(12) United States Patent
Narjes et al.

(10) Patent No.: US 10,988,445 B2
(45) Date of Patent: *Apr. 27, 2021

(54) COMPOUNDS

(71) Applicant: AstraZeneca AB, Södertälje (SE)

(72) Inventors: Frank Narjes, Mölndal (SE); Roine Ingemar Olsson, Mölndal (SE); Stefan Von Berg, Mölndal (SE); Sarah Lever, Mölndal (SE)

(73) Assignee: AstraZeneca AB, Södertälje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/693,866

(22) Filed: Nov. 25, 2019

(65) Prior Publication Data

US 2020/0181084 A1  Jun. 11, 2020

Related U.S. Application Data

(63) Continuation of application No. 15/997,310, filed on Jun. 4, 2018, now Pat. No. 10,526,286, which is a continuation of application No. 15/378,360, filed on Dec. 14, 2016, now Pat. No. 10,011,566.

(60) Provisional application No. 62/267,391, filed on Dec. 15, 2015.

(51) Int. Cl.
| | |
|---|---|
| *C07D 209/44* | (2006.01) |
| *C07D 407/06* | (2006.01) |
| *A61K 31/4035* | (2006.01) |
| *C07D 405/06* | (2006.01) |

(52) U.S. Cl.
CPC ........ *C07D 209/44* (2013.01); *A61K 31/4035* (2013.01); *C07D 405/06* (2013.01); *C07D 407/06* (2013.01)

(58) Field of Classification Search
CPC .................................................. C07D 209/44
See application file for complete search history.

(56) References Cited

U.S. PATENT DOCUMENTS

| | | |
|---|---|---|
| 2005/0165218 A1 | 7/2005 | Beerli et al. |
| 2015/0218160 A1 | 8/2015 | Claremon et al. |
| 2016/0122318 A1 | 5/2016 | Claremon et al. |
| 2016/0122345 A1 | 5/2016 | Claremon et al. |
| 2017/0050974 A1 | 2/2017 | Yamamoto et al. |
| 2017/0107240 A1 | 4/2017 | Yamamoto et al. |
| 2017/0233390 A1 | 8/2017 | Schnute et al. |

FOREIGN PATENT DOCUMENTS

| | | |
|---|---|---|
| EP | 2076260 B1 | 3/2011 |
| EP | 3018123 A1 | 5/2016 |
| EP | 3018126 A1 | 5/2016 |
| JP | 2009051827 | 3/2009 |
| JP | 2009051828 | 3/2009 |
| WO | WO1996002537 A1 | 2/1996 |
| WO | WO1997027852 A1 | 8/1997 |
| WO | WO1999043672 A1 | 9/1999 |
| WO | WO2000054759 A2 | 9/2000 |
| WO | WO2001003705 A1 | 1/2001 |
| WO | WO2001085695 A1 | 11/2001 |
| WO | WO2002020463 A2 | 3/2002 |
| WO | WO2002046164 A1 | 6/2002 |
| WO | WO2002058690 A2 | 8/2002 |
| WO | WO2003041641 A2 | 5/2003 |
| WO | WO2003082198 A2 | 10/2003 |
| WO | WO2005009383 A2 | 2/2005 |
| WO | WO2005013946 A2 | 2/2005 |
| WO | WO2005055998 A1 | 6/2005 |
| WO | WO2006091862 A2 | 8/2006 |
| WO | WO2007055374 | 5/2007 |
| WO | WO2007058990 A2 | 5/2007 |
| WO | WO2007088999 A1 | 8/2007 |
| WO | WO2007106525 A1 | 9/2007 |
| WO | WO2007146712 A2 | 12/2007 |
| WO | WO2008008020 A1 | 1/2008 |
| WO | WO2008008022 A1 | 1/2008 |
| WO | WO2011115892 A1 | 9/2011 |
| WO | WO2012027965 A1 | 3/2012 |
| WO | WO2012028100 A1 | 3/2012 |
| WO | WO2012100732 A1 | 8/2012 |
| WO | WO2012100734 A1 | 8/2012 |
| WO | WO2012106995 A1 | 8/2012 |
| WO | WO2012158784 A2 | 11/2012 |
| WO | WO2013029338 A1 | 3/2013 |
| WO | WO2013100027 A1 | 7/2013 |

(Continued)

OTHER PUBLICATIONS

U.S. Appl. No. 10/011,566, filed Jul. 3, 2018, Narjes et al.

(Continued)

*Primary Examiner* — Shawquia Jackson

(57) ABSTRACT

The present specification provides a compound of formula (I):

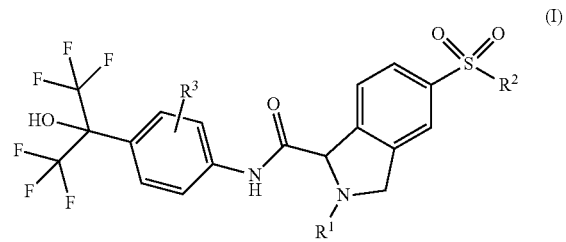

or a pharmaceutically acceptable salt thereof; a process for preparing such a compound; and to the use of such a compound in the treatment of an RORγ and/or RORγt mediated disease state.

9 Claims, No Drawings

Specification includes a Sequence Listing.

(56) References Cited

FOREIGN PATENT DOCUMENTS

| | | | |
|---|---|---|---|
| WO | WO2013120835 A1 | 8/2013 |
| WO | WO2013159095 A1 | 10/2013 |
| WO | WO2013166013 A1 | 11/2013 |
| WO | WO2013166015 A1 | 11/2013 |
| WO | WO2013171729 A2 | 11/2013 |
| WO | WO2014125426 A1 | 8/2014 |
| WO | WO2014165816 A1 | 10/2014 |
| WO | WO2014179564 A1 | 11/2014 |
| WO | WO2015017335 A1 | 2/2015 |
| WO | WO2015035032 A1 | 3/2015 |
| WO | WO2015082533 A1 | 6/2015 |
| WO | WO2015083130 A1 | 6/2015 |
| WO | WO2015101928 A1 | 7/2015 |
| WO | WO2015116904 A1 | 8/2015 |
| WO | WO2015129853 A1 | 9/2015 |
| WO | WO2015145371 A1 | 10/2015 |
| WO | WO2015159233 A1 | 10/2015 |
| WO | WO2015160654 A1 | 10/2015 |
| WO | WO2016002968 A1 | 1/2016 |
| WO | WO2016020288 A1 | 2/2016 |
| WO | WO2016046755 A1 | 3/2016 |
| WO | WO2016061160 A1 | 4/2016 |
| WO | WO2016073633 A1 | 5/2016 |
| WO | WO2016176399 A1 | 11/2016 |
| WO | WO2016185342 A1 | 11/2016 |
| WO | WO2016193452 A1 | 12/2016 |
| WO | WO2016193459 A1 | 12/2016 |
| WO | WO2016193461 A1 | 12/2016 |
| WO | WO2016193468 A1 | 12/2016 |
| WO | WO2016193470 A1 | 12/2016 |
| WO | WO2017010399 A1 | 1/2017 |
| WO | WO2017024018 A1 | 2/2017 |
| WO | WO2017058831 A1 | 4/2017 |

OTHER PUBLICATIONS

U.S. Appl. No. 10/526,286, filed Jan. 7, 2020, Narjes et al.
Bartlett et al., Targeting the IL-17-$T_H$17, Nature Reviews, 2015, pp. 11-12, vol. 14.
CAS Registry No. 1009689-67-1, Entered STN Mar. 23, 2008, CHEMCATS (Chemical Catalogs Online).
CAS Registry No. 1030916-68-7, Entered STN Jun. 26, 2008, CHEMCATS (Chemical Catalogs Online).
CAS Registry No. 1792962-73-2, Entered STN Jul. 1, 2015, CHEMCATS (Chemical Catalogs Online).
Cheng et al., Bioorganic and Medicinal Chemistry Letters 16 (2006) 3484-3488.
Cheng et al., Heteroaryl substituted bis-trifluoromethyl carbinols as malonyl-CoA decarboxylase inhibitors, Bioorganic & Medicinal Chemistry Letters, 2006, pp. 3484-3488, vol. 16.
Cosmi, et al., Th17 regulating lower airway disease, Curr. Opin. Allergy Clin. Immunol., 2016, 16(1): 1-6.
Diabetes Mellitus (DM) Online; retrieved from the internet on May 29, 2017; URL; http://www.merckmanuals.com/professional/endocrine-and-metabolic-disorders/diabetes-mellitus-dm.
Fauber et al., Journal of Medicinal Chemistry 2014 5871-5892.
Gaffen et al., IL-23-IL-17 immune axis: Discovery, Mechanistic Understanding, and Clinical Testing, Nat. Rev. Immunol., 2014, pp. 585-600, vol. 14 (9).
He et al., RORγt, a Novel Isoform of an Orphan Receptor, Negatively Regulates Fas Ligand Expression and IL-2 Production in T Cells, Immunity, 1998, pp. 797-806, vol. 9 (6).
Ivanov et al., The Orphan Nuclear Receptor RORgt Directs the Differentiation Program of Proinflammatory IL-17+ T Helper Cells, Cell, 2006, pp. 1121-1133, vol. 126.
Jetten et al., The RoR Nuclear Orphan Receptor Subfamily: Critical Regulators of Multiple Biological Processes, Progress in Nucleic Acid Research and Molecular Biology, 2001, pp. 205-247, vol. 69.
Kamenecka et al., Med. Chem. Comm. 2013 764-776.
Mease, Philip J., Inhibition of interleukin-17, interleukin-23 and the TH17 cell pathway in the treatment of psoriatic arthritis and psoriasis, Curr. Opin. Rheumatol., 2015, 27(2):127-133.
Morán-Ramallal, Dynamic Kinetic Resolution of 1,3-Dihydro-2H-isoindole-1-carboxylic Acid Methyl Ester: Asymmetric Transformations toward Isoindoline Carbamates, Organic Letters, 2012, pp. 1696-1699, vol. 14 (7).
Narjes et al., Potent and Orally Bioavailable Inverse Agonists of RORγt Resulting from Structure-Based Design, J. Med. Chem., 2018, pp. 7796-7813, vol. 61.
Narjes, The discovery of AZD0284, Symposium presentation, Sep. 13, 2017, 1-31, Cambridge, United Kingdom.
Narjes, "The discovery of AZD0284, an inverse agonist of the nuclear receptor RORγ," American Chemical Society, 2017 Drug Design and Delivery Symposium Webinar, Oct. 26, 2017 (Webinar Slides).
Narjes, "The discovery of AZD0284, an inverse agonist of the nuclear receptor RORγ," American Chemical Society, 2017 Drug Design and Delivery Symposium Webinar, Oct. 26, 2017 (Slides posted at https://www.acs.org/content/dam/acsorg/events/drug-discovery/slides/2017-10-26-ddds9-psoriasis-public-slides.pdf).
Nishimura, Small Molecule Disruptors of the Glucokinase—Glucokinase Regulatory Protein Interaction: 3. Structure—Activity Relationships within the Aryl Carbinol Region of the N-Arylsulfonamido-N'-arylpiperazine Series, J. Med. Chem., 2014, pp. 3094-3116, vol. 57.
Psoriasis [Online], retrieved from the internet on Nov. 26, 2017; URL https://medicinenet.com/psoriasis/article.htm.
Von Berg, et al., Discovery of Potent and Orally Bioavailable Inverse Agonists of the Retinoic Acid Receptor-Related Orphan Receptor C2, ACS Med. Chem. Lett., 2019, 10(6):972-977.
Wang et al., ACS Medicinal Chemistry Letters 2015 787-792.
Wang et al., Bioorganic and Medicinal Chemistry 2015 5293-5302.
Wilke, Deciphering the role of Th17 cells in human disease, Trends Immunol., 2011, pp. 603-611, vol. 32 (12).
Zhang et al., Acta Pharmacologica Sinica 2015 71-87.
International Search Report and Written Opinion dated Mar. 14, 2017 for Application No. PCT/EP2016/080885.

SEQUENCE LISTING

```
<160> NUMBER OF SEQ ID NOS: 2

<210> SEQ ID NO 1
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

His Asn His Asn His Asn His Asn His Asn His Asn Gly Gly Leu Asn
1               5                   10                  15

Asp Ile Phe Glu Ala Gln Lys Ile Glu Trp His Glu Gly Ser Pro Ile
                20                  25                  30

Leu Gly Tyr Trp Lys Ile Lys Gly Leu Val Gln Pro Thr Arg Leu Leu
            35                  40                  45

Leu Glu Tyr Leu Glu Glu Lys Tyr Glu Glu His Leu Tyr Glu Arg Asp
        50                  55                  60

Glu Gly Asp Lys Trp Arg Asn Lys Lys Phe Glu Leu Gly Leu Glu Phe
65                  70                  75                  80

Pro Asn Leu Pro Tyr Tyr Ile Asp Gly Asp Val Lys Leu Thr Gln Ser
                85                  90                  95

Met Ala Ile Ile Arg Tyr Ile Ala Asp Lys His Asn Met Leu Gly Gly
            100                 105                 110

Cys Pro Lys Glu Arg Ala Glu Ile Ser Met Leu Glu Gly Ala Val Leu
        115                 120                 125

Asp Ile Arg Tyr Gly Val Ser Arg Ile Ala Tyr Ser Lys Asp Phe Glu
    130                 135                 140

Thr Leu Lys Val Asp Phe Leu Ser Lys Leu Pro Glu Met Leu Lys Met
145                 150                 155                 160

Phe Glu Asp Arg Leu Cys His Lys Thr Tyr Leu Asn Gly Asp His Val
                165                 170                 175
```

```
Thr His Pro Asp Phe Met Leu Tyr Asp Ala Leu Asp Val Val Leu Tyr
            180                 185                 190

Met Asp Pro Met Cys Leu Asp Ala Phe Pro Lys Leu Val Cys Phe Lys
        195                 200                 205

Lys Arg Ile Glu Ala Ile Pro Gln Ile Asp Lys Tyr Leu Lys Ser Ser
    210                 215                 220

Lys Tyr Ile Ala Trp Pro Leu Gln Gly Trp Gln Ala Thr Phe Gly Gly
225                 230                 235                 240

Gly Asp His Pro Pro Lys Ser Asp Tyr Asp Ile Pro Thr Thr Gly Ser
                245                 250                 255

Gly Ser Gly Ser Leu Val Pro Arg Gly Ser Thr Pro Glu Ala Pro Tyr
            260                 265                 270

Ala Ser Leu Thr Glu Ile Glu His Leu Val Gln Ser Val Cys Lys Ser
        275                 280                 285

Tyr Arg Glu Thr Cys Gln Leu Arg Leu Glu Asp Leu Leu Arg Gln Arg
    290                 295                 300

Ser Asn Ile Phe Ser Arg Glu Glu Val Thr Gly Tyr Gln Arg Lys Ser
305                 310                 315                 320

Met Trp Glu Met Trp Glu Arg Cys Ala His His Leu Thr Glu Ala Ile
                325                 330                 335

Gln Tyr Val Val Glu Phe Ala Lys Arg Leu Ser Gly Phe Met Glu Leu
            340                 345                 350

Cys Gln Asn Asp Gln Ile Val Leu Leu Lys Ala Gly Ala Met Glu Val
        355                 360                 365

Val Leu Val Arg Met Cys Arg Ala Tyr Asn Ala Asp Asn Arg Thr Val
    370                 375                 380

Phe Phe Glu Gly Lys Tyr Gly Gly Met Glu Leu Phe Arg Ala Leu Gly
385                 390                 395                 400

Cys Ser Glu Leu Ile Ser Ser Ile Phe Asp Phe Ser His Ser Leu Ser
                405                 410                 415

Ala Leu His Phe Ser Glu Asp Glu Ile Ala Leu Tyr Thr Ala Leu Val
            420                 425                 430

Leu Ile Asn Ala His Arg Pro Gly Leu Gln Glu Lys Arg Lys Val Glu
        435                 440                 445

Gln Leu Gln Tyr Asn Leu Glu Leu Ala Phe His His His Leu Cys Lys
    450                 455                 460

Thr His Arg Gln Ser Ile Leu Ala Lys Leu Pro Pro Lys Gly Lys Leu
465                 470                 475                 480

Arg Ser Leu Cys Ser Gln His Val Glu Arg Leu Gln Ile Phe Gln His
                485                 490                 495

Leu His Pro Ile Val Val Gln Ala Ala Phe Pro Pro Leu Tyr Lys Glu
            500                 505                 510

Leu Phe Ser Thr Glu Thr Glu Ser Pro Val Gly Leu Ser Lys
        515                 520                 525

<210> SEQ ID NO 2
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met His Asn His Asn His Asn His Asn His Asn His Asn Gly Gly Leu
```

-continued

```
1               5                   10                  15
Asn Asp Ile Phe Glu Ala Gln Lys Ile Glu Trp His Glu Gly Met Lys
                20                  25                  30

Ile Glu Glu Gly Lys Leu Val Ile Trp Ile Asn Gly Asp Lys Gly Tyr
                35                  40                  45

Asn Gly Leu Ala Glu Val Gly Lys Lys Phe Glu Lys Asp Thr Gly Ile
50                              55                  60

Lys Val Thr Val Glu His Pro Asp Lys Leu Glu Glu Lys Phe Pro Gln
65                  70                  75                  80

Val Ala Ala Thr Gly Asp Gly Pro Asp Ile Ile Phe Trp Ala His Asp
                    85                  90                  95

Arg Phe Gly Gly Tyr Ala Gln Ser Gly Leu Leu Ala Glu Ile Thr Pro
                    100                 105                 110

Asp Lys Ala Phe Gln Asp Lys Leu Tyr Pro Phe Thr Trp Asp Ala Val
                    115                 120                 125

Arg Tyr Asn Gly Lys Leu Ile Ala Tyr Pro Ile Ala Val Glu Ala Leu
                130                 135                 140

Ser Leu Ile Tyr Asn Lys Asp Leu Leu Pro Asn Pro Pro Lys Thr Trp
145                 150                 155                 160

Glu Glu Ile Pro Ala Leu Asp Lys Glu Leu Lys Ala Lys Gly Lys Ser
                    165                 170                 175

Ala Leu Met Phe Asn Leu Gln Glu Pro Tyr Phe Thr Trp Pro Leu Ile
                180                 185                 190

Ala Ala Asp Gly Gly Tyr Ala Phe Lys Tyr Glu Asn Gly Lys Tyr Asp
                195                 200                 205

Ile Lys Asp Val Gly Val Asp Asn Ala Gly Ala Lys Ala Gly Leu Thr
210                 215                 220

Phe Leu Val Asp Leu Ile Lys Asn Lys His Met Asn Ala Asp Thr Asp
225                 230                 235                 240

Tyr Ser Ile Ala Glu Ala Ala Phe Asn Lys Gly Glu Thr Ala Met Thr
                    245                 250                 255

Ile Asn Gly Pro Trp Ala Trp Ser Asn Ile Asp Thr Ser Lys Val Asn
                260                 265                 270

Tyr Gly Val Thr Val Leu Pro Thr Phe Lys Gly Gln Pro Ser Lys Pro
                275                 280                 285

Phe Val Gly Val Leu Ser Ala Gly Ile Asn Ala Ala Ser Pro Asn Lys
                290                 295                 300

Glu Leu Ala Lys Glu Phe Leu Glu Asn Tyr Leu Leu Thr Asp Glu Gly
305                 310                 315                 320

Leu Glu Ala Val Asn Lys Asp Lys Pro Leu Gly Ala Val Ala Leu Lys
                    325                 330                 335

Ser Tyr Glu Glu Leu Ala Lys Asp Pro Arg Ile Ala Ala Thr Met
                340                 345                 350

Glu Asn Ala Gln Lys Gly Glu Ile Met Pro Asn Ile Pro Gln Met Ser
                355                 360                 365

Ala Phe Trp Tyr Ala Val Arg Thr Ala Val Ile Asn Ala Ala Ser Gly
                370                 375                 380

Arg Gln Thr Val Asp Glu Ala Leu Lys Asp Ala Gln Thr Gly Ser Asp
385                 390                 395                 400

Tyr Asp Ile Pro Thr Thr Gly Ser Gly Ser Gly Ser Leu Val Pro Arg
                    405                 410                 415

Gly Ser Thr Pro Glu Ala Pro Tyr Ala Ser Leu Thr Glu Ile Glu His
                    420                 425                 430
```

-continued

```
Leu Val Gln Ser Val Cys Lys Ser Tyr Arg Glu Thr Cys Gln Leu Arg
        435                 440                 445
Leu Glu Asp Leu Leu Arg Gln Arg Ser Asn Ile Phe Ser Arg Glu Glu
    450                 455                 460
Val Thr Gly Tyr Gln Arg Lys Ser Met Trp Glu Met Trp Glu Arg Cys
465                 470                 475                 480
Ala His His Leu Thr Glu Ala Ile Gln Tyr Val Val Glu Phe Ala Lys
                485                 490                 495
Arg Leu Ser Gly Phe Met Glu Leu Cys Gln Asn Asp Gln Ile Val Leu
                500                 505                 510
Leu Lys Ala Gly Ala Met Glu Val Val Leu Val Arg Met Cys Arg Ala
        515                 520                 525
Tyr Asn Ala Asp Asn Arg Thr Val Phe Phe Glu Gly Lys Tyr Gly Gly
    530                 535                 540
Met Glu Leu Phe Arg Ala Leu Gly Cys Ser Glu Leu Ile Ser Ser Ile
545                 550                 555                 560
Phe Asp Phe Ser His Ser Leu Ser Ala Leu His Phe Ser Glu Asp Glu
                565                 570                 575
Ile Ala Leu Tyr Thr Ala Leu Val Leu Ile Asn Ala His Arg Pro Gly
                580                 585                 590
Leu Gln Glu Lys Arg Lys Val Glu Gln Leu Gln Tyr Asn Leu Glu Leu
        595                 600                 605
Ala Phe His His His Leu Cys Lys Thr His Arg Gln Ser Ile Leu Ala
    610                 615                 620
Lys Leu Pro Pro Lys Gly Lys Leu Arg Ser Leu Cys Ser Gln His Val
625                 630                 635                 640
Glu Arg Leu Gln Ile Phe Gln His Leu His Pro Ile Val Val Gln Ala
                645                 650                 655
Ala Phe Pro Pro Leu Tyr Lys Glu Leu Phe Ser Thr Glu Thr Glu Ser
                660                 665                 670
Pro Val Gly Leu Ser Lys
                675
```

COMPOUNDS

CROSS-REFERENCE TO RELATED APPLICATIONS

This application is a continuation of U.S. application Ser. No. 15/997,310, filed on Jun. 4, 2018, which is a continuation of U.S. application Ser. No. 15/378,360, filed on Dec. 14, 2016, which claims the benefit under 35 U.S.C. § 119(e) of U.S. Provisional Patent Application No. 62/267,391, filed on Dec. 15, 2015. All of the above listed applications are incorporated by reference herein in its entirety for all purposes.

REFERENCE TO THE SEQUENCE LISTING

This application incorporates by reference a Sequence Listing submitted with this application as text file entitled 200357-US-CNT-2_SL, created on Nov. 25, 2019, and having a size of 10.5 KB.

This specification relates to arylamide compounds having pharmaceutical activity, to processes for preparing such compounds, to pharmaceutical compositions comprising such compounds and to the use of such compounds as active therapeutic agents.

Retinoic acid receptor-related orphan receptors (RORs) are a family of transcription factors which belong to the nuclear receptor superfamily. The family is comprised of three genes, RORA, RORB, and RORC, all of which express more than one isoform of the protein (Jetten, A M; Kurebayashi, S; Ueda, E. (2006) *Prog. Nucleic Acid Res. Mol. Biol.* 69:205-47). RORC (also known as RORγ or NR1F3) is translated into two major protein isoforms which share most of the amino acid sequence, including the ligand binding domain, but differ 21 amino acids in length in the N-terminal end. The two isoforms are differentially expressed. The longer form (RORγ) is found in many tissues such as liver, kidney, muscle and some cells of hematopoetic origin whereas the shorter form (RORγt) is expressed in the thymus and cells of the immune system (He, Y W; Deftos, M L; Ojala, E W; Bevan, M J (1998) *Immunity* 9(6):797-806). RORγt has been shown to be required for differentiation and function of Th17 cells and coordinates the expression of IL17 in many immune cells (Ivanov, II; McKenzie, BS; Zhou, L; Littman, D R et al. (2006) *Cell* 126:1121-1133). Th17 cells are a subset of T helper cells that produce IL17, IL22, and other cytokines. They attain their Th17 phenotype through local exposure to a combination of cytokines such as TGFβ, IL1β and IL2β. The mediators and transcription factors that are required for their differentiation, polarization and effector function are referred to as the Th17 axis, and the Th17 axis includes other cell types which produce the same cytokines (and corresponding receptors), such as innate lymphoid cells (ILCs) and γδ T cells.

The Th17 axis of biological processes has been implicated in the pathology of many human diseases with an immune component or autoimmune pathology, such as psoriasis, ankylosing spondylitis, psoriatic arthritis, asthma, chronic obstructive pulmonary disease, ulcerative cholitis, Crohn's disease, multiple sclerosis, inflammatory bowel disease, rheumatoid arthritis, graft versus host disease, systemic lupus erythematosis, lupus nephritis, insulin dependent diabetes type I, and also in cancer (Wilke C M, Bishop K, Fox D, Zou W (2011) *Trends Immunol.* 32(12):603-11; Bartlett, H S; Million, R P (2015) *Nat. Rev. Drug Discovery* 14:11-12). Many of these diseases share genetic associations to genes contained in the Th17 axis (Gaffen S L, Jain R, Garg A V, Cua D J (2014) *Nat. Rev. Immunol.* 14(9):585-600).

RORγt is central to the Th17 axis since it is required for the function of Th17 cells and governs cytokine production and related biological processes in many other cell types. Due to the central role of RORγt it is desirable to regulate RORγt activity as a means of treatment of diseases where the Th17 axis is perturbed. Accordingly there is a need for new therapeutic agents which modulate RORγt.

Briefly, this specification describes, in part, a compound of formula (I):

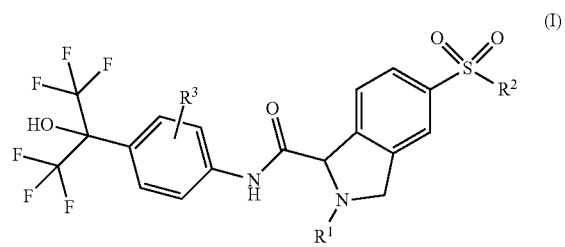

wherein:

$R^1$ is H or $(CO)R^4$;

$R^2$ is $C_{1-6}$ alkyl, cyclopropyl, $CH_2$-cyclopropyl, or $NR^5R^6$, wherein said $C_{1-6}$ alkyl is optionally substituted with OH or $C_{1-6}$ alkoxy and said $CH_2$-cyclopropyl is optionally substituted with halo, OH, CN or $C_{1-6}$ alkoxy;

$R^3$ is H, $C_{1-6}$ alkyl, $C_{1-6}$ alkoxy, halo or CN.

$R^4$ is:

H;

$C_{1-6}$ alkyl optionally substituted with $(R^7)_a$;

$C_{3-7}$ cycloalkyl optionally substituted with halo, $C_{1-6}$ alkyl, OH, CN, $C_{1-6}$ alkoxy, or $C_{1-3}$ alkyl-$OR^8$;

heterocycloalkyl optionally substituted with $C_{1-6}$ alkyl or OH;

$C_{1-6}$ alkoxy; or $NHR^{13}$;

a is 1, 2 or 3;

$R^6$ is H, $C_{1-6}$ alkyl or $C_{3-7}$ cycloalkyl;

$R^7$ is independently selected from the group consisting of halo, OH, CN, $C_{1-6}$ alkoxy, $NR^9R^{10}$, $C_{3-7}$ cycloalkyl, heterocycloalkyl and aryl, wherein said $C_{3-7}$ cycloalkyl, heterocycloalkyl or aryl groups are further optionally substituted with 1, 2 or 3 groups independently selected from the group consisting of $C_{1-6}$ alkyl, CN, OH, $C_{1-6}$ alkoxy and $NR^{11}R^{12}$;

$R^{13}$ is H, $C_{1-6}$ alkyl or $C_{3-7}$ cycloalkyl;

$R^5$, $R^8$, $R^9$, $R^{10}$, $R^{11}$ and $R^{12}$ are each independently H or $C_{1-6}$ alkyl;

or a pharmaceutically acceptable salt thereof.

This specification also describes, in part, pharmaceutical compositions which comprise a compound of the formula (I), or a pharmaceutically acceptable salt thereof, and at least one pharmaceutically acceptable excipient.

This specification also describes, in part, a compound of formula (I), or a pharmaceutically acceptable salt thereof, for use in therapy.

This specification also describes, in part, a compound of formula (I), or a pharmaceutically acceptable salt thereof, for the treatment or prevention of an RORγ and/or RORγt mediated disease state.

This specification also describes, in part, the use of a compound of formula (I), or a pharmaceutically acceptable salt thereof, in the manufacture of a medicament for the treatment or prevention of an RORγ and/or RORγt mediated disease state.

This specification also describes, in part, a method of treating or of preventing an RORγ and/or RORγt mediated disease state in a mammal suffering from, or at risk of, said disease, which comprises administering to a mammal in need of such treatment a therapeutically effective amount of a compound of formula (I), or a pharmaceutically acceptable salt thereof.

Further aspects of the specification will be apparent to one skilled in the art from reading this specification.

The compounds of the specification may exist in salt-form or in non-salt form (ie. as a free base), and the present specification covers both salt forms and non-salt forms. Compounds described in this specification may form acid addition salts or base addition salts. In general, an acid addition salt can be prepared using various inorganic or organic acids. Such salts can typically be formed by, for example, mixing the compound with an acid (e.g. a stoichiometric amount of an acid) using various methods known in the art. This mixing may occur in water, an organic solvent (e.g. ether, ethyl acetate, ethanol, methanol, isopropanol, or acetonitrile), or an aqueous/organic mixture. In another aspect of the specification acid addition salts are, for example, trifluoroacetate, formate, acetate or hydrochloric. In general, a base addition salt can be prepared using various inorganic or organic bases, for example an alkali or alkaline earth metal salt such as a sodium, calcium or magnesium salt, or other metal salts, such as potassium or zinc, or an ammonium salt, or a salt with an organic base such as methylamine, dimethylamine, trimethylamine, piperidine or morpholine. The skilled person will be aware of the general principles and techniques of preparing pharmaceutical salts, such as those described in, for example, Berge et al., *J. Pharm. Sci.*, 66, 1-19 (1977).

Compounds and salts described in this specification include one or more chiral (i.e. asymmetric) centres. To the extent a structure or chemical name in this specification does not indicate the chirality, the structure or name is intended to encompass any single stereoisomer (i.e. any single chiral isomer) corresponding to that structure or name, as well as any mixture of stereoisomers (e.g. a racemate). In some embodiments, a single stereoisomer is obtained by isolating it from a mixture of isomers (e.g. a racemate) using, for example, chiral chromatographic separation. In other embodiments, a single stereoisomer is obtained through direct synthesis from, for example, a chiral starting material. A particular enantiomer of a compound described herein may be more active than other enantiomers of the same compound.

According to one embodiment there is provided a compound of formula (I), or a pharmaceutically acceptable salt thereof, which is a single enantiomer being in an enantiomeric excess (% ee) of ≥95, ≥98% or ≥99%. Conveniently, the single enantiomer is present in an enantiomeric excess (% ee) of ≥99%.

According to another embodiment there is provided a pharmaceutical composition, which comprises a compound of formula (I), which is a single enantiomer being in an enantiomeric excess (% ee) of ≥95, ≥98% or ≥99% or a pharmaceutically acceptable salt thereof, in association with one or more pharmaceutically acceptable excipients. Conveniently, the single enantiomer is present in an enantiomeric excess (% ee) of ≥99%.

When in solid crystalline form a compound of formula (I) can be in the form of a co-crystal with another chemical entity and the specification encompasses all such co-crystals.

The compounds of the specification may exist as a solvate (such as a hydrate) as well as unsolvated forms, and the present specification covers all such solvates.

Compounds and salts described in this specification may exist in various tautomeric forms and the specification encompasses all such tautomeric forms. "Tautomers" are structural isomers that exist in equilibrium resulting from the migration of a hydrogen atom.

Compounds and salts described in this specification may be isotopically-labeled (or "radio-labeled"). In that instance, one or more atoms are replaced by an atom having an atomic mass or mass number different from the atomic mass or mass number typically found in nature. The specification encompasses isotopically-labelled forms of compounds disclosed herein. Examples of isotopes that may be incorporated include $^{2}$H (also written as "D" for deuterium), $^{3}$H (also written as "T" for tritium), $^{11}$C, $^{13}$C, $^{14}$C, $^{13}$N, $^{15}$N, $^{15}$O, $^{17}$O, $^{18}$O and $^{36}$Cl. The isotope that is used will depend on the specific application of that radio-labeled derivative. For example, for in vitro receptor labeling and competition assays, H or $^{14}$C are often useful. For radio-imaging applications, $^{11}$C is often useful. In some embodiments, the radionuclide is $^{3}$H. In some embodiments, the radionuclide is $^{14}$C. In some embodiments, the radionuclide is $^{11}$C.

Unless otherwise stated, halo is selected from chloro (Cl), fluoro (F), bromo (Br) and iodo (I), such as fluoro.

Cycloalkyl is a non-aromatic carbocyclic ring. The carbocyclic ring may be saturated or unsaturated, and may be bridged or unbridged. $C_{3-7}$ cycloalkyl is any such carbocyclic ring containing 3 to 7 carbon atoms. An example of $C_{3-7}$ cycloalkyl is an unsaturated non-aromatic carbocyclic ring containing 3 to 7 carbon atoms. Examples of suitable cycloalkyl groups are cyclopropyl, cyclobutyl, cyclopentyl, cyclohexyl and cycloheptyl, such as cyclopropyl and cyclobutyl.

Heterocycloalkyl is a 3 to 9 membered non-aromatic, mono- or bi-cyclic ring comprising one or two heteroatoms independently selected from nitrogen, oxygen or sulphur; or an N-oxide thereof, or an S-oxide or S-dioxide thereof. The ring may be saturated or unsaturated, and may be bridged or unbridged. An example of heterocycloalkyl is an unsaturated 4 to 6 membered non-aromatic, mono-cyclic ring comprising one heteroatom independently selected from nitrogen or oxygen; or an N-oxide thereof. Examples of suitable heterocycloalkyl groups include oxiranyl, aziridinyl, azetidinyl, oxetanyl, tetrahydrofuranyl, pyrrolidinyl, tetrahydropyranyl, piperidinyl, morpholinyl, thiomorpholinyl, and piperazinyl, such as azetidinyl, oxetanyl, pyrrolidinyl or tetrahydrofuranyl, for example oxetanyl or tetrahydrofuranyl. For the avoidance of doubt, substituents on the heterocycloalkyl ring may be linked via either a carbon atom or a heteroatom.

Aryl is an aromatic ring containing 6 or 10 carbon atoms. Examples of suitable aryl groups include phenyl and naphthyl, such as phenyl.

Unless otherwise stated alkyl, alkoxy and haloalkyl groups containing the requisite number of carbon atoms can be branched or unbranched. Examples of suitable $C_{1-6}$ alkyl groups include methyl (Me), ethyl (Et), n-propyl, i-propyl, n-butyl, sec-butyl, i-butyl, t-butyl, n-pentyl, i-pentyl, neopentyl, n-hexyl and i-hexyl, such as methyl, ethyl, n-propyl, i-propyl, and i-butyl. Examples of suitable $C_{1-6}$ alkoxy groups include methoxy, ethoxy, n-propoxy, i-propoxy, n-butoxy, sec-butoxy, t-butoxy, n-pentoxy, i-pentoxy, n-hexoxy, i-hexoxy, methoxyethyl, methoxypropyl, ethoxyethyl and methoxybutyl, such as methoxy, ethoxy, i-propoxy and t-butoxy. Examples of suitable $C_{1-3}$ alkyl-OH groups include —$CH_2OH$ and —$CH_2CH_2OH$, such as —$CH_2OH$.

For the avoidance of doubt, where multiple substituents are independently selected from a given group, the selected substituents may comprise the same substituents or different substituents from within the given group. By way of example only, where $R^4$ is $C_{1-6}$ alkyl optionally substituted with $(R^7)_a$, and where a is 2, the two $R^7$ substituents could be the same, for instance both fluoro, or could be different, for instance one fluoro and one OH.

In one embodiment $R^1$ is H.

In another embodiment $R^1$ is $(CO)R^4$.

In one embodiment $R^2$ is $C_{1-6}$ alkyl (optionally substituted with OH or $C_{1-6}$ alkoxy), cyclopropyl, unsubstituted $CH_2$-cyclopropyl, or $NR^5R^6$.

In one embodiment $R^2$ is $C_{1-6}$ alkyl (optionally substituted with OH or $C_{1-6}$ alkoxy), or $CH_2$-cyclopropyl (optionally substituted with halo, OH, CN or $C_{1-6}$ alkoxy).

In one embodiment $R^2$ is $C_{1-6}$ alkyl (optionally substituted with OH or $C_{1-6}$ alkoxy), or $CH_2$-cyclopropyl (optionally substituted with OH, CN or $C_{1-6}$ alkoxy).

In another embodiment $R^2$ is unsubstituted $C_{1-6}$ alkyl or unsubstituted $CH_2$-cyclopropyl.

In another embodiment $R^2$ is $C_{1-6}$ alkyl optionally substituted with OH or $C_{1-6}$ alkoxy.

In another embodiment $R^2$ is $C_{1-6}$ alkyl substituted with OH, such as —$CH_2CH_2OH$, —$CH_2CH_2CH_2OH$ or —$CH_2CH(OH)CH_3$, for example —$CH_2CH_2OH$.

In another embodiment $R^2$ is $C_{1-6}$ alkyl substituted with $C_{1-6}$ alkoxy, such as —$CH_2CH_2OCH_3$, or —$CH_2CH_2CH_2OCH_3$, for example —$CH_2CH_2OCH_3$.

In another embodiment $R^2$ is unsubstituted $C_{1-6}$ alkyl, such as methyl, ethyl or i-propyl.

In another embodiment $R^2$ is unsubstituted methyl or unsubstituted ethyl. In a further embodiment $R^2$ is unsubstituted methyl.

In another embodiment $R^2$ is cyclopropyl or $CH_2$-cyclopropyl (optionally substituted with OH, CN or $C_{1-6}$ alkoxy).

In another embodiment $R^2$ is $CH_2$-cyclopropyl (optionally substituted with halo, OH, CN or $C_{1-6}$ alkoxy).

In another embodiment $R^2$ is $CH_2$-cyclopropyl substituted with halo, such as fluoro.

In another embodiment $R^2$ is $CH_2$-cyclopropyl (optionally substituted with OH, CN or $C_{1-6}$ alkoxy).

In another embodiment $R^2$ is unsubstituted $CH_2$-cyclopropyl.

In another embodiment $R^2$ is $NR^5R^6$.

In one embodiment $R^3$ is H, $C_{1-6}$ alkyl or halo.

In another embodiment $R^3$ is H, methyl or fluoro.

In another embodiment $R^3$ is H.

In another embodiment $R^3$ is $C_{1-6}$ alkyl such as methyl, ethyl or i-propyl, for example methyl.

In another embodiment $R^3$ is halo, for example fluoro.

In one embodiment $R^4$ is:
H;
$C_{1-6}$ alkyl optionally substituted with $(R^7)_a$;
$C_{3-7}$ cycloalkyl optionally substituted with $C_{1-6}$ alkyl, OH, CN, $C_{1-6}$ alkoxy, or $C_{1-3}$ alkyl-$OR^8$;
heterocycloalkyl optionally substituted with $C_{1-6}$ alkyl or OH; or
$C_{1-6}$ alkoxy;

In another embodiment $R^4$ is H.

In one embodiment $R^4$ is $C_{1-6}$ alkyl optionally substituted with $(R^7)_a$.

In another embodiment $R^4$ is unsubstituted $C_{1-6}$ alkyl. In a further embodiment, $R^4$ is unsubstituted methyl. In a further embodiment, $R^4$ is unsubstituted ethyl.

In another embodiment a is 1 or 2. In another embodiment a is 2 or 3. In another embodiment a is 1. In another embodiment a is 2. In another embodiment a is 3.

In another embodiment $R^4$ is $C_{3-7}$ cycloalkyl (such as cyclopropyl or cyclobutyl) optionally substituted with $C_{1-6}$ alkyl, OH, CN, $C_{1-6}$ alkoxy or $C_{1-3}$ alkyl-$OR^8$. In another embodiment, $R^4$ is unsubstituted $C_{3-7}$ cycloalkyl.

In another embodiment $R^4$ is $C_{3-7}$ cycloalkyl (such as cyclopropyl) optionally substituted with halo.

In another embodiment $R^4$ is cyclopropyl optionally substituted with OH, CN, $C_{1-6}$ alkoxy (such as methoxy or ethoxy) or $C_{1-3}$ alkyl-$OR^8$ (such as —$CH_2OH$).

In another embodiment $R^4$ is cyclobutanyl optionally substituted with OH, CN, $C_{1-6}$ alkoxy (such as methoxy or ethoxy) or $C_{1-3}$ alkyl-$OR^8$ (such as —$CH_2OH$), for example OH.

In another embodiment $R^4$ is heterocycloalkyl optionally substituted with $C_{1-6}$ alkyl or OH. In another embodiment, $R^4$ is unsubstituted heterocycloalkyl.

In a further embodiment $R^4$ is tetrahydrofuranyl optionally substituted with $C_{1-6}$ alkyl or OH.

In a further embodiment $R^4$ is oxetanyl optionally substituted with $C_{1-6}$ alkyl or OH.

In another embodiment $R^4$ is $C_{1-6}$ alkoxy, such as methoxy, ethoxy, i-propoxy or t-butoxy, for example methoxy.

In one embodiment $R^4$ is $NHR^{13}$.

In one embodiment $R^6$ is $C_{1-6}$ alkyl, such as methyl.

In another embodiment $R^6$ is $C_{3-7}$ cycloalkyl, such as cyclopropyl.

In one embodiment $R^7$ is independently selected from the group consisting of halo (such as fluoro), OH, CN, $C_{1-6}$ alkoxy (such as methoxy), $NR^9R^{10}$, $C_{3-7}$ cycloalkyl (such as cyclopropyl or cyclobutyl), heterocycloalkyl (such as oxetanyl) and aryl (such as phenyl), wherein said $C_{3-7}$ cycloalkyl, heterocycloalkyl or aryl groups are further optionally substituted with 1, 2 or 3 groups independently selected from the group consisting of CN, OH, $C_{1-6}$ alkoxy (such as methoxy) and $NR^{11}R^{12}$.

In another embodiment $R^7$ is independently selected from the group consisting of fluoro, OH, CN, methoxy, $NH_2$, cyclopropyl, cyclobutyl, oxetanyl and phenyl, wherein said cyclopropyl, cyclobutyl, oxetanyl or phenyl groups are further optionally substituted with 1, 2 or 3 groups independently selected from the group consisting of CN, OH, methoxy and $NR^{11}R^{12}$.

In another embodiment $R^7$ is independently selected from the group consisting of halo (such as fluoro) and $C_{3-7}$ cycloalkyl (such as cyclopropyl).

In another embodiment $R^7$ is halo, such as fluoro.

In another embodiment $R^7$ is OH.

In another embodiment $R^7$ is CN.

In another embodiment $R^7$ is $C_{1-6}$ alkoxy, such as methoxy or ethoxy.

In another embodiment $R^7$ is $NR^9R^{10}$, such as —$NH_2$ or —$N(CH_3)_2$.

In another embodiment $R^7$ is $C_{3-7}$ cycloalkyl (such as cyclopropyl or cyclobutyl) optionally substituted with 1, 2 or 3 groups (such as 1 or 2 groups, for example 1 group) independently selected from the group consisting of CN, OH, $C_{1-6}$ alkoxy (such as methoxy) and $NR^{11}R^{12}$ (such as —$N(CH_3)_2$). In another embodiment, $R^7$ is unsubstituted $C_{3-7}$ cycloalkyl.

In another embodiment $R^7$ is heterocycloalkyl (such as oxetanyl) optionally substituted with 1, 2 or 3 groups (such as 1 or 2 groups, for example 1 group) independently selected from the group consisting of CN, OH, $C_{1-6}$ alkoxy (such as methoxy) and $NR^{11R12}$. In another embodiment, $R^7$ is unsubstituted heterocycloalkyl.

In another embodiment $R^7$ is phenyl optionally substituted with 1, 2 or 3 groups (such as 1 or 2 groups, for example 1 group) independently selected from the group consisting of CN, OH, halo, $C_{1-6}$ alkoxy (such as methoxy) or $NR^{11}R^{12}$. In another embodiment, $R^7$ is unsubstituted phenyl.

In one embodiment $R^9$ and $R^{10}$ are independently H or methyl.

In one embodiment $R^{11}$ and $R^{12}$ are independently H or methyl.

In a further embodiment, there is provided a compound of formula (II), or a pharmaceutically acceptable salt thereof, wherein $R^2$, $R^3$ and $R^4$ are as defined in the compound of formula (I):

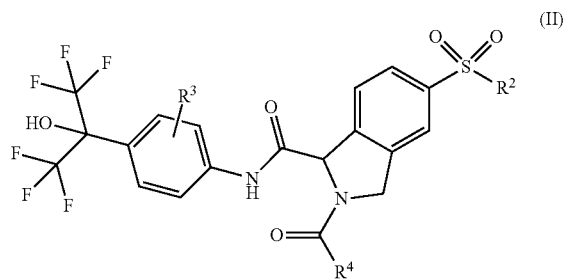

In a further embodiment, there is provided the compound of formula (II), or a pharmaceutically acceptable salt thereof, wherein $R^2$ is $C_{1-6}$ alkyl optionally substituted with OH or $C_{1-6}$ alkoxy, such as methyl, ethyl, —$CH_2CH_2OH$, or —$CH_2CH_2OCH_3$.

In a further embodiment, there is provided the compound of formula (II), or a pharmaceutically acceptable salt thereof, wherein $R^2$ is cyclopropyl or $CH_2$-cyclopropyl (optionally substituted with halo, OH, CN or $C_{1-6}$ alkoxy), such as $CH_2$-cyclopropyl (optionally substituted with OH, CN or $C_{1-6}$ alkoxy).

In a further embodiment, there is provided the compound of formula (II), or a pharmaceutically acceptable salt thereof, wherein $R^2$ is $NR^5R^6$, such as —$NHR^6$ where $R^6$ is methyl or cyclopropyl.

In a further embodiment, there is provided the compound of formula (II), or a pharmaceutically acceptable salt thereof, wherein $R^2$ is unsubstituted $C_{1-6}$ alkyl or unsubstituted $CH_2$-cyclopropyl.

In a further embodiment, there is provided the compound of formula (II), or a pharmaceutically acceptable salt thereof, wherein $R^2$ is unsubstituted $C_{1-6}$ alkyl.

In a further embodiment, there is provided the compound of formula (II), or a pharmaceutically acceptable salt thereof, wherein $R^2$ is unsubstituted methyl or unsubstituted ethyl.

In a further embodiment, there is provided the compound of formula (II), or a pharmaceutically acceptable salt thereof, wherein $R^2$ is unsubstituted methyl.

In a further embodiment, there is provided the compound of formula (II), or a pharmaceutically acceptable salt thereof, wherein $R^2$ is unsubstituted ethyl.

In a further embodiment, there is provided the compound of formula (II), or a pharmaceutically acceptable salt thereof, wherein $R^2$ is cyclopropyl.

In a further embodiment, there is provided the compound of formula (II), or a pharmaceutically acceptable salt thereof, wherein $R^2$ is $CH_2$-cyclopropyl optionally substituted with halo, OH, CN or $C_{1-6}$ alkoxy.

In a further embodiment, there is provided the compound of formula (II), or a pharmaceutically acceptable salt thereof, wherein $R^2$ is $CH_2$-cyclopropyl optionally substituted with OH, CN or $C_{1-6}$ alkoxy.

In a further embodiment, there is provided the compound of formula (II), or a pharmaceutically acceptable salt thereof, wherein $R^2$ is unsubstituted $CH_2$-cyclopropyl.

In a further embodiment, there is provided the compound of formula (II), or a pharmaceutically acceptable salt thereof, wherein $R^2$ is —$CH_2CH_2OCH_3$.

In a further embodiment, there is provided the compound of formula (II), or a pharmaceutically acceptable salt thereof, wherein $R^2$ is —$CH_2CH_2OH$.

In a further embodiment, there is provided the compound of formula (II), or a pharmaceutically acceptable salt thereof, wherein $R^2$ is —$CH_2CH(OH)CH_3$.

In a further embodiment, there is provided the compound of formula (II), or a pharmaceutically acceptable salt thereof, wherein $R^2$ is —$NHCH_3$.

In a further embodiment, there is provided the compound of formula (II), or a pharmaceutically acceptable salt thereof, wherein $R^2$ is —NH-cyclopropyl.

In a further embodiment, there is provided the compound of formula (II), or a pharmaceutically acceptable salt thereof, wherein $R^3$ is H.

In a further embodiment, there is provided the compound of formula (II), or a pharmaceutically acceptable salt thereof, wherein $R^3$ is $C_{1-6}$ alkyl, such as methyl.

In a further embodiment, there is provided the compound of formula (II), or a pharmaceutically acceptable salt thereof, wherein $R^3$ is fluoro.

In a further embodiment, there is provided the compound of formula (II), or a pharmaceutically acceptable salt thereof, wherein $R^4$ is H.

In a further embodiment, there is provided the compound of formula (II), or a pharmaceutically acceptable salt thereof, wherein $R^4$ is $C_{1-6}$ alkyl optionally substituted with $(R^7)_a$. In a further embodiment a is 1 or 2, such as 1. In another embodiment, $R^4$ is unsubstituted $C_{1-6}$ alkyl. In another embodiment, $R^4$ is unsubstituted methyl. In another embodiment, $R^4$ is unsubstituted ethyl.

In a further embodiment, there is provided the compound of formula (II), or a pharmaceutically acceptable salt thereof, wherein $R^4$ is $C_{3-7}$ cycloalkyl (such as cyclopropyl or cyclobutyl) optionally substituted with $C_{1-6}$ alkyl, OH, CN, $C_{1-6}$ alkoxy (such as methoxy or ethoxy) or $C_{1-3}$ alkyl-$OR^8$ (such as —$CH_2OH$). In another embodiment, $R^4$ is unsubstituted $C_{3-7}$ cycloalkyl.

In a further embodiment, there is provided the compound of formula (II), or a pharmaceutically acceptable salt thereof, wherein $R^4$ is heterocycloalkyl (such as oxetanyl or tetrahydrofuranyl) optionally substituted with $C_{1-6}$ alkyl or OH. In another embodiment, $R^4$ is unsubstituted heterocycloalkyl.

In a further embodiment, there is provided the compound of formula (II), or a pharmaceutically acceptable salt thereof, wherein $R^4$ is $C_{1-6}$ alkoxy (such as methoxy, ethoxy, i-propoxy or t-butoxy).

In a further embodiment, there is provided the compound of formula (II), or a pharmaceutically acceptable salt thereof, wherein R$^4$ is NHR$^{13}$ (such as —NH$_2$, —NHCH$_3$, —NHCH$_2$CH$_3$ or —NH-cyclopropyl).

In one embodiment, there is provided the compound of formula (II), or a pharmaceutically acceptable salt thereof, wherein R$^2$ is C$_{1-6}$ alkyl (optionally substituted with OH or C$_{1-6}$ alkoxy) or CH$_2$-cyclopropyl (optionally substituted with halo, OH, CN or C$_{1-6}$ alkoxy); R$^3$ is H; and R$^4$ is C$_{1-6}$ alkyl (optionally substituted with (R$^7$)$_a$), C$_{3-7}$ cycloalkyl (optionally substituted with halo, C$_{1-6}$ alkyl, OH, CN, C$_{1-6}$ alkoxy or C$_{1-3}$ alkyl-OR$^8$), heterocycloalkyl (optionally substituted with C$_{1-6}$ alkyl or OH) or C$_{1-6}$ alkoxy.

In one embodiment, there is provided the compound of formula (II), or a pharmaceutically acceptable salt thereof, wherein R$^2$ is C$_{1-6}$ alkyl (optionally substituted with OH or C$_{1-6}$ alkoxy) or CH$_2$-cyclopropyl (optionally substituted with halo, OH, CN or C$_{1-6}$ alkoxy); R$^3$ is H; and R$^4$ is C$_{1-6}$ alkyl (optionally substituted with (R$^7$)$_a$) or C$_{3-7}$ cycloalkyl (optionally substituted with halo, C$_{1-6}$ alkyl, OH, CN, C$_{1-6}$ alkoxy or C$_{1-3}$ alkyl-ORs).

In one embodiment, there is provided the compound of formula (II), or a pharmaceutically acceptable salt thereof, wherein R$^2$ is C$_{1-6}$ alkyl (optionally substituted with OH or C$_{1-6}$ alkoxy) or CH$_2$-cyclopropyl (optionally substituted with halo, OH, CN or C$_{1-6}$ alkoxy); R$^3$ is H; and R$^4$ is C$_{1-6}$ alkyl optionally substituted with (R$^7$)$_a$.

In one embodiment, there is provided the compound of formula (II), or a pharmaceutically acceptable salt thereof, wherein R$^2$ is unsubstituted C$_{1-6}$ alkyl or unsubstituted CH$_2$-cyclopropyl; R$^3$ is H; and R$^4$ is C$_{1-6}$ alkyl optionally substituted with (R$^7$)$_a$.

In one embodiment, there is provided the compound of formula (II), or a pharmaceutically acceptable salt thereof, wherein R$^2$ is unsubstituted C$_{1-6}$ alkyl; R$^3$ is H; and R$^4$ is C$_{1-6}$ alkyl optionally substituted with (R$^7$)$_a$.

In one embodiment, there is provided the compound of formula (II), or a pharmaceutically acceptable salt thereof, wherein R$^2$ is unsubstituted CH$_2$-cyclopropyl; R$^3$ is H; and R$^4$ is C$_{1-6}$ alkyl optionally substituted with (R$^7$)$_a$.

In another embodiment, there is provided the compound of formula (II), or a pharmaceutically acceptable salt thereof, wherein R$^2$ is unsubstituted methyl or unsubstituted ethyl; R$^3$ is H; and R$^4$ is C$_{1-6}$ alkyl optionally substituted with (R$^7$)$_a$.

In another embodiment, there is provided the compound of formula (II), or a pharmaceutically acceptable salt thereof, wherein R$^2$ is unsubstituted methyl; R$^3$ is H; and R$^4$ is C$_{1-6}$ alkyl optionally substituted with (R$^7$)$_a$.

In another embodiment, there is provided the compound of formula (II), or a pharmaceutically acceptable salt thereof, wherein R$^2$ is unsubstituted ethyl; R$^3$ is H; and R$^4$ is C$_{1-6}$ alkyl optionally substituted with (R$^7$)$_a$.

In another embodiment, there is provided the compound of formula (II), or a pharmaceutically acceptable salt thereof, wherein R$^2$ is unsubstituted CH$_2$-cyclopropyl; R$^3$ is H; and R$^4$ is C$_{1-6}$ alkyl optionally substituted with (R$^7$)$_a$.

In one embodiment, there is provided the compound of formula (II), or a pharmaceutically acceptable salt thereof, wherein R$^2$ is unsubstituted C$_{1-6}$ alkyl or unsubstituted CH$_2$-cyclopropyl; R$^3$ is H; and R$^4$ is unsubstituted C$_{1-6}$ alkyl.

In another embodiment, there is provided the compound of formula (II), or a pharmaceutically acceptable salt thereof, wherein R$^2$ is unsubstituted C$_{1-6}$ alkyl; R$^3$ is H; and R$^4$ is unsubstituted C$_{1-6}$ alkyl.

In another embodiment, there is provided the compound of formula (II), or a pharmaceutically acceptable salt thereof, wherein R$^2$ is unsubstituted CH$_2$-cyclopropyl; R$^3$ is H; and R$^4$ is unsubstituted C$_{1-6}$ alkyl.

In another embodiment, there is provided the compound of formula (II), or a pharmaceutically acceptable salt thereof, wherein R$^2$ is unsubstituted methyl; R$^3$ is H; and R$^4$ is unsubstituted methyl.

In another embodiment, there is provided the compound of formula (II), or a pharmaceutically acceptable salt thereof, wherein R$^2$ is unsubstituted ethyl; R$^3$ is H; and R$^4$ is unsubstituted methyl.

In another embodiment, there is provided the compound of formula (II), or a pharmaceutically acceptable salt thereof, wherein R$^2$ is unsubstituted CH$_2$-cyclopropyl; R$^3$ is H; and R$^4$ is unsubstituted methyl.

In another embodiment, there is provided the compound of formula (II), or a pharmaceutically acceptable salt thereof, wherein R$^2$ is unsubstituted methyl; R$^3$ is H; and R$^4$ is unsubstituted ethyl.

In another embodiment, there is provided the compound of formula (II), or a pharmaceutically acceptable salt thereof, wherein R$^2$ is unsubstituted ethyl; R$^3$ is H; and R$^4$ is unsubstituted ethyl.

In another embodiment, there is provided the compound of formula (II), or a pharmaceutically acceptable salt thereof, wherein R$^2$ is unsubstituted CH$_2$-cyclopropyl; R$^3$ is H; and R$^4$ is unsubstituted ethyl.

In another embodiment, there is provided the compound of formula (I) or formula (II) which exhibits R-stereochemistry at the carbon atom marked with an asterisk as shown below:

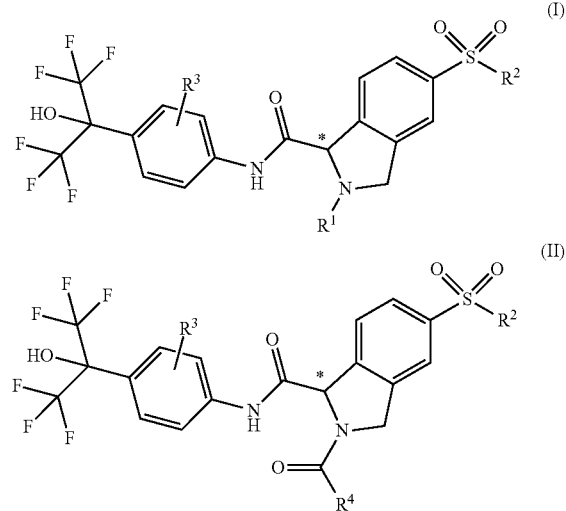

or a pharmaceutically acceptable salt thereof.

Where any embodiment within this specification includes a group which is said to be "optionally substituted", then unless otherwise stated the said group may be unsubstituted or may be substituted with 1, 2 or 3 substituents (such as 1 or 2 substituents, for example 1 substituent) independently selected from the list of substituents provided. For the avoidance of doubt a further embodiment will include that embodiment wherein the said group is unsubstituted.

Where any embodiment within this specification includes a sub-selection of a smaller group (using the words "such as" or "for example"), then for the avoidance of doubt each sub-selected group represents an additional embodiment.

An example of a compound of the specification is:

5-(Ethylsulfonyl)-N-[4-(1,1,1,3,3,3-hexafluoro-2-hydroxypropan-2-yl)phenyl]-2,3-dihydro-1H-isoindole-1-carboxamide;

5-(Ethylsulfonyl)-2-formyl-N-[4-(1,1,1,3,3,3-hexafluoro-2-hydroxypropan-2-yl)phenyl]-2,3-dihydro-1H-isoindole-1-carboxamide;

2-[(1-Cyanocyclopropyl)acetyl]-5-(ethylsulfonyl)-N-[4-(1,1,1,3,3,3-hexafluoro-2-hydroxypropan-2-yl)phenyl]-2,3-dihydro-1H-isoindole-1-carboxamide;

2-Acetyl-5-(ethylsulfonyl)-N-[4-(1,1,1,3,3,3-hexafluoro-2-hydroxypropan-2-yl)phenyl]-2,3-dihydro-1H-isoindole-1-carboxamide;

2-[Cyclopropyl(difluoro)acetyl]-5-(ethylsulfonyl)-N-[4-(1,1,1,3,3,3-hexafluoro-2-hydroxypropan-2-yl)phenyl]-2,3-dihydro-1H-isoindole-1-carboxamide;

2-[(1-Cyanocyclopropyl)carbonyl]-5-(ethylsulfonyl)-N-[4-(1,1,1,3,3,3-hexafluoro-2-hydroxypropan-2-yl)phenyl]-2,3-dihydro-1H-isoindole-1-carboxamide;

5-(Ethylsulfonyl)-N-[4-(1,1,1,3,3,3-hexafluoro-2-hydroxypropan-2-yl)phenyl]-2-(3-hydroxy-3-methylbutanoyl)-2,3-dihydro-1H-isoindole-1-carboxamide;

5-(Ethylsulfonyl)-N-[4-(1,1,1,3,3,3-hexafluoro-2-hydroxypropan-2-yl)phenyl]-2-[(1-hydroxycyclopropyl)acetyl]-2,3-dihydro-1H-isoindole-1-carboxamide;

5-(Ethylsulfonyl)-2-(3-fluoropropanoyl)-N-[4-(1,1,1,3,3,3-hexafluoro-2-hydroxypropan-2-yl)phenyl]-2,3-dihydro-1H-isoindole-1-carboxamide;

2-(Cyclobutylacetyl)-5-(ethylsulfonyl)-N-[4-(1,1,1,3,3,3-hexafluoro-2-hydroxypropan-2-yl)phenyl]-2,3-dihydro-1H-isoindole-1-carboxamide;

5-(Ethylsulfonyl)-N-[4-(1,1,1,3,3,3-hexafluoro-2-hydroxypropan-2-yl)phenyl]-2-(oxetan-2-ylcarbonyl)-2,3-dihydro-1H-isoindole-1-carboxamide;

2-(3-Cyanopropanoyl)-5-(ethylsulfonyl)-N-[4-(1,1,1,3,3,3-hexafluoro-2-hydroxypropan-2-yl)phenyl]-2,3-dihydro-1H-isoindole-1-carboxamide;

5-(Ethylsulfonyl)-N-[4-(1,1,1,3,3,3-hexafluoro-2-hydroxypropan-2-yl)phenyl]-2-[(1-methoxycyclopropyl)acetyl]-2,3-dihydro-1H-isoindole-1-carboxamide;

5-(Ethylsulfonyl)-N-[4-(1,1,1,3,3,3-hexafluoro-2-hydroxypropan-2-yl)phenyl]-2-(tetrahydrofuran-3-ylcarbonyl)-2,3-dihydro-1H-isoindole-1-carboxamide;

5-(Ethylsulfonyl)-N-[4-(1,1,1,3,3,3-hexafluoro-2-hydroxypropan-2-yl)phenyl]-2-(tetrahydrofuran-2-ylcarbonyl)-2,3-dihydro-1H-isoindole-1-carboxamide;

2-{[1-(Dimethylamino)cyclopropyl]acetyl}-5-(ethylsulfonyl)-N-[4-(1,1,1,3,3,3-hexafluoro-2-hydroxypropan-2-yl)phenyl]-2,3-dihydro-1H-isoindole-1-carboxamide;

5-[(Cyclopropylmethyl)sulfonyl]-N-[4-(1,1,1,3,3,3-hexafluoro-2-hydroxypropan-2-yl)phenyl]-2,3-dihydro-1H-isoindole-1-carboxamide;

2-Acetyl-5-[(cyclopropylmethyl)sulfonyl]-N-[4-(1,1,1,3,3,3-hexafluoro-2-hydroxypropan-2-yl)phenyl]-2,3-dihydro-1H-isoindole-1-carboxamide;

5-[(cyclopropylmethyl)sulfonyl]-2-formyl-N-[4-(1,1,1,3,3,3-hexafluoro-2-hydroxypropan-2-yl)phenyl]-2,3-dihydro-1H-isoindole-1-carboxamide;

5-[(Cyclopropylmethyl)sulfonyl]-N-[4-(1,1,1,3,3,3-hexafluoro-2-hydroxypropan-2-yl)phenyl]-2-(methoxyacetyl)-2,3-dihydro-1H-isoindole-1-carboxamide;

Ethyl 5-[(cyclopropylmethyl)sulfonyl]-1-{[4-(1,1,1,3,3,3-hexafluoro-2-hydroxypropan-2-yl)phenyl]carbamoyl}-1,3-dihydro-2H-isoindole-2-carboxylate;

5-[(Cyclopropylmethyl)sulfonyl]-N-[4-(1,1,1,3,3,3-hexafluoro-2-hydroxypropan-2-yl)phenyl]-2-[(1-methoxycyclopropyl)acetyl]-2,3-dihydro-1H-isoindole-1-carboxamide;

5-[(Cyclopropylmethyl)sulfonyl]-N-[4-(1,1,1,3,3,3-hexafluoro-2-hydroxypropan-2-yl)phenyl]-2-[(1-hydroxycyclopropyl)acetyl]-2,3-dihydro-1H-isoindole-1-carboxamide;

5-[(Cyclopropylmethyl)sulfonyl]-N-[4-(1,1,1,3,3,3-hexafluoro-2-hydroxypropan-2-yl)phenyl]-2-(3-hydroxy-3-methylbutanoyl)-2,3-dihydro-1H-isoindole-1-carboxamide;

5-[(Cyclopropylmethyl)sulfonyl]-N-[4-(1,1,1,3,3,3-hexafluoro-2-hydroxypropan-2-yl)phenyl]-2-(tetrahydrofuran-2-ylcarbonyl)-2,3-dihydro-1H-isoindole-1-carboxamide;

2-[(1-Cyanocyclopropyl)carbonyl]-5-[(cyclopropylmethyl)sulfonyl]-N-[4-(1,1,1,3,3,3-hexafluoro-2-hydroxypropan-2-yl)phenyl]-2,3-dihydro-1H-isoindole-1-carboxamide;

5-[(Cyclopropylmethyl)sulfonyl]-N-[4-(1,1,1,3,3,3-hexafluoro-2-hydroxypropan-2-yl)phenyl]-2-(tetrahydrofuran-3-ylcarbonyl)-2,3-dihydro-1H-isoindole-1-carboxamide;

2-[Amino(cyclopropyl)acetyl]-5-[(cyclopropylmethyl)sulfonyl]-N-[4-(1,1,1,3,3,3-hexafluoro-2-hydroxypropan-2-yl)phenyl]-2,3-dihydro-1H-isoindole-1-carboxamide;

5-[(Cyclopropylmethyl)sulfonyl]-N-[4-(1,1,1,3,3,3-hexafluoro-2-hydroxypropan-2-yl)phenyl]-2-[(1-methoxycyclopropyl)carbonyl]-2,3-dihydro-1H-isoindole-1-carboxamide;

Methyl 5-[(cyclopropylmethyl)sulfonyl]-1-{[4-(1,1,1,3,3,3-hexafluoro-2-hydroxypropan-2-yl)phenyl]carbamoyl}-1,3-dihydro-2H-isoindole-2-carboxylate;

2-[Cyclopropyl(difluoro)acetyl]-5-[(cyclopropylmethyl)sulfonyl]-N-[4-(1,1,1,3,3,3-hexafluoro-2-hydroxypropan-2-yl)phenyl]-2,3-dihydro-1H-isoindole-1-carboxamide;

N-[4-(1,1,1,3,3,3-hexafluoro-2-hydroxypropan-2-yl)phenyl]-5-(methylsulfamoyl)-2,3-dihydro-1H-isoindole-1-carboxamide;

2-Acetyl-N-[4-(1,1,1,3,3,3-hexafluoro-2-hydroxypropan-2-yl)phenyl]-5-(methylsulfamoyl)-2,3-dihydro-1H-isoindole-1-carboxamide;

2-Formyl-N-[4-(1,1,1,3,3,3-hexafluoro-2-hydroxypropan-2-yl)phenyl]-5-(methylsulfamoyl)-2,3-dihydro-1H-isoindole-1-carboxamide;

N-[4-(1,1,1,3,3,3-Hexafluoro-2-hydroxypropan-2-yl)phenyl]-2-[(2R)-2-hydroxybutanoyl]-5-(methylsulfamoyl)-2,3-dihydro-1H-isoindole-1-carboxamide;

Methyl 1-{[4-(1,1,1,3,3,3-hexafluoro-2-hydroxypropan-2-yl)phenyl]carbamoyl}-5-(methylsulfamoyl)-1,3-dihydro-2H-isoindole-2-carboxylate;

Ethyl 1-{[4-(1,1,1,3,3,3-Hexafluoro-2-hydroxypropan-2-yl)phenyl]carbamoyl}-5-(methylsulfamoyl)-1,3-dihydro-2H-isoindole-2-carboxylate;

N-[4-(1,1,1,3,3,3-Hexafluoro-2-hydroxypropan-2-yl)phenyl]-2-[(1-methoxycyclopropyl)carbonyl]-5-(methylsulfamoyl)-2,3-dihydro-1H-isoindole-1-carboxamide;

N-[4-(1,1,1,3,3,3-Hexafluoro-2-hydroxypropan-2-yl)phenyl]-2-[(2S)-2-hydroxybutanoyl]-5-(methylsulfamoyl)-2,3-dihydro-1H-isoindole-1-carboxamide;

N-[4-(1,1,1,3,3,3-Hexafluoro-2-hydroxypropan-2-yl)phenyl]-2-(methoxyacetyl)-5-(methylsulfamoyl)-2,3-dihydro-1H-isoindole-1-carboxamide;

N-[4-(1,1,1,3,3,3-Hexafluoro-2-hydroxypropan-2-yl)phenyl]-5-(methylsulfamoyl)-2-(oxetan-2-ylcarbonyl)-2,3-dihydro-1H-isoindole-1-carboxamide;

N-[4-(1,1,1,3,3,3-Hexafluoro-2-hydroxypropan-2-yl)phenyl]-5-(methylsulfamoyl)-2-[(2R)-tetrahydrofuran-2-ylcarbonyl]-2,3-dihydro-1H-isoindole-1-carboxamide;

N-[4-(1,1,1,3,3,3-Hexafluoro-2-hydroxypropan-2-yl)phenyl]-5-(methylsulfamoyl)-2-[(2S)-tetrahydrofuran-2-ylcarbonyl]-2,3-dihydro-1H-isoindole-1-carboxamide;

N-[4-(1,1,1,3,3,3-Hexafluoro-2-hydroxypropan-2-yl)phenyl]-5-(methylsulfonyl)-2,3-dihydro-1H-isoindole-1-carboxamide;

2-Acetyl-N-[4-(1,1,1,3,3,3-hexafluoro-2-hydroxypropan-2-yl)phenyl]-5-(methylsulfonyl)-2,3-dihydro-1H-isoindole-1-carboxamide;

N-[4-(1,1,1,3,3,3-Hexafluoro-2-hydroxypropan-2-yl)phenyl]-5-(methylsulfonyl)-2-(phenylacetyl)-2,3-dihydro-1H-isoindole-1-carboxamide;

Methyl 1-{[4-(1,1,1,3,3,3-hexafluoro-2-hydroxypropan-2-yl)phenyl]carbamoyl}-5-(methylsulfonyl)-1,3-dihydro-2H-isoindole-2-carboxylate;

N-[4-(1,1,1,3,3,3-Hexafluoro-2-hydroxypropan-2-yl)phenyl]-2-[(1-methoxycyclopropyl)carbonyl]-5-(methylsulfonyl)-2,3-dihydro-1H-isoindole-1-carboxamide;

2-[(1-Cyanocyclopropyl)carbonyl]-N-[4-(1,1,1,3,3,3-hexafluoro-2-hydroxypropan-2-yl)phenyl]-5-(methylsulfonyl)-2,3-dihydro-1H-isoindole-1-carboxamide;

2-Formyl-N-[4-(1,1,1,3,3,3-hexafluoro-2-hydroxypropan-2-yl)phenyl]-5-(methylsulfonyl)-2,3-dihydro-1H-isoindole-1-carboxamide;

N-[4-(1,1,1,3,3,3-Hexafluoro-2-hydroxypropan-2-yl)phenyl]-5-(methylsulfonyl)-2-(oxetan-2-ylcarbonyl)-2,3-dihydro-1H-isoindole-1-carboxamide;

2-(3-Fluoro-2-methylpropanoyl)-N-[4-(1,1,1,3,3,3-hexafluoro-2-hydroxypropan-2-yl)phenyl]-5-(methylsulfonyl)-2,3-dihydro-1H-isoindole-1-carboxamide;

N-[4-(1,1,1,3,3,3-Hexafluoro-2-hydroxypropan-2-yl)phenyl]-2-[(2R)-2-hydroxybutanoyl]-5-(methylsulfonyl)-2,3-dihydro-1H-isoindole-1-carboxamide;

N-[4-(1,1,1,3,3,3-Hexafluoro-2-hydroxypropan-2-yl)phenyl]-2-(3-methylbutanoyl)-5-(methylsulfonyl)-2,3-dihydro-1H-isoindole-1-carboxamide;

2-(Cyclopropylacetyl)-N-[4-(1,1,1,3,3,3-hexafluoro-2-hydroxypropan-2-yl)phenyl]-5-(methylsulfonyl)-2,3-dihydro-1H-isoindole-1-carboxamide;

N-[4-(1,1,1,3,3,3-Hexafluoro-2-hydroxypropan-2-yl)phenyl]-2-[(1-hydroxycyclopropyl)acetyl]-5-(methylsulfonyl)-2,3-dihydro-1H-isoindole-1-carboxamide;

2-[(3S)-3-Fluorobutanoyl]-N-[4-(1,1,1,3,3,3-hexafluoro-2-hydroxypropan-2-yl)phenyl]-5-(methylsulfonyl)-2,3-dihydro-1H-isoindole-1-carboxamide;

N-[4-(1,1,1,3,3,3-Hexafluoro-2-hydroxypropan-2-yl)phenyl]-2-(methoxyacetyl)-5-(methylsulfonyl)-2,3-dihydro-1H-isoindole-1-carboxamide;

2-(3-Fluoropropanoyl)-N-[4-(1,1,1,3,3,3-hexafluoro-2-hydroxypropan-2-yl)phenyl]-5-(methylsulfonyl)-2,3-dihydro-1H-isoindole-1-carboxamide;

2-[(1-Ethoxycyclopropyl)carbonyl]-N-[4-(1,1,1,3,3,3-hexafluoro-2-hydroxypropan-2-yl)phenyl]-5-(methylsulfonyl)-2,3-dihydro-1H-isoindole-1-carboxamide;

N-[4-(1,1,1,3,3,3-Hexafluoro-2-hydroxypropan-2-yl)phenyl]-2-[(1-methoxycyclopropyl)acetyl]-5-(methylsulfonyl)-2,3-dihydro-1H-isoindole-1-carboxamide;

2-[(3R)-3-Fluorobutanoyl]-N-[4-(1,1,1,3,3,3-hexafluoro-2-hydroxypropan-2-yl)phenyl]-5-(methylsulfonyl)-2,3-dihydro-1H-isoindole-1-carboxamide;

N-[4-(1,1,1,3,3,3-Hexafluoro-2-hydroxypropan-2-yl)phenyl]-2-(2-methoxy-2-methylpropanoyl)-5-(methylsulfonyl)-2,3-dihydro-1H-isoindole-1-carboxamide;

Propan-2-yl 1-{[4-(1,1,1,3,3,3-hexafluoro-2-hydroxypropan-2-yl)phenyl]carbamoyl}-5-(methylsulfonyl)-1,3-dihydro-2H-isoindole-2-carboxylate;

N-[4-(1,1,1,3,3,3-Hexafluoro-2-hydroxypropan-2-yl)phenyl]-2-(3-hydroxy-3-methylbutanoyl)-5-(methylsulfonyl)-2,3-dihydro-1H-isoindole-1-carboxamide;

N-[4-(1,1,1,3,3,3-Hexafluoro-2-hydroxypropan-2-yl)phenyl]-2-[(2R)-2-hydroxy-3-methylbutanoyl]-5-(methylsulfonyl)-2,3-dihydro-1H-isoindole-1-carboxamide;

N-[4-(1,1,1,3,3,3-Hexafluoro-2-hydroxypropan-2-yl)phenyl]-2-[(2S)-2-hydroxy-3-methylbutanoyl]-5-(methylsulfonyl)-2,3-dihydro-1H-isoindole-1-carboxamide;

N-[4-(1,1,1,3,3,3-Hexafluoro-2-hydroxypropan-2-yl)phenyl]-2-[(2S)-2-hydroxybutanoyl]-5-(methylsulfonyl)-2,3-dihydro-1H-isoindole-1-carboxamide;

N-[4-(1,1,1,3,3,3-Hexafluoro-2-hydroxypropan-2-yl)phenyl]-2-(3-hydroxy-2-methylpropanoyl)-5-(methylsulfonyl)-2,3-dihydro-1H-isoindole-1-carboxamide;

N-[4-(1,1,1,3,3,3-Hexafluoro-2-hydroxypropan-2-yl)phenyl]-5-(methylsulfonyl)-2-(oxetan-3-ylacetyl)-2,3-dihydro-1H-isoindole-1-carboxamide;

2-[(1-Cyanocyclopropyl)acetyl]-N-[4-(1,1,1,3,3,3-hexafluoro-2-hydroxypropan-2-yl)phenyl]-5-(methylsulfonyl)-2,3-dihydro-1H-isoindole-1-carboxamide;

N-[4-(1,1,1,3,3,3-Hexafluoro-2-hydroxypropan-2-yl)phenyl]-2-[(1-hydroxycyclopropyl)carbonyl]-5-(methylsulfonyl)-2,3-dihydro-1H-isoindole-1-carboxamide;

2-(3-Cyanopropanoyl)-N-[4-(1,1,1,3,3,3-hexafluoro-2-hydroxypropan-2-yl)phenyl]-5-(methylsulfonyl)-2,3-dihydro-1H-isoindole-1-carboxamide;

N-[4-(1,1,1,3,3,3-Hexafluoro-2-hydroxypropan-2-yl)phenyl]-2-[(trans-3-hydroxycyclobutyl)carbonyl]-5-(methylsulfonyl)-2,3-dihydro-1H-isoindole-1-carboxamide;

N-[4-(1,1,1,3,3,3-Hexafluoro-2-hydroxypropan-2-yl)phenyl]-2-[(cis-3-hydroxycyclobutyl)carbonyl]-5-(methylsulfonyl)-2,3-dihydro-1H-isoindole-1-carboxamide;

N-[4-(1,1,1,3,3,3-Hexafluoro-2-hydroxypropan-2-yl)phenyl]-2-[(3R)-3-hydroxybutanoyl]-5-(methylsulfonyl)-2,3-dihydro-1H-isoindole-1-carboxamide;

N-[4-(1,1,1,3,3,3-Hexafluoro-2-hydroxypropan-2-yl)phenyl]-2-[(3S)-3-hydroxybutanoyl]-5-(methylsulfonyl)-2,3-dihydro-1H-isoindole-1-carboxamide;

2-Acetyl-N-[3-fluoro-4-(1,1,1,3,3,3-hexafluoro-2-hydroxypropan-2-yl)phenyl]-5-(methylsulfonyl)-2,3-dihydro-1H-isoindole-1-carboxamide;

2-[(1-cyanocyclopropyl)carbonyl]-N-[2-fluoro-4-(1,1,1,3,3,3-hexafluoro-2-hydroxypropan-2-yl)phenyl]-5-(methylsulfonyl)-2,3-dihydro-1H-isoindole-1-carboxamide;

2-Acetyl-N-[2-fluoro-4-(1,1,1,3,3,3-hexafluoro-2-hydroxypropan-2-yl)phenyl]-5-(methylsulfonyl)-2,3-dihydro-1H-isoindole-1-carboxamide;

N-[2-Fluoro-4-(1,1,1,3,3,3-hexafluoro-2-hydroxypropan-2-yl)phenyl]-5-(methylsulfonyl)-2,3-dihydro-1H-isoindole-1-carboxamide;

2-[(1-Cyanocyclopropyl)carbonyl]-N-[3-fluoro-4-(1,1,1,3,3,3-hexafluoro-2-hydroxypropan-2-yl)phenyl]-5-(methylsulfonyl)-2,3-dihydro-1H-isoindole-1-carboxamide;

N-[3-Fluoro-4-(1,1,1,3,3,3-hexafluoro-2-hydroxypropan-2-yl)phenyl]-2-[(1-methoxycyclopropyl)carbonyl]-5-(methylsulfonyl)-2,3-dihydro-1H-isoindole-1-carboxamide;

2-Acetyl-5-(cyclopropylsulfamoyl)-N-[4-(1,1,1,3,3,3-hexafluoro-2-hydroxypropan-2-yl)phenyl]-2,3-dihydro-1H-isoindole-1-carboxamide;

5-(Cyclopropylsulfonyl)-N-[4-(1,1,1,3,3,3-hexafluoro-2-hydroxypropan-2-yl)phenyl]-2,3-dihydro-1H-isoindole-1-carboxamide;

2-Acetyl-5-(cyclopropylsulfonyl)-N-[4-(1,1,1,3,3,3-hexafluoro-2-hydroxypropan-2-yl)phenyl]-2,3-dihydro-1H-isoindole-1-carboxamide;

Methyl 5-(cyclopropylsulfonyl)-1-{[4-(1,1,1,3,3,3-hexafluoro-2-hydroxypropan-2-yl)phenyl]carbamoyl}-1,3-dihydro-2H-isoindole-2-carboxylate;

5-(cyclopropylsulfonyl)-N-[4-(1,1,1,3,3,3-hexafluoro-2-hydroxypropan-2-yl)phenyl]-2-[(1-methoxycyclopropyl)carbonyl]-2,3-dihydro-1H-isoindole-1-carboxamide;

5-(cyclopropylsulfonyl)-2-formyl-N-[4-(1,1,1,3,3,3-hexafluoro-2-hydroxypropan-2-yl)phenyl]-2,3-dihydro-1H-isoindole-1-carboxamide;

N-[4-(1,1,1,3,3,3-Hexafluoro-2-hydroxypropan-2-yl)phenyl]-5-[(2-methoxyethyl)sulfonyl]-2,3-dihydro-1H-isoindole-1-carboxamide;

2-Formyl-N-[4-(1,1,1,3,3,3-hexafluoro-2-hydroxypropan-2-yl)phenyl]-5-[(2-methoxyethyl)sulfonyl]-2,3-dihydro-1H-isoindole-1-carboxamide;

2-Acetyl-N-[4-(1,1,1,3,3,3-hexafluoro-2-hydroxypropan-2-yl)phenyl]-5-[(2-methoxyethyl)sulfonyl]-2,3-dihydro-1H-isoindole-1-carboxamide;

N-[4-(1,1,1,3,3,3-hexafluoro-2-hydroxypropan-2-yl)phenyl]-2-[(1-methoxycyclopropyl)carbonyl]-5-[(2-methoxyethyl)sulfonyl]-2,3-dihydro-1H-isoindole-1-carboxamide;

N-[4-(1,1,1,3,3,3-hexafluoro-2-hydroxypropan-2-yl)phenyl]-5-[(2-hydroxyethyl)sulfonyl]-2,3-dihydro-1H-isoindole-1-carboxamide;

2-Acetyl-N-[4-(1,1,1,3,3,3-hexafluoro-2-hydroxypropan-2-yl)phenyl]-5-[(2-hydroxyethyl)sulfonyl]-2,3-dihydro-1H-isoindole-1-carboxamide;

N-[4-(1,1,1,3,3,3-hexafluoro-2-hydroxypropan-2-yl)phenyl]-5-[(2-hydroxyethyl)sulfonyl]2-[(1-methoxycyclopropyl)carbonyl]-2,3-dihydro-1H-isoindole-1-carboxamide;

(1R)-2-Acetyl-5-(ethylsulfonyl)-N-[4-(1,1,1,3,3,3-hexafluoro-2-hydroxypropan-2-5 yl)phenyl]-2,3-dihydro-1H-isoindole-1-carboxamide;

(1S)-2-Acetyl-5-(ethylsulfonyl)-N-[4-(1,1,1,3,3,3-hexafluoro-2-hydroxypropan-2-yl)phenyl]-2,3-dihydro-1H-isoindole-1-carboxamide;

(1R)-2-Acetyl-5-[(cyclopropylmethyl)sulfonyl]-N-[4-(1,1,3,3,3-hexafluoro-2-hydroxypropan-2-yl)phenyl]-2,3-dihydro-1H-isoindole-1-carboxamide; 10

(1S)-2-Acetyl-5-[(cyclopropylmethyl)sulfonyl]-N-[4-(1,1,3,3,3-hexafluoro-2-hydroxypropan-2-yl)phenyl]-2,3-dihydro-1H-isoindole-1-carboxamide;

(1R)—N-[4-(1,1,1,3,3,3-Hexafluoro-2-hydroxypropan-2-yl)phenyl]-2-[(2R)-2-hydroxybutanoyl]-5-(methylsulfamoyl)-2,3-dihydro-1H-isoindole-1-carboxamide;

(1S)—N-[4-(1,1,1,3,3,3-Hexafluoro-2-hydroxypropan-2-yl)phenyl]-2-[(2R)-2-15 hydroxybutanoyl]-5-(methylsulfamoyl)-2,3-dihydro-1H-isoindole-1-carboxamide;

(1R)—N-[4-(1,1,1,3,3,3-Hexafluoro-2-hydroxypropan-2-yl)phenyl]-2-[(2S)-2-hydroxybutanoyl]-5-(methylsulfamoyl)-2,3-dihydro-1H-isoindole-1-carboxamide;

(1S)—N-[4-(1,1,1,3,3,3-Hexafluoro-2-hydroxypropan-2-yl)phenyl]-2-[(2S)-2-hydroxybutanoyl]-5-(methylsulfamoyl)-2,3-dihydro-1H-isoindole-1-carboxamide; 20

(1R)-2-Acetyl-N-[4-(1,1,1,3,3,3-hexafluoro-2-hydroxypropan-2-yl)phenyl]-5-(methylsulfonyl)-2,3-dihydro-1H-isoindole-1-carboxamide;

(1S)-2-Acetyl-N-[4-(1,1,1,3,3,3-hexafluoro-2-hydroxypropan-2-yl)phenyl]-5-(methylsulfonyl)-2,3-dihydro-1H-isoindole-1-carboxamide;

(1R)—N-[4-(1,1,1,3,3,3-Hexafluoro-2-hydroxypropan-2-yl)phenyl]-2-[(1-25 methoxycyclopropyl)carbonyl]-5-(methylsulfonyl)-2,3-dihydro-1H-isoindole-1-carboxamide;

(1S)—N-[4-(1,1,1,3,3,3-Hexafluoro-2-hydroxypropan-2-yl)phenyl]-2-[(1-methoxycyclopropyl)carbonyl]-5-(methylsulfonyl)-2,3-dihydro-1H-isoindole-1-carboxamide;

(1R)—N-[4-(1,1,1,3,3,3-Hexafluoro-2-hydroxypropan-2-yl)phenyl]-2-[(2R)-2-hydroxybutanoyl]-5-(methylsulfonyl)-2,3-dihydro-1H-isoindole-1-carboxamide;

(1S)—N-[4-(1,1,1,3,3,3-Hexafluoro-2-hydroxypropan-2-yl)phenyl]-2-[(2R)-2-hydroxybutanoyl]-5-(methylsulfonyl)-2,3-dihydro-1H-isoindole-1-carboxamide;

(1R)—N-[4-(1,1,1,3,3,3-Hexafluoro-2-hydroxypropan-2-yl)phenyl]-2-[(2S)-2-5 hydroxybutanoyl]-5-(methylsulfonyl)-2,3-dihydro-1H-isoindole-1-carboxamide;

(1S)—N-[4-(1,1,1,3,3,3-Hexafluoro-2-hydroxypropan-2-yl)phenyl]-2-[(2S)-2-hydroxybutanoyl]-5-(methylsulfonyl)-2,3-dihydro-1H-isoindole-1-carboxamide;

or a pharmaceutically acceptable salt thereof.

A further example of a compound of the specification is:

2-(Cyanoacetyl)-5-(ethylsulfonyl)-N-[4-(1,1,1,3,3,3-hexafluoro-2-hydroxypropan-2-yl)phenyl]-2,3-dihydro-1H-isoindole-1-carboxamide;

5-(Ethylsulfonyl)-N-[4-(1,1,1,3,3,3-hexafluoro-2-hydroxypropan-2-yl)phenyl]-2-{[1-(hydroxymethyl)cyclopropyl]carbonyl}-2,3-dihydro-1H-isoindole-1-carboxamide;

N-[4-(1,1,1,3,3,3-Hexafluoro-2-hydroxypropan-2-yl)phenyl]-2-(2-methoxybutanoyl)-5-(methylsulfamoyl)-2,3-dihydro-1H-isoindole-1-carboxamide;

N-[4-(1,1,1,3,3,3-Hexafluoro-2-hydroxypropan-2-yl)phenyl]-2-(hydroxyacetyl)-5-(methylsulfamoyl)-2,3-dihydro-1H-isoindole-1-carboxamide;

N-[2-Fluoro-4-(1,1,1,3,3,3-hexafluoro-2-hydroxypropan-2-yl)phenyl]-2-[(1-methoxycyclopropyl)carbonyl]-5-(methylsulfonyl)-2,3-dihydro-1H-isoindole-1-carboxamide;

N-[2-Fluoro-4-(1,1,1,3,3,3-hexafluoro-2-hydroxypropan-2-yl)phenyl]-5-(methylsulfonyl) 2,3-dihydro-1H-isoindole-1-carboxamide;

N-[4-(1,1,1,3,3,3-Hexafluoro-2-hydroxypropan-2-yl)phenyl]-2-[(3-methyloxetan-3-yl)carbonyl]-5-(methylsulfonyl)-2,3-dihydro-1H-isoindole-1-carboxamide;

N-[4-(1,1,1,3,3,3-Hexafluoro-2-hydroxypropan-2-yl)phenyl]-5-(methylsulfonyl)-2-(oxetan-3-ylcarbonyl)-2,3-dihydro-1H-isoindole-1-carboxamide;

N-[4-(1,1,1,3,3,3-Hexafluoro-2-hydroxypropan-2-yl)phenyl]-2-[(2-methyloxetan-2-yl)carbonyl]-5-(methylsulfonyl)-2,3-dihydro-1H-isoindole-1-carboxamide;

2-[(1-Fluorocyclopropyl)carbonyl]-N-[4-(1,1,1,3,3,3-hexafluoro-2-hydroxypropan-2-yl)phenyl]-5-(methylsulfonyl)-2,3-dihydro-1H-isoindole-1-carboxamide;

N-[4-(1,1,1,3,3,3-Hexafluoro-2-hydroxypropan-2-yl)phenyl]-2-(2-methoxybutanoyl)-5-(methylsulfonyl)-2,3-dihydro-1H-isoindole-1-carboxamide;

N-[4-(1,1,1,3,3,3-Hexafluoro-2-hydroxypropan-2-yl)phenyl]-2-[(1-methoxycyclobutyl)carbonyl]-5-(methylsulfonyl)-2,3-dihydro-1H-isoindole-1-carboxamide;

N-[4-(1,1,1,3,3,3-hexafluoro-2-hydroxypropan-2-yl)phenyl]-2-[(2R)-2-methoxypropanoyl]-5-(methylsulfonyl)-2,3-dihydro-1H-isoindole-1-carboxamide;

2-Acetyl-N-[4-(1,1,1,3,3,3-hexafluoro-2-hydroxypropan-2-yl)phenyl]-5-(methylsulfonyl)(1-$^2$H)-2,3-dihydro-1H-isoindole-1-carboxamide;

(1R)—N-[4-(1,1,1,3,3,3-Hexafluoro-2-hydroxypropan-2-yl)phenyl]-2-[(2-methyloxetan-2-yl)carbonyl]-5-(methylsulfonyl)-2,3-dihydro-1H-isoindole-1-carboxamide;

5-(Cyclopropylsulfonyl)-N-[4-(1,1,1,3,3,3-hexafluoro-2-hydroxypropan-2-yl)phenyl]-2-(hydroxyacetyl)-2,3-dihydro-1H-isoindole-1-carboxamide;

5-(Cyclopropylsulfonyl)-N-[4-(1,1,1,3,3,3-hexafluoro-2-hydroxypropan-2-yl)phenyl]-2-(methoxyacetyl)-2,3-dihydro-1H-isoindole-1-carboxamide;

2-[(1-Cyanocyclopropyl)carbonyl]-5-(cyclopropylsulfonyl)-N-[4-(1,1,1,3,3,3-hexafluoro-2-hydroxypropan-2-yl)phenyl]-2,3-dihydro-1H-isoindole-1-carboxamide;

5-(Cyclopropylsulfonyl)-N-[4-(1,1,1,3,3,3-hexafluoro-2-hydroxypropan-2-yl)phenyl]-2-[(2S)-tetrahydrofuran-2-ylcarbonyl]-2,3-dihydro-1H-isoindole-1-carboxamide;

5-(Cyclopropylsulfonyl)-N-[4-(1,1,1,3,3,3-hexafluoro-2-hydroxypropan-2-yl)phenyl]-2-[(2R)-tetrahydrofuran-2-ylcarbonyl]-2,3-dihydro-1H-isoindole-1-carboxamide;

Methyl 1-{[4-(1,1,1,3,3,3-hexafluoro-2-hydroxypropan-2-yl)phenyl]carbamoyl}-5-[(2-methoxyethyl)sulfonyl]-1,3-dihydro-2H-isoindole-2-carboxylate;

N-[4-(1,1,1,3,3,3-Hexafluoro-2-hydroxypropan-2-yl)phenyl]-2-(hydroxyacetyl)-5-[(2-methoxyethyl)sulfonyl]-2,3-dihydro-1H-isoindole-1-carboxamide;

N-[4-(1,1,1,3,3,3-Hexafluoro-2-hydroxypropan-2-yl)phenyl]-2-(methoxyacetyl)-5-[(2-methoxyethyl)sulfonyl]-2,3-dihydro-1H-isoindole-1-carboxamide;

5-{[(1-Cyanocyclopropyl)methyl]sulfonyl}-N-[4-(1,1,1,3,3,3-hexafluoro-2-hydroxypropan-2-yl)phenyl]-2,3-dihydro-1H-isoindole-1-carboxamide;

2-Acetyl-5-{[(1-cyanocyclopropyl)methyl]sulfonyl}-N-[4-(1,1,1,3,3,3-hexafluoro-2-hydroxypropan-2-yl)phenyl]-2,3-dihydro-1H-isoindole-1-carboxamide;

Methyl 5-{[(1-cyanocyclopropyl)methyl]sulfonyl}-1-{[4-(1,1,1,3,3,3-hexafluoro-2-hydroxypropan-2-yl)phenyl]carbamoyl}-1,3-dihydro-2H-isoindole-2-carboxylate;

N-[4-(1,1,1,3,3,3-Hexafluoro-2-hydroxypropan-2-yl)phenyl]-5-[(2-methylpropyl)sulfonyl]-2,3-dihydro-1H-isoindole-1-carboxamide;

2-Acetyl-N-[4-(1,1,1,3,3,3-hexafluoro-2-hydroxypropan-2-yl)phenyl]-5-[(2-methylpropyl)sulfonyl]-2,3-dihydro-1H-isoindole-1-carboxamide;

N-[4-(1,1,1,3,3,3-Hexafluoro-2-hydroxypropan-2-yl)phenyl]-5-{[(1-hydroxycyclopropyl)methyl]sulfonyl}-2,3-dihydro-1H-isoindole-1-carboxamide;

2-Acetyl-N-[4-(1,1,1,3,3,3-hexafluoro-2-hydroxypropan-2-yl)phenyl]-5-{[(1-hydroxycyclopropyl)methyl]sulfonyl}-2,3-dihydro-1H-isoindole-1-carboxamide;

2-Formyl-N-[4-(1,1,1,3,3,3-hexafluoro-2-hydroxypropan-2-yl)phenyl]-5-{[(1-hydroxycyclopropyl)methyl]sulfonyl}-2,3-dihydro-1H-isoindole-1-carboxamide;

N-[4-(1,1,1,3,3,3-Hexafluoro-2-hydroxypropan-2-yl)phenyl]-2-(hydroxyacetyl)-5-{[(1-hydroxycyclopropyl)methyl]sulfonyl}-2,3-dihydro-1H-isoindole-1-carboxamide;

2-Acetyl-N-[4-(1,1,1,3,3,3-hexafluoro-2-hydroxypropan-2-yl)phenyl]-5-[(2-hydroxypropyl)sulfonyl]-2,3-dihydro-1H-isoindole-1-carboxamide;

(1R)-2-[(1-Cyanocyclopropyl)carbonyl]-N-[4-(1,1,1,3,3,3-hexafluoro-2-hydroxypropan-2-yl)phenyl]-5-(methylsulfonyl)-2,3-dihydro-1H-isoindole-1-carboxamide;

(1S)-2-[(1-Cyanocyclopropyl)carbonyl]-N-[4-(1,1,1,3,3,3-hexafluoro-2-hydroxypropan-2-yl)phenyl]-5-(methylsulfonyl)-2,3-dihydro-1H-isoindole-1-carboxamide;

(1R)-2-Acetyl-N-[4-(1,1,1,3,3,3-hexafluoro-2-hydroxypropan-2-yl)phenyl]-5-(methylsulfonyl)(1-$^2$H)-2,3-dihydro-1H-isoindole-1-carboxamide;

(1S)-2-Acetyl-N-[4-(1,1,1,3,3,3-hexafluoro-2-hydroxypropan-2-yl)phenyl]-5-(methylsulfonyl)(1-$^2$H)-2,3-dihydro-1H-isoindole-1-carboxamide;

(1R)—N-[4-(1,1,1,3,3,3-Hexafluoro-2-hydroxypropan-2-yl)phenyl]-2-[(2R)-(2-methyloxetan-2-yl)carbonyl]-5-(methylsulfonyl)-2,3-dihydro-1H-isoindole-1-carboxamide;

(1R)—N-[4-(1,1,1,3,3,3-Hexafluoro-2-hydroxypropan-2-yl)phenyl]-2-[(2S)-(2-methyloxetan-2-yl)carbonyl]-5-(methylsulfonyl)-2,3-dihydro-1H-isoindole-1-carboxamide;

$N^2$—Cyclopropyl-$N^1$-[4-(1,1,1,3,3,3-hexafluoro-2-hydroxypropan-2-yl)phenyl]-5-(methylsulfamoyl)-1,3-dihydro-2H-isoindole-1,2-dicarboxamide;

$N^1$-[4-(1,1,1,3,3,3-Hexafluoro-2-hydroxypropan-2-yl)phenyl]-$N^2$-methyl-5-(methylsulfonyl)-1,3-dihydro-2H-isoindole-1,2-dicarboxamide;

$N^2$-Ethyl-$N^1$-[4-(1,1,1,3,3,3-hexafluoro-2-hydroxypropan-2-yl)phenyl]-5-(methylsulfonyl)-1,3-dihydro-2H-isoindole-1,2-dicarboxamide;

$N^1$-[4-(1,1,1,3,3,3-Hexafluoro-2-hydroxypropan-2-yl)phenyl]-5-(methylsulfonyl)-1,3-dihydro-2H-isoindole-1,2-dicarboxamide;

$N^2$—Cyclopropyl-N-[4-(1,1,1,3,3,3-hexafluoro-2-hydroxypropan-2-yl)phenyl]-5-(methylsulfonyl)-1,3-dihydro-2H-isoindole-1,2-dicarboxamide;

5-(Cyclopropylsulfonyl)-$N^1$-[4-(1,1,1,3,3,3-hexafluoro-2-hydroxypropan-2-yl)phenyl]-$N^2$-methyl-1,3-dihydro-2H-isoindole-1,2-dicarboxamide;

$N^1$-[4-(1,1,1,3,3,3-Hexafluoro-2-hydroxypropan-2-yl)phenyl]-5-[(2-methoxyethyl)sulfonyl]-$N^2$-methyl-1,3-dihydro-2H-isoindole-1,2-dicarboxamide;

or a pharmaceutically acceptable salt thereof.

A further feature is any of the embodiments described above with the proviso that any of the specific Examples are individually disclaimed. For example, a further feature is any of the embodiments described above with the proviso that any one or more of the compounds selected from the above list of examples of compounds of the specification are individually disclaimed.

In some embodiments, the compound is a compound of formula (I) excluding at least one compound recited in the Examples below. To illustrate, in some such embodiments, the compound is a compound of formula (I) excluding the compound disclosed in Example X, wherein X may be 1, 2, 3, etc. In other embodiments, the compound is a compound of formula (I) excluding the compounds disclosed in Examples Y, wherein Y may be any combination of 1, 2, 3, etc.

The compounds of general Formula I described in the present invention can be readily prepared according to the following reaction schemes. Furthermore, a skilled organic chemist will appreciate that where specific reaction conditions are used, it is understood that other suitable reaction conditions may be used to achieve the same transformation and are thus included in the present invention. It will also be clear to the skilled person that where synthetic schemes contain functionality which may interfere with the desired reaction, suitable protecting groups can be applied. For examples of protecting groups see T. W. Greene and P. G. M. Wuts, "Protective Groups in Organic Synthesis", Third Edition, John Wiley & Sons, New York, 1999.

Scheme 1 represents a general reaction scheme for preparing compounds of Formula (I), where $R^2$ and $R^3$ are defined as above, and where Z is defined below. An intermediate (IV) is condensed under standard amide bond forming conditions with intermediate (III). Conditions for this transformation include, but are not limited to the use of reagents such as EDC and HOBt, HATU and T3P and are conducted in solvents such as DCM, ethyl actetate or DMF in the presence of bases such as triethylamine, DMAP, diisopropyl ethylamine (DIPEA) or 2,6-lutidine. The intermediates (IV) and (III) and the reagents described are either commercially available or can be prepared using methods known to those skilled in the art.

Scheme 1

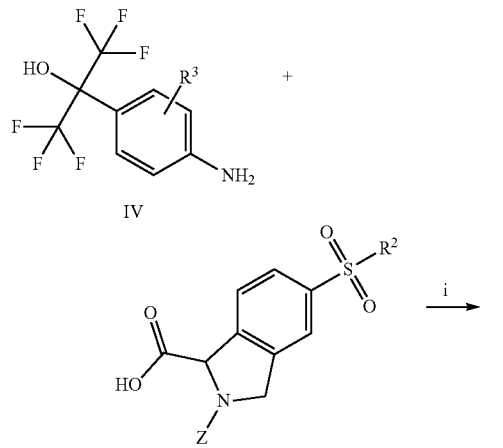

Exemplary conditions: i) EDC, DIPEA, DCM, rt, or T3P, EtOAc, NEt$_3$, rt.

Z is either $R^1$ which is defined as above, but excluding $R^1$=H, leading directly to compounds of Formula (I), or it is a commonly used amine protecting group such as, but not limited to tert-butyl carbamate (Boc), 9-Fluorenylmethyl carbamate (Fmoc) or benzyl carbamate (Cbz), which is removed to give the amine (V), a special case of formula I where $R^1$=H, either as a free base or a salt, depending on the deprotection and isolation conditions (Scheme 2).

Scheme 2

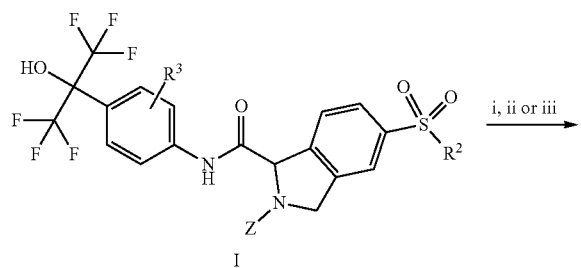

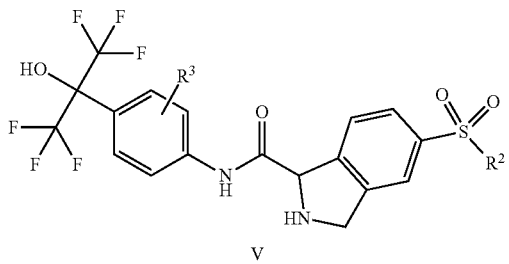

Exemplary conditions: i) Boc deprotection: TFA, DCM; or TBDMSOTf, DCM; or HCl, solvent; ii) Fmoc-deprotection: HNEt$_2$, CH$_3$CN; or morpholine, solvent; iii) Cbz-deprotection: H$_2$, Pd/C, solvent.

As shown in Scheme 3, amine (V) can then be transformed to an amide, a urea or a carbamate using standard organic chemistry procedures to give compounds of Formula (II). The reagents for these transformations such as, but not limited to, carboxylic acids, acid chlorides or anhydrides ($R^4CO_2H$, $R^4COCl$, ($R^4CO)_2O$), isocyanates ($R^{13}N$=C=O) and chloroformates ($R^{4'}OCOCl$) are either commercially available or can be prepared using methods known to those skilled in the art. For the avoidance of doubt, $R^{4'}O$ represents $R^4$ as defined as above, wherein the final atom of the corresponding $R^4$ is oxygen.

Scheme 3

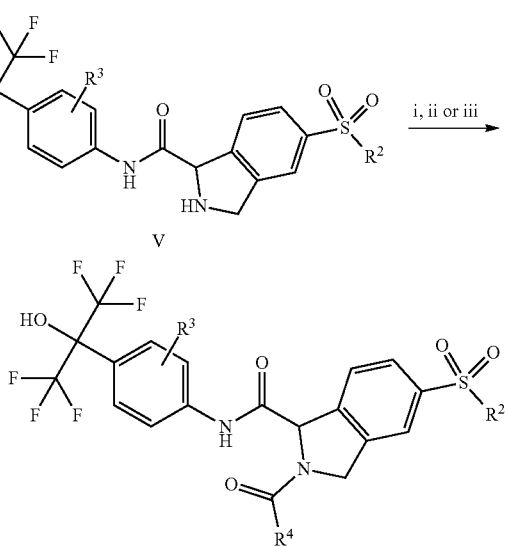

Exemplary conditions: i) Amide bond formation: $R^4CO_2H$, HATU, solvent, base or $R^4COCl$, solvent, base or ($R^4CO)_2O$, base; ii) carbamate formation: $R^{4'}OCOCl$, base, solvent; iii) urea formation: $R^{13}N$=C=O, base, solvent.

Another possibility is to use the functionality present in the $R^4$ substituent of compounds of Formula (II) to transform it into other compounds of Formula (II). For some of these reactions, it might be advantageous to protect the hydroxy group with known protecting groups, such as, but not limited to, benzyl ethers. Scheme 4 shows an example of this approach.

Scheme 4

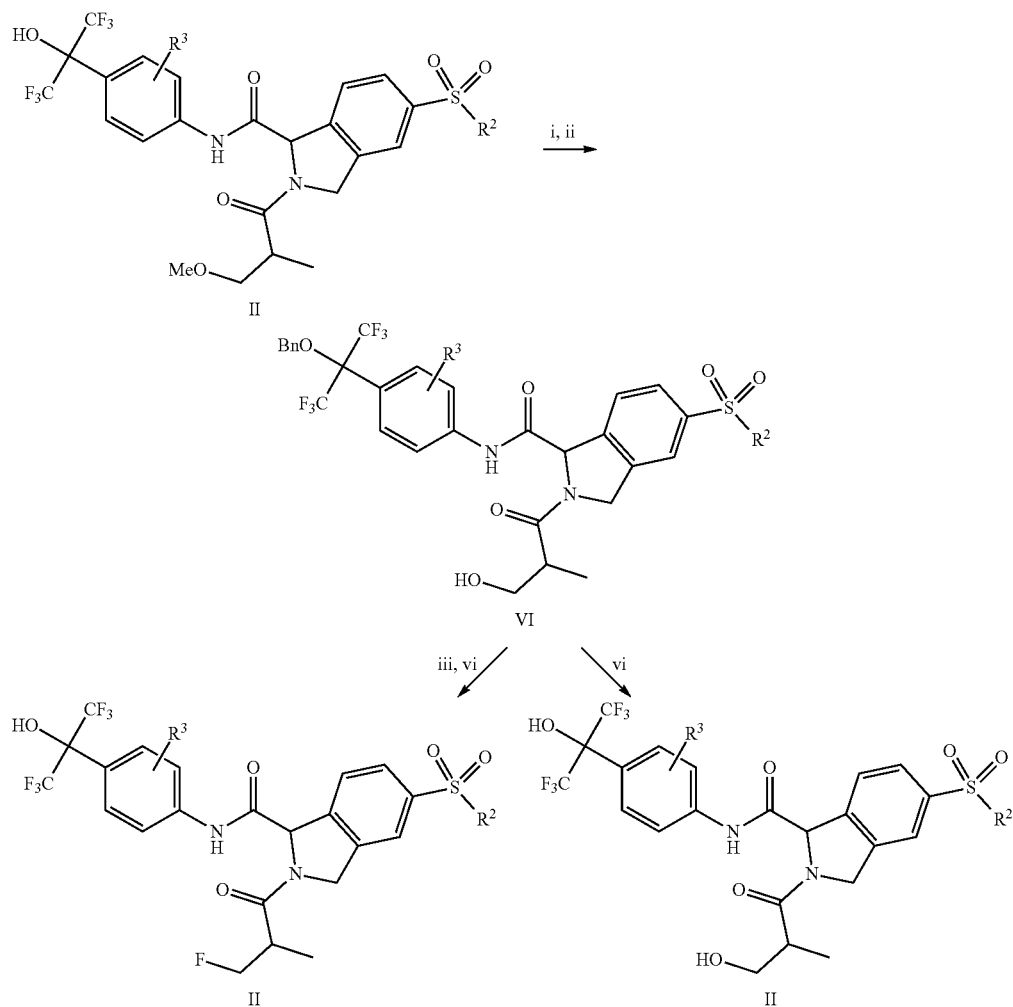

Exemplary conditions: i) Protection of hydroxy group: benzyl bromide, base, solvent; ii) Manipulation of $R^4$: BBr$_3$, DCM; iii) Manipulation of $R^4$: DAST, DCM; iv) Deprotection: H$_2$, Pd/C, solvent.

Intermediates such as (IV) are either commercially available or may be prepared by the method shown in Scheme 5 from anilines. Other methods for the preparation of intermediates (IV) can be found for example in: Cheng, J. F. et al. Bioorganic & Medicinal Chemistry Letters 2006,16, 3484 or Nishimura, N. et al., Journal of Medicinal Chemistry 2014, 57, 3094.

Scheme 5

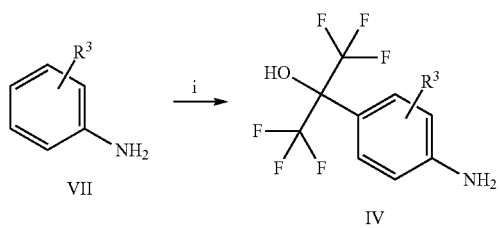

Exemplary conditions: i) 1,1,1,3,3,3-hexafluoropropan-2-one trihydrate, TsOH, microwave, heat.

Intermediates (III) can be prepared by one of the general methods shown in the following Schemes. Introduction of the sulphur residue onto bromo lactam (VIII) can be conducted in several ways, by base-catalyzed or metal catalyzed substitution of the bromine with $R^2$SH, where $R^2$ is as defined above, but not NR$^5$R$^6$. This leads to thioethers (IX), which after protection of the lactam NH with a suitable protecting group, such as, but not limited to Boc, gives compounds (X), which can be subsequently oxidized to sulphones (XI) (Scheme 6). The order of the protection and oxidation step may be changed.

Scheme 6

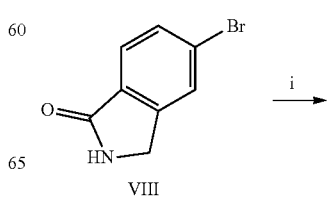

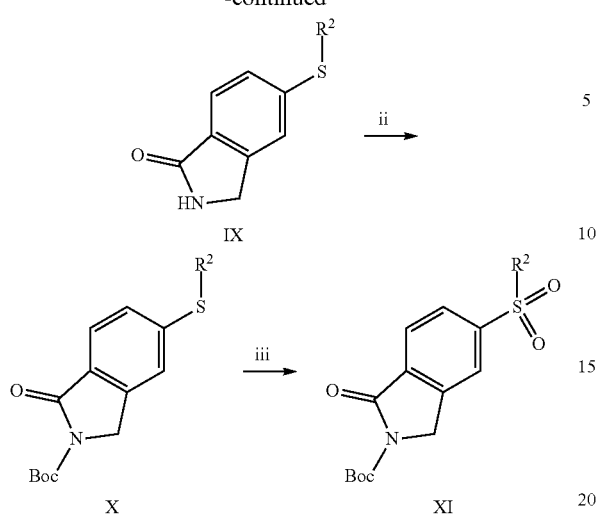

Exemplary conditions: i) R²SH, base solvent, heat; or R²SNa, DMF, or Pd catalyst, ligand, R²SH, solvent, heat ii) Boc₂O, base solvent; iii) mCPBA, DCM;

Another approach to thioethers (IX) is shown in Scheme 7. A thioether is formed from the bromo lactam as shown in Scheme 6, but the substituent on the sulphur is a protecting group, for example, but not limited to, benzyl or a methylpropanoate group. Removal of the protecting group and alkylation of the resulting thiol then leads to thioethers (IX).

Scheme 7

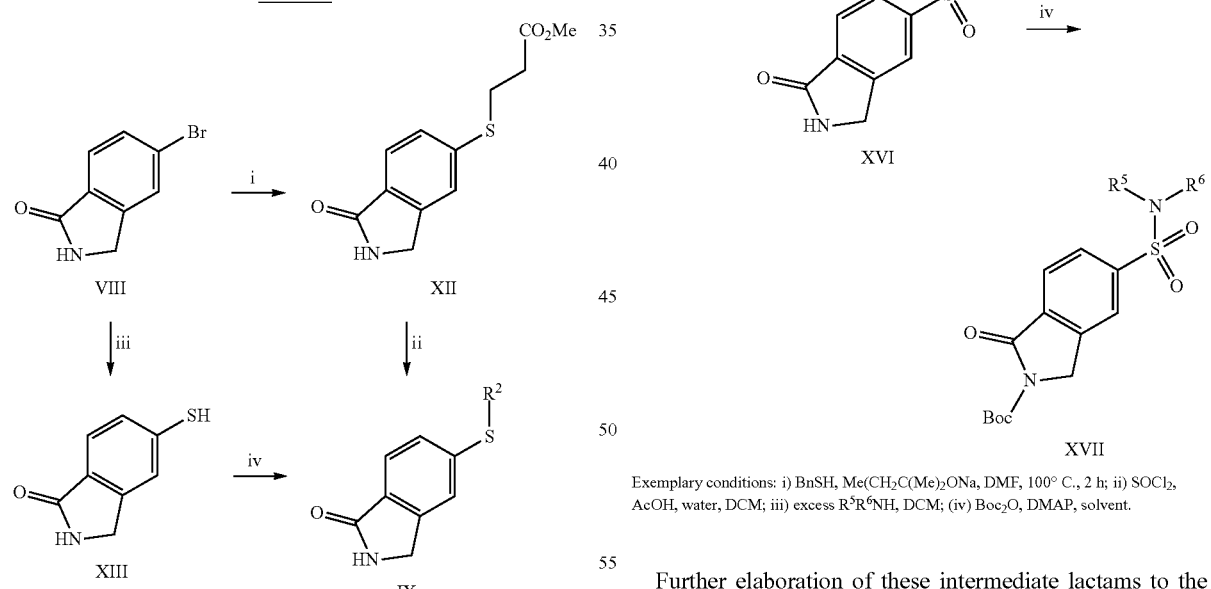

Exemplary conditions: i) Pd₂(dba)₃, Xantphos, DIPEA, HS(CH₂)₂CO₂Me, dioxane; ii) KOᵗBu, THF, then R²Br; iii) BnSH, Me(CH₂C(Me)₂ONa, DMF, 100° C., 12 h; iv) Alkylation of thiol XIII: R²Br, solvent, base.

For R²=NR⁵R⁶ the route in Scheme 8 can be used. Benzyl thioether (XIV) is oxidized to the sulphonylchloride, which reacts with amines HNR⁵R⁶ to give sulphonamides (XVI). These can then be protected on the lactam nitrogen with a suitable protecting group, such as, but not limited to, Boc.

Scheme 8

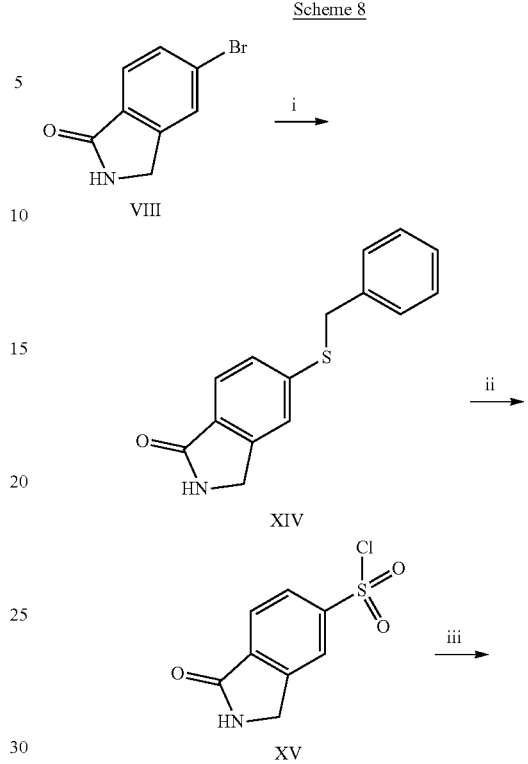

Exemplary conditions: i) BnSH, Me(CH₂C(Me)₂ONa, DMF, 100° C., 2 h; ii) SOCl₂, AcOH, water, DCM; iii) excess R⁵R⁶NH, DCM; (iv) Boc₂O, DMAP, solvent.

Further elaboration of these intermediate lactams to the isoindoline carboxylic acids (III) is shown in Scheme 9. Similar chemistry is described in Moran-Ramallal et al. Org. Lett. 2012, 14, 1696-1699. Reduction of protected lactams (XI) or (XVII) is followed by introduction of the cyano group, which is subsequently hydrolyzed to the carboxylic acid. The resulting isoindoline (XX) is then protected at the nitrogen with a suitable protecting group such as, but not limited to Fmoc or Boc. Alternatively, the group R⁴CO can be introduced at this stage.

Scheme 9

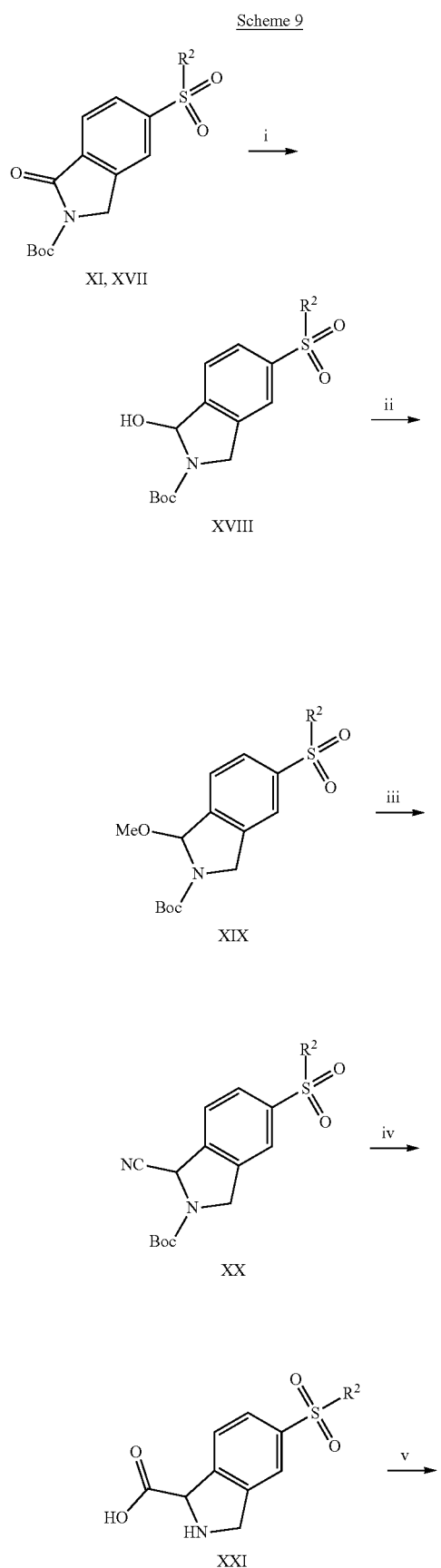

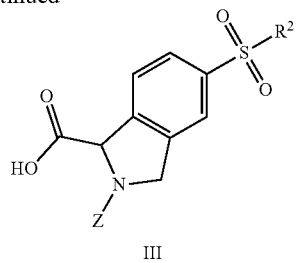

Exemplary conditions: i) DIBAL—H, THF, -78° C.; or DIBAL—H, DCM, 0° C.; ii) PPTs, MeOH; iii) TMSCN, BF$_3$•OEt$_2$, DCM; iv) 6M HCl, heat; or NaOH, heat; v) Boc$_2$O, base, solvent; or Fmoc—Cl, base, solvent; or R$^4$COCl, base, solvent; or (R$^4$CO)$_2$O, base solvent; R$^4$OC(O)Cl, base, solvent; or R$^{13}$N=C=O, base, solvent.

Scheme 10 shows a further possibility to access building blocks (III). Here, the R$^2$-moiety is introduced after elaboration of the lactam to the carboxylic acid by alkylation of the thiol with electrophiles R$^2$X, where X is a typical leaving group such as tosylate or halogen.

Scheme 10

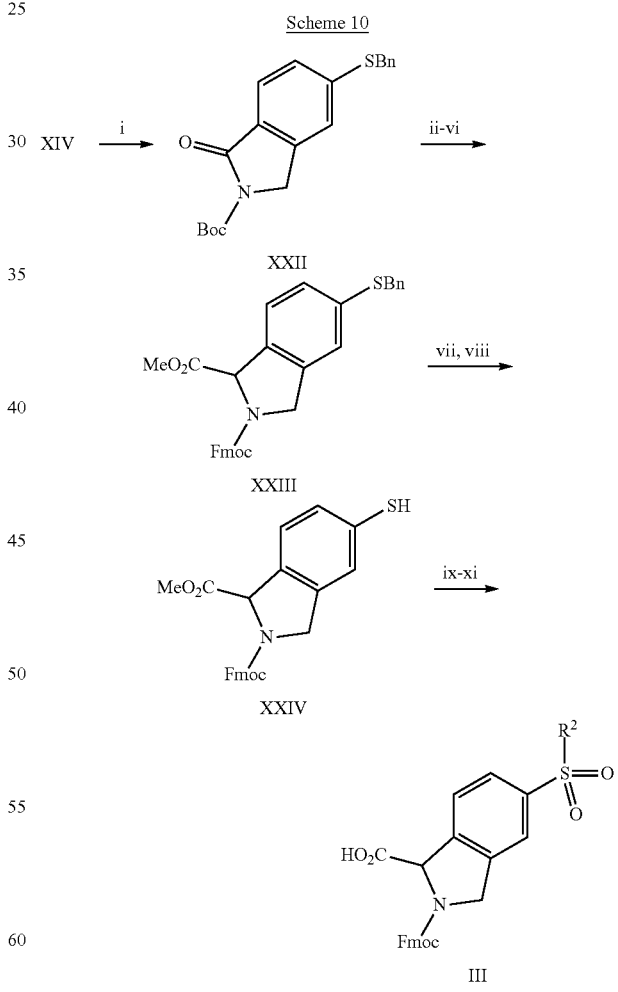

Exemplary conditions: i) Boc$_2$O, base, solvent; ii) Li(AlO$^t$Bu)$_3$H, THF, 0-25° C.; iii) Ag$_2$O, MeI; iv) TMSCN, BF$_3$•OEt$_2$, DCM; v) HCl, heat; MeOH vi) Fmoc—Cl, base solvent; vii) HCOOH, NCS, NaCl; viii) Ph$_3$P, DCM; ix) K$_2$CO$_3$, R$^2$X; x) mCPBA; xi) Ester hydrolysis.

In Scheme 11, bromo lactam (VIII) is converted to intermediate (XXV), which is transformed to the advanced intermediate (XXVI). Subsequently, the bromine can be converted to a protected thiol derivative, as in (XXVII), or converted directly to precursor of the desired sulfone $R^2$ and eventually to compounds of formula (II).

able (for example from NetChem), or may be synthesised using procedures known to those skilled in the art. Where Z is a commonly used amine protecting group, such as those described for Scheme 2, then deprotection leads to the chiral amine (V), which can then react under conditions described for Scheme 3 to give compounds of formula (R)-II.

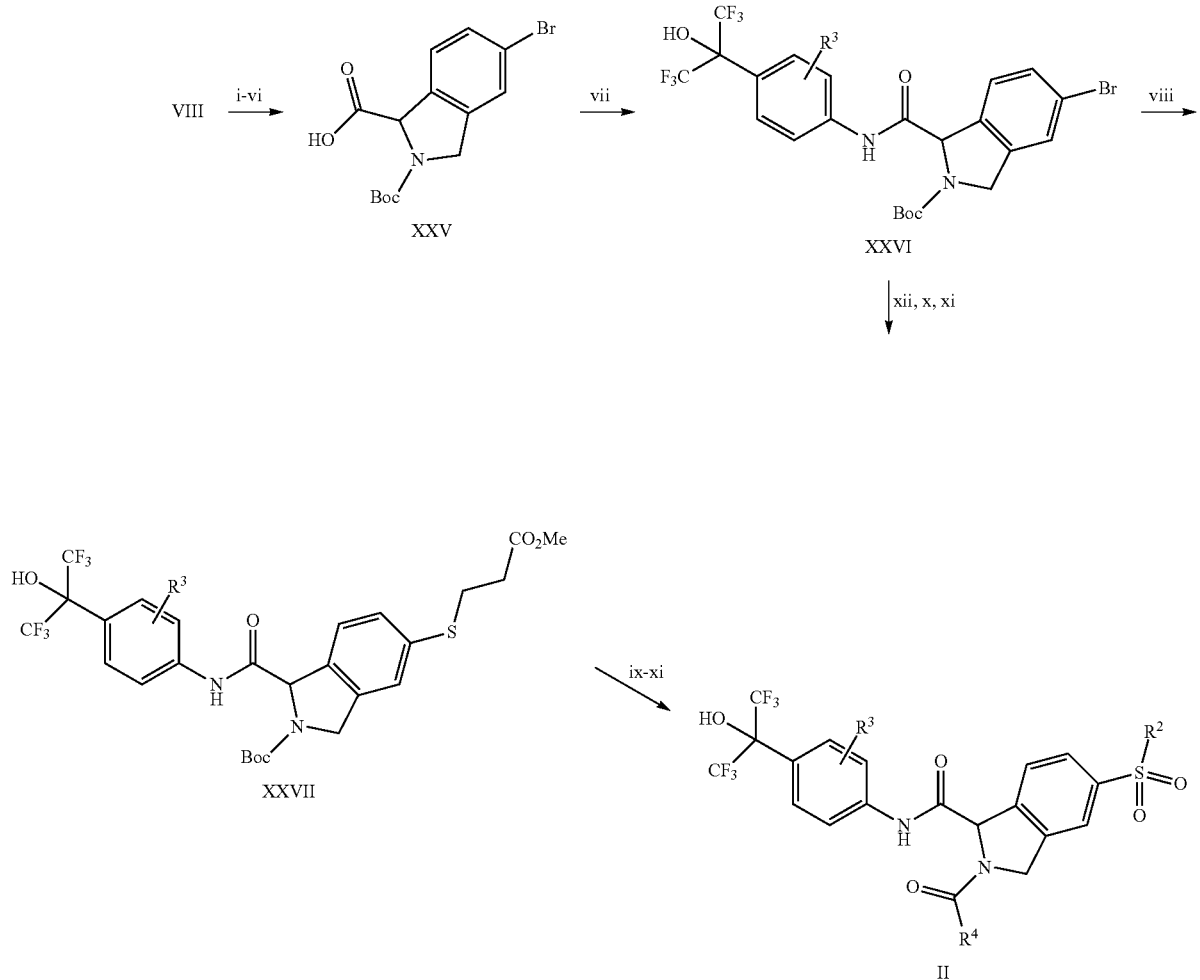

Exemplary conditions: i) Boc$_2$O, base, solvent; ii) Li(AlO$^t$Bu)$_3$H, THF; iii) PPTs, MeOH; iv) TMSCN, BF$_3$·OEt$_2$, DCM; v) 6M HCl, heat; or NaOH, heat; vi) Boc$_2$O, base, solvent; vii) T3P, compound IV, DCM; viii) Pd$_2$(dba)$_3$, Xantphos, DIPEA, HS(CH$_2$)$_2$CO$_2$Me; ix) KO$^t$Bu, R$^2$X, THF; x) mCPBA; xi) see Scheme 2 and 3; xii) Pd$_2$(dba)$_3$, Xantphos, DIPEA, R$^2$SH.

Compounds of formula (I) contain a stereogenic center in the isoindoline moiety. Compounds of formula (I) can be separated into the (R)- and (S)-stereoisomers using appropriate chromatographic methods, as shown generically in Scheme 12 and described in the examples provided below. These stereoisomers can also be obtained by condensing intermediate (IV) under standard amide bond forming conditions with a chiral intermediate (III) as described in Scheme 1. Chiral intermediate III may be obtained from the corresponding unprotected chiral amino-acid using routine protection protocols known to those skilled in the art. The said unprotected chiral amino-acids are commercially avail-

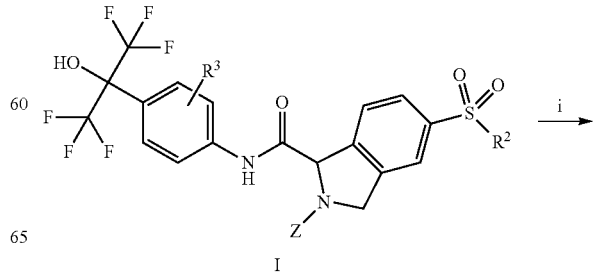

-continued

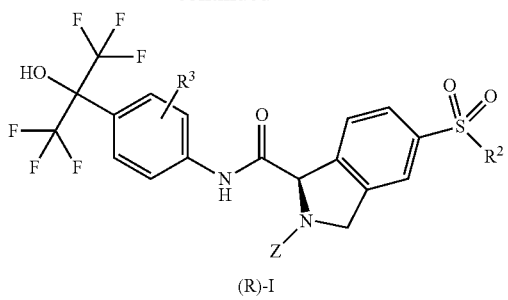

(R)-I

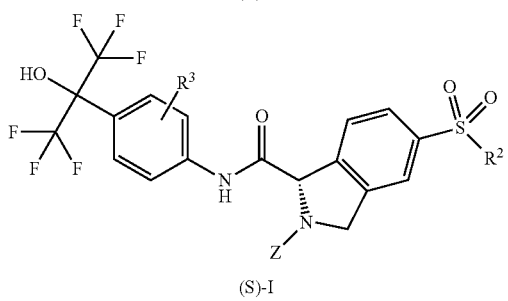

(S)-I

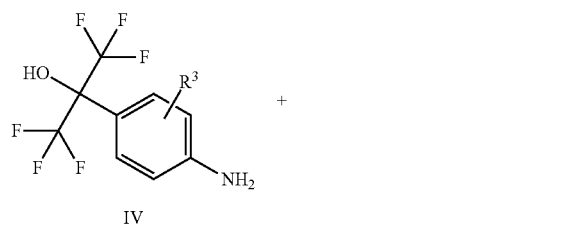

IV

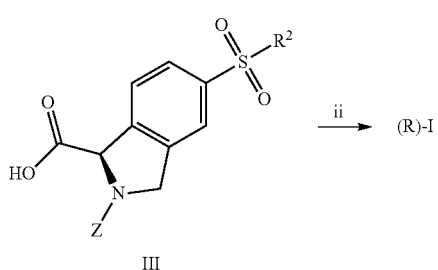

III

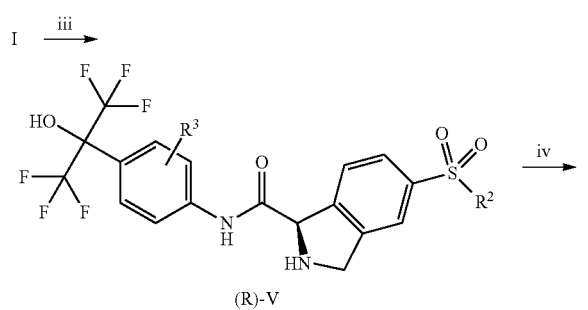

(R)-V

-continued

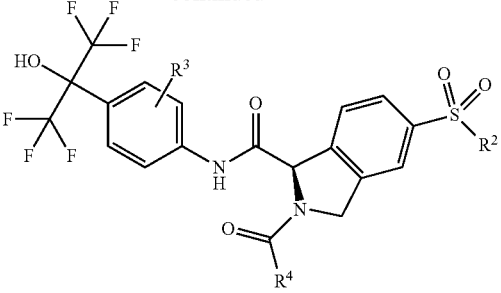

(R)-II

Exemplary conditions: i) Chromatographic separation of enantiomers either by RP-HPLC or SFC using chiral stationary phases; ii) see Scheme 1; iii) see Scheme 2; iv) see Scheme 3.

Detailed processes to the compounds of the specification are further described in the Examples below.

Compounds and salts described in this specification generally may be used in methods to treat various disorders in animals, particularly mammals. Mammals include, for example, humans.

The compounds of the specification, and pharmaceutically acceptable salts thereof, have activity as pharmaceuticals, in particular as modulators of RORγ and/or RORγt, and can be used in the treatment of an RORγ and/or RORγt mediated disease state. Disease states that may be treated with a compound of the specification, or a pharmaceutically acceptable salt thereof, include but are not limited to immune disorders such as psoriasis, ankylosing spondylitis, psoriatic arthritis, ulcerative cholitis, Crohn's disease, multiple sclerosis, inflammatory bowel disease, rheumatoid arthritis, graft versus host disease, systemic lupus erythematosis, lupus nephtritis and insulin dependent diabetes type I, and to respiratory disorders such as chronic obstructive pulmonary disease (COPD) and asthma, and to cancer.

The present specification further provides a compound of formula (I) to (II) as hereinbefore defined, or a pharmaceutically acceptable salt thereof, for use in therapy.

In another aspect, the specification provides the use of a compound of formula (I) to (II) as hereinbefore defined, or a pharmaceutically acceptable salt thereof, in the manufacture of a medicament for use in therapy.

In the context of the present specification, the term "therapy" also includes "prophylaxis" unless there are specific indications to the contrary. The terms "therapeutic" and "therapeutically" should be construed accordingly.

A further aspect provides a method of treating a disease state in a mammal suffering from, or at risk of, said disease, which comprises administering to a mammal in need of such treatment a therapeutically effective amount of a compound of formula (I) to (II) as hereinbefore defined, or a pharmaceutically acceptable salt thereof.

The present specification also provides the use of a compound of formula (I) to (II) as hereinbefore defined, or a pharmaceutically acceptable salt thereof, in the manufacture of a medicament for use in the treatment of chronic obstructive pulmonary disease (COPD), asthma or psoriasis.

The present specification further provides the use of a compound of formula (I) to (II) as hereinbefore defined, or a pharmaceutically acceptable salt thereof, in the manufacture of a medicament for use in the treatment of psoriasis. In a further aspect, the use is in the treatment of ankylosing spondylitis or psoriatic arthritis.

The present specification also provides the use of a compound of formula (I) to (II) as hereinbefore defined, or a pharmaceutically acceptable salt thereof, for treating chronic obstructive pulmonary disease (COPD), asthma or psoriasis.

The present specification further provides the use of a compound of formula (I) to (II) as hereinbefore defined, or a pharmaceutically acceptable salt thereof, for treating psoriasis. In a further aspect, the use is in the treatment of ankylosing spondylitis or psoriatic arthritis.

The present specification further provides a method of treating chronic obstructive pulmonary disease (COPD), asthma or psoriasis in a warm-blooded animal, such as man, which comprises administering to a mammal in need of such treatment a therapeutically effective amount of a compound of formula (I) to (II) as hereinbefore defined, or a pharmaceutically acceptable salt thereof.

The present specification further provides a method of treating psoriasis in a warm-blooded animal, such as man, which comprises administering to a mammal in need of such treatment a therapeutically effective amount of a compound of formula (I) to (II) as hereinbefore defined, or a pharmaceutically acceptable salt thereof. In a further aspect is a method of treating ankylosing spondylitis or psoriatic arthritis.

When a compound or salt described in this specification is administered to treat a disorder, a "therapeutically effective amount" is an amount sufficient to reduce or completely alleviate symptoms or other detrimental effects of the disorder; cure the disorder; reverse, completely stop, or slow the progress of the disorder; or reduce the risk of the disorder getting worse.

In some embodiments in which a combination therapy is used, the amount of the compound or salt described in this specification and the amount of the other pharmaceutically active agent(s) are, when combined, therapeutically effective to treat a targeted disorder in the animal patient. In this context, the combined amounts are "therapeutically effective amounts" if they are, when combined, sufficient to reduce or completely alleviate symptoms or other detrimental effects of the disorder; cure the disorder; reverse, completely stop, or slow the progress of the disorder; or reduce the risk of the disorder getting worse. Typically, such amounts may be determined by one skilled in the art by, for example, starting with the dosage range described in this specification for the compound or salt and an approved or otherwise published dosage range(s) of the other pharmaceutically active compound(s).

In order to use a compound of the specification, or a pharmaceutically acceptable salt thereof, for the therapeutic treatment of a mammal, such as human, said ingredient is normally formulated in accordance with standard pharmaceutical practice as a pharmaceutical composition. Therefore in another aspect the present specification provides a pharmaceutical composition which comprises a compound of the formula (I), or a pharmaceutically acceptable salt thereof (active ingredient), and at least one pharmaceutically acceptable excipient.

The pharmaceutical composition is typically intended for use in the therapeutic and/or prophylactic treatment of a warm-blooded animal, such as man.

Therefore the present specification provides a pharmaceutical composition that comprises a compound of the specification (or a pharmaceutically acceptable salt thereof) and one or more pharmaceutically acceptable excipients.

By the term "pharmaceutically acceptable excipient" we mean a substance that serves as a vehicle or medium for the compound of the specification (or a pharmaceutically acceptable salt thereof), i.e. so as to prepare the active ingredient in a form suitable for administration. Generally the pharmaceutically acceptable excipients are pharmacologically inactive. Each excipient should be compatible with the other ingredients in the composition and should be acceptable for administration to a warm-blooded animal, such as man.

The excipient(s) selected for inclusion in a particular composition will depend on factors such as the mode of administration and the form of the composition provided. Suitable pharmaceutically acceptable excipients are well known to persons skilled in the art and are described, for example, in the Handbook of Pharmaceutical Excipients, Sixth edition, Pharmaceutical Press, edited by Rowe, Ray C; Sheskey, Paul J; Quinn, Marian. Pharmaceutically acceptable excipients may function as, for example, adjuvants, diluents, carriers, stabilisers, flavorings, colourants, fillers, binders, disintegrants, lubricants, glidants, thickening agents and coating agents. As persons skilled in the art will appreciate, certain pharmaceutically acceptable excipients may serve more than one function and may serve alternative functions depending on how much of the excipient is present in the composition and what other excipents are present in the composition.

A pharmaceutical composition of the specification may comprise one or more further active ingredients, as appropriate, examples of combinations of a compound of the specification (or a pharmaceutically acceptable salt thereof) and one or more additional active ingredients are described herein.

A process for the preparation of the pharmaceutical composition may comprise the step of mixing a compound of the specification (or a pharmaceutically acceptable salt thereof) with one or more pharmaceutically acceptable excipients. The process may further comprise the step of mixing one or more further active ingredients with a compound of the specification (or a pharmaceutically acceptable salt thereof) and one or more pharmaceutically acceptable excipients. The processes are conducted using techniques and methods known to persons skilled in the art.

The pharmaceutical composition of the specification may be administered in a standard manner for the disease that it is desired to treat and/or prevent. For example, suitable modes of administration include oral, intravenous, rectal, parenteral, topical, ocular, nasal, buccal or pulmonary administration. For these purposes a compound of the specification (or a pharmaceutically acceptable salt thereof) may be formulated by means known in the art into the form of, for example, tablets, capsules, syrups, powders, granules, aqueous or oily solutions or suspensions, (lipid) emulsions, dispersible powders, suppositories, ointments, creams, drops, aerosols, dry powder formulations, and sterile injectable aqueous or oily solutions or suspensions.

The magnitude of prophylactic or therapeutic dose of a compound of the specification (or a pharmaceutically acceptable salt thereof) will vary depending upon a range of factors, including the activity of the specific compound (or pharmaceutically acceptable salt thereof) that is used, the age, body weight, diet, general health and sex of the patient, time of administration, the route of administration, the rate of excretion, the use of any other active ingredients, and the severity of the disease undergoing treatment.

Depending on the mode of administration, the pharmaceutical composition of the specification will comprise from 0.05 to 99% w/w (percent by weight), such as from 0.05 to 80% w/w, for example from 0.10 to 70% w/w, such as from 0.10 to 50% w/w, of a compound of the specification (or a pharmaceutically acceptable salt thereof), all percentages by weight being based on the total composition.

The present specification provides a pharmaceutical composition comprising a compound of the specification (or a pharmaceutically acceptable salt thereof) and one or more pharmaceutically acceptable excipients, which composition is formulated for oral administration.

A pharmaceutical composition of the specification that is suitable for oral administration may be provided in unit dosage form, for example in the form of a tablet or capsule. Such a unit dosage form may contain from 0.1 mg to 1 g, for example from 5 mg to 250 mg, of a compound of the specification (or a pharmaceutically acceptable salt thereof) as active ingredient.

For oral administration a compound of the specification (or a pharmaceutically acceptable salt thereof) may be admixed with one or more excipients, such as a carrier and/or a binder and/or a lubricant. Suitable carriers include, for example, lactose, saccharose, sorbitol, mannitol, a starch (for example, potato starch, corn starch or amylopectin) and a cellulose derivative. Suitable binders include, for example, gelatine or polyvinylpyrrolidone. Suitable lubricants include, for example, magnesium stearate, calcium stearate, polyethylene glycol, a wax, paraffin, and the like. The mixture may then be compressed into tablets using known techniques. If coated tablets are required, the cores, prepared as described above, may be coated with a suitable coating agent, for example with a concentrated sugar solution which may contain, for example, gum arabic, gelatine, talcum and/or titanium dioxide. Alternatively, the tablet may be coated with a suitable polymer dissolved in a readily volatile organic solvent.

For the preparation of soft gelatine capsules, a compound of the specification (or a pharmaceutically acceptable salt thereof) may be admixed with one or more excipients, such as a diluent. Suitable diluents include, for example, a vegetable oil or polyethylene glycol. Hard gelatine capsules may contain granules of the compound (or salt) using the above-mentioned excipients for tablets. Also liquid or semi-solid formulations of a compound of the specification (or a pharmaceutically acceptable salt thereof) may be filled into hard gelatine capsules.

Liquid preparations for oral application may be in the form of syrups or suspensions, for example, solutions containing a compound of the specification (or a pharmaceutically acceptable salt thereof), the balance being sugar and a mixture of ethanol, water, glycerol and propylene glycol. Optionally such liquid preparations may contain colourants, flavours, saccharine and/or carboxymethylcellulose as a thickening agent or other excipients known to those skilled in art.

The present specification further provides a pharmaceutical composition comprising a compound of the specification (or a pharmaceutically acceptable salt thereof) and one or more pharmaceutically acceptable excipients, which composition is formulated for topical administration. Topical administration may, for example, be in the form of creams, lotions, ointments or transdermal patches. Creams and ointments may comprise an aqueous or oily base to which suitable thickening or gelling agents are applied. Lotions may comprise an aqueous or oily base to which one or more emulsifying agents, stabilising agents, dispersing agents, suspending agents or thickening agents are applied.

A pharmaceutical composition of a compound of the specification that is suitable for pulmonary administration may be provided for inhaled administration. Administration may be by oral inhalation. In another embodiment administration may be by intra-nasal administration. The present specification therefore provides a pharmaceutical composition comprising a compound of the specification (or a pharmaceutically acceptable salt thereof) and one or more pharmaceutically acceptable excipients, which composition is formulated for inhaled administration (particularly for oral inhaled administration).

When administered by oral inhalation, a compound of the specification (or a pharmaceutically acceptable salt thereof) may be used effectively at a daily dose in the µg range, for example up to 500 µg, such as from 0.1 to 50 µg, from 0.1 to 40 µg, from 0.1 to g, from 0.1 to 20 µg or from 0.1 to 10 µg, of a compound of the specification (or a pharmaceutically acceptable salt thereof) as active ingredient.

A pharmaceutical composition of the specification may be administered by oral inhalation in any suitable form and using any suitable inhaler device. Suitable inhaler devices are known to persons skilled in the art and may be manual or breath actuated. The pharmaceutical composition may be formulated as a dry powder, as a suspension (in a liquid or gas) or as a solution (in a liquid) for administration by oral inhalation by means of a suitable inhaler device.

Inhaler devices suitable for pulmonary administration include metered dose inhalers (MDIs), dry powder inhalers (DPIs), nebulisers and soft mist inhalers. Multi-chamber devices may be used to allow for delivery of a compound of the specification (or a pharmaceutically acceptable salt thereof) and one or more further active ingredients (when present).

The specification further relates to a combination therapy wherein a compound of the specification, or a pharmaceutically acceptable salt thereof, and a second active ingredient are administered concurrently, sequentially or in admixture, for the treatment of one or more of the conditions listed above. Such a combination may be used in combination with one or more further active ingredients.

In one aspect there is provided a combination (for example, for use as a medicament for the treatment of one of the diseases or conditions listed herein, such as psoriasis, COPD or asthma, for example COPD or asthma) comprising a compound of the specification, or a pharmaceutically acceptable salt thereof, and at least one active ingredient selected from:

a) a beta-adrenoceptor agonist;

b) a muscarinic receptor antagonist;

c) a joint muscarinic receptor antagonist and beta-adrenoceptor agonist; and d) a glucocorticoid receptor agonist (steroidal or non-steroidal).

In another aspect there is provided a combination (for example, for use as a medicament for the treatment of one of the diseases or conditions listed herein, such as psoriasis, COPD or asthma) comprising a compound of the specification, or a pharmaceutically acceptable salt thereof, and a phosphodiesterase-4 (PDE4) inhibitor.

In a further aspect of the present specification there is provided a pharmaceutical composition (for example, for use as a medicament for the treatment of one of the diseases or conditions listed herein, such as psoriasis, COPD or asthma) comprising a compound of the specification, or a pharmaceutically acceptable salt thereof, and at least one active ingredient selected from:

a) a beta-adrenoceptor agonist;

b) a muscarinic receptor antagonist;

c) a joint muscarinic receptor antagonist and beta-adrenoceptor agonist; and d) a glucocorticoid receptor agonist (steroidal or nonsteroidal).

In another aspect there is provided a pharmaceutical composition (for example, for use as a medicament for the treatment of one of the diseases or conditions listed herein, such as psoriasis, COPD or asthma) comprising a compound of the specification, or a pharmaceutically acceptable salt thereof, and a phosphodiesterase-4 (PDE4) inhibitor.

The compounds described in this specification are further illustrated in the following Examples. These Examples are given by way of illustration only and are non-limiting.

Chemical names are preferably IUPAC names which were generated using ACD Labs 2014, or ChemDraw Ultra version 11.0.

Abbreviations

ACN acetonitrile
Boc$_2$O di-tert-butyl dicarbonate
CDI 1,1'-carbonyldiimidazole
DCM dichloromethane
DAST diethylaminosulfur trifluoride
DBU 2,3,4,6,7,8,9,10-octahydropyrimido[1,2-a]azepine
DIBAL-H diisobutylaluminum hydride
DIPEA diisopropylethylamine
DMAP 4-N,N-dimethylamino pyridine
DMF dimethylformamide
DMSO dimethylsulfoxide
dppf 1,1'-bis(diphenylphosphino)ferrocene
EDC N$^1$-((ethylimino)methylene)-N$^3$,N$^3$-dimethylpropane-1,3-diamine hydrochloride
ESI electrospray ionization
EtOH ethanol
EtOAc ethyl acetate
Fmoc-Cl 9-fluorenylmethyl chloroformate
h hour
HATU 1-[bis(dimethylamino)methylene]-1H-1,2,3-triazolo[4,5-b]pyridinium 3-oxid hexafluorophosphate
HOBt 1H-benzo[d][1,2,3]triazol-1-ol hydrate
HPLC high-performance liquid chromatography
IPA isopropyl alcohol
LC/MS liquid chromatography-mass spectroscopy
LHMDS lithium bis(trimethylsilyl)amide
mCPBA 3-chloroperoxybenzoic acid
MeOH methanol
MsCl methanesulfonyl chloride
MTBE methyl tert-butyl ether
NBS N-bromosuccinimide
NCS N-chlorosuccinimide
NsCl 4-nitrobenzenesulfonyl chloride
(PinB)$_2$ bis(pinacolato)diboron
PPTs pyridinium para-toluenesulphonate
rt room temperature
RP-HPLC reverse phase HPLC
SFC supercritical fluid chromatography
TEA triethylamine
T3P 2,4,6-tripropyl-1,3,5,2,4,6-trioxatriphosphinane 2,4,6-trioxide
TBAF tetra-n-butylammonium fluoride
TBDMSCl tert-Butyldimethylsilyl chloride
TBDMSOTf tert-butyldimethylsilyl trifluoromethanesulfonate
TBTU 2-(1H-benzo[d][1,2,3]triazol-1-yl)-1,1,3,3-tetramethylisouronium tetrafluoroborate
TFA trifluoroacetic acid
TFAA trifluoroacetic anhydride
THF tetrahydrofuran
TMSCN trimethylsilyl cyanide
TsCl para-toluenesulphonyl chloride
TsOH para-toluenesulphonic acid General Methods NMR spectra were recorded on a Bruker Avance, Avance II or Avance III spectrometer at a proton frequency of 300, 400, 500 or 600 MHz. The central peaks of chloroform-δ (H 7.26 ppm), CD$_3$OD (H 3.30 ppm) or DMSO-d$_6$ (H 2.49 ppm) were used as internal references.

Optical rotations were measured on a Perkin Elmer 341 polarimeter.

LC/MS experiments were performed using a Waters Acquity system combined with a Waters Xevo Q-ToF Mass or a Shimadzu 2010EV UPLC system in ESI mode. LC was run in two set ups: 1) BEH C18 column (1.7 μm 2.1×50 mm) in combination with a gradient (2-95% B in 5 minutes) of aqueous 46 mM ammonium carbonate/ammonia buffer at pH 10 (A) and MeCN (B) at a flow rate of 1.0 mL/min or in combination with a gradient (5-95% B in 2 minutes) of water and TFA (0.05%) (A) and CH$_3$CN and TFA (0.05%) at a flow rate of 1.0 mL/min (B).

Optical purity, indicated as enantiomeric excess (% ee), was determined either on by HPLC using an Agilent 1100 series chromatograph, or on a Novasep Supersep 2. Preparative HPLC was performed with a Waters FractionLynx system with integrated MS detection and equipped with Prep C18 OBD 5 μm 19×150 mm columns from X-Bridge or Sunfire. Alternatively Gilson GX-281 with intregrated UV detection was used, equipped with either Kromasil C8 10 μm, 20×250 ID or 50×250 ID mm. As eluent (acidic) gradients of water/MeCN/acetic acid (95/5/0.1) or water/0.05% TFA (A) and MeCN/0.05% TFA (B) or (basic) MeCN or MeOH (A) and 0.03% ammonia in water or 0.03% NH$_4$HCO$_3$ (B) were applied.

Preparative SCF was performed with a Waters Prep100 SCF system with integrated MS detection, equipped with Waters Viridis 2-EP or Phenomenex Luna Hilic, 30×250 mm, 5 m. As eluent gradients of CO$_2$ (100 g/min, 120 bar, 40° C.) (A) and MeOH/NH3 (20 mM) or MeOH (5% formic acid) or MeOH (B) were applied.

Unless otherwise stated, starting materials were commercially available or previously described in the literature. All solvents and commercial reagents were of laboratory grade and were used as received unless otherwise stated.

Intermediate 1: 9H-Fluoren-9-yl 1-{[4-(1,1,1,3,3,3-hexafluoro-2-hydroxypropan-2-yl)phenyl]carbamoyl}-5-(ethylsulfonyl)-1,3-dihydro-2H-isoindole-2-carboxylate

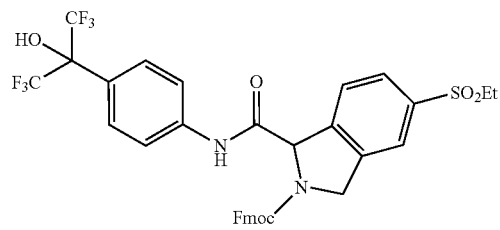

Step 1: 5-(Ethylthio)isoindolin-1-one

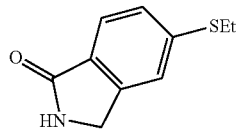

5-Bromoisoindolin-1-one (10 g, 47.16 mmol) and sodium ethanethiolate (9.92 g, 117.90 mmol) were mixed together in DMF (100 mL) and the reaction heated to 100° C. for 20 min. The reaction was cooled to room temperature, poured into water (100 mL) and the product extracted with EtOAc (3×200 mL). The combined organic extracts were washed with brine (4×50 mL). LCMS indicated product in the aqueous washings consequently they were combined and extracted with EtOAc (4×50 mL). The organic extracts were combined, dried using a phase separator cartridge and concentrated in vacuo. The solid obtained was dried under high vacuum overnight. 5-(Ethylthio)isoindolin-1-one (8.68 g, 95%) was obtained as a yellow solid. The material was used in the next step without further purification.

LC/MS: m/z=194 [M+H]$^+$. $^1$H NMR (500 MHz, DMSO-d$_6$) δ 1.27 (t, 3H), 3.06 (q, 2H), 4.33 (s, 2H), 7.36 (dd, 1H), 7.47-7.48 (m, 1H), 7.57 (d, 1H), 8.45 (s, 1H).

Step 2: tert-Butyl 5-(ethylthio)-1-oxoisoindoline-2-carboxylate

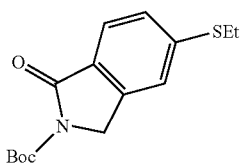

5-(Ethylthio)isoindolin-1-one (8.68 g, 44.91 mmol) was suspended in acetonitrile (400 mL) and DMAP (7.68 g, 62.88 mmol) was added in one portion. After 10 min Boc-anhydride (13.72 g, 62.88 mmol) was added and the mixture was stirred at room temperature for 30 min. The reaction was concentrated in vacuo. The residue was dissolved in EtOAc and washed with 0.1M aqueous HCl (4×100 mL). The organic extract was dried using a phase separator cartridge and concentrated in vacuo to afford tert-butyl 5-(ethylthio)-1-oxoisoindoline-2-carboxylate (12.50 g, 95%) as an orange solid. The material was used in the next step without further purification.

$^1$H NMR (500 MHz, DMSO-d$_6$) δ 1.29 (t, 3H), 1.51 (s, 9H), 3.09 (q, 2H), 4.74 (s, 2H), 7.39 (dd, 1H), 7.52-7.53 (m, 1H), 7.65 (d, 1H) 1H).

Step 3: tert-Butyl 5-(ethylsulfonyl)-1-oxoisoindoline-2-carboxylate

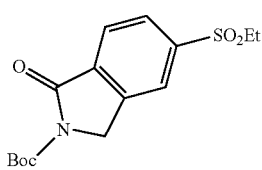

tert-Butyl 5-(ethylthio)-1-oxoisoindoline-2-carboxylate (13.18 g, 44.91 mmol) was dissolved in DCM (500 mL) and to this mCPBA (≥77%) (24.16 g, 107.78 mmol) was added portionwise (an increase of the temperature to ca 35° C. was observed). The reaction was stirred at room temperature for 30 min. The reaction was washed twice with 1M aq NaOH and the DCM phase was dried using a phase separator cartridge and concentrated in vacuo. tert-Butyl 5-(ethylsulfonyl)-1-oxoisoindoline-2-carboxylate (14.00 g, 96%) was obtained as a yellow solid. The material was used in the next step without purification. LC/MS: m/z=324 [M–H]$^-$.
$^1$H NMR (500 MHz, DMSO-d$_6$) δ 1.12 (t, 3H), 1.53 (s, 9H), 3.38 (q, 2H), 4.89 (s, 2H), 7.99-8.04 (m, 2H), 8.21 (s, 1H).

Step 4: tert-Butyl 5-(ethylsulfonyl)-1-hydroxyisoindoline-2-carboxylate

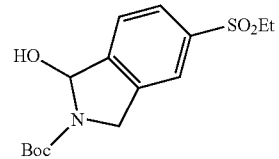

tert-Butyl 5-(ethylsulfonyl)-1-oxoisoindoline-2-carboxylate (12 g, 36.88 mmol) was dissolved in DCM (300 mL) and the mixture was cooled in an ice bath. DIBAL-H (63 mL, 63.00 mmol) 1M solution in THF was added and the reaction stirred at this temperature for 15 min. Saturated aqueous Rochelle's salt (300 mL) was added and the mixture stirred for 20 min. DCM (300 mL) was added and the layers separated. The aqueous phase was extracted with DCM. The combined organic extracts were dried using a phase separator cartridge and concentrated in vacuo. The material was used crude in the next step. LC/MS: m/z=326 [M–H]$^-$.

Step 5: tert-Butyl 5-(ethylsulfonyl)-1-methoxyisoindoline-2-carboxylate

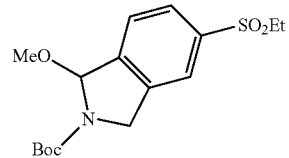

tert-Butyl 5-(ethylsulfonyl)-1-hydroxyisoindoline-2-carboxylate (12.07 g, 36.88 mmol) was dissolved in MeOH (210 mL) and to this PPTs (0.927 g, 3.69 mmol) was added and the reaction stirred at room temperature. After 20 min LCMS indicated that no starting material remained and a single product formed however, the desired mass ion was not seen. The reaction was quenched by addition of triethylamine (81 mL, 581.14 mmol) and concentrated in vacuo to afford a dark purple oil. This was used without further purification in the next step.

Step 6: tert-Butyl 1-cyano-5-(ethylsulfonyl)isoindoline-2-carboxylate

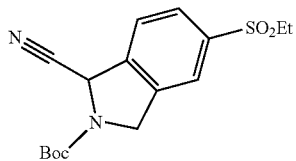

tert-Butyl 5-(ethylsulfonyl)-1-methoxyisoindoline-2-carboxylate (12.59 g, 36.88 mmol) was dissolved in DCM (300 mL) and the solution cooled to −78° C. TMS-CN (7.42 mL, 55.32 mmol) and then $BF_3.OEt_2$ (7.01 mL, 55.32 mmol) was added. The reaction was stirred at −78° C. for 15 min. Sat. aq $NaHCO_3$ solution (300 mL) and DCM (300 mL) were added and the reaction allowed to warm to room temperature. The two layers were separated and the aqueous extracted with DCM. The combined organic extracts were dried using a phase separator cartridge and concentrated in vacuo. The material was purified by flash chromatography eluting with 40% EtOAc in heptane. tert-Butyl 1-cyano-5-(ethylsulfonyl)isoindoline-2-carboxylate (7.58 g, 61.1%) was obtained as a pink solid. LC/MS: m/z=335 [M−H]$^-$. $^1$H NMR (500 MHz, DMSO-$d_6$, mixture of rotamers, 1:1) δ 1.11 (t, 3H), 1.49, 1.51 (s, 9H), 3.29-3.36 (m, 2H), 4.75, 4.77 (s, 2H), 6.18, 6.20 (s, 1H), 7.83, 7.85 (s, 1H), 7.93, 7.95 (s, 1H), 7.96, 7.99 (s, 1H).

Step 7: 5-(Ethylsulfonyl)isoindoline-1-carboxylic acid, hydrochloride salt

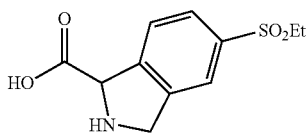

6M aq HCl (50 ml, 300.00 mmol) was added to tert-butyl 1-cyano-5-(ethylsulfonyl)isoindoline-2-carboxylate (5 g, 14.86 mmol) and the mixture heated at 70° C. for 2 h. The reaction was cooled to room temperature and concentrated to dryness in vacuo. The dark solid obtained was used crude in the next step.
LC/MS: m/z=254 [M−H]$^-$.

Step 8: 2-((9H-Fluoren-9-yl)methoxy)carbonyl)-5-(ethylsulfonyl)isoindoline-1-carboxylic acid

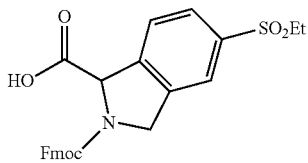

To 5-(ethylsulfonyl)isoindoline-1-carboxylic acid, HCl (4.35 g, 14.9 mmol) in dioxane (80 mL)/water (80 mL) was added potassium carbonate (10.30 g, 74.50 mmol) and 9-fluorenylmethyl chloroformate (3.47 g, 13.41 mmol). The reaction was stirred at room temperature overnight. The dioxane was removed in vacuo and the aqueous acidified with 1M aq HCl and extracted with EtOAc until no product remained in the aqueous (as judged by LCMS). The combined organic extracts were dried using a phase separator cartridge and concentrated in vacuo. This material was used crude in the next step.

Step 9: (9H-Fluoren-9-yl)methyl 5-(ethylsulfonyl)-1-((4-(1,1,1,3,3,3-hexafluoro-2-hydroxypropan-2-yl)phenyl)carbamoyl)isoindoline-2-carboxylate

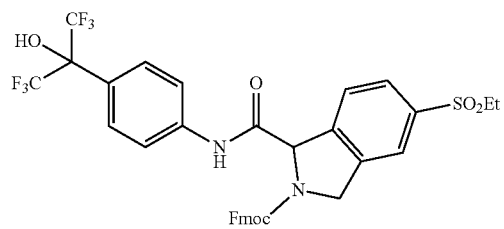

T3P (50% solution in EtOAc) (22.17 mL, 37.25 mmol) was added to a mixture of 2-(((9H-fluoren-9-yl)methoxy)carbonyl)-5-(ethylsulfonyl)isoindoline-1-carboxylic acid (7.12 g, 14.9 mmol), 2-(4-aminophenyl)-1,1,1,3,3,3-hexafluoropropan-2-ol (2.317 g, 8.94 mmol) and triethylamine (4.15 mL, 29.80 mmol) in DCM (200 mL). This was stirred at room temperature for 30 min. The reaction mixture was partitioned between DCM and water. The layers were separated in a phase separator cartridge and the organic layer was concentrated in vacuo. The residue was purified by flash chromatography eluting with 20%-50% EtOAc in heptane. All product containing fractions were combined and concentrated in vacuo. The residue was triturated with methanol and a solid was obtained. This was collected by filtration and washed with methanol. The mother liquor was concentrated in vacuo and the trituration process repeated. A second batch of product was obtained which was less pure however, the two batches were combined (5.40 g, 50.4%) and used in the next step.
LC/MS: m/z=719 [M+H]$^+$. $^1$H NMR (500 MHz, DMSO-$d_6$, mixture of rotamers, 1:1) δ 1.09-1.14 (m, 3H), 3.28-3.33 (m, 2H), 4.14-4.39 (m, 3H), 4.87-5.05 (m, 2H), 5.72, 5.81 (s, 1H), 6.93-6.99 (m, 1H), 7.23-7.47 (m, 3H), 7.56-7.95 (m, 10H), 8.01-8.05 (m, 1H), 8.64, 8.66 (s, 1H), 10.82, 10.87 (s, 1H).

Intermediate 2: 9H-Fluoren-9-yl 5-[(cyclopropylmethyl)sulfonyl]-1-{[4-(1,1,1,3,3,3-hexafluoro-2-hydroxypropan-2-yl)phenyl]carbamoyl}-1,3-dihydro-2H-isoindole-2-carboxylate

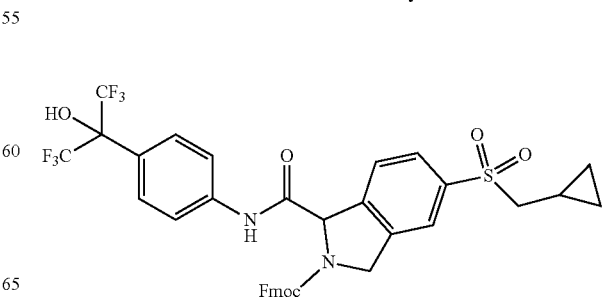

Step 1: Methyl 3-((1-oxoisoindolin-5-yl)thio)propanoate

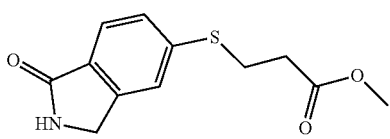 [SMILES: COC(=O)CCSc1ccc2c(c1)CNC2=O]

A solution of 5-bromoisoindolin-1-one (10 g, 47.16 mmol) in dioxane (450 mL) was degassed before Xantphos (2.73 g, 4.72 mmol), DIPEA (9.88 mL, 56.59 mmol), $Pd_2(dba)_3$ (2.159 g, 2.36 mmol) and methyl 3-mercaptopropanoate (32.6 mL, 330.12 mmol) was added. The reaction was heated to 80° C. for 1 h. The reaction was concentrated in vacuo. Approximately half of the material was purified by flash chromatography eluting with 0-5% methanol in EtOAc to afford 4.69 g of product. Only half the material was purified this way because the crude material solidified part way through loading onto the column. The solidified material was triturated with methanol and 4.48 g of product was collected by filtration as a colorless solid. The mother liquor was concentrated in vacuo and purified by flash chromatography eluting with 0-5% methanol in EtOAc to afford 1. g product. This was combined with the material from the first column to give 10.27 g (86%) of the title compound.

LC/MS: m/z=252 $[M+H]^+$. $^1$H NMR (500 MHz, DMSO) δ 2.69 (t, 2H), 3.26 (t, 2H), 3.60 (s, 3H), 4.34 (s, 2H), 7.38 (d, 1H), 7.52 (s, 1H), 7.58 (d, 1H), 8.48 (s, 1H).

Step 2: 5-((Cyclopropylmethyl)thio)isoindolin-1-one

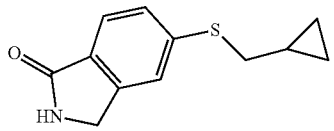 [SMILES: O=C1NCc2cc(SCC3CC3)ccc21]

To a suspension of methyl 3-((1-oxoisoindolin-5-yl)thio)propanoate (5.79 g, 23.04 mmol) in THF (250 mL) was added potassium tert-butoxide (46.1 mL, 46.08 mmol, 1M solution in THF). The reaction was stirred for 5 min at room temperature, followed by addition of (bromomethyl)cyclopropane (6.22 g, 46.08 mmol). The reaction was stirred for 30 min at room temperature. The reaction was poured into water and the product extracted into EtOAc. The combined organic extracts were washed with brine, dried using a phase separator cartridge and concentrated in vacuo. The solid obtained was slurried in EtOAc, collected by filtration and then washed with diethyl ether to afford 5-((cyclopropylmethyl)thio)isoindolin-1-one (2.35 g, 46%).

LC/MS: m/z=220 $[M+H]^+$. $^1$H NMR (500 MHz, DMSO-$d_6$) δ 0.17-0.33 (m, 2H), 0.44-0.62 (m, 2H), 0.94-1.11 (m, 1H), 3.01 (d, 2H), 4.33 (s, 2H), 7.38 (d, 1H), 7.50 (s, 1H), 7.55 (d, 1H), 8.45 (s, 1H).

Step 3: tert-Butyl 5-((cyclopropylmethyl)thio)-1-oxoisoindoline-2-carboxylate

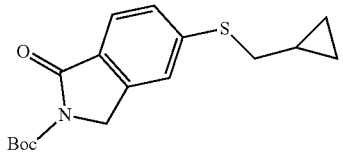 [SMILES: CC(C)(C)OC(=O)N1Cc2cc(SCC3CC3)ccc2C1=O]

5-((Cyclopropylmethyl)thio)isoindolin-1-one (4.13 g, 18.83 mmol) was suspended in acetonitrile (150 mL) and DMAP (3.22 g, 26.37 mmol) was added in one portion. Boc-anhydride (5.75 g, 26.37 mmol) was then added and the reaction stirred at room temperature for 20 min. The acetonitrile was removed in vacuo. The residue was dissolved in EtOAc and washed with 0.5M aqueous HCl (3×200 mL). The organic extract was dried using a phase separator cartridge and concentrated in vacuo. tert-Butyl 5-((cyclopropylmethyl)thio)-1-oxoisoindoline-2-carboxylate was obtained as a brown oil that solidified on standing. The material was used in the next step without further purification $^1$H NMR (500 MHz, DMSO-$d_6$) δ 0.23-0.34 (m, 2H), 0.5-0.6 (m, 2H), 1-1.13 (m, 1H), 1.51 (s, 9H), 3.04 (d, 2H), 4.73 (s, 2H), 7.41 (d, 1H), 7.55 (s, 1H), 7.64 (d, 1H).

Step 4: tert-Butyl 5-((cyclopropylmethyl)sulfonyl)-1-oxoisoindoline-2-carboxylate

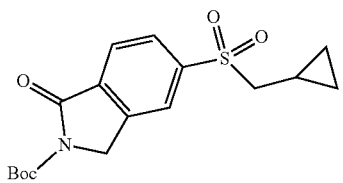 [SMILES: CC(C)(C)OC(=O)N1Cc2cc(S(=O)(=O)CC3CC3)ccc2C1=O]

tert-Butyl 5-((cyclopropylmethyl)thio)-1-oxoisoindoline-2-carboxylate (6.01 g, 18.83 mmol) was dissolved in DCM (200 mL) and to this mCPBA (≥77%) (10.13 g, 45.19 mmol) was added (an exotherm of ca 36° C. was observed). The reaction was stirred at room temperature for 20 min. The reaction mixture was washed twice with 1M aq NaOH. The DCM was dried using a phase separator cartridge and concentrated in vacuo to afford tert-butyl 5-((cyclopropylmethyl)sulfonyl)-1-oxoisoindoline-2-carboxylate (5.98 g, 90%) as an off-white solid. The material was used in the next step without further purification. LC/MS: m/z=350 $[M-H]^-$. $^1$H NMR (500 MHz, DMSO-$d_6$) δ 0.01-0.2 (m, 2H), 0.33-0.5 (m, 2H), 0.78-0.93 (m, 1H), 1.53 (s, 9H), 3.35 (d, 2H), 4.89 (s, 2H), 7.97-8.05 (m, 2H), 8.21 (s, 1H).

Step 5: tert-Butyl 5-((cyclopropylmethyl)sulfonyl)-1-hydroxyisoindoline-2-carboxylate

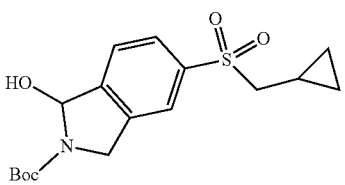 [SMILES: CC(C)(C)OC(=O)N1Cc2cc(S(=O)(=O)CC3CC3)ccc2C1O]

tert-Butyl 5-((cyclopropylmethyl)sulfonyl)-1-oxoisoindoline-2-carboxylate (5.48 g, 15.59 mmol) was dissolved in DCM (150 mL) and the mixture was cooled in an ice bath. DIBAL-H (26.5 mL, 26.51 mmol) 1M solution in THF was added and the reaction stirred at this temperature for 15 min. 100 ml saturated aq Rochelle's salt was added and the resultant mixture was stirred for 20 min whilst warming to room temperature. DCM (150 mL) was added and the layers separated. The aqueous layer was extracted with DCM. The combined organic extracts were dried using a phase separator cartridge and concentrated in vacuo. The product was obtained as a pink gum/foam. The material was used as such in the next step.

LC/MS: m/z=352 [M−H]⁻.

Step 6: tert-Butyl 5-((cyclopropylmethyl)sulfonyl)-1-methoxyisoindoline-2-carboxylate

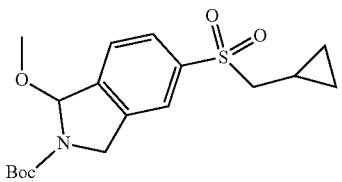 [SMILES: COC1c2ccc(S(=O)(=O)CC3CC3)cc2CN1C(=O)OC(C)(C)C]

tert-Butyl 5-((cyclopropylmethyl)sulfonyl)-1-hydroxyisoindoline-2-carboxylate (5.51 g, 15.59 mmol) was dissolved in MeOH (110 mL) and to this PPTs (0.392 g, 1.56 mmol) was added and the reaction stirred at room temperature. After 20 min LCMS indicated no starting material remained and a single product had formed however, the desired mass ion was not seen. The reaction was quenched by addition of triethylamine (34.8 mL, 249.44 mmol) and concentrated in vacuo to afford a dark purple oil. This was used without further purification in the next step.

Step 7: tert-butyl 1-cyano-5-((cyclopropylmethyl)sulfonyl)isoindoline-2-carboxylate

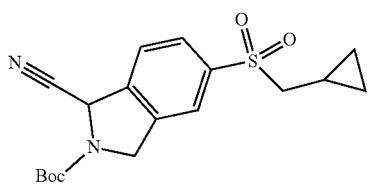 [SMILES: CC(C)(C)OC(=O)N1Cc2cc(S(=O)(=O)CC3CC3)ccc2C1C#N]

tert-Butyl 5-((cyclopropylmethyl)sulfonyl)-1-methoxyisoindoline-2-carboxylate (5.73 g, 15.59 mmol) was dissolved in DCM (110 mL). This was cooled to −78° C. before TMS-CN (3.14 mL, 23.39 mmol) and BF₃.OEt₂ (2.96 mL, 23.39 mmol) was added. The reaction was stirred at −78° C. for 15 min. Sat. aq NaHCO₃ and DCM was added and the reaction allowed to warm to room temperature. The two layers were separated and the aqueous extracted with DCM. The combined organic extracts were dried using a phase separator cartridge and concentrated in vacuo. The residue was purified on silica eluting with 25-50% EtOAc in heptane. tert-Butyl 1-cyano-5-((cyclopropylmethyl)sulfonyl) isoindoline-2-carboxylate (3.22 g, 57%) was obtained as a pale pink foam.

LC/MS: m/z=361 [M−H]⁻. ¹H NMR (500 MHz, DMSO) δ 0.06-0.16 (m, 2H), 0.33-0.53 (m, 2H), 0.7-0.95 (m, 1H), 1.49, 1.51 (s, 9H), 3.27-3.31 (m, 2H), 4.75, 4.77 (s, 2H), 6.18, 6.20 (s, 1H), 7.82, 7.84 (s, 1H), 7.94, 7.96 (s, 1H), 7.97, 7.99 (s, 1H).

Step 8: 5-((Cyclopropylmethyl)sulfonyl)isoindoline-1-carboxylic acid, hydrochloride salt

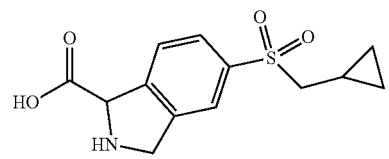 [SMILES: O=C(O)C1NCc2cc(S(=O)(=O)CC3CC3)ccc21]

6M aq HCl (35 ml, 210.00 mmol) was added to tert-butyl 1-cyano-5-((cyclopropylmethyl)sulfonyl)isoindoline-2-carboxylate (3.48 g, 9.60 mmol) and the mixture heated at 70° C. for 2.5 h. The reaction was cooled to room temperature and concentrated to dryness in vacuo. The dark solid obtained was used crude in the next step. LC/MS: m/z=280 [M−H]⁻.

Step 9: 5-[(Cyclopropylmethyl)sulfonyl]-2-[(9H-fluoren-9-yloxy)carbonyl]-2,3-dihydro-1H-isoindole-1-carboxylic acid

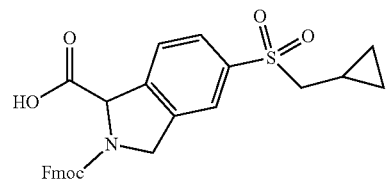

To 5-((cyclopropylmethyl)sulfonyl)isoindoline-1-carboxylic acid, HCl (3.05 g, 9.6 mmol) in dioxane (70 mL)/water (70 mL) was added potassium carbonate (6.63 g, 48.00 mmol) and 9-fluorenylmethyl chloroformate (2.235 g, 8.64 mmol). The reaction was stirred at room temperature overnight. The dioxane was removed in vacuo. The aqueous was then acidified with 1M aq HCl and extracted with EtOAc. The organic extracts were combined, dried using a phase separator cartridge and concentrated in vacuo. The material was used as such in the next step.

LC/MS: m/z=504 [M+H]⁺.

Step 10: 9H-Fluoren-9-yl 5-[(cyclopropylmethyl)sulfonyl]-1-{[4-(1,1,1,3,3,3-hexafluoro-2-hydroxypropan-2-yl)phenyl]carbamoyl}-1,3-dihydro-2H-isoindole-2-carboxylate

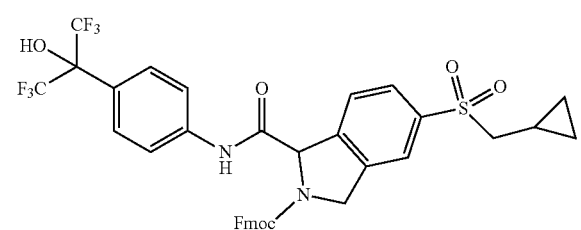

T3P (50% solution in EtOAc, 10.29 mL, 17.28 mmol) was added to a mixture 5-[(cyclopropylmethyl)sulfonyl]-2-[(9H-fluoren-9-yloxy)carbonyl]-2,3-dihydro-1H-isoindole-1-carboxylic acid (4.35 g, 8.64 mmol), 2-(4-aminophenyl)-1,1,1,3,3,3-hexafluoropropan-2-ol (1.791 g, 6.91 mmol) and triethylamine (2.408 mL, 17.28 mmol) in DCM (100 mL). This reaction was stirred at room temperature for 30 min. The reaction mixture was washed with water and the layers separated using a phase separator cartridge. The DCM was removed in vacuo to afford a black tar. This was triturated with methanol and the solid (1.8 g) obtained was collected by filtration and washed with methanol. The mother liquor was concentrated in vacuo and purified on silica eluting with 25-50% EtOAc in heptane. An additional 1.4 g of material was obtained. The two batches were combined and used directly in the next step.

LC/MS: m/z=754 [M+H]$^+$. $^1$H NMR (500 MHz, DMSO-d$_6$, mixture of rotamers, 1:1) δ 0.05-0.2 (m, 2H), 0.4-0.52 (m, 2H), 0.84 (m, 1H), 3.22-3.3 (m, 2H), 4.13-4.4 (m, 3H), 4.83-5.04 (m, 2H), 5.72, 5.81 (s, 1H), 6.92-7 (m, 1H), 7.22-7.48 (m, 3H), 7.56-7.83 (m, 8H), 7.87-7.95 (m, 2H), 8-8.05 (m, 1H), 8.66 (br s, 1H), 10.82, 10.86 (s, 1H).

Intermediate 3: tert-Butyl 1-{[4-(1,1,1,3,3,3-hexafluoro-2-hydroxypropan-2-yl)phenyl]carbamoyl}-5-(methylsulfamoyl)-1,3-dihydro-2H-isoindole-2-carboxylate

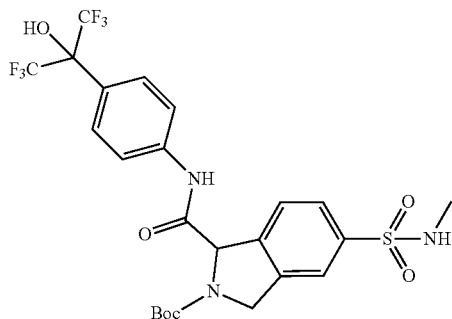 [SMILES: CNS(=O)(=O)c1ccc2c(c1)CN(C(=O)OC(C)(C)C)C2C(=O)Nc1ccc(C(O)(C(F)(F)F)C(F)(F)F)cc1]

Step 1: 5-(Benzylthio)isoindolin-1-one

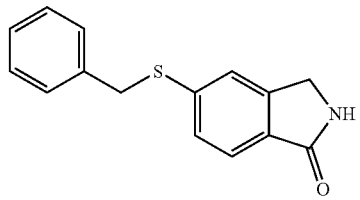 [SMILES: O=C1NCc2cc(SCc3ccccc3)ccc21]

Benzyl mercaptan (11.71 g, 94.32 mmol) was added to 5-bromoisoindolin-1-one (10 g, 47.16 mmol) and sodium 2-methyl-2-butoxide (5.19 g, 47.16 mmol) in DMF (100 mL) under nitrogen. The resulting mixture was stirred at 100° C. for 2 hours. The reaction mixture was quenched with water (300 mL) and extracted with EtOAc (3×300 mL). The organic layer was dried over Na$_2$SO$_4$, filtered and evaporated to dryness to afford 5-(benzylthio)isoindolin-1-one (7.00 g, 58.1%) as a yellow solid.

LC/MS: m/z=256 [M+H]$^+$. $^1$H NMR (300 MHz, DMSO-d$_6$) δ 4.33 (s, 2H), 4.35 (s, 2H), 7.23-7.61 (m, 8H), 8.48 (s, 1H).

Step 2: 1-Oxoisoindoline-5-sulfonyl chloride

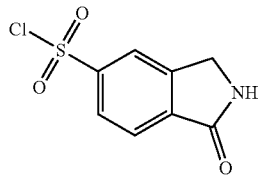 [SMILES: O=C1NCc2cc(S(=O)(=O)Cl)ccc21]

SOCl$_2$ (6.86 mL, 93.99 mmol) was added to 5-(benzylthio)isoindolin-1-one (6 g, 23.50 mmol), AcOH (6.73 mL, 117.49 mmol) and water (1.69 mL, 93.99 mmol) in DCM (80 mL) cooled to 0° C. under nitrogen. The resulting mixture was stirred at room temperature for 2 hours. The reaction mixture was quenched with saturated NaHCO$_3$ (100 mL), extracted with DCM (3×125 mL), the organic layer was dried over Na$_2$SO$_4$, filtered and evaporated to afford 1-oxoisoindoline-5-sulfonyl chloride (5.00 g, crude) as a yellow solid. The product was used directly in the next step without further purification.

LC/MS: m/z=232 [M+H]$^+$.

Step 3: N-Methyl-1-oxoisoindoline-5-sulfonamide

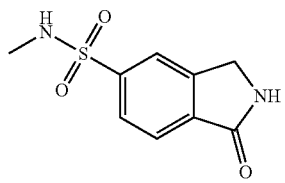

Methanamine (4.02 g, 129.50 mmol) was added to 1-oxoisoindoline-5-sulfonyl chloride (10 g, 43.17 mmol) in DCM (200 mL) under nitrogen. The resulting mixture was stirred at room temperature for 2 hours. The reaction mixture was quenched with water (100 mL), extracted with DCM (3×250 mL), the organic layer was dried over Na$_2$SO$_4$, filtered and evaporated to afford N-methyl-1-oxoisoindoline-5-sulfonamide (8.0 g, 82%) as an orange solid. The product was used in the next step directly without further purification.

LC/MS: m/z=227 [M+H]+.

Step 4: tert-Butyl 5-(N-(tert-butoxycarbonyl)-N-methylsulfamoyl)-1-oxoisoindoline-2-carboxylate

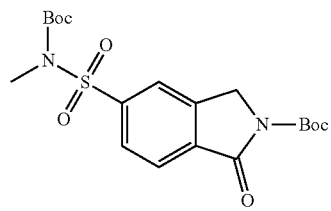 [SMILES: CN(C(=O)OC(C)(C)C)S(=O)(=O)c1ccc2c(c1)CN(C(=O)OC(C)(C)C)C2=O]

Di-tert-butyl dicarbonate (10.80 g, 49.50 mmol) was added to N-methyl-1-oxoisoindoline-5-sulfonamide (8 g, 35.36 mmol) and DMAP (6.05 g, 49.50 mmol) in MeCN (200 mL) under nitrogen. The resulting mixture was stirred at room temperature for 2 hours. The reaction mixture was quenched with water (100 mL), extracted with EtOAc (3×150 mL), the organic layer was dried over $Na_2SO_4$, filtered and evaporated to afford tert-butyl 5-(N-(tert-butoxycarbonyl)-N-methylsulfamoyl)-1-oxoisoindoline-2-carboxylate (7.00 g, 46.4%) as a pale yellow oil.

LC/MS: m/z=490 [M+Na+MeCN]$^+$. $^1$H NMR (400 MHz, $CDCl_3$) δ 1.38 (s, 9H), 1.65 (s, 9H), 3.42 (s, 3H), 4.87 (s, 2H), 8.01-8.09 (m, 3H).

Step 5: tert-Butyl 5-(N-(tert-butoxycarbonyl)-N-methylsulfamoyl)-1-hydroxyisoindoline-2-carboxylate

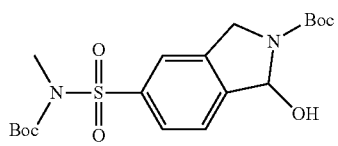

Lithium triethylborohydride (3.97 g, 37.52 mmol) was added to tert-butyl 5-(N-(tert-butoxycarbonyl)-N-methylsulfamoyl)-1-oxoisoindoline-2-carboxylate (8 g, 18.76 mmol) in DCM (200 mL) cooled to 0° C. under nitrogen. The resulting mixture was stirred at 0° C. for 30 minutes. Another part of lithium triethylborohydride (1.987 g, 18.76 mmol) was added. The resulting mixture was stirred at 0° C. for more 30 minutes. The reaction mixture was quenched with saturated Rochelle's salt (100 mL), extracted with EtOAc (3×100 mL), the organic layer was dried over $Na_2SO_4$, filtered and evaporated to afford tert-butyl 5-(N-(tert-butoxycarbonyl)-N-methylsulfamoyl)-1-hydroxyisoindoline-2-carboxylate (8.0 g) as a pale yellow oil.

LC/MS: m/z=411 [M-OH]$^+$.

Step 6: tert-Butyl 5-(N-(tert-butoxycarbonyl)-N-methylsulfamoyl)-1-methoxyisoindoline-2-carboxylate

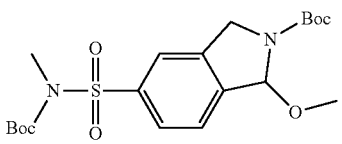

PPTs (0.47 g, 1.87 mmol) was added to tert-butyl 5-(N-(tert-butoxycarbonyl)-N-methylsulfamoyl)-1-hydroxyisoindoline-2-carboxylate (8 g, 18.67 mmol) in MeOH (150 mL) under nitrogen. The resulting mixture was stirred at room temperature for 2 hours. The reaction was quenched by addition of $Et_3N$ (41.6 mL, 298.72 mmol) and concentrated in vacuo to afford tert-butyl 5-(N-(tert-butoxycarbonyl)-N-methylsulfamoyl)-1-methoxyisoindoline-2-carboxylate (8.00 g) as a purple oil.

LC/MS: m/z=411 [M-MeO]$^+$.

Step 7: tert-Butyl 5-(N-(tert-butoxycarbonyl)-N-methylsulfamoyl)-1-cyanoisoindoline-2-carboxylate

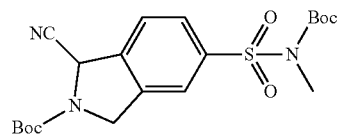

tert-Butyl 5-(N-(tert-butoxycarbonyl)-N-methylsulfamoyl)-1-methoxyisoindoline-2-carboxylate (1.20 g, 2.71 mmol) in DCM (20 mL) cooled to −78° C. over a period of 5 minutes under nitrogen. Trimethylsilanecarbonitrile (0.40 g, 4.07 mmol) and $BF_3.Et_2O$ (0.51 mL, 4.07 mmol) was added to. The resulting mixture was stirred at −78° C. for 30 minutes. The reaction mixture was quenched with saturated $NaHCO_3$ (150 mL), extracted with DCM (3×150 mL), the organic layer was dried over $Na_2SO_4$, filtered and evaporated to afford yellow oil. The crude product was purified by flash silica chromatography, elution gradient 20 to 40% EtOAc in petroleum ether. Pure fractions were evaporated to dryness to afford tert-butyl 5-(N-(tert-butoxycarbonyl)-N-methylsulfamoyl)-1-cyanoisoindoline-2-carboxylate (0.80 g, 67.4%) as a yellow solid.

LC/MS: m/z=455 [M+H+$NH_3$]+. $^1$H NMR (400 MHz, $CDCl_3$, mixture of rotamers, 1.6*:1) δ 1.41 (s, 9H), 1.57, 1.61*(s, 9H), 3.39 (3H, s), 4.79, 4.83*(s, 2H), 5.80*, 5.85 (s, 1H), 7.61-7.66*, 7.66-7.70 (m, 1H), 7.89-8.01 (m, 2H).

Step 8: 5-(N-Methylsulfamoyl)isoindoline-1-carboxylic acid

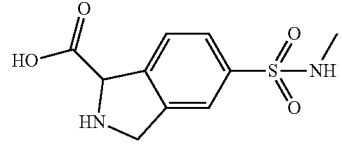 [SMILES: CNS(=O)(=O)c1ccc2c(c1)CNC2C(=O)O]

tert-Butyl 5-(N-(tert-butoxycarbonyl)-N-methylsulfamoyl)-1-cyanoisoindoline-2-carboxylate (7 g, 16.00 mmol) was added to HCl (6 M) (140 mL, 840.00 mmol) under nitrogen. The resulting mixture was stirred at 70° C. for 2 hours. The solvent was removed under reduced pressure to afford 5-(N-methylsulfamoyl)isoindoline-1-carboxylic acid (4.0 g) as a black solid.

LC/MS: m/z=257 [M+H]$^+$.

Step 9: 2-(tert-Butoxycarbonyl)-5-(N-methylsulfamoyl)isoindoline-1-carboxylic acid

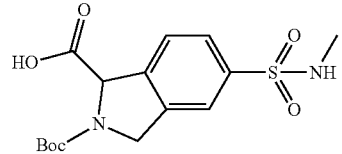 [SMILES: CNS(=O)(=O)c1ccc2c(c1)CN(C(=O)OC(C)(C)C)C2C(=O)O]

Di-tert-butyl dicarbonate (5.13 g, 23.50 mmol) was added to 5-(N-methylsulfamoyl)isoindoline-1-carboxamide (4 g, 15.67 mmol) and Et₃N (3.28 mL, 23.50 mmol) in DCM (50 mL) under nitrogen. The resulting mixture was stirred at room temperature for 2 hours. The reaction mixture was quenched with 0.1M HCl (100 mL), extracted with DCM (2×100 mL), the organic layer was dried over Na₂SO₄, filtered and evaporated to afford dark solid. The crude product was purified by flash silica chromatography, elution gradient 5 to 10% MeOH in DCM. Pure fractions were evaporated to dryness to afford 2-(tert-butoxycarbonyl)-5-(N-methylsulfamoyl)isoindoline-1-carboxylic acid (3.0 g, 53.7%) as a black solid.

LC/MS: m/z=301 [M+H-tBu]⁺. ¹H NMR (300 MHz, DMSO-d₆, mixture of rotamers, 1.5*:1) δ 1.41*, 1.46 (s, 9H), 2.42 (d, 3H), 4.67-4.78 (m, 2H), 5.42 (s, 1H), 7.48-7.60 (m, 2H), 7.73-7.82 (m, 2H), 13.20 (brs, 1H).

Step 10: tert-Butyl 1-{[4-(1,1,1,3,3,3-hexafluoro-2-hydroxypropan-2-yl)phenyl]carbamoyl}-5-(methylsulfamoyl)-1,3-dihydro-2H-isoindole-2-carboxylate

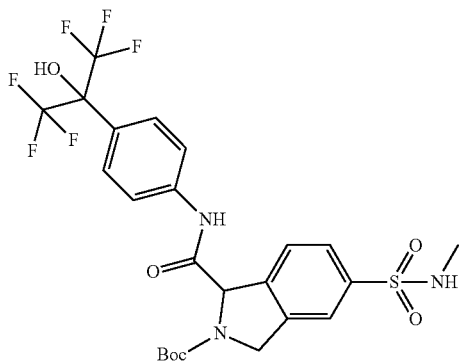 [SMILES: CNS(=O)(=O)c1ccc2c(c1)CN(C(=O)OC(C)(C)C)C2C(=O)Nc1ccc(C(O)(C(F)(F)F)C(F)(F)F)cc1]

2-(4-Aminophenyl)-1,1,1,3,3,3-hexafluoropropan-2-ol (2.84 g, 10.94 mmol) was added to a mixture of 2-(tert-butoxycarbonyl)-5-(N-methylsulfamoyl)isoindoline-1-carboxylic acid (3 g, 8.42 mmol), HATU (4.16 g, 10.94 mmol) and DIPEA (2.94 mL, 16.84 mmol) in DCM (50 mL) under nitrogen. The resulting mixture was stirred at room temperature for 2 hours. The reaction mixture was quenched with saturated NH₄Cl (75 mL), extracted with DCM (3×75 mL), the organic layer was dried over Na₂SO₄, filtered and evaporated to afford orange solid. The crude product was purified by flash silica chromatography, elution gradient 30 to 50% EtOAc in petroleum ether. Pure fractions were evaporated to dryness to afford tert-butyl 1-((4-(1,1,1,3,3,3-hexafluoro-2-hydroxypropan-2-yl)phenyl)carbamoyl)-5-(N-methylsulfamoyl)isoindoline-2-carboxylate (3.00 g, 59.6%) as a yellow solid.

LC/MS: m/z=598 [M+H]⁺. ¹H NMR (300 MHz, DMSO-d₆, mixture of rotamers, 1.8*:1) δ 1.36*, 1.48 (s, 9H), 2.43 (d, 3H), 4.63-4.87 (m, 2H), 5.60-5.77 (m, 1H), 7.49-7.85 (m, 8H), 8.66*, 8.67 (s, 1H), 10.75 (s, 1H).

Intermediate 4: 9H-Fluoren-9-yl 1-{[4-(1,1,1,3,3,3-hexafluoro-2-hydroxypropan-2-yl)phenyl]carbamoyl}-5-(methylsulfonyl)-1,3-dihydro-2H-isoindole-2-carboxylate

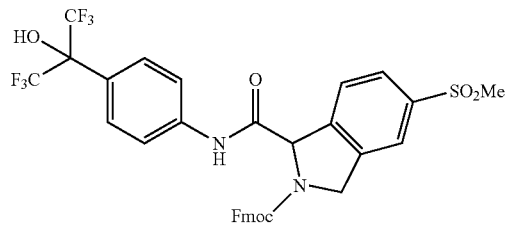

Step 1: 5-(Methylthio)isoindolin-1-one

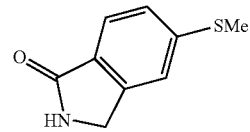 [SMILES: CSc1ccc2c(c1)CNC2=O]

5-Bromoisoindolin-1-one (15 g, 70.74 mmol) and sodium methyl mercaptide (12.40 g, 176.85 mmol) were mixed together in DMF (150 mL) and heated to 100° C. for 1 h. The reaction mixture was cooled to room temperature and poured into water (160 mL). The product extracted with EtOAc (400 mL). The layers were then separated and the aqueous was extracted with EtOAc (3×200 mL). The combined organic extracts were washed with brine (3×100 mL). The organic extracts were combined, dried using a phase separator cartridge and concentrated in vacuo. 5-(Methylthio)isoindolin-1-one (12.00 g, 95%) was obtained as a yellow solid. The material was used in the next step without further purification.

LC/MS: m/z=180 [M–H]⁻. ¹H NMR (500 MHz, DMSO-d₆) δ 2.54 (s, 3H), 4.33 (s, 2H), 7.33 (d, 1H), 7.44 (s, 1H), 7.56 (d, 1H), 8.43 (s, 1H).

Step 2: tert-Butyl 5-(methylthio)-1-oxoisoindoline-2-carboxylate

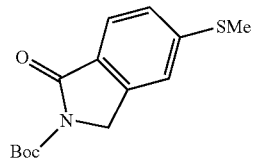 [SMILES: CSc1ccc2c(c1)CN(C(=O)OC(C)(C)C)C2=O]

5-(Methylthio)isoindolin-1-one (12.68 g, 70.74 mmol) was suspended in acetonitrile (500 mL) and DMAP (12.10 g, 99.04 mmol) was added in one portion. Boc-anhydride (21.61 g, 99.04 mmol) was then added and the reaction stirred for 20 min at room temperature. The acetonitrile was removed in vacuo. The residue was dissolved in EtOAc and washed with 0.5M aq HCl (3×200 ml). The organic extract was dried using a phase separator cartridge and concentrated in vacuo. tert-Butyl 5-(methylthio)-1-oxoisoindoline-2-carboxylate (15.60 g, 79%) was obtained as a brown oil that solidified on standing. The material was used in the next step without further purification.

¹H NMR (500 MHz, DMSO-d₆) δ 1.51 (s, 9H), 2.55 (s, 3H), 4.74 (s, 2H), 7.37 (d, 1H), 7.49 (s, 1H), 7.64 (d, 1H).

Step 3: tert-Butyl 5-(methylsulfonyl)-1-oxoisoindoline-2-carboxylate

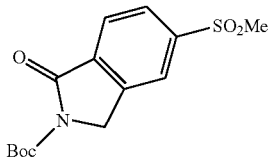 [SMILES: CC(C)(C)OC(=O)N1Cc2cc(S(C)(=O)=O)ccc2C1=O]

tert-Butyl 5-(methylthio)-1-oxoisoindoline-2-carboxylate (15.58 g, 55.77 mmol) was dissolved in DCM (500 mL) and to this mCPBA (≥77%) (30.0 g, 133.85 mmol) was added portionwise (an exotherm to ca. 38° C. was observed). The reaction was stirred at room temperature for 20 min. The reaction was washed twice with 1M aq NaOH. The organic layer was dried using a phase separator cartridge and concentrated in vacuo to afford tert-butyl 5-(methylsulfonyl)-1-oxoisoindoline-2-carboxylate (15.56 g, 90%) as a yellow solid.

The material was used in the next step without further purification.

LC/MS: m/z=310 [M−H]⁻. ¹H NMR (500 MHz, DMSO-d₆) δ 1.53 (s, 9H), 3.31 (s, 3H), 4.88 (s, 2H), 8.00 (d, 1H), 8.08 (d, 1H), 8.25 (s, 1H).

Step 4: tert-Butyl 1-hydroxy-5-(methylsulfonyl) isoindoline-2-carboxylate

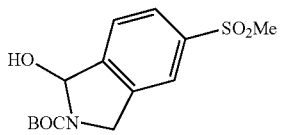

tert-Butyl 5-(methylsulfonyl)-1-oxoisoindoline-2-carboxylate (15.56 g, 49.98 mmol) was dissolved in DCM (375 mL), cooled in an ice bath and kept under a nitrogen atmosphere. DIBAL-H (85 mL, 84.96 mmol) 1M solution in THF was added gradually over 10 min. The reaction was stirred at this temperature for 15 min. Sat. aq Rochelle's salt (100 ml) was added and the resultant mixture was stirred for 20 min whilst warming to room temperature. DCM (200 mL) was added and the layers separated. The aqueous layer was extracted with DCM. The combined organic extracts were dried using a phase separator cartridge and concentrated in vacuo. The product was obtained as a pink-brown gum/foam which was used crude in the next step.

LC/MS: m/z=312 [M−H]⁻.

Step 5: tert-Butyl 1-methoxy-5-(methylsulfonyl) isoindoline-2-carboxylate

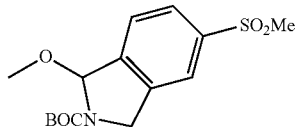

tert-Butyl 1-hydroxy-5-(methylsulfonyl)isoindoline-2-carboxylate (15.66 g, 49.98 mmol) was dissolved in MeOH (300 mL) and to this PPTs (1.256 g, 5.00 mmol) was added and the reaction stirred at room temperature. After 20 min LCMS indicated that no starting material remained and one product had formed but the desired mass ion was not seen. The reaction was quenched by addition of triethylamine (111 mL, 799.68 mmol) and concentrated in vacuo to afford a dark purple oil. This was used crude in the next step.

Step 6: tert-Butyl 1-cyano-5-(methylsulfonyl)isoindoline-2-carboxylate

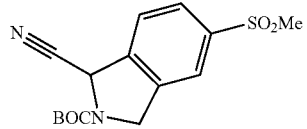

tert-Butyl 1-methoxy-5-(methylsulfonyl)isoindoline-2-carboxylate (16.36 g, 49.98 mmol) was dissolved in DCM (375 mL). This was cooled to −78° C. before TMS-CN (10.05 mL, 74.97 mmol) and BF₃.OEt₂ (9.50 mL, 74.97 mmol) was added. The reaction was stirred at −78° C. for 15 min. Sat aq NaHCO₃ and DCM was added and the reaction allowed to warm to room temperature. The two layers were separated and the aqueous extracted with DCM. The combined organic extracts were dried using a phase separator cartridge and concentrated in vacuo. The material was purified by flash chromatography eluting with 40-50% EtOAc in heptane. tert-Butyl 1-cyano-5-(methylsulfonyl) isoindoline-2-carboxylate (10.6 g, 65.8%) was obtained as a slightly pink solid.

LC/MS: m/z=321 [M−H]⁻. ¹H NMR (500 MHz, DMSO-d₆, mixture of rotamers, 1:1) δ 1.50, 1.51 (s, 9H), 3.24, 3.25 (s, 3H), 4.74, 4.76 (s, 2H), 6.17, 6.19 (s, 1H), 7.83 (d, 1H), 7.96-8.05 (m, 2H).

Step 7: 5-(Methylsulfonyl)isoindoline-1-carboxylic acid, hydrochloride salt

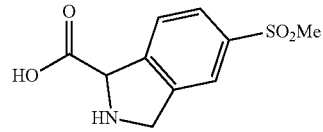 [SMILES: CS(=O)(=O)c1ccc2c(c1)CNC2C(=O)O]

6M aq HCl (110 mL, 660.00 mmol) was added to tert-butyl 1-cyano-5-(methylsulfonyl)isoindoline-2-carboxylate (10.6 g, 32.88 mmol) and the mixture was heated at 70° C. for 2.5 h. The reaction was cooled to room temperature and concentrated to dryness to afford a dark solid, which was used in the next step without further purification.

LC/MS: m/z=240 [M−H]⁻.

Step 8: 2-[(9H-Fluoren-9-yloxy)carbonyl]-5-(methylsulfonyl)-2,3-dihydro-1H-isoindole-1-carboxylic acid

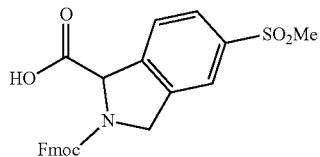

To 5-(methylsulfonyl)isoindoline-1-carboxylic acid, HCl (9.13 g, 32.88 mmol) in dioxane (230 mL)/water (230 mL) was added potassium carbonate (22.72 g, 164.40 mmol) and 9-fluorenylmethyl chloroformate (7.66 g, 29.59 mmol). The reaction was stirred at room temperature overnight. The dioxane was removed in vacuo. The aqueous was then acidified with 1M aq HCl and extracted with EtOAc. These organic extracts were combined, dried using a phase separator and concentrated in vacuo. The material was used crude in the next step.

LC/MS: m/z=462 [M−H]⁻.

Step 9: 9H-Fluoren-9-yl 1-{[4-(1,1,1,3,3,3-hexafluoro-2-hydroxypropan-2-yl)phenyl]carbamoyl}-5-(methylsulfonyl)-1,3-dihydro-2H-isoindole-2-carboxylate

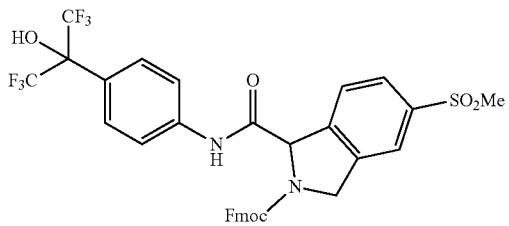

T3P (50% solution in EtOAc, 37.7 mL, 63.40 mmol) was added to a mixture of 2-[(9H-fluoren-9-yloxy)carbonyl]-5-(methylsulfonyl)-2,3-dihydro-1H-isoindole-1-carboxylic acid (14.69 g, 31.7 mmol), 2-(4-aminophenyl)-1,1,1,3,3,3-hexafluoropropan-2-ol (6.57 g, 25.36 mmol) and triethylamine (8.84 mL, 63.40 mmol) in DCM (300 mL). This was stirred at room temperature for 30 min. The reaction mixture was washed with water and the layers separated using a phase separator cartridge. The DCM was removed in vacuo to afford a black tar. The first attempt to purify by flash chromatography was unsuccessful because the main impurity crystallised and blocked the column. The column had to be flushed with 1:1 EtOAc:methanol to unblock it. The product containing solution obtained was concentrated in vacuo. This was then purified by flash chromatography eluting with 30%-50% EtOAc in heptane to afford (9H-fluoren-9-yl)methyl 1-((4-(1,1,1,3,3,3-hexafluoro-2-hydroxypropan-2-yl)phenyl)carbamoyl)-5-(methylsulfonyl)isoindoline-2-carboxylate (10.64 g, 47.6%).

LC/MS: m/z=705 [M+H]⁺. ¹H NMR (500 MHz, DMSO-d₆, mixture of rotamers, 1:1) δ 3.22, 3.23 (s, 3H), 4.14-4.39 (m, 3H), 4.88-5.03 (m, 2H), 5.72, 5.81 (s, 1H), 6.93-6.99 (m, 1H), 7.21-7.48 (m, 3H), 7.56-7.83 (m, 8H), 7.9-7.95 (m, 2H), 8.03-8.09 (m, 1H), 8.64, 8.66 (s, 1H), 10.82, 10.87 (s, 1H).

Intermediate 5: tert-Butyl 1-{[4-(1,1,1,3,3,3-hexafluoro-2-hydroxypropan-2-yl)phenyl]carbamoyl}-5-(methylsulfonyl)-1,3-dihydro-2H-isoindole-2-carboxylate

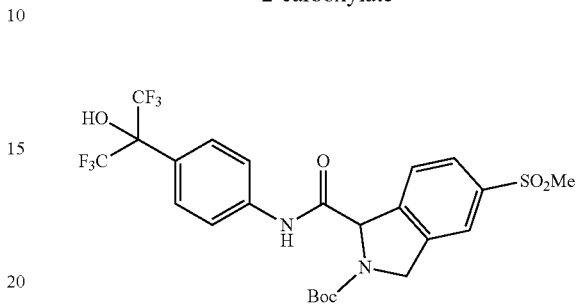

Step 1: 5-(Methylsulfonyl)isoindoline-1-carboxylic acid, hydrochloride salt

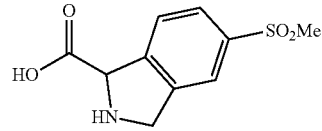 [SMILES: CS(=O)(=O)c1ccc2c(c1)CNC2C(=O)O]

6M aq HCl (110 mL, 660.00 mmol) was added to tert-butyl 1-cyano-5-(methylsulfonyl)isoindoline-2-carboxylate (10.6 g, 32.88 mmol) with stirring, and the mixture was heated at 70° C. for 3 h. The reaction was concentrated to 13.3 g of a sticky black solid, which was used as such in the next step.

¹H NMR (400 MHz, DMSO-d₆) δ 3.25 (s, 3H), 4.61 (q, 1H), 4.69 (q, 1H), 5.75 (s, 1H), 7.81 (d, 1H), 7.99 (d, 1H), 8.04 (s, 1H).

Step 2: 2-(tert-Butoxycarbonyl)-5-(methylsulfonyl)isoindoline-1-carboxylic acid

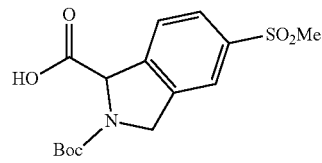 [SMILES: CC(C)(C)OC(=O)N1Cc2cc(S(C)(=O)=O)ccc2C1C(=O)O]

The hydrochloride salt of 5-(methylsulfonyl)isoindoline-1-carboxylic acid (7.78 g, 28 mmol) was dissolved in water (130 mL) and 1,4-dioxane (200 mL) and 2M aq potassium carbonate (70.0 mL, 140.00 mmol) was added. Di-tert-butyl dicarbonate (6.11 g, 28.00 mmol) was added in one portion, and the solution was stirred at room temperature overnight. The dioxane was removed in vacuo and DCM (100 mL) was added. A black precipitate formed in the aqueous which was removed by filtration. The aqueous solution was washed a second time with DCM and the organic washes discarded.

The aqueous solution was then chilled with stirring on an ice water bath before adding EtOAc (100 mL). The pH was gradually adjusted to 2 by the slow addition of chilled 3.8M aq HCl; the biphasic mixture was stirred for a few minutes before the EtOAc phase was separated. The aqueous solution was washed with EtOAc (2×100 mL). The combined EtOAc extracts were washed with water (1×100 mL) and brine (50 mL) before drying over MgSO₄. This was filtered and concentrated in vacuo to afford 2-(tert-butoxycarbonyl)-5-(methylsulfonyl)isoindoline-1-carboxylic acid (4.55 g, 47.5%) as solid.

LC/MS: m/z=681 [2M−H]⁻. ¹H NMR (400 MHz, DMSO-d₆, mixture of rotamers, 1.6*:1) δ 1.41*, 1.46 (s, 9H), 3.21, 3.22* (s, 3H), 4.68-4.8 (m, 2H), 5.44 (s, 1H), 7.60*, 7.63 (d, 1H), 7.87-7.92 (m, 1H), 7.95, 7.98* (s, 1H).

Step 3: tert-Buyl 1-{[4-(1,1,1,3,3,3-hexafluoro-2-hydroxypropan-2-yl)phenyl]carbamoyl}-5-(methylsulfonyl)-1,3-dihydro-2H-isoindole-2-carboxylate

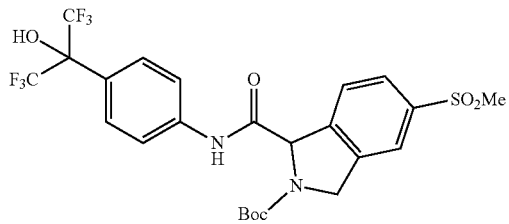 [SMILES: CC(C)(C)OC(=O)N1Cc2cc(S(C)(=O)=O)ccc2C1C(=O)Nc1ccc(C(O)(C(F)(F)F)C(F)(F)F)cc1]

2-(tert-Butoxycarbonyl)-5-(methylsulfonyl)isoindoline-1-carboxylic acid (4.40 g, 12.89 mmol) and 2-(4-aminophenyl)-1,1,1,3,3,3-hexafluoropropan-2-ol (3.34 g, 12.89 mmol) were combined in ethyl acetate (50 mL) to give a suspension, before the addition of triethylamine (5.39 mL, 38.67 mmol) gave a dark brown solution. The solution was chilled by stirring on an ice/water bath before the addition of T3P (50% in EtOA, 15.35 mL, 25.78 mmol) by dropping funnel. The addition was controlled to ensure temperature did not exceed 5° C. After one hour the reaction solution was washed with water (2×50 mL). The combined water washes were extracted with EtOAc (50 mL). The combined organic extracts were washed with 0.1M aq HCl (2×50 mL) and brine (25 mL) before drying over MgSO₄. This was filtered and concentrated in vacuo. The residue was purified by flash chromatography eluting with 0-60% EtOAc in n-heptane to give the title compound (4.95 g, 66%) as a solid.

LC/MS: m/z=581 [M−H]⁻. ¹H NMR (400 MHz, DMSO-d₆, mixture of rotamers, 1.8*:1) δ 1.35*, 1.47 (s, 9H), 3.20, 3.21* (s, 3H), 4.69-4.88 (m, 2H), 5.61*, 5.63 (s, 1H), 7.6-7.76 (m, 5H), 7.86-7.92 (m, 1H), 7.98, 8.01* (s, 1H), 8.63*, 8.65 (s, 1H), 10.75 (s, 1H).

Intermediate 6: 2-Acetyl-5-(cyclopropylsulfamoyl)-2,3-dihydro-1H-isoindole-1-carboxylic acid

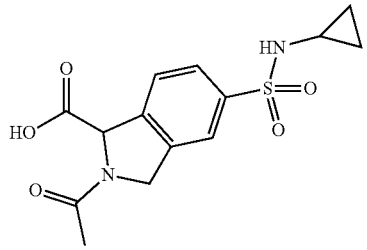 [SMILES: CC(=O)N1Cc2cc(S(=O)(=O)NC3CC3)ccc2C1C(=O)O]

Step 1:
N-Cyclopropyl-1-oxoisoindoline-5-sulfonamide

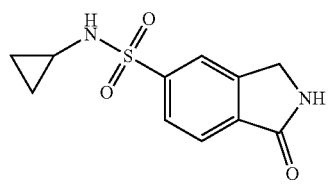 [SMILES: O=C1NCc2cc(S(=O)(=O)NC3CC3)ccc21]

Cyclopropanamine (1.848 g, 32.38 mmol) was added to 1-oxoisoindoline-5-sulfonyl chloride (2.5 g, 10.79 mmol, prepared as described for intermediate 3, step 1 and 2) in DCM (30 mL) under nitrogen. The resulting mixture was stirred at room temperature for 2 hours. The reaction mixture was quenched with water (125 mL), extracted with DCM (3×100 mL), the organic layer was dried over Na₂SO₄, filtered and evaporated to afford N-cyclopropyl-1-oxoisoindoline-5-sulfonamide (1.60 g, 58.8%) as a yellow solid. The product was used in the next step directly without further purification.

LC/MS: m/z=253 [M+H]⁺

Step 2: tert-Butyl 5-(N-(tert-butoxycarbonyl)-N-cyclopropylsulfamoyl)-1-oxoisoindoline-2-carboxylate

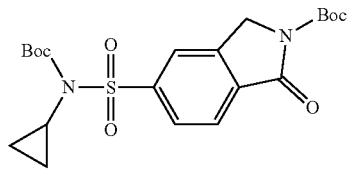 [SMILES: CC(C)(C)OC(=O)N1Cc2cc(S(=O)(=O)N(C(=O)OC(C)(C)C)C3CC3)ccc2C1=O]

Di-tert-butyl dicarbonate (1.938 g, 8.88 mmol) was added to N-cyclopropyl-1-oxoisoindoline-5-sulfonamide (1.6 g, 6.34 mmol) and DMAP (1.085 g, 8.88 mmol) in MeCN (20 mL) under nitrogen. The resulting mixture was stirred at room temperature for 2 hours. The reaction mixture was quenched with water (100 mL), extracted with EtOAc (3×75 mL), the organic layer was dried over Na₂SO₄, filtered and evaporated to afford yellow solid. The crude product was purified by flash silica chromatography, elution gradient 30 to 40% EtOAc in petroleum ether. Pure fractions were evaporated to dryness to afford tert-butyl 5-(N-(tert-butoxycarbonyl)-N-cyclopropylsulfamoyl)-1-oxoisoindoline-2-carboxylate (1.10 g, 38.3%) as a pale yellow oil.

LC/MS: m/z=397 [M+H-tBu]$^+$. $^1$H NMR (300 MHz, DMSO-d$_6$) δ 0.88-0.92 (m, 2H), 1.11-1.14 (m, 2H), 1.39 (s, 9H), 1.61 (s, 9H), 2.82-2.87 (m, 1H), 4.87 (s, 2H), 8.05-8.06 (m, 2H), 8.13 (s, 1H).

Step 3: tert-Butyl 5-(N-(tert-butoxycarbonyl)-N-cyclopropylsulfamoyl)-1-hydroxyisoindoline-2-carboxylate

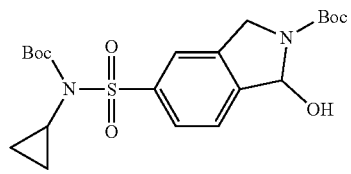

DIBAL-H (1M in THF) (4.42 mL, 4.42 mmol) was added to tert-butyl 5-(N-(tert-butoxycarbonyl)-N-cyclopropylsulfamoyl)-1-oxoisoindoline-2-carboxylate (1 g, 2.21 mmol) in DCM (25 mL) cooled to 0° C. under nitrogen. The resulting mixture was stirred at 0° C. for 1 hour. The reaction mixture was quenched with saturated aq. Rochelle's salt (25 mL), extracted with EtOAc (3×100 mL), the organic layer was dried over Na$_2$SO$_4$, filtered and evaporated to afford tert-butyl 5-(N-(tert-butoxycarbonyl)-N-cyclopropylsulfamoyl)-1-hydroxyisoindoline-2-carboxylate (0.92 g, 92%) as a pale yellow oil. The crude product was used in the next step directly without further purification.

LC/MS: m/z=437 [M-OH]$^+$.

Step 4: tert-Butyl 5-(N-(tert-butoxycarbonyl)-N-cyclopropylsulfamoyl)-1-methoxyisoindoline-2-carboxylate

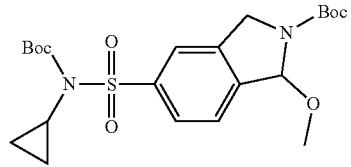 [SMILES: COC1c2ccc(S(=O)(=O)N(C(=O)OC(C)(C)C)C3CC3)cc2CN1C(=O)OC(C)(C)C]

PPTs (50.9 mg, 0.20 mmol) was added to tert-butyl 5-(N-(tert-butoxycarbonyl)-N-cyclopropylsulfamoyl)-1-hydroxyisoindoline-2-carboxylate (920 mg, 2.02 mmol) in MeOH (2 mL) under nitrogen. The resulting mixture was stirred at room temperature for 2 hours. The reaction was quenched by addition of Et$_3$N (4.51 mL, 32.38 mmol) and concentrated in vacuo to afford tert-butyl 5-(N-(tert-butoxycarbonyl)-N-cyclopropylsulfamoyl)-1-methoxyisoindoline-2-carboxylate (940 mg, 99%) as a dark purple oil. The crude product was used to the next step directly without further purification.

LC/MS: m/z=437 [M−MeO]$^+$

Step 5: tert-Butyl 5-(N-(tert-butoxycarbonyl)-N-cyclopropylsulfamoyl)-1-cyanoisoindoline-2-carboxylate

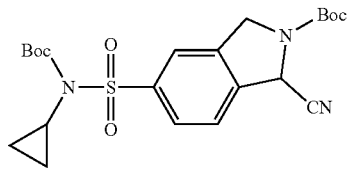 [SMILES: CC(C)(C)OC(=O)N1Cc2cc(S(=O)(=O)N(C(=O)OC(C)(C)C)C3CC3)ccc2C1C#N]

BF$_3$.Et$_2$O (0.38 mL, 3.01 mmol) was added to tert-butyl 5-(N-(tert-butoxycarbonyl)-N-cyclopropylsulfamoyl)-1-methoxyisoindoline-2-carboxylate (940 mg, 2.01 mmol) and trimethylsilanecarbonitrile (299 mg, 3.01 mmol) in DCM (25 mL) cooled to −78° C. under nitrogen. The resulting mixture was stirred at −78° C. for 30 minutes. The reaction mixture was quenched with saturated NaHCO$_3$ (25 mL), extracted with DCM (3×25 mL), the organic layer was dried over Na$_2$SO$_4$, filtered and evaporated to afford dark oil. The crude product was purified by flash silica chromatography, elution gradient 0 to 60% EtOAc in petroleum ether. Pure fractions were evaporated to dryness to afford tert-butyl 5-(N-(tert-butoxycarbonyl)-N-cyclopropylsulfamoyl)-1-cyanoisoindoline-2-carboxylate (240 mg, 25.8%) as a solid.

LC/MS: m/z=464 [M+H]$^+$. $^1$H NMR (300 MHz, CDCl$_3$) δ 0.82-0.85 (m, 2H), 1.03-1.10 (m, 2H), 1.40 (s, 9H), 1.56 (d, 9H), 2.77-2.82 (m, 1H), 4.77-4.80 (m, 2H), 5.80 (d, 1H), 7.59-7.66 (m, 1H), 7.93-7.99 (m, 2H).

Step 6: 5-(N-cyclopropylsulfamoyl)isoindoline-1-carboxylic acid

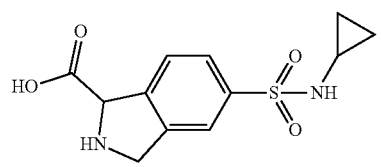 [SMILES: O=C(O)C1NCc2cc(S(=O)(=O)NC3CC3)ccc21]

tert-Butyl 5-(N-(tert-butoxycarbonyl)-N-cyclopropylsulfamoyl)-1-cyanoisoindoline-2-carboxylate (240 mg, 0.52 mmol) was added to 6M aq HCl (2.4 mL, 14.40 mmol). The resulting mixture was stirred at 70° C. for 2 hours. The reaction mixture was concentrated under reduced pressure to afford 5-(N-cyclopropylsulfamoyl)isoindoline-1-carboxylic acid (110 mg, 75%) as solid, which was used without further purification.

LC/MS: m/z=283 [M+H]$^+$.

Step 7: 2-Acetyl-5-(cyclopropylsulfamoyl)-2,3-dihydro-1H-isoindole-1-carboxylic acid

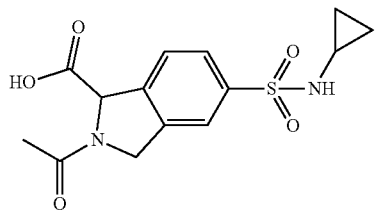 [SMILES: CC(=O)N1Cc2cc(S(=O)(=O)NC3CC3)ccc2C1C(=O)O]

Acetic anhydride (39.8 mg, 0.39 mmol) was added to 5-(N-cyclopropylsulfamoyl)-isoindoline-1-carboxylic acid (110 mg, 0.39 mmol) and Et$_3$N (0.217 mL, 1.56 mmol) in DCM (2 mL) under nitrogen. The resulting solution was stirred at room temperature for 2 hours. The reaction mixture was concentrated under vacuum to afford the crude 2-acetyl-5-(cyclopropylsulfamoyl)-2,3-dihydro-1H-isoindole-1-carboxylic acid (110 mg, 87%), which was used without further purification.

LC/MS: m/z=325 [M+H]$^+$.

Intermediate 7: Tert-Butyl 5-(Cyclopropylsulfonyl)-1-{[4-(1,1,1,3,3,3-Hexafluoro-2-Hydroxypropan-2-Yl)Phenyl]Carbamoyl}-1,3-Dihydro-2H-Isoindole-2-Carboxylate

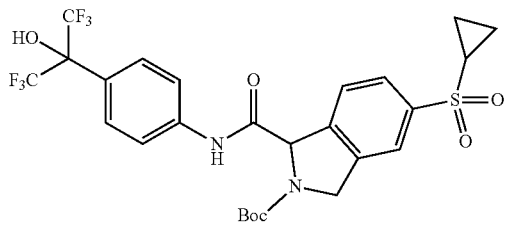 [SMILES: CC(C)(C)OC(=O)N1Cc2cc(S(=O)(=O)C3CC3)ccc2C1C(=O)Nc1ccc(C(O)(C(F)(F)F)C(F)(F)F)cc1]

Step 1: 5-mercaptoisoindolin-1-one

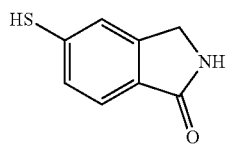 [SMILES: O=C1NCc2cc(S)ccc21]

Sodium 2-methylbutan-2-olate (31.2 g, 282.96 mmol) was added to 5-bromoisoindolin-1-one (30 g, 141.48 mmol) and phenylmethanethiol (35.1 g, 282.96 mmol) in DMF (300 mL) under nitrogen. The resulting mixture was stirred at 100° C. for 12 hours. The reaction mixture was quenched with water (300 mL), extracted with EtOAc (3×300 mL), the organic layer was dried over Na$_2$SO$_4$, filtered and evaporated to afford 5-(benzylthio)isoindolin-1-one (6.00 g, 16.61%) as a yellow solid. The water layer was acidified with 2M HCl and the mixture was extracted with EtOAc (3×150 mL). The organic layer was dried over Na$_2$SO$_4$, filtered and evaporated to dryness to afford 5-mercaptoisoindolin-1-one (15.00 g, 64.2%) as a solid.

LC/MS: m/z=166 [M+H]$^+$. $^1$H NMR (300 MHz, DMSO-d$_6$) δ 4.32 (s, 2H), 5.88 (s, 1H), 7.37-7.40 (m, 1H), 7.49-7.54 (m, 2H), 8.45 (s, 1H).

Step 2: 5-(Cyclopropylthio)isoindolin-1-one

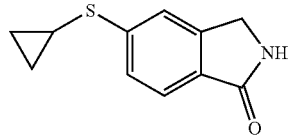 [SMILES: O=C1NCc2cc(SC3CC3)ccc21]

5-Mercaptoisoindolin-1-one (8 g, 48.42 mmol) was added to bromocyclopropane (8.79 g, 72.63 mmol) and NaH (2.32 g, 96.85 mmol) in DMF (100 mL) under nitrogen. The resulting mixture was stirred at 100° C. for 12 hours. The reaction mixture was quenched with water (300 mL), extracted with EtOAc (3×300 mL), the organic layer was dried over Na$_2$SO$_4$, filtered and evaporated to afford yellow solid. The crude product was purified by flash silica chromatography, elution gradient 30 to 50% EtOAc in petroleum ether. Pure fractions were evaporated to dryness to afford 5-(cyclopropylthio)isoindolin-1-one (5.00 g, 50.3%) as a solid.

LC/MS: m/z=206 [M+H]$^+$.

Step 3: 5-(Cyclopropylsulfonyl)isoindolin-1-one

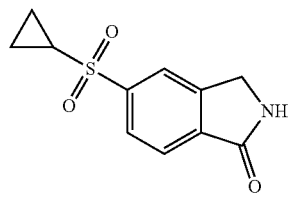 [SMILES: O=C1NCc2cc(S(=O)(=O)C3CC3)ccc21]

mCPBA (10.51 g, 60.89 mmol) was added to 5-(cyclopropylthio)isoindolin-1-one (5 g, 24.36 mmol) in DCM (100 mL) cooled to 0° C. over a period of 5 minutes under nitrogen. The resulting mixture was stirred at room temperature for 2 hours. The reaction mixture was quenched with saturated NaHCO$_3$ (200 mL), extracted with DCM (3×200 mL), the organic layer was dried over Na$_2$SO$_4$, filtered and evaporated to afford 5-(cyclopropylsulfonyl)isoindolin-1-one (6.00 g, crude) as a white solid.

LC/MS: m/z=238 [M+H]$^+$.

Step 4: tert-Butyl 5-(cyclopropylsulfonyl)-1-oxoisoindoline-2-carboxylate

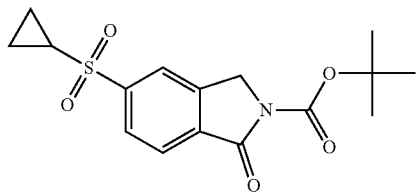 [SMILES: CC(C)(C)OC(=O)N1Cc2cc(S(=O)(=O)C3CC3)ccc2C1=O]

Boc-anhydride (8.81 mL, 37.93 mmol) was added to 5-(cyclopropylsulfonyl)isoindolin-1-one (6 g, 25.29 mmol) and DMAP (4.63 g, 37.93 mmol) in DCM (120 mL) under nitrogen. The resulting solution was stirred at room temperature for 4 hours. The reaction mixture was quenched with saturated NH$_4$Cl (100 mL), extracted with DCM (3×100 mL), the organic layer was dried over Na$_2$SO$_4$, filtered and evaporated to afford yellow solid. The crude product was purified by flash silica chromatography, elution gradient 0 to 50% EtOAc in petroleum ether. Pure fractions were evaporated to dryness to afford tert-butyl 5-(cyclopropylsulfonyl)-1-oxoisoindoline-2-carboxylate (7.10 g, 83%) as a solid.

LC/MS: m/z=401 [M+Na+MeCN]$^+$. $^1$H NMR (400 MHz, CDCl$_3$) δ 1.10-1.13 (m, 2H), 1.39-1.43 (m, 2H), 1.62 (s, 9H), 2.48-2.54 (m, 1H), 4.87 (s, 2H), 8.02-8.10 (m, 3H).

Step 5: tert-Butyl 5-(cyclopropylsulfonyl)-1-hydroxyisoindoline-2-carboxylate

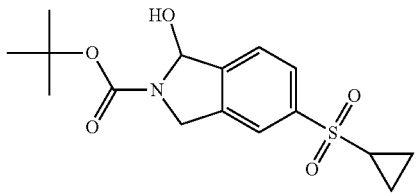

DIBAL-H (42.1 mL, 42.09 mmol) was added dropwise to tert-butyl 5-(cyclopropylsulfonyl)-1-oxoisoindoline-2-carboxylate (7.1 g, 21.04 mmol) in DCM (140 mL) cooled to 0° C. over a period of 10 minutes under nitrogen. The resulting solution was stirred at 0° C. for 1 hour. The reaction mixture was quenched with saturated aq. Rochelle's salt (200 mL), extracted with DCM (3×200 mL), the organic layer was dried over Na$_2$SO$_4$, filtered and evaporated to afford tert-butyl 5-(cyclopropylsulfonyl)-1-hydroxyisoindoline-2-carboxylate (6.80 g).

LC/MS: m/z=266 [M-OH-tBu]$^+$.

Step 6: tert-Butyl 5-(cyclopropylsulfonyl)-1-methoxyisoindoline-2-carboxylate

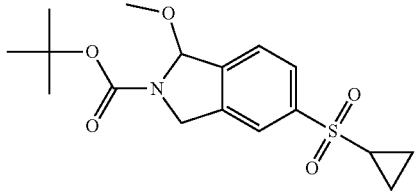 [SMILES: COC1c2ccc(S(=O)(=O)C3CC3)cc2CN1C(=O)OC(C)(C)C]

PPTs (0.067 g, 0.27 mmol) was added to tert-butyl 5-(cyclopropylsulfonyl)-1-hydroxyisoindoline-2-carboxylate (0.9 g, 2.65 mmol) in MeOH (20 mL) under nitrogen. The resulting solution was stirred at room temperature for 1 hour. The reaction mixture was quenched with Et$_3$N (50 mL), The resulting mixture was concentrated under reduced pressure to afford crude tert-butyl 5-(cyclopropylsulfonyl)-1-methoxyisoindoline-2-carboxylate (5.80 g, 83%).

LC/MS: m/z=266 [M-MeO-tBu]$^+$.

Step 7: tert-Butyl 1-cyano-5-(cyclopropylsulfonyl)isoindoline-2-carboxylate

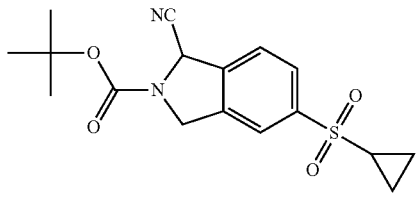 [SMILES: CC(C)(C)OC(=O)N1Cc2cc(S(=O)(=O)C3CC3)ccc2C1C#N]

BF$_3$·Et$_2$O (3.12 mL, 24.62 mmol) was added dropwise to tert-butyl 5-(cyclopropylsulfonyl)-1-methoxyisoindoline-2-carboxylate (5.8 g, 16.41 mmol) and TMS-CN (3.30 mL, 24.62 mmol) in DCM (120 mL) at −78° C. under nitrogen. The resulting solution was stirred at −78° C. for 1 hour. The reaction mixture was quenched with saturated NaHCO$_3$ (150 mL), extracted with DCM (3×100 mL), the organic layer was dried over Na$_2$SO$_4$, filtered and evaporated to afford dark solid. The crude product was purified by flash silica chromatography, elution gradient 0 to 50% EtOAc in petroleum ether. Pure fractions were evaporated to dryness to afford tert-butyl 1-cyano-5-(cyclopropylsulfonyl)isoindoline-2-carboxylate (2.400 g, 42.0.

LC/MS: m/z=366 [M+H+NH$_3$]+. $^1$H NMR (300 MHz, CDCl$_3$) δ 1.06-1.15 (m, 2H), 1.35-1.51 (m, 2H), 1.62 (s, 9H), 2.48-2.54 (m, 1H), 4.82-4.89 (m, 2H), 5.82-5.88 (m, 1H), 7.66-7.74 (m, 1H), 7.89-8.07 (m, 2H).

Step 8: 5-(Cyclopropylsulfonyl)isoindoline-1-carboxylic acid

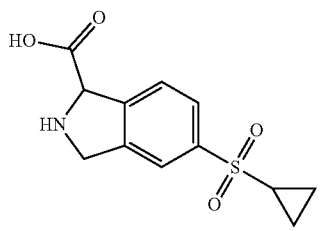 [SMILES: O=C(O)C1NCc2cc(S(=O)(=O)C3CC3)ccc21]

A mixture of tert-butyl 1-cyano-5-(cyclopropylsulfonyl)isoindoline-2-carboxylate (2.38 g, 6.83 mmol) in HCl (6M, 24 mL, 144.00 mmol) was stirrd at 70° C. for 3 hours. The reaction mixture was concentrated under reduced pressure to afford 5-(cyclopropylsulfonyl)isoindoline-1-carboxylic acid 2.2 g of a dark solid, which was used without further purification.

LC/MS: m/z=268 [M+H]+.

Step 9: 2-(tert-Butoxycarbonyl)-5-(cyclopropylsulfonyl)isoindoline-1-carboxylic acid

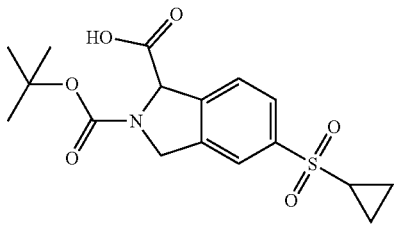 [SMILES: CC(C)(C)OC(=O)N1Cc2cc(S(=O)(=O)C3CC3)ccc2C1C(=O)O]

Boc₂O (1.91 mL, 8.23 mmol) was added to 5-(cyclopropylsulfonyl)isoindoline-1-carboxylic acid (2.2 g, 8.23 mmol) and Et₃N (4.59 mL, 32.92 mmol) in DCM (40 mL) under nitrogen. The resulting solution was stirred at room temperature for 12 hours. The reaction mixture was acidified with 1M HCl. The resulting mixture was extracted with DCM (3×50 mL), the organic layer was dried over Na₂SO₄, filtered and evaporated to afford dark oil. The crude product was purified by flash silica chromatography, elution gradient 0 to 10% MeOH in DCM. Pure fractions were evaporated to dryness to afford 2-(tert-butoxycarbonyl)-5-(cyclopropylsulfonyl)isoindoline-1-carboxylic acid (2.20 g, 72.8 LC/MS: m/z=268 [M+H-Boc]⁺. ¹H NMR (300 MHz, DMSO-d₆) δ 1.00-1.27 (m, 4H), 1.45 (s, 9H), 2.82-2.88 (m, 1H), 4.68-4.78 (m, 2H), 5.40 (s, 1H), 7.60-7.66 (m, 1H), 7.82-7.93 (m, 2H).

Step 10: Tert-Butyl 5-(Cyclopropylsulfonyl)-1-{[4-(1,1,1,3,3,3-Hexafluoro-2-Hydroxypropan-2-Yl)Phenyl]Carbamoyl}-1,3-Dihydro-2H-Isoindole-2-Carboxylate

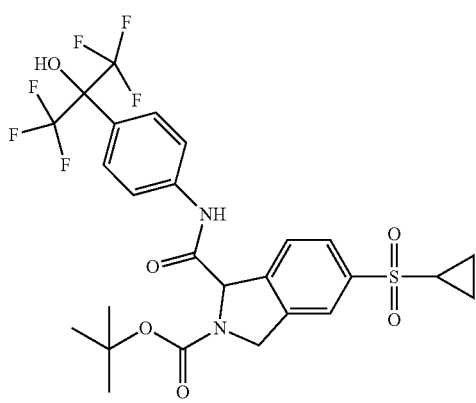 [SMILES: CC(C)(C)OC(=O)N1Cc2cc(S(=O)(=O)C3CC3)ccc2C1C(=O)Nc1ccc(C(O)(C(F)(F)F)C(F)(F)F)cc1]

DIPEA (1.426 mL, 8.17 mmol) was added to 2-(tert-butoxycarbonyl)-5-(cyclopropylsulfonyl)isoindoline-1-carboxylic acid (1 g, 2.72 mmol), HATU (1.138 g, 2.99 mmol) and 2-(4-aminophenyl)-1,1,1,3,3,3-hexafluoropropan-2-ol (0.705 g, 2.72 mmol) in DCM (10 mL) under nitrogen. The resulting solution was stirred at room temperature for 1 hour. The reaction mixture was quenched with saturated NH₄Cl (20 mL), extracted with DCM (3×25 mL), the organic layer was dried over Na₂SO₄, filtered and evaporated to afford dark oil. The crude product was purified by flash silica chromatography, elution gradient 0 to 50% EtOAc in petroleum ether. Pure fractions were evaporated to dryness to afford the title compound (1.3 g, 77%) as a pale yellow solid.
LC/MS: m/z=609 [M+H]⁺. ¹H NMR (400 MHz, DMSO-d₆, mixture of rotamers, 1.8*:1) δ 1.04-1.21 (m, 4H), 1.35*, 1.47 (s, 9H), 2.84-2.86 (m, 1H), 4.73-4.86 (m, 2H), 5.61*, 5.63 (s, 1H), 7.61-7.78 (m, 5H), 7.83-7.89 (m, 1H), 7.94-8.01 (m, 1H), 8.65*, 8.67 (s, 1H), 10.76 (s, 1H).

Intermediate 8: tert-Butyl 1-{[4-(1,1,1,3,3,3-hexafluoro-2-hydroxypropan-2-yl)phenyl]carbamoyl}-5-[(2-methoxyethyl)sulfonyl]-1,3-dihydro-2H-isoindole-2-carboxylate

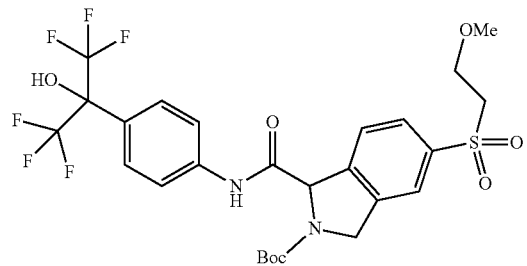 [SMILES: COCCS(=O)(=O)c1ccc2c(c1)CN(C(=O)OC(C)(C)C)C2C(=O)Nc1ccc(C(O)(C(F)(F)F)C(F)(F)F)cc1]

Step 1: 5-(2-Methoxyethylthio)isoindolin-1-one

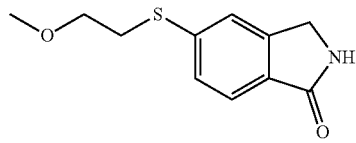

1-Bromo-2-methoxyethane (12.62 g, 90.79 mmol) was added to 5-mercaptoisoindolin-1-one (10 g, 60.53 mmol) and K₂CO₃ (16.73 g, 121.06 mmol) in DMF (200 mL) under nitrogen. The resulting mixture was stirred at room temperature for 12 hours. The reaction mixture was quenched with water (200 mL), extracted with EtOAc (2×200 mL), the organic layer was washed with water (2×200 mL) and brine (1×200 mL), dried over Na₂SO₄, filtered and evaporated to afford brown oil. The crude product was purified by flash silica chromatography, elution gradient 30 to 50% EtOAc in petroleum ether. Pure fractions were evaporated to dryness to afford 5-((2-methoxyethyl)thio)isoindolin-1-one (9.60 g, 71%).
LC/MS: m/z=224 [M+H]⁺. ¹H NMR (400 MHz, DMSO-d₆) δ 3.25 (t, 2H), 3.27 (s, 3H), 3.56 (t, 2H), 4.34 (s, 2H), 7.39-7.58 (m, 3H), 8.49 (s, 1H).

Step 2: 5-((2-Methoxyethyl)sulfonyl)isoindolin-1-one

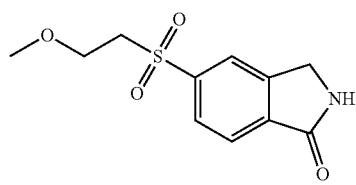 [SMILES: COCCS(=O)(=O)c1ccc2c(c1)CNC2=O]

mCPBA (15.58 g, 90.29 mmol) was added portionwise to 5-((2-methoxyethyl)thio)isoindolin-1-one (9.6 g, 42.99 mmol) in DCM (60 mL) under nitrogen. The resulting mixture was stirred at room temperature for 3 hours. The reaction mixture was quenched with saturated Na$_2$CO$_3$ (200 mL), extracted with DCM (6×150 mL), the organic layer was dried over Na$_2$SO$_4$, filtered and evaporated to afford 5-((2-methoxyethyl)sulfonyl)isoindolin-1-one (8.20 g, 75%) as pale yellow solid. The crude product was used to the next step directly.

LC/MS: m/z=256 [M+H]$^+$. $^1$H NMR (300 MHz, DMSO-d$_6$) δ 3.09 (s, 3H), 3.61-3.71 (m, 4H), 4.50 (s, 2H), 7.91 (d, 1H), 8.00 (d, 1H), 8.14 (s, 1H), 8.96 (s, 1H).

Step 3: tert-Butyl 5-(2-methoxyethylsulfonyl)-1-oxoisoindoline-2-carboxylate

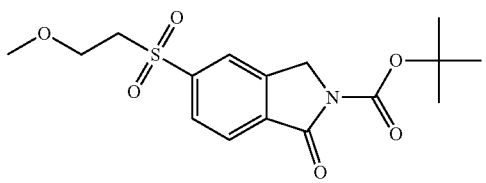 [SMILES: COCCS(=O)(=O)c1ccc2c(c1)CN(C(=O)OC(C)(C)C)C2=O]

DMAP (5.81 g, 47.59 mmol) was added to 5-((2-methoxyethyl)sulfonyl)isoindolin-1-one (8.1 g, 31.73 mmol) and (Boc)$_2$O (11.05 mL, 47.59 mmol) in MeCN (160 mL) under nitrogen. The resulting solution was stirred at room temperature for 2 hours. The reaction mixture was quenched with saturated NH$_4$Cl (200 mL), extracted with DCM (3×200 mL), the organic layer was dried over Na$_2$SO$_4$, filtered and evaporated to afford brown oil. The crude product was purified by flash silica chromatography, elution gradient 0 to 50% EtOAc in petroleum ether. Pure fractions were evaporated to dryness to afford tert-butyl 5-((2-methoxyethyl)sulfonyl)-1-oxoisoindoline-2-carboxylate (7.20 g, 63.2%) as a brown solid.

LC/MS: m/z=300 [M+H-tBu]$^+$. $^1$H NMR (300 MHz, DMSO-d$_6$) δ 1.55 (s, 9H), 3.08 (s, 3H), 3.65-3.72 (m, 4H), 4.90 (s, 2H), 7.98-8.06 (m, 2H), 8.22 (s, 1H).

Step 4: tert-Butyl 1-hydroxy-5-((2-methoxyethyl)sulfonyl)isoindoline-2-carboxylate

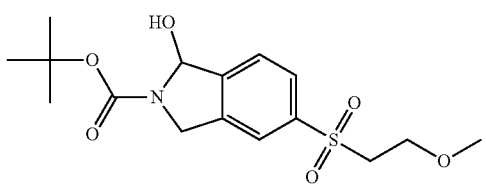 [SMILES: COCCS(=O)(=O)c1ccc2c(c1)CN(C(=O)OC(C)(C)C)C2O]

DIBAL-H (5.76 g, 40.52 mmol) was added to tert-butyl 5-((2-methoxyethyl)sulfonyl)-1-oxoisoindoline-2-carboxylate (7.2 g, 20.26 mmol) in DCM (140 mL) cooled to 0° C. under nitrogen. The resulting solution was stirred at room temperature for 5 hours. The reaction mixture was quenched with sat Rochelle's salt (50 mL), extracted with DCM (3×50 mL), the organic layer was dried over Na$_2$SO$_4$, filtered and evaporated to afford tert-butyl 1-hydroxy-5-((2-methoxyethyl)sulfonyl)isoindoline-2-carboxylate (6.50 g, 90%).

LC/MS: m/z=340 [M-OH]$^+$.

Step 5: tert-Butyl 1-methoxy-5-((2-methoxyethyl)sulfonyl)isoindoline-2-carboxylate

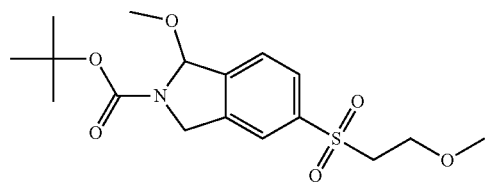 [SMILES: COCCS(=O)(=O)c1ccc2c(c1)CN(C(=O)OC(C)(C)C)C2OC]

PPTs (0.457 g, 1.82 mmol) was added to tert-butyl 1-hydroxy-5-((2-methoxyethyl)sulfonyl)isoindoline-2-carboxylate (6.5 g, 18.19 mmol) in MeOH (130 mL) at room temperature under nitrogen. The resulting solution was stirred at room temperature for 5 hours. The reaction mixture was quenched with Et$_3$N (150 mL), the organic layer was filtered and evaporated to afford tert-butyl 1-methoxy-5-((2-methoxyethyl)sulfonyl)isoindoline-2-carboxylate (6.50 g, 96%) as brown oil.

LC/MS: m/z=340 [M-MeO]$^+$.

Step 6: tert-Butyl 1-cyano-5-(2-methoxyethylsulfonyl)isoindoline-2-carboxylate

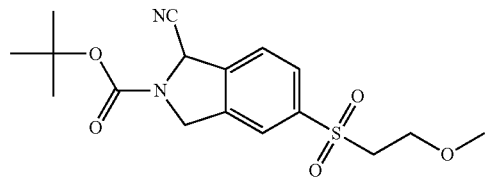 [SMILES: COCCS(=O)(=O)c1ccc2c(c1)CN(C(=O)OC(C)(C)C)C2C#N]

BF$_3$.Et$_2$O (3.79 mL, 29.88 mmol) was added dropwise to tert-butyl 1-methoxy-5-((2-methoxyethyl)sulfonyl)isoindoline-2-carboxylate (7.4 g, 19.92 mmol) and TMS-CN (4.01 mL, 29.88 mmol) in DCM (148 mL) cooled to -78° C. under nitrogen. The resulting solution was stirred at -78° C. for 45 minutes. The reaction mixture was quenched with saturated NaHCO$_3$ (150 mL), extracted with DCM (3×150 mL), the organic layer was dried over Na$_2$SO$_4$, filtered and evaporated to afford purple oil. The crude product was purified by flash silica chromatography. Pure fractions were evaporated to dryness to afford tert-butyl 1-cyano-5-((2-methoxyethyl)sulfonyl)isoindoline-2-carboxylate (3.20 g, 43.8%).

LC/MS: m/z=384 [M+H+NH$_3$]+. $^1$H NMR (300 MHz, DMSO-d$_6$) δ 1.52 (s, 9H), 3.11 (s, 3H), 3.64 (s, 4H), 4.77 (s, 2H), 6.21 (s, 1H), 7.82-8.00 (m, 3H).

Step 7: 5-((2-Methoxyethyl)sulfonyl)isoindoline-1-carboxylic acid

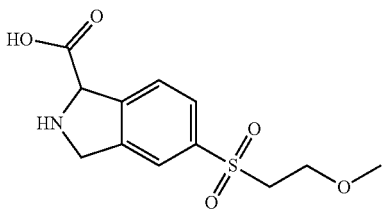 [SMILES: COCCS(=O)(=O)c1ccc2c(c1)CNC2C(=O)O]

A mixture of tert-butyl 1-cyano-5-((2-methoxyethyl)sulfonyl)isoindoline-2-carboxylate (3.2 g, 8.73 mmol) in HCl (6M, 0.2 mL, 1.20 mmol) was heated to 70° C. for 2 hours. The reaction mixture was concentrated under vacuum to afford the crude 5-((2-methoxyethyl)sulfonyl)isoindoline-1-carboxylic acid (3.2 g), which was used without further purification.

LC/MS: m/z=286 [M+H]+.

Step 8: 2-(tert-Butoxycarbonyl)-5-(2-methoxyethyl-sulfonyl)isoindoline-1-carboxylic acid

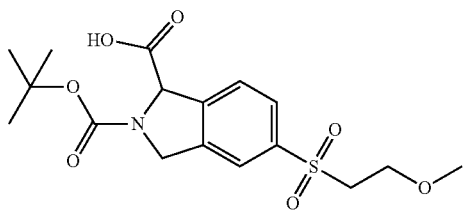 [SMILES: COCCS(=O)(=O)c1ccc2c(c1)CN(C(=O)OC(C)(C)C)C2C(=O)O]

Boc-anhydride (2.60 mL, 11.22 mmol) was added to 5-((2-methoxyethyl)sulfonyl)-isoindoline-1-carboxylic acid (3.2 g, 11.22 mmol) and Et$_3$N (6.25 mL, 44.86 mmol) in DCM (64 mL) under nitrogen. The resulting solution was stirred at room temperature for 4 hours. The reaction mixture was acidified with 1M HCl. The resulting mixture was extracted with DCM (3×60 ml), the organic layer was dried over Na$_2$SO$_4$, filtered and evaporated to afford dark solid. The crude product was purified by flash silica chromatography, elution gradient 0 to 10% MeOH in DCM. Pure fractions were evaporated to dryness to afford 2-(tert-butoxycarbonyl)-5-((2-methoxyethyl)sulfonyl)isoindoline-1-carboxylic acid (2.80 g, 64.8%).

LC/MS: m/z=286 [M+H-Boc]+.

$^1$H NMR (300 MHz, DMSO-d$_6$, mixture of rotamers, 1.3*:1) δ 1.43*, 1.48 (s, 9H), 3.11 (s, 3H), 3.63 (s, 4H), 4.73-4.76 (m, 2H), 5.47 (s, 1H), 7.60-7.96 (m, 3H), 13.28 (1H, brs).

Step 9: tert-Butyl 1-{[4-(1,1,1,3,3,3-hexafluoro-2-hydroxypropan-2-yl)phenyl]carbamoyl}-5-[(2-methoxyethyl)sulfonyl]-1,3-dihydro-2H-isoindole-2-carboxylate

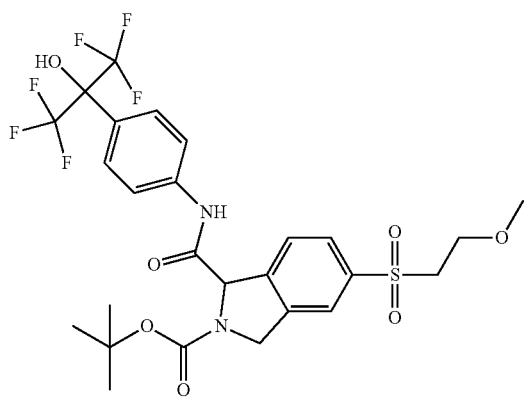 [SMILES: COCCS(=O)(=O)c1ccc2c(c1)CN(C(=O)OC(C)(C)C)C2C(=O)Nc1ccc(C(O)(C(F)(F)F)C(F)(F)F)cc1]

DIPEA (3.81 mL, 21.79 mmol) was added to 2-(tert-butoxycarbonyl)-5-((2-methoxyethyl)sulfonyl)isoindoline-1-carboxylic acid (2.8 g, 7.26 mmol), 2-(4-aminophenyl)-1,1,1,3,3,3-hexafluoropropan-2-ol (1.883 g, 7.26 mmol) and HATU (3.04 g, 7.99 mmol) in DCM (56 mL) under nitrogen. The resulting solution was stirred at room temperature for 1 hour. The reaction mixture was quenched with saturated aqueous NH$_4$Cl (20 mL), extracted with DCM (3×100 mL), the organic layer was dried over Na$_2$SO$_4$, filtered and evaporated to afford dark solid. The crude product was purified by flash silica chromatography, elution gradient 0 to 60% EtOAc in petroleum ether. Pure fractions were evaporated to dryness to afford tert-butyl 1-((4-(1,1,1,3,3,3-hexafluoro-2-hydroxypropan-2-yl)phenyl)carbamoyl)-5-((2-methoxyethyl)sulfonyl)isoindoline-2-carboxylate (3.53 g, 96%).

LC/MS: m/z=571 [M+H-tBu]+. $^1$H NMR (300 MHz, DMSO-d$_6$, mixture of rotamers, 1.8*:1) δ 1.34*, 1.48 (s, 9H), 3.09 (s, 3H), 3.58-3.60 (m, 4H), 4.66-4.89 (m, 2H), 5.60*, 5.62 (s, 1H), 7.59-7.78 (m, 5H), 7.81-7.87 (m, 1H), 7.91-7.99 (m, 1H), 8.63*, 8.64 (s, 1H), 10.74 (1H, s).

Intermediate 9: (9H-Fluoren-9-yl)methyl 1-(4-(1,1,1,3,3,3-hexafluoro-2-hydroxypropan-2-yl)phenylcarbamoyl)-5-(2-hydroxyethylsulfonyl)isoindoline-2-carboxylate

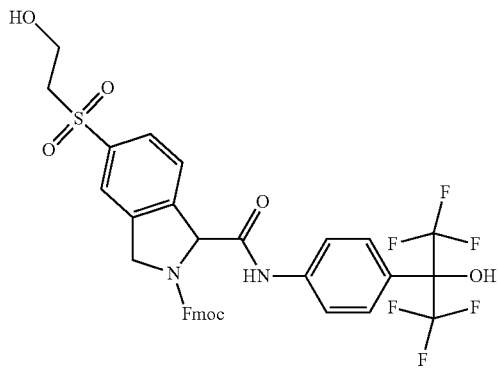

Step 1: (9H-Fluoren-9-yl)methyl 1-(4-(1,1,1,3,3,3-hexafluoro-2-hydroxypropan-2-yl)phenylcarbamoyl)-5-(2-methoxyethylsulfonyl)isoindoline-2-carboxylate

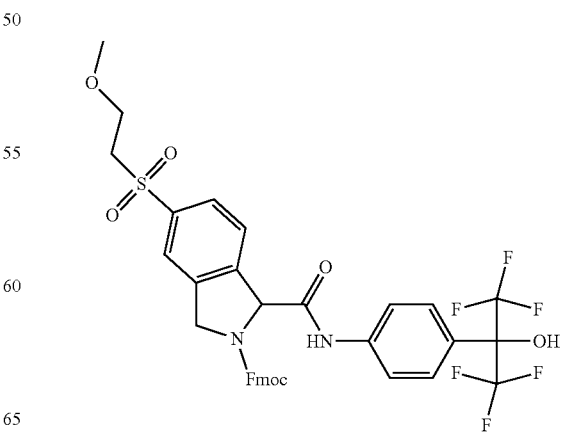

9-Fluorenylmethyl chloroformate (73.7 mg, 0.28 mmol) was added to N-(4-(1,1,1,3,3,3-hexafluoro-2-hydroxypropan-2-yl)phenyl)-5-((2-methoxyethyl)sulfonyl)isoindoline-1-carboxamide (100 mg, 0.19 mmol, prepared as described in Example 700) and sat. aq. NaHCO₃ (4 mL) in DCM (2 mL). The resulting mixture was stirred at room temperature for 6 hours. The reaction mixture was quenched with water (10 mL), extracted with DCM (3×10 mL), the organic layer was dried over Na₂SO₄, filtered and evaporated to afford brown oil. The crude product was purified by flash silica chromatography, elution gradient 30 to 50% EtOAc in petroleum ether. Pure fractions were evaporated to dryness to afford (9H-fluoren-9-yl)methyl 1-((4-(1,1,1,3,3,3-hexafluoro-2-hydroxypropan-2-yl)phenyl)carbamoyl)-5-((2-methoxyethyl)sulfonyl)isoindoline-2-carboxylate (120 mg, 84%).

LC/MS: m/z=749 [M+H]⁺. ¹H NMR (400 MHz, DMSO-d₆, mixture of rotamers, 1.1*:1) δ 3.11*, 3.12 (s, 3H), 3.60-3.64 (m, 4H), 4.14-4.42 (m, 3H), 4.78-5.03 (m, 2H), 5.72, 5.82* (s, 1H), 6.92-7.00 (m, 1H), 7.22-7.50 (m, 3H), 7.55-7.84 (m, 8H), 7.86-7.96 (m, 2H), 8.00-8.05 (m, 1H), 8.67, 8.69* (s, 1H), 10.84, 10.88* (s, 1H).

Step 2: (9H-Fluoren-9-yl)methyl 1-(4-(1,1,1,3,3,3-hexafluoro-2-hydroxypropan-2-yl)phenylcarbamoyl)-5-(2-hydroxyethylsulfonyl)isoindoline-2-carboxylate

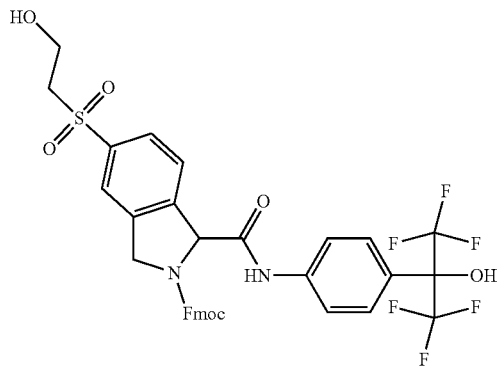

Tribromoborane (1088 mg, 4.34 mmol) was added dropwise to (9H-fluoren-9-yl)methyl 1-((4-(1,1,1,3,3,3-hexafluoro-2-hydroxypropan-2-yl)phenyl)carbamoyl)-5-((2-methoxyethyl)sulfonyl)isoindoline-2-carboxylate (650 mg, 0.87 mmol) in DCM (20 mL) cooled to −40° C. over a period of 20 minutes under nitrogen. The resulting solution was stirred at 0° C. for 2 hours. The reaction mixture was quenched with ice (50 mL), extracted with DCM (3×75 mL), the organic layer was dried over Na₂SO₄, filtered and evaporated to afford pale yellow solid. The crude product was purified by flash silica chromatography, elution gradient 0 to 80% EtOAc in petroleum ether. Pure fractions were evaporated to dryness to afford (9H-fluoren-9-yl)methyl 1-((4-(1,1,1,3,3,3-hexafluoro-2-hydroxypropan-2-yl)phenyl)carbamoyl)-5-((2-hydroxyethyl)sulfonyl)isoindoline-2-carboxylate (442 mg, 69.3%).

LC/MS: m/z=735 [M+H]⁺. ¹H NMR (400 MHz, DMSO-d₆, mixture of rotamers, 1.2*:1) δ 3.46-3.49 (m, 2H), 3.68-3.71 (m, 2H), 4.16-4.38 (m, 3H), 4.88-5.03 (m, 3H), 5.72, 5.82* (s, 1H), 6.94-7.00 (m, 1H), 7.23-7.32 (m, 1H), 7.34- 7.49 (m, 2H), 7.56-7.85 (m, 8H), 7.87-7.96 (m, 2H), 8.01-8.06 (m, 1H), 8.67, 8.69* (s, 1H), 10.85, 10.90* (s, 1H).

Intermediate 10: 5-((2-((tert-Butyldimethylsilyl)oxy)ethyl)sulfonyl)-N-(4-(1,1,1,3,3,3-hexafluoro-2-hydroxypropan-2-yl)phenyl)isoindoline-1-carboxamide

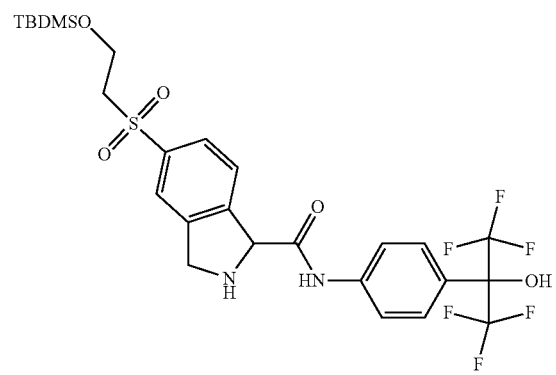 [SMILES: CC(C)(C)[Si](C)(C)OCCS(=O)(=O)c1ccc2c(c1)CNC2C(=O)Nc1ccc(C(O)(C(F)(F)F)C(F)(F)F)cc1]

Step 1: (9H-Fluoren-9-yl)methyl 5-((2-((tert-butyldimethylsilyl)oxy)ethyl)sulfonyl)-1-((4-(1,1,1,3,3,3-hexafluoro-2-hydroxypropan-2-yl)phenyl)carbamoyl)isoindoline-2-carboxylate

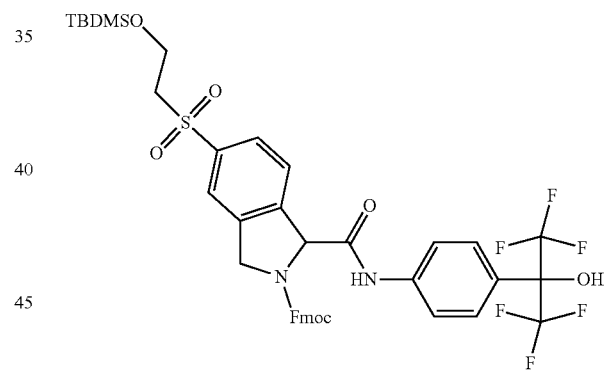

tert-Butylchlorodimethylsilane (451 mg, 2.99 mmol) was added to (9H-fluoren-9-yl)methyl 1-((4-(1,1,1,3,3,3-hexafluoro-2-hydroxypropan-2-yl)phenyl)carbamoyl)-5-((2-hydroxyethyl)sulfonyl)isoindoline-2-carboxylate (440 mg, 0.60 mmol), 2,6-dimethylpyridine (193 mg, 1.80 mmol) in DCM (10 mL) under nitrogen. The resulting solution was stirred at 25° C. for 4 hours. The reaction mixture was quenched with water (15 mL), extracted with DCM (3×20 mL), the organic layer was dried over Na₂SO₄, filtered and evaporated to afford pale yellow solid. The crude product was purified by flash silica chromatography, elution gradient 0 to 70% EtOAc in petroleum ether. Pure fractions were evaporated to dryness to afford (9H-fluoren-9-yl)methyl 5-((2-((tert-butyldimethylsilyl)oxy)ethyl)sulfonyl)-1-((4-(1,1,3,3,3-hexafluoro-2-hydroxypropan-2-yl)phenyl)carbamoyl)isoindoline-2-carboxylate (320 mg, 62.9%).

LC/MS: m/z=849 [M+H]⁺.

Step 2: 5-((2-(((tert-Butyldimethylsilyl)oxy)ethyl)sulfonyl)-N-(4-(1,1,1,3,3,3-hexafluoro-2-hydroxy-propan-2-yl)phenyl)isoindoline-11-carboxamide

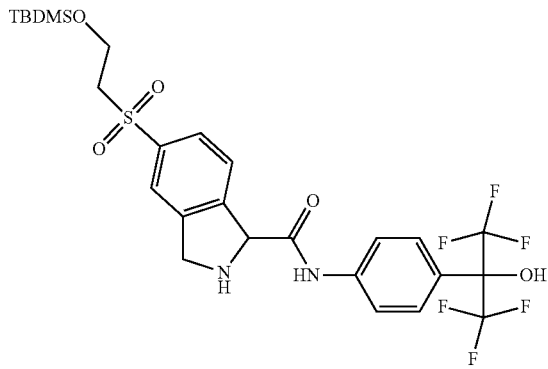 [SMILES: CC(C)(C)[Si](C)(C)OCCS(=O)(=O)c1ccc2c(c1)CNC2C(=O)Nc1ccc(C(O)(C(F)(F)F)C(F)(F)F)cc1]

Diethylamine (267 mg, 3.65 mmol) was added to (9H-fluoren-9-yl)methyl 5-((2-((tert-butyldimethylsilyl)oxy)ethyl)sulfonyl)-1-((4-(1,1,1,3,3,3-hexafluoro-2-hydroxy-propan-2-yl)phenyl)carbamoyl)isoindoline-2-carboxylate (310 mg, 0.37 mmol) in DCM (2 mL) under nitrogen. The resulting solution was stirred at room temperature for 2 hours. The crude product was purified by flash silica chromatography, elution gradient 0 to 70% EtOAc in petroleum ether. Pure fractions were evaporated to dryness to afford 5-((2-((tert-butyldimethylsilyl)oxy)ethyl)sulfonyl)-N-(4-(1,1,1,3,3,3-hexafluoro-2-hydroxypropan-2-yl)phenyl)isoindoline-1-carboxamide (210 mg, 92%).

LC/MS: m/z=627 [M+H]+.

Intermediate 11: 2-(4-amino-3-fluorophenyl)-1,1,1,3,3,3-hexafluoropropan-2-ol

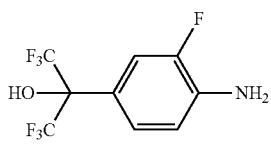

2-Fluoroaniline (3 g, 27.00 mmol), 1,1,1,3,3,3-hexafluoropropan-2-one sesquihydrate (4.23 ml, 34.60 mmol) and 4-methylbenzenesulfonic acid hydrate (0.54 g, 2.84 mmol) were mixed in a vial under nitrogen. The mixture was heated to 90° C. overnight. The reaction contents were then diluted with 600 mL ethyl acetate and washed with NaHCO$_3$(sat.). The ethyl acetate phase was then washed with brine, dried using a phase separator, and concentrated in vacuo. Flash chromatography on silica gel eluting with 0 to 20% EtOAc in heptanes gave impure product, which was purified again under the same conditions to afford 2-(4-amino-3-fluorophenyl)-1,1,1,3,3,3-hexafluoropropan-2-ol (2.3 g, 31%). LC/MS: m/z=276 [M−H]−. $^1$H NMR (500 MHz, DMSO) δ 5.55 (s, 2H), 6.82 (t, 1H), 7.15 (d, 1H), 7.19 (d, 1H), 8.44 (s, 1H).

Intermediate 12: 2-(4-Amino-2-fluorophenyl)-1,1,1,3,3,3-hexafluoropropan-2-ol

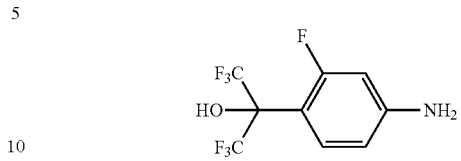

To 3-fluoroaniline (3 g, 27.00 mmol) in a vial was added 1,1,1,3,3,3-hexafluoropropan-2-one sesquihydrate (4.23 ml, 34.60 mmol) and 4-methylbenzenesulfonic acid hydrate (0.54 g, 2.84 mmol). The tube was then purged with nitrogen, sealed and heated overnight at 90° C. The reaction contents were then diluted with ethyl acetate and washed 3× with NaHCO$_3$(sat.). The ethyl acetate phase was then washed with brine, dried using a phase separator, and concentrated in vacuo. The desired product was isolated by flash chromatography on silica using 0 to 20% ethyl acetate in heptane. This resulted in a solid that was recrystallised using hexanes and ethyl acetate. 2-(4-Amino-2-fluorophenyl)-1,1,1,3,3,3-hexafluoropropan-2-ol (1.22 g, 16.3%) was obtained as a solid.

LC/MS: m/z=276 [M−H]−. $^1$H NMR (500 MHz, DMSO) δ 5.78 (s, 2H), 6.33 (dd, 1H), 6.44 (dd, 1H), 7.35 (t, 1H), 8.33 (s, 1H).

Intermediate 13: tert-Butyl 1-{[3-fluoro-4-(1,1,1,3,3,3-hexafluoro-2-hydroxypropan-2-yl)phenyl]carbamoyl}-5-(methylsulfonyl)-1,3-dihydro-2H-isoindole-2-carboxylate

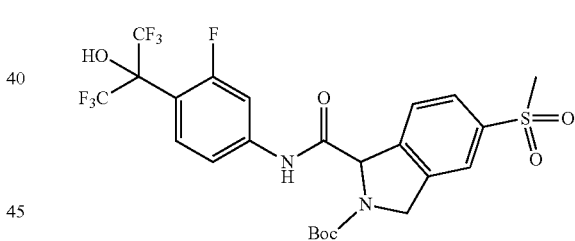

2-(tert-Butoxycarbonyl)-5-(methylsulfonyl)isoindoline-1-carboxylic acid (345 mg, 1.01 mmol) was suspended in DCM (5 mL) and to this 2-(4-amino-2-fluorophenyl)-1,1,1,3,3,3-hexafluoropropan-2-ol (280 mg, 1.01 mmol) and triethylamine (0.282 mL, 2.02 mmol) was added. To the solution obtained T3P (643 mg, 2.02 mmol, 50% in EtOAc) was then added. The reaction was stirred at rt for 30 mins. LCMS indicated complete conversion to product. The reaction was diluted with DCM and washed with 0.5M HCl. The layers were separated using a phase separator and concentrated in vacuo. The residue was purified on silica eluting with 40% EtOAc in heptane. Pure fractions were combined and concentrated in vacuo to afford tert-butyl 1-((3-fluoro-4-(1,1,1,3,3,3-hexafluoro-2-hydroxypropan-2-yl)phenyl) carbamoyl)-5-(methylsulfonyl)isoindoline-2-carboxylate (422 mg, 69.5%) as a solid.

LC/MS: m/z=601 [M+H]+. $^1$H NMR (500 MHz, DMSO-d$_6$, mixture of rotamers, 2*:1) δ 1.34*, 1.47 (s, 9H), 3.21, 3.22* (s, 3H), 4.71-4.86, (m, 2H), 5.6*, 5.62 (s, 1H), 7.51

(td, 1H), 7.63-7.71 (m, 2H), 7.75-7.81 (m, 1H), 7.85-7.91 (m, 1H), 7.98, 8.02* (s, 1H), 8.84*, 8.86 (s, 1H), 10.94 (s, 1H).

Intermediate 14: tert-Butyl 1-{[2-fluoro-4-(1,1,1,3,3,3-hexafluoro-2-hydroxypropan-2-yl)phenyl]carbamoyl}-5-(methylsulfonyl)-1,3-dihydro-2H-isoindole-2-carboxylate

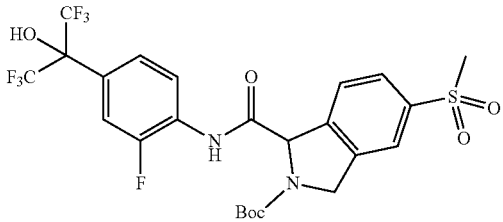 [SMILES: CC(C)(C)OC(=O)N1Cc2cc(S(C)(=O)=O)ccc2C1C(=O)Nc1ccc(C(O)(C(F)(F)F)C(F)(F)F)cc1F]

2-(tert-Butoxycarbonyl)-5-(methylsulfonyl)isoindoline-1-carboxylic acid (345 mg, 1.01 mmol) was suspended in DCM (5 mL) and to this 2-(4-amino-3-fluorophenyl)-1,1,1,3,3,3-hexafluoropropan-2-ol (280 mg, 1.01 mmol) and triethylamine (0.282 mL, 2.02 mmol) was added. To the resulting solution T3P (1.203 mL, 2.02 mmol) 50% in EtOAc was then added. The reaction was stirred at rt for 30 mins. LCMS indicated complete conversion to product. The reaction was diluted with DCM and washed with 0.5M HCl. The layers were separated using a phase separator and concentrated in vacuo. The residue was purified on silica eluting with 40% EtOAc in heptane. Completely pure fractions were combined and concentrated in vacuo to afford tert-butyl 1-((2-fluoro-4-(1,1,1,3,3,3-hexafluoro-2-hydroxypropan-2-yl)phenyl)carbamoyl)-5-(methylsulfonyl)isoindoline-2-carboxylate (402 mg, 66.3%) as a solid.

LC/MS: m/z=601 [M+H]$^+$. $^1$H NMR (500 MHz, DMSO-d$_6$, mixture of rotamers, 2*:1) δ 1.38*, 1.47 (s, 9H), 3.21, 3.23* (s, 3H), 4.7-4.85 (m, 2H), 5.81*, 5.85 (s, 1H), 7.42-7.58 (m, 2H), 7.67*, 7.72 (d, 1H), 7.88-8.06 (m, 3H), 8.92 (s, 1H), 10.60, 10.63* (s, 1H).

Intermediate 15: tert-Butyl 1-{[4-(1,1,1,3,3,3-hexafluoro-2-hydroxypropan-2-yl)phenyl]carbamoyl}-5-[(3-methoxy-3-oxopropyl)sulfonyl]-1,3-dihydro-2H-isoindole-2-carboxylate

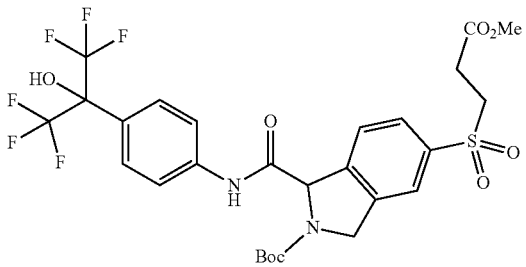 [SMILES: COC(=O)CCS(=O)(=O)c1ccc2c(c1)CN(C(=O)OC(C)(C)C)C2C(=O)Nc1ccc(C(O)(C(F)(F)F)C(F)(F)F)cc1]

Step 1: tert-Butyl 5-bromo-1-oxoisoindoline-2-carboxylate

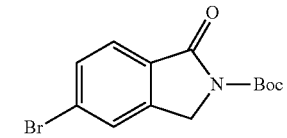 [SMILES: CC(C)(C)OC(=O)N1Cc2cc(Br)ccc2C1=O]

(Boc)$_2$O (69.5 g, 318.33 mmol) was added slowly to 5-bromoisoindolin-1-one (45 g, 212.22 mmol) and DMAP (38.9 g, 318.33 mmol) in acetonitrile (1000 mL) at room temperature over a period of 30 minutes under nitrogen. The resulting solution was stirred at this temperature for 12 hours. The solvent was removed under reduced pressure. The residue was treated with water (500 mL), extracted with DCM (3×500 mL), the organic layer was dried over Na$_2$SO$_4$, filtered and evaporated to afford brown oil. The crude product was purified by flash silica chromatography, elution gradient 0 to 10% EtOAc in petroleum ether. Pure fractions were evaporated to dryness to afford tert-butyl 5-bromo-1-oxoisoindoline-2-carboxylate (55.0 g, 83%).

LC/MS: m/z=256,258 [M-tBu+H]$^+$. $^1$H NMR (400 MHz, CDCl$_3$) δ 1.62 (s, 9H), 4.76 (s, 2H), 7.63-7.66 (m, 2H), 7.78 (d, J=8.0 Hz, 1H).

Step 2: tert-Butyl 5-bromo-1-hydroxyisoindoline-2-carboxylate

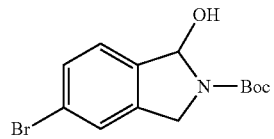

Lithium tri-tert-butoxyaluminum hydride (61.1 g, 240.26 mmol) was added slowly to tert-butyl 5-bromo-1-oxoisoindoline-2-carboxylate (50 g, 160.17 mmol) in THF (800 mL) at 0° C. over a period of 45 minutes under nitrogen. The resulting solution was stirred at 25° C. for 12 hours. The reaction mixture was quenched with ice (500 mL), extracted with EtOAc (3×250 mL), the organic layer was dried over Na$_2$SO$_4$, filtered and evaporated to afford brown oil. The crude product was purified by flash silica chromatography, elution gradient 10 to 20% EtOAc in petroleum ether. Pure fractions were evaporated to dryness to afford tert-butyl 5-bromo-1-hydroxyisoindoline-2-carboxylate (40.0 g, 79%).

LC/MS: m/z=240,242 [M-tBu-OH]$^+$.

Step 3: tert-Butyl 5-bromo-1-methoxyisoindoline-2-carboxylate

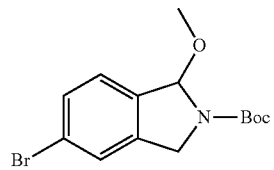 [SMILES: COC1c2ccc(Br)cc2CN1C(=O)OC(C)(C)C]

PPTs (3.20 g, 12.73 mmol) was added slowly to tert-butyl 5-bromo-1-hydroxyisoindoline-2-carboxylate (20 g, 63.66 mmol) in MeOH (400 mL) at room temperature over a period of 15 minutes under nitrogen. The resulting solution was stirred at this temperature for 2 hours. The reaction mixture was treated with Et$_3$N (100 mL). The solvent was removed under reduced pressure to afford tert-butyl 5-bromo-1-methoxyisoindoline-2-carboxylate (20.00 g, 96%). The product was used in the next step directly without further purification.

$^1$H NMR (300 MHz, CDCl$_3$, mixture of rotamers, 1:1) δ 1.55 (s, 9H), 3.23, 3.32 (s, 3H), 4.57-4.75 (m, 2H), 6.23, 6.33 (s, 1H), 7.29-7.34 (m, 1H), 7.42-7.50 (m, 2H).

Step 4: tert-Butyl 5-bromo-1-cyanoisoindoline-2-carboxylate

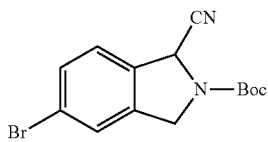 [SMILES: CC(C)(C)OC(=O)N1Cc2cc(Br)ccc2C1C#N]

BF$_3$.Et$_2$O (11.58 mL, 91.41 mmol) was added dropwise to tert-butyl 5-bromo-1-methoxyisoindoline-2-carboxylate (20 g, 60.94 mmol) and TMS-CN (12.25 mL, 91.41 mmol) in DCM (400 mL) at −78° C. over a period of 45 minutes under nitrogen. The resulting solution was stirred at −78° C. for 2 hours. The reaction mixture was treated with ice/water (300 mL), extracted with DCM (3×200 mL), the organic layer was dried over Na$_2$SO$_4$, filtered and evaporated to afford brown oil. The crude product was purified by flash silica chromatography, elution gradient 10 to 20% EtOAc in petroleum ether. Pure fractions were evaporated to dryness to afford tert-butyl 5-bromo-1-cyanoisoindoline-2-carboxylate (15.0 g, 76%).

$^1$H NMR (300 MHz, CDCl$_3$, mixture of rotamers, 1.5*:1) δ 1.54, 1.58* (s, 9H), 4.68, 4.72* (s, 2H), 5.65*, 5.70 (s, 1H), 7.28-7.41 (m, 1H), 7.42-7.58 (m, 2H).

Step 5: 5-Bromoisoindoline-1-carboxylic acid

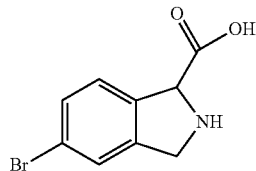 [SMILES: O=C(O)C1NCc2cc(Br)ccc21]

tert-Butyl 5-bromo-1-cyanoisoindoline-2-carboxylate (7 g, 21.66 mmol) was added slowly to 6M HCl (140 mL) at room temperature over a period of 35 minutes under nitrogen. The resulting mixture was stirred at 70° C. for 3 hours. The solvent was removed under reduced pressure to afford 5-bromoisoindoline-1-carboxylic acid (5.0 g, 95%). The product was used in the next step directly without further purification.

LC/MS: m/z=242,244 [M+H]$^+$. $^1$H NMR (300 MHz, DMSO-d$_6$) δ 4.52 (d, J=15.0 Hz, 1H), 4.61 (d, J=15.1 Hz, 1H), 5.57 (s, 1H), 7.49 (d, J=8.4 Hz, 1H), 7.61 (dd, J=8.4, 1.8 Hz, 1H), 7.69 (d, J=1.8 Hz, 1H), 9.54 (brs, 1H), 11.29 (brs, 1H).

Step 6: 5-Bromo-2-(tert-butoxycarbonyl)isoindoline-1-carboxylic acid

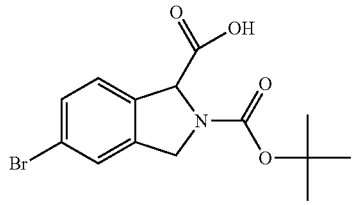 [SMILES: CC(C)(C)OC(=O)N1Cc2cc(Br)ccc2C1C(=O)O]

(Boc)$_2$O (5.41 g, 24.79 mmol) was added slowly to 5-bromoisoindoline-1-carboxylic acid (5 g, 20.66 mmol) and Et$_3$N (11.52 mL, 82.62 mmol) in DCM (100 mL) at 0° C. over a period of 30 minutes under nitrogen. The resulting mixture was stirred at room temperature for 12 hours. The reaction mixture was treated with water (100 mL), extracted with DCM (3×50 mL), the organic layer was dried over Na$_2$SO$_4$, filtered and evaporated to afford brown oil. The crude product was purified by flash silica chromatography, elution gradient 10 to 20% EtOAc in petroleum ether. Pure fractions were evaporated to dryness to afford 5-bromo-2-(tert-butoxycarbonyl)isoindoline-1-carboxylic acid (3.0 g, 42.4%). $^1$H NMR (300 MHz, CDCl$_3$, mixture of rotamers, 1.6*: 1) δ 1.47*, 1.49 (s, 9H), 4.61-4.83 (m, 2H), 5.25-5.32 (m, 1H), 7.32-7.43 (m, 3H).

Step 7: tert-Butyl 5-bromo-1-(4-(1, 1,1,3,3,3-hexafluoro-2-hydroxypropan-2-yl)phenylcarbamoyl) isoindoline-2-carboxylate

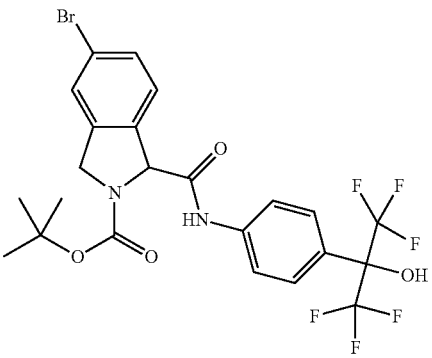 [SMILES: CC(C)(C)OC(=O)N1Cc2cc(Br)ccc2C1C(=O)Nc1ccc(C(O)(C(F)(F)F)C(F)(F)F)cc1]

Et$_3$N (5.50 mL, 39.45 mmol) was added to 5-bromo-2-(tert-butoxycarbonyl)isoindoline-1-carboxylic acid (4.5 g, 13.15 mmol), 2-(4-aminophenyl)-1,1,1,3,3,3-hexafluoropropan-2-ol (3.41 g, 13.15 mmol) and T3P (12.55 g, 39.45 mmol) in DCM (100 mL) under nitrogen. The resulting solution was stirred at room temperature for 2 hours. The reaction mixture was treated with saturated NH$_4$Cl (100 mL), extracted with DCM (3×100 mL), the organic layer was dried over Na$_2$SO$_4$, filtered and evaporated to afford yellow solid. The crude product was purified by flash C18-flash chromatography, elution gradient 0 to 60% MeCN in water. Pure fractions were evaporated to dryness to afford tert-butyl 5-bromo-1-((4-(1,1,1,3,3,3-hexafluoro-2-hydroxypropan-2-yl)phenyl)carbamoyl)isoindoline-2-carboxylate (5.70 g, 74.3%).

LC/MS: m/z=583,585 [M+H]+. 1H NMR (300 MHz, DMSO-d6, mixture of rotamers, 1.7*:1) δ 1.34*, 1.45 (s, 9H), 4.61-4.77 (m, 2H), 5.43-5.47 (m, 1H), 7.36 (dd, J=10.8, 8.1 Hz, 1H), 7.50 (dd, J=8.1, 1.8 Hz, 1H), 7.61-7.74 (m, 5H), 8.61*, 8.63 (s, 1H), 10.63, 10.64* (s, 1H).

Step 8: tert-Butyl 1-(4-(1,1,1,3,3,3-hexafluoro-2-hydroxypropan-2-yl)phenylcarbamoyl)-5-(3-methoxy-3-oxopropylthio)isoindoline-2-carboxylate

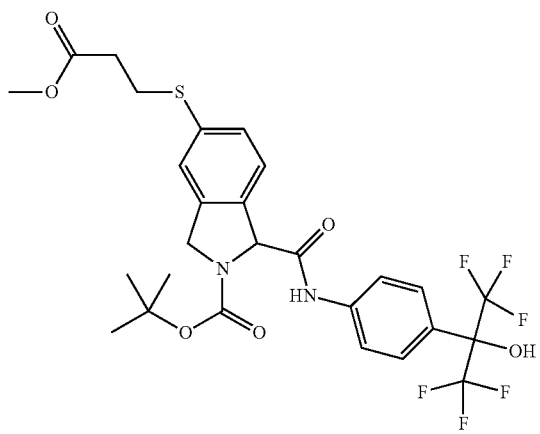 [SMILES: COC(=O)CCSc1ccc2c(c1)CN(C(=O)OC(C)(C)C)C2C(=O)Nc1ccc(C(O)(C(F)(F)F)C(F)(F)F)cc1]

DIPEA (5.14 mL, 29.40 mmol) was added to tert-butyl 5-bromo-1-((4-(1,1,1,3,3,3-hexafluoro-2-hydroxypropan-2-yl)phenyl)carbamoyl)isoindoline-2-carboxylate (5.7 g, 9.77 mmol), methyl 3-mercaptopropanoate (1.174 g, 9.77 mmol), Pd2(dba)3 (0.447 g, 0.49 mmol) and Xantphos (0.565 g, 0.98 mmol) in 1,4-dioxane (120 mL) under nitrogen. The resulting mixture was stirred at 80° C. for 2 hours. The reaction mixture was quenched with water (100 mL), extracted with DCM (3×125 mL), the organic layer was dried over Na2SO4, filtered and evaporated to afford white solid. The crude product was purified by flash silica chromatography, elution gradient 0 to 25% EtOAc in petroleum ether. Pure fractions were evaporated to dryness to afford tert-butyl 1-((4-(1,1,1,3,3,3-hexafluoro-2-hydroxypropan-2-yl)phenyl)carbamoyl)-5-((3-methoxy-3-oxopropyl)thio)isoindoline-2-carboxylate (5.5 g, 90%).

LC/MS: m/z=623 [M+H]+. 1H NMR (300 MHz, CDCl3) δ 1.54 (s, 9H), 2.65 (t, J=7.5 Hz, 2H), 3.19 (t, J=7.5 Hz, 2H), 3.70 (s, 3H), 4.77-4.90 (m, 2H), 5.48-5.65 (m, 1H), 7.31-7.63 (m, 7H), 9.38 (brs, 1H).

Intermediate 16: tert-Butyl 1-{[4-(1,1,1,3,3,3-hexafluoro-2-hydroxypropan-2-yl)phenyl]carbamoyl}-5-[(2-methylpropyl)sulfonyl]-1,3-dihydro-2H-isoindole-2-carboxylate

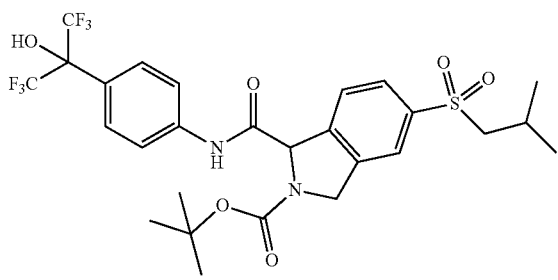 [SMILES: CC(C)CS(=O)(=O)c1ccc2c(c1)CN(C(=O)OC(C)(C)C)C2C(=O)Nc1ccc(C(O)(C(F)(F)F)C(F)(F)F)cc1]

Step 1: tert-Butyl 1-{[4-(1,1,1,3,3,3-hexafluoro-2-hydroxypropan-2-yl)phenyl]carbamoyl}-5-[(2-methylpropyl)sulfanyl]-1,3-dihydro-2H-isoindole-2-carboxylate

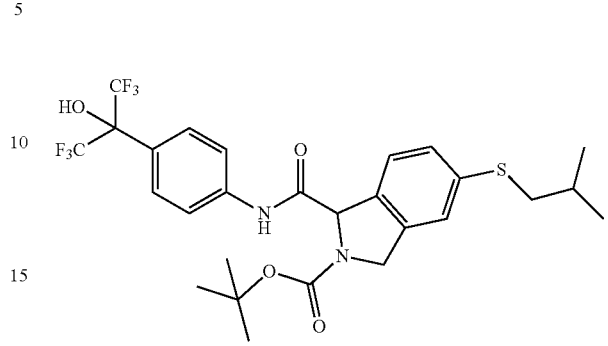

A solution of tert-butyl 5-bromo-1-((4-(1,1,1,3,3,3-hexafluoro-2-hydroxypropan-2-yl)phenyl)carbamoyl)isoindoline-2-carboxylate (150 mg, 0.26 mmol) in dioxane (3 mL) was degassed before Xantphos (14.88 mg, 0.03 mmol), DIPEA (0.054 mL, 0.31 mmol). Pd2(dba)3 (11.77 mg, 0.01 mmol) and 2-methylpropane-1-thiol (162 mg, 1.80 mmol) were added. The reaction was heated to 80° C. for 40 min. The reaction was judged to be complete by LCMS. The reaction was cooled to room temperature and concentrated in vacuo. The residue was purified by flash chromatography eluting with 0-40% EtOAc in heptane. tert-Butyl 1-{[4-(1,1,1,3,3,3-hexafluoro-2-hydroxypropan-2-yl)phenyl]carbamoyl}-5-[(2-methylpropyl)sulfanyl]-1,3-dihydro-2H-isoindole-2-carboxylate (130 mg, 85%) was obtained as a foam.

LC/MS: m/z=591 [M−H]−. 1H NMR (500 MHz, DMSO-d6, mixture of rotamers, 3*:1) 0.98 (d, 6H), 1.34*, 1.45 (s, 9H), 1.73-1.83 (m, 1H), 2.82-2.89 (m, 2H), 4.53-4.74 (m, 2H), 5.43*, 5.46 (d, 1H), 7.23-7.26 (m, 1H), 7.28-7.4 (m, 2H), 7.6-7.66 (m, 2H), 7.7-7.75 (m, 2H), 8.61*, 8.63 (s, 1H), 10.60, 10.61* (s, 1H).

Step 2: tert-Butyl 1-{[4-(1,1,1,3,3,3-hexafluoro-2-hydroxypropan-2-yl)phenyl]carbamoyl}-5-[(2-methylpropyl)sulfonyl]-1,3-dihydro-2H-isoindole-2-carboxylate

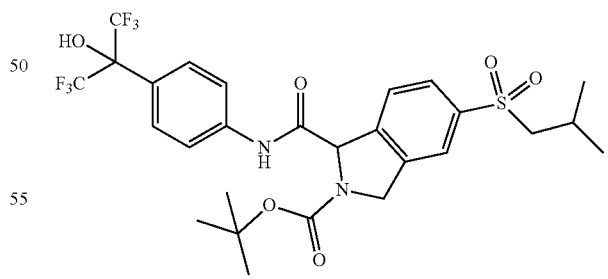

tert-Butyl 1-{[4-(1,1,1,3,3,3-hexafluoro-2-hydroxypropan-2-yl)phenyl]carbamoyl}-5-[(2-methylpropyl)sulfanyl]-1,3-dihydro-2H-isoindole-2-carboxylate (127 mg, 0.21 mmol) was dissolved in DCM (5 mL) and to this mCPBA (≥77%) (115 mg, 0.51 mmol) was added. The reaction was stirred at room temperature for 20 min. After this time LCMS indicated that approximately 20% of the sulphoxide remained. mCPBA (≥77%) (30 mg, 0.13 mmol) was added and the reaction stirred at rt for 10 min. LCMS indicated complete clean conversion to the sulphone had been achieved. The reaction was diluted with DCM and washed twice with 1M aqueous NaOH. The DCM was dried using a phase separator cartridge and concentrated in vacuo to afford tert-butyl 1-{[4-(1,1,1,3,3,3-hexafluoro-2-hydroxypropan-2-yl)phenyl]carbamoyl}-5-[(2-methylpropyl)sulfonyl]-1,3-dihydro-2H-isoindole-2-carboxylate. (130 mg, 97%) as a foam. The material was used in the next step without purification.

LC/MS: m/z=625 [M+H]$^+$. $^1$H NMR (500 MHz, DMSO-d$_6$, mixture of rotamers, 2*:1) δ 0.92-1 (m, 6H), 1.35*, 1.47 (s, 9H), 2-2.08 (m, 1H), 3.2 (t, 2H), 4.69-4.86 (m, 2H), 5.61*, 5.63 (d, 1H), 7.61-7.76 (m, 5H), 7.84-7.88 (m, 1H), 7.95, 7.98* (s, 1H), 8.65 (br s, 1H), 10.76, 10.77* (s, 1H).

Intermediate 17: 2-Acetyl-5-bromo-N-(4-(1,1,1,3,3,3-hexafluoro-2-hydroxypropan-2-yl)phenyl)isoindoline-1-carboxamide

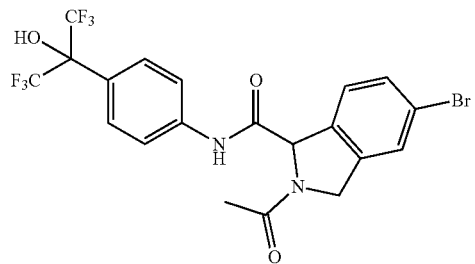 [SMILES: CC(=O)N1Cc2cc(Br)ccc2C1C(=O)Nc1ccc(C(O)(C(F)(F)F)C(F)(F)F)cc1]

Step 1: 5-Bromo-N-(4-(1,1,1,3,3,3-hexafluoro-2-hydroxypropan-2-yl)phenyl)isoindoline-1-carboxamide

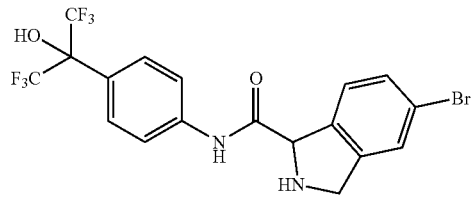 [SMILES: O=C(Nc1ccc(C(O)(C(F)(F)F)C(F)(F)F)cc1)C1NCc2cc(Br)ccc21]

tert-Butyl 5-bromo-1-((4-(1,1,1,3,3,3-hexafluoro-2-hydroxypropan-2-yl)phenyl)carbamoyl)-isoindoline-2-carboxylate (300 mg, 0.51 mmol) was dissolved in DCM (4 mL) and to this TFA (2 mL, 25.96 mmol) was added. The reaction was stirred at room temperature for 1 h. The reaction was concentrated in vacuo and the residue obtained was dissolved in methanol. This was loaded onto a O1 g Isolute™ SCX cartridge (previously flushed with methanol). The cartridge was flushed with methanol and then the product was eluted with 7M NH$_3$ in methanol. The methanolic ammonia was removed in vacuo to afford 5-bromo-N-(4-(1,1,1,3,3,3-hexafluoro-2-hydroxypropan-2-yl)phenyl)isoindoline-1-carboxamide (180 mg, 72.4%). The material was used in the next step without purification.

LC/MS: m/z=483/485 [M+H]$^+$.

Step 2: 2-Acetyl-5-bromo-N-(4-(1,1,1,3,3,3-hexafluoro-2-hydroxypropan-2-yl)phenyl)isoindoline-1-carboxamide

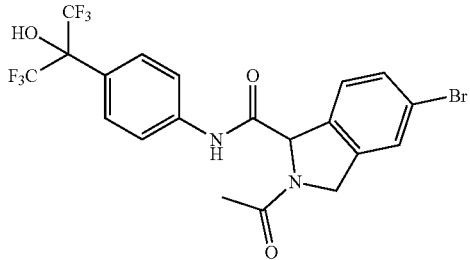 [SMILES: CC(=O)N1Cc2cc(Br)ccc2C1C(=O)Nc1ccc(C(O)(C(F)(F)F)C(F)(F)F)cc1]

5-Bromo-N-(4-(1,1,1,3,3,3-hexafluoro-2-hydroxypropan-2-yl)phenyl)isoindoline-1-carboxamide (180 mg, 0.37 mmol) was suspended in DCM (2 mL) and to this triethylamine (0.104 mL, 0.75 mmol)), acetic acid (0.043 mL, 0.75 mmol) and T3P (50% solution in EtOAc) (0.444 mL, 0.75 mmol) were added. The reaction was stirred at room temperature for 30 min. The reaction was diluted with DCM and washed with 0.5M aqueous HCl and then saturated aqueous NaHCO$_3$. The layers were separated using a phase separator cartridge and the DCM removed in vacuo. The yield was assumed quantitative and the material was used without further purification.

LC/MS: m/z=523/525 [M−H]$^−$

Intermediate 18: (1-(tert-Butyldimethylsilyloxy)cyclopropyl)methyl methanesulphonate

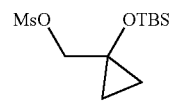

Step 1: 1-(Benzyloxymethyl)cyclopropanol

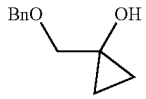

Ethylmagnesium bromide in Et$_2$O (154 mL, 463.36 mmol) was added dropwise to ethyl 2-(benzyloxy)acetate (20 g, 102.98 mmol) and titanium (IV) isopropoxide (30.18 mL, 102.98 mmol) in Et$_2$O (200 mL) cooled to 0'C over a period of 30 minutes under nitrogen. The reaction mixture was quenched with saturated NH$_4$Cl (200 mL) in a bath of ice, extracted with EtOAc (3×250 mL), the organic layer was dried over Na$_2$SO$_4$, filtered and evaporated to afford grey oil. The crude product was purified by flash silica chromatography, elution gradient 0 to 20% EtOAc in petroleum ether. Pure fractions were evaporated to dryness to afford 1-((benzyloxy)methyl)cyclopropan-1-ol (15.0 g, 82%). $^1$H NMR (300 MHz, DMSO-d$_6$) δ 0.47-0.52 (m, 2H), 0.56-0.60 (m, 2H), 3.46 (s, 2H), 4.54 (s, 2H), 5.39 (s, 1H), 7.23-7.40 (m, 5H).

Step 2: 1-(Benzyloxymethyl)cyclopropoxy)(tert-butyl)dimethylsilane

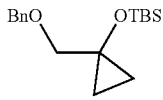

Imidazole (2.86 g, 42.08 mmol) was added to 1-((benzyloxy)methyl)cyclopropan-1-ol (5 g, 28.05 mmol) and TBDMSCl (4.65 g, 30.86 mmol) in DCM (4 mL) cooled to 0° C. under nitrogen. The resulting mixture was stirred at room temperature for 12 hours. The reaction mixture was quenched with water (20 mL), extracted with DCM (3×20 mL), the organic layer was dried over $Na_2SO_4$, filtered and evaporated to afford pale yellow oil. The crude product was purified by flash silica chromatography, elution gradient 0 to 5% EtOAc in petroleum ether. Pure fractions were evaporated to dryness to afford (1-((benzyloxy)methyl)cyclopropoxy)(tert-butyl)dimethylsilane (5.30 g, 64.6%). $^1$H NMR (300 MHz, DMSO-$d_6$) δ 0.09 (s, 6H), 0.60-0.65 (m, 4H), 0.82 (s, 9H), 3.47 (s, 2H), 4.51 (s, 2H), 7.29-7.37 (m, 5H).

Step 3: (1-tert-Butyldimethylsilyloxy)cyclopropyl)methanol

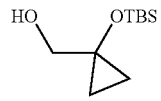

Pd—C (40 mg, 0.38 mmol) was added to (1-((benzyloxy)methyl)cyclopropoxy)(tert-butyl)dimethylsilane (5.3 g, 18.12 mmol) in MeOH (100 mL) under nitrogen. The resulting mixture was stirred at room temperature for 12 hours under hydrogen. The reaction mixture was filtered through celite. The solvent was removed under reduced pressure. The crude product was purified by flash silica chromatography, elution gradient 0 to 5% EtOAc in petroleum ether. Pure fractions were evaporated to dryness to afford (1-((tert-butyldimethylsilyl)oxy)cyclopropyl)methanol (2.3 g, 62.7%).
$^1$H NMR (300 MHz, DMSO-$d_6$) δ 0.10 (s, 6H), 0.53-0.57 (m, 4H), 0.82 (s, 9H), 3.43 (d, J=5.7 Hz, 2H), 4.65 (t, J=5.7 Hz, 1H).

Step 4: (2-(9H-Fluoren-9-yl)methyl 1-methyl 5-(benzylthio)isoindoline-1,2-dicarboxylate

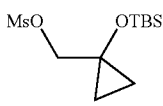

Et$_3$N (1.891 mL, 13.56 mmol) was added to (1-((tert-butyldimethylsilyl)oxy)cyclopropyl)methanol (1.83 g, 9.04 mmol) and MsCl (0.846 mL, 10.85 mmol) in DCM (30 mL) cooled to 0° C. under nitrogen. The resulting solution was stirred at room temperature for 3 hours. The reaction mixture was quenched with water (25 mL), extracted with DCM (2×25 mL), the organic layer was dried over $Na_2SO_4$, filtered and evaporated to afford (1-((tert-butyldimethylsilyl)oxy)cyclopropyl)methyl methanesulfonate (1.85 g, 72.9%).
$^1$H NMR (300 MHz, CDCl$_3$) δ 0.17 (s, 6H), 0.76-0.95 (m, 13H), 3.09 (s, 3H), 4.22 (s, 2H).

Intermediate 19: (1-Cyanocyclopropyl)methyl 4-methylbenzenesulphonate

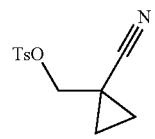 [SMILES: Cc1ccc(S(=O)(=O)OCC2(C#N)CC2)cc1]

Et$_3$N (8.97 mL, 64.36 mmol) was added to 1-(hydroxymethyl)cyclopropane-1-carbonitrile (5 g, 51.48 mmol) and TsCl (11.78 g, 61.78 mmol) in DCM (100 mL) cooled to 0° C. under nitrogen. The resulting solution was stirred at room temperature for 2 hours. The reaction mixture was quenched with water (20 mL), extracted with DCM (3×20 mL), the organic layer was dried over $Na_2SO_4$, filtered and evaporated to afford white solid. The crude product was purified by flash silica chromatography, elution gradient 0 to 100% DCM in petroleum ether. Pure fractions were evaporated to dryness to afford (1-cyanocyclopropyl)methyl 4-methylbenzenesulfonate (5.20 g, 40%).
LC/MS: m/z=252 [M+H]$^+$. $^1$H NMR (300 MHz, CDCl$_3$) δ 1.09 (dd, J=7.5, 5.7 Hz, 2H), 1.38 (dd, J=7.5, 5.4 Hz, 2H), 2.48 (s, 3H), 4.01 (s, 2H), 7.40 (d, J=8.1 Hz, 2H), 7.84 (d, J=8.1 Hz, 2H).

Intermediate 20: 9H-Fluoren-9-yl 5-{[(1-cyanocyclopropyl)methyl]sulfonyl}-1-{[4-(1,1,1,3,3,3-hexafluoro-2-hydroxypropan-2-yl)phenyl]carbamoyl}-1,3-dihydro-2H-isoindole-2-carboxylate

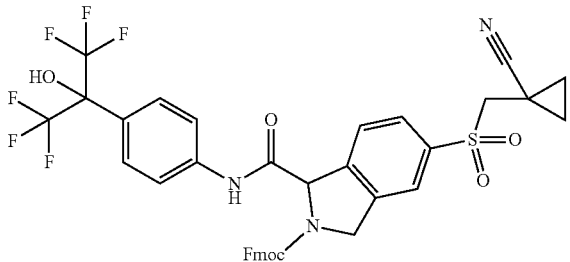

Step 1: tert-Butyl 5-(benzylthio)1-oxoisoindoline-2-carboxylate

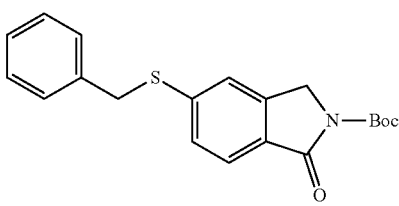 [SMILES: CC(C)(C)OC(=O)N1Cc2cc(SCc3ccccc3)ccc2C1=O]

(Boc)₂O (87.20 g, 400.00 mmol) was added to 5-(benzylthio)isoindolin-1-one (68.00 g, 266.7 mmol) and DMAP (48.80 g, 400 mmol) in MeCN (900 mL) under nitrogen. The resulting mixture was stirred at room temperature for 3 hours. The solvent was removed under reduced pressure. The crude product was purified by crystallisation from MeCN to afford tert-butyl 5-(benzylthio)-1-oxoisoindoline-2-carboxylate (60.0 g, 63%). LC/MS: m/z=300 [M-tBu+H]⁺. ¹H NMR (300 MHz, DMSO-d₆) δ 1.50 (s, 9H), 4.37 (s, 2H), 4.72 (s, 2H), 7.25-7.64 (m, 8H).

Step 2: tert-Butyl 5-(benzylthio)1-hydroxyisoindoline-2-carboxylate

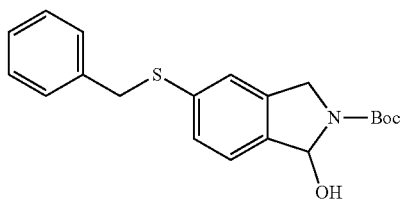 [SMILES: CC(C)(C)OC(=O)N1Cc2cc(SCc3ccccc3)ccc2C1O]

Lithium tri-tert-butoxyaluminum hydride (32.2 g, 126.60 mmol) was added to tert-butyl 5-(benzylthio)-1-oxoisoindoline-2-carboxylate (30 g, 84.40 mmol) in THF (750 mL) cooled to 0° C. under nitrogen. The resulting solution was stirred at room temperature for 2 hours. The reaction mixture was quenched with saturated NH₄Cl (500 mL), extracted with EtOAc (3×500 mL), the organic layer was dried over Na₂SO₄, filtered and evaporated to afford tert-butyl 5-(benzylthio)-1-hydroxyisoindoline-2-carboxylate (29.6 g, 98%).

LC/MS: m/z=340 [M-OH]⁺. ¹H NMR (300 MHz, DMSO-d₆) δ 1.48 (s, 9H), 4.27 (s, 2H), 4.45-4.48 (m, 2H), 6.03-6.25 (m, 2H), 7.24-7.40 (m, 8H).

Step 3: tert-Butyl 5-(benzylthio)1-methoxyisoindoline-2-carboxylate

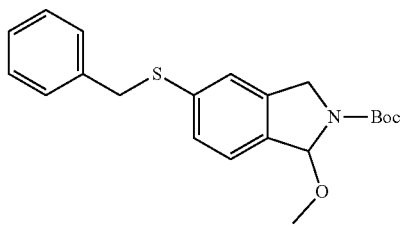 [SMILES: COC1c2ccc(SCc3ccccc3)cc2CN1C(=O)OC(C)(C)C]

Silver (I) oxide (77 g, 331.22 mmol) was added to tert-butyl 5-(benzylthio)-1-hydroxyisoindoline-2-carboxylate (29.6 g, 82.80 mmol) and MeI (31.1 mL, 496.83 mmol) in toluene (650 mL) under nitrogen. The resulting mixture was stirred at 80° C. for 4 hours. The reaction mixture was filtered through celite. The solvent was removed under reduced pressure. The product tert-butyl 5-(benzylthio)-1-methoxyisoindoline-2-carboxylate (29.6 g, 96%) was used in the next step directly without further purification.

LC/MS: m/z=340 [M-MeO]⁺. ¹H NMR (400 MHz, DMSO-d₆, mixture of rotamers, 1:1) δ 1.47 (s, 9H), 3.14 (brs, 3H), 4.27 (s, 2H), 4.44-4.57 (m, 2H), 6.14, 6.19 (s, 1H), 7.22-7.38 (m, 8H).

Step 4: tert-Butyl 5-(benzylthio)1-cyanoisoindoline-2-carboxylate

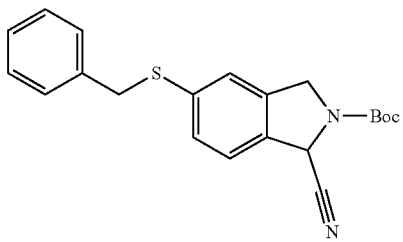 [SMILES: CC(C)(C)OC(=O)N1Cc2cc(SCc3ccccc3)ccc2C1C#N]

BF₃.Et₂O (15.15 mL, 119.52 mmol) was added dropwise to tert-butyl 5-(benzylthio)-1-methoxyisoindoline-2-carboxylate (29.6 g, 79.68 mmol) and trimethylsilanecarbonitrile (11.86 g, 119.52 mmol) in DCM (600 mL) cooled to −78'C under nitrogen. The resulting solution was stirred at −78° C. for 1 hour. The reaction mixture was quenched with saturated NaHCO₃ (5 mL), extracted with DCM (3×10 mL), the organic layer was dried over Na₂SO₄, filtered and evaporated to afford red oil. The crude product was purified by flash silica chromatography, elution gradient 0 to 5% EtOAc in petroleum ether. Pure fractions were evaporated to dryness to afford tert-butyl 5-(benzylthio)-1-cyanoisoindoline-2-carboxylate (15.50 g, 53.1%).

LC/MS: m/z=430 [M+Na+MeCN]⁺. ¹H NMR (300 MHz, DMSO-d₆, mixture of rotamers, 1.1*:1) δ 1.49, 1.50* (s, 9H), 4.30 (s, 2H), 4.61*, 4.63 (s, 2H), 5.99, 6.00* (s, 1H), 7.22-7.47 (m, 8H).

Step 5: Methyl 5-(benzylthio)isoindoline-1-carboxylate

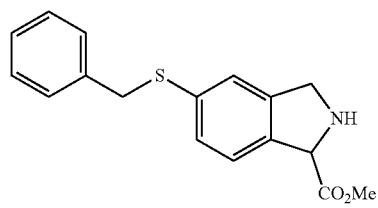 [SMILES: COC(=O)C1NCc2cc(SCc3ccccc3)ccc21]

Hydrogen chloride (12N, 43 mL, 516.00 mmol) was added slowly to tert-butyl 5-(benzylthio)-1-cyanoisoindoline-2-carboxylate (19 g, 51.91 mmol) in MeOH (30 mL) cooled to 0° C. The resulting mixture was stirred at room temperature for 18 hours. The reaction mixture was basified with 2M NaOH (200 mL), extracted with DCM (3×200 mL), the organic layer was dried over Na₂SO₄, filtered and evaporated to afford dark oil. The crude product was purified by flash silica chromatography, elution gradient 0 to 10% MeOH in DCM. Pure fractions were evaporated to dryness to afford methyl 5-(benzylthio)isoindoline-1-carboxylate (8.0 g, 51.5%).

LC/MS: m/z=300 [M+H]⁺. ¹H NMR (300 MHz, DMSO-d₆) δ 3.65 (s, 3H), 4.02-4.24 (m, 4H), 4.89 (s, 1H), 7.18-7.37 (m, 8H).

Step 6: 2-(9H-Fluoren-9-yl)methyl 1-methyl 5-(benzylthio)isoindoline-1,2-dicarboxylate

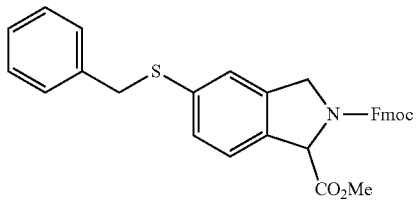

K$_2$CO$_3$ (44.6 g, 322.83 mmol) was added to (9H-fluoren-9-yl)methyl carbonochloridate (3.48 g, 13.45 mmol), methyl 5-(benzylthio)-1H-isoindole-1-carboxylate (4 g, 13.45 mmol) in 1,4-dioxane (15 mL) and water (60.0 mL) at 0° C. under air. The resulting solution was stirred at room temperature for 2 hours. The reaction mixture was treated with water (75 mL), extracted with DCM (3×75 mL), the organic layer was dried over Na$_2$SO$_4$, filtered and evaporated to afford black solid. The crude product was purified by flash silica chromatography, elution gradient 0 to 5% EtOAc in petroleum ether. Pure fractions were evaporated to dryness to afford 2-((9H-fluoren-9-yl)methyl)-1-methyl-5-(benzylthio)isoindoline-1,2-dicarboxylate (4.50 g, 64.1%).

LC/MS: m/z=522 [M+H]$^+$. $^1$H NMR (300 MHz, DMSO-d$_6$, mixture of rotamers, 1.1*:1) δ 3.59, 3.66* (s, 3H), 4.19-4.50 (m, 5H), 4.64-4.74 (m, 2H), 5.41, 5.48* (s, 1H), 7.21-7.93 (m, 16H).

Step 7: 2-(9H-Fluoren-9-yl)methyl 1-methyl 5-(chlorosulphonyl)isoindoline-1,2-dicarboxylate

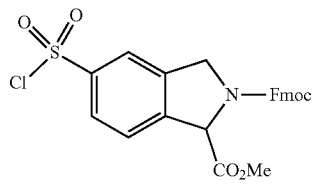

Formic acid (60 mL, 1604.35 mmol) was added to 2-((9H-fluoren-9-yl)methyl) 1-methyl 5-(benzylthio)isoindoline-1,2-dicarboxylate (5.08 g, 9.74 mmol), NCS (6.50 g, 48.69 mmol) and sodium chloride (2.85 g, 48.69 mmol) in DCM (140 mL) and water (60 mL) under nitrogen. The resulting solution was stirred at 25° C. for 2 hours. The reaction mixture was treated with water (150 mL), extracted with DCM (3×200 mL), the organic layer was dried over Na$_2$SO$_4$, filtered and evaporated to afford 2-((9H-fluoren-9-yl)methyl) 1-methyl 5-(chlorosulfonyl)isoindoline-1,2-dicarboxylate (4.40 g, 90%). The product was used in the next step directly without further purification.

LC/MS: m/z=498 [M+H]$^+$.

Step 8: 2-(9H-Fluoren-9-yl)methyl 1-methyl 5-mercaptoisoindoline-1,2-dicarboxylate

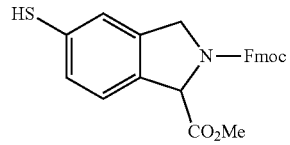

Ph$_3$P (9.48 g, 36.15 mmol) was added to 2-((9H-fluoren-9-yl)methyl) 1-methyl 5-(chlorosulfonyl)isoindoline-1,2-dicarboxylate (6 g, 12.05 mmol) in DMF (18 mL) and DCM (180 mL) at 0° C. under nitrogen. The resulting solution was stirred at 30° C. for 4 hours. The reaction mixture was quenched with water (100 mL), extracted with DCM (3×100 mL), the organic layer was dried over Na$_2$SO$_4$, filtered and evaporated to afford brown oil. The crude product was purified by flash C18-flash chromatography, elution gradient 0 to 60% MeCN in water. Pure fractions were evaporated to dryness to afford 2-((9H-fluoren-9-yl)methyl) 1-methyl 5-mercaptoisoindoline-1,2-dicarboxylate (1.6 g, 30.8%).

LC/MS: m/z=432 [M+H]$^+$. $^1$H NMR (300 MHz, CDCl$_3$, mixture of rotamers, 1.1*:1) δ 3.53, 3.55* (s, 1H), 3.67, 3.79* (s, 3H), 4.24, 4.36* (t, J=6.7 Hz, 1H), 4.43-4.59 (m, 2H), 4.74-4.91 (m, 2H), 5.39-5.43, 5.52-5.56 (m, 1H), 7.18-7.25 (m, 2H), 7.28-7.48 (m, 5H), 7.55-7.72 (m, 2H), 7.76-7.82 (m, 2H).

Step 9: 2-(9H-Fluoren-9-yl)methyl 1-methyl 5-((1-cyanocyclopropyl)methylthio)isoindoline-1,2-dicarboxylate

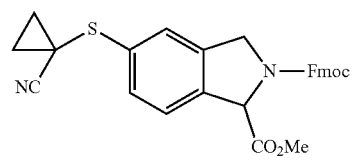

K$_2$CO$_3$ (4.68 g, 14.37 mmol) was added to 2-((9H-fluoren-9-yl)methyl) 1-methyl 5-mercaptoisoindoline-1,2-dicarboxylate (3.1 g, 7.18 mmol) and (1-cyanocyclopropyl)methyl 4-methylbenzenesulfonate (2.72 g, 10.78 mmol) in DMF (100 mL) at 0° C. under nitrogen. The resulting solution was stirred at room temperature for 2 hours. The reaction mixture was quenched with water (100 mL), extracted with DCM (3×125 mL), the organic layer was dried over Na$_2$SO$_4$, filtered and evaporated to afford white solid. The crude product was purified by flash silica chromatography, elution gradient 0 to 25% EtOAc in petroleum ether. Pure fractions were evaporated to dryness to afford 2-((9H-fluoren-9-yl)methyl) 1-methyl 5-(((1-cyanocyclopropyl)methyl)thio)isoindoline-1,2-dicarboxylate (3.39 g, 92%).

LC/MS: m/z=511 [M+H]$^+$. $^1$H NMR (300 MHz, CDCl$_3$, mixture of rotamers, 1.1*:1) δ 0.89-0.93 (m, 2H), 1.29-1.34 (m, 2H), 3.07, 3.08* (s, 2H), 3.67, 3.81* (s, 3H), 4.22, 4.33* (t, J=6.7 Hz, 1H), 4.39-4.60 (m, 2H), 4.74-4.94 (m, 2H), 5.40, 5.60* (brs, 1H), 7.29-7.47 (m, 7H), 7.54-7.71 (m, 2H), 7.74-7.83 (m, 2H).

Step 10: 2-(9H-Fluoren-9-yl)methyl 1-methyl 5-((1-cyanocyclopropyl)methylsulfonyl)isoindoline-1,2-dicarboxylate

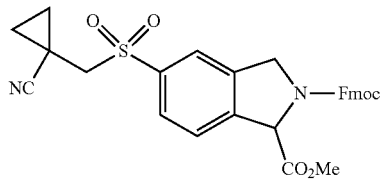

mCPBA (3.44 g, 19.92 mmol) was added to 2-((9H-fluoren-9-yl)methyl) 1-methyl 5-(((1-cyanocyclopropyl)methyl)thio)isoindoline-1,2-dicarboxylate (3.39 g, 6.64 mmol) in DCM (100 mL) under nitrogen. The resulting solution was stirred at room temperature for 2 hours. The reaction mixture was treated with saturated NaHCO$_3$ (100 mL), extracted with DCM (3×150 mL), the organic layer was dried over Na$_2$SO$_4$, filtered and evaporated to afford white solid. The crude product was purified by flash silica chromatography, elution gradient 0 to 30% EtOAc in petroleum ether. Pure fractions were evaporated to dryness to afford 2-((9H-fluoren-9-yl)methyl) 1-methyl 5-(((1-cyanocyclopropyl)methyl)sulfonyl)isoindoline-1,2-dicarboxylate (3.20 g, 89%).

LC/MS: m/z=543 [M+H]$^+$. $^1$H NMR (300 MHz, CDCl$_3$, mixture of rotamers, 1.1*:1) δ 1.19-1.27 (m, 2H), 1.39-1.49 (m, 2H), 3.22, 3.24* (s, 2H), 3.64, 3.79* (s, 3H), 4.22, 4.34* (t, J=6.7 Hz, 1H), 4.42-4.65 (m, 2H), 4.79-5.03 (m, 2H), 5.51, 5.69* (brs, 1H), 7.28-7.49 (m, 4H), 7.53-7.85 (m, 5H), 7.90-8.02 (m, 2H).

Step 11: 2-(((9H-Fluoren-9-yl)methoxy)carbonyl)-5-((1-cyanocyclopropyl)methylsulfonyl)isoindoline-1-carboxylic acid

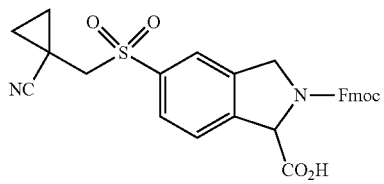

Lithium iodide (0.740 g, 5.53 mmol) was added to 2-((9H-fluoren-9-yl)methyl) 1-methyl 5-(((1-cyanocyclopropyl)methyl)sulfonyl)isoindoline-1,2-dicarboxylate (3 g, 5.53 mmol) in EtOAc (100 mL) under nitrogen. The resulting solution was stirred at 70° C. for 15 hours. The reaction mixture was treated with 0.1M HCl (50 mL), extracted with EtOAc (3×100 mL), the organic layer was dried over Na$_2$SO$_4$, filtered and evaporated to afford white solid. The crude product was purified by flash silica chromatography, elution gradient 0 to 10% MeOH in DCM. Pure fractions were evaporated to dryness to afford 2-(((9H-fluoren-9-yl)methoxy)carbonyl)-5-(((1-cyanocyclopropyl)methyl)sulfonyl)isoindoline-1-carboxylic acid (2.2 g, 75%).

LC/MS: m/z=529 [M+H]$^+$. $^1$H NMR (300 MHz, DMSO-d$_6$) δ 1.01-1.05 (m, 2H), 1.30-1.34 (m, 2H), 3.70 (s, 2H), 4.10-4.39 (m, 3H), 4.78-4.86 (m, 2H), 5.23-5.39 (m, 1H), 7.32-7.95 (m, 11H).

Step 12: (9H-Fluoren-9-yl)methyl 5-{[(1-cyanocyclopropyl)methyl]sulfonyl}-1-{[4-(1,1,1,3,3,3-hexafluoro-2-hydroxypropan-2-yl)phenyl]carbamoyl}-1,3-dihydro-2H-isoindole-2-carboxylate

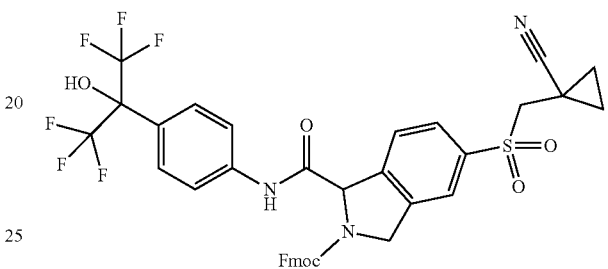

DIPEA (0.991 mL, 5.68 mmol) was added to 2-(((9H-fluoren-9-yl)methoxy)carbonyl)-5-(((1-cyanocyclopropyl)methyl)sulfonyl)isoindoline-1-carboxylic acid (1 g, 1.89 mmol), 2-(4-aminophenyl)-1,1,1,3,3,3-hexafluoropropan-2-ol (0.981 g, 3.78 mmol) and HATU (1.439 g, 3.78 mmol) in DCM (20 mL) under nitrogen. The resulting solution was stirred at room temperature for 2 hours. The reaction mixture was treated with saturated NH$_4$Cl (20 mL), extracted with DCM (3×25 mL), the organic layer was dried over Na$_2$SO$_4$, filtered and evaporated to afford (9H-fluoren-9-yl)methyl 5-(((1-cyanocyclopropyl)methyl)sulfonyl)-1-((4-(1,1,1,3,3,3-hexafluoro-2-hydroxypropan-2-yl)phenyl)carbamoyl)isoindoline-2-carboxylate (1.200 g, 82%), which was used in the next step without further purification.

LC/MS: m/z=770 [M+H]$^+$. $^1$H NMR (300 MHz, DMSO-d$_6$) δ 0.99-1.07 (m, 2H), 1.29-1.34 (m, 2H), 3.73 (s, 2H), 4.15-4.39 (m, 3H), 4.93-5.05 (m, 2H), 5.75-5.85 (m, 1H), 6.95-8.08 (m, 15H), 8.67 (s, 1H), 10.86-10.92 (m, 1H).

Intermediate 21: tert-Butyl 5-{[(1-{[tert-butyl(dimethyl)silyl]oxy}cyclopropyl)methyl]sulfonyl}-1-{[4-(1,1,1,3,3,3-hexafluoro-2-hydroxypropan-2-yl)phenyl]carbamoyl}-1,3-dihydro-2H-isoindole-2-carboxylate

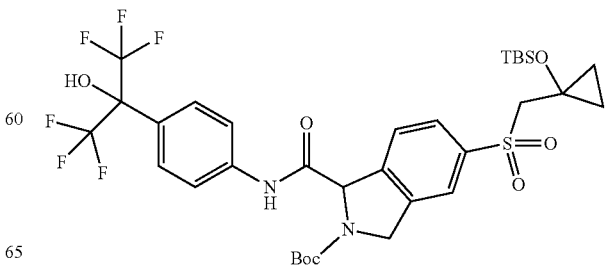

Step 1: tert-Butyl 5-{[(1-{[tert-butyl(dimethyl)silyl]oxy}cyclopropyl)methyl]sulfanyl}-1-{[4-(1,1,1,3,3,3-hexafluoro-2-hydroxypropan-2-yl)phenyl]carbamoyl}-1,3-dihydro-2H-isoindole-2-carboxylate

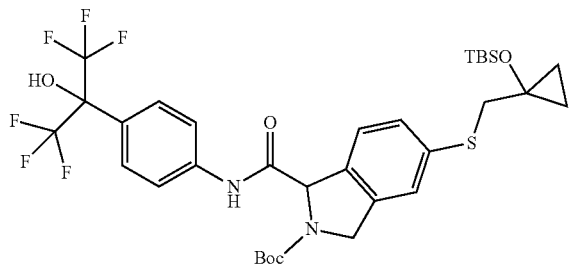 [SMILES: CC(C)(C)OC(=O)N1Cc2cc(SCC3(O[Si](C)(C)C(C)(C)C)CC3)ccc2C1C(=O)Nc1ccc(C(O)(C(F)(F)F)C(F)(F)F)cc1]

(1-((tert-Butyldimethylsilyl)oxy)cyclopropyl)methyl methanesulfonate (1.8 g, 6.42 mmol) was added to tert-butyl 1-((4-(1,1,1,3,3,3-hexafluoro-2-hydroxypropan-2-yl)phenyl)carbamoyl)-5-((3-methoxy-3-oxopropyl)thio)isoindoline-2-carboxylate (2.7 g, 4.34 mmol) and potassium 2-methylpropan-2-olate (1.947 g, 17.35 mmol) in THF (70 mL) at −78° C. under nitrogen. The resulting solution was stirred at 60° C. for 3 hours. The reaction mixture was treated with water (75 mL), extracted with DCM (3×100 mL), the organic layer was dried over $Na_2SO_4$, filtered and evaporated to afford white solid. The crude product was purified by flash silica chromatography, elution gradient 0 to 25% EtOAc in petroleum ether. Pure fractions were evaporated to dryness to afford tert-butyl 5-(((1-((tert-butyldimethylsilyl)oxy)cyclopropyl)methyl)thiohi)-1-((4-(1,1,1,3,3,3-hexafluoro-2-hydroxypropan-2-yl)phenyl)carbamoyl)isoindoline-2-carboxylate (2.60 g, 83%).

LC/MS: m/z=721 [M+H]$^+$. $^1$H NMR (300 MHz, DMSO-$d_6$, mixture of rotamers, 1.5*:1) δ 0.10 (s, 6H), 0.61-0.68 (m, 2H), 0.72-0.77 (m, 2H), 0.82 (s, 9H), 1.35*, 1.46 (s, 9H), 3.22, 3.23* (s, 2H), 4.54-4.77 (m, 2H), 5.39-5.49 (m, 1H), 7.21-7.43 (m, 3H), 7.56-7.77 (m, 4H), 8.61*, 8.63 (s, 1H), 10.60 (s, 1H).

Step 2: tert-Butyl 5-{[(1-{[tert-butyl(dimethyl)silyl]oxy}cyclopropyl)methyl]sulfonyl}-1-{[4-(1,1,1,3,3,3-hexafluoro-2-hydroxypropan-2-yl)phenyl]carbamoyl}-1,3-dihydro-2H-isoindole-2-carboxylate

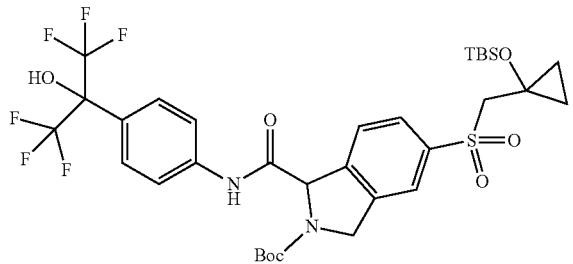 [SMILES: CC(C)(C)OC(=O)N1Cc2cc(S(=O)(=O)CC3(O[Si](C)(C)C(C)(C)C)CC3)ccc2C1C(=O)Nc1ccc(C(O)(C(F)(F)F)C(F)(F)F)cc1]

mCPBA (1.867 g, 10.82 mmol) was added to tert-butyl 5-(((1-((tert-butyldimethylsilyl)oxy)cyclopropyl)methyl)thio)-1-((4-(1,1,1,3,3,3-hexafluoro-2-hydroxypropan-2-yl)phenyl)carbamoyl)isoindoline-2-carboxylate (2.6 g, 3.61 mmol) in DCM (50 mL) under nitrogen. The resulting solution was stirred at rt for 1 hour. The reaction mixture was treated with saturated $Na_2CO_3$ (50 mL), extracted with DCM (3×75 mL), the organic layer was dried over $Na_2SO_4$, filtered and evaporated to afford white solid. The crude product was purified by flash silica chromatography, elution gradient 0 to 25% EtOAc in petroleum ether. Pure fractions were evaporated to dryness to afford tert-butyl 5-(((1-((tert-butyldimethylsilyl)oxy)cycloplfonyl)-1-((4-(1,1,1,3,3,3-hexafluoro-2-hydroxypropan-2-yl)phenyl)carbamoyl)isoindoline-2-carboxylate (2.2 g, 81%).

LC/MS: m/z=753 [M+H]$^+$. $^1$H NMR (300 MHz, DMSO-$d_6$, mixture of rotamers, 1.8*:1) δ−0.12, −0.08* (s, 6H), 0.61 (s, 9H), 0.66-0.79 (m, 4H), 1.37*, 1.48 (s, 9H), 3.45-3.65 (m, 2H), 4.66-4.90 (m, 2H), 5.60*, 5.62 (brs, 1H), 7.59-7.78 (m, 5H), 7.82-7.98 (m, 2H), 8.61*, 8.62 (s, 1H), 10.71 (s, 1H).

Intermediate 22: (R)-tert-Butyl 1-((4-(1,1,1,3,3,3-hexafluoro-2-hydroxypropan-2-yl)phenyl)carbamoyl)-5-(methylsulfonyl)isoindoline-2-carboxylate

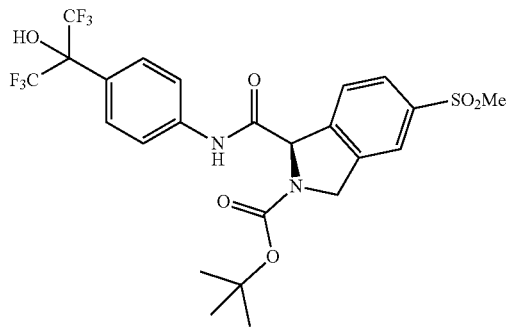 [SMILES: CC(C)(C)OC(=O)N1Cc2cc(S(C)(=O)=O)ccc2[C@@H]1C(=O)Nc1ccc(C(O)(C(F)(F)F)C(F)(F)F)cc1]

A 2 L reactor, equipped with a thermometer, was charged with (R)-2-(tert-butoxycarbonyl)-5-(methylsulfonyl)isoindoline-1-carboxylic acid (110 g, 307.08 mmol) under nitrogen. EtOAc (1000 mL) was added and the resulting mixture was stirred for 1 min. The vessel was then charged with 2-(4-aminophenyl)-1,1,1,3,3,3-hexafluoropropan-2-ol (84 g, 307.08 mmol), the resulting mixture was cooled to +10 OC and then pyridine (27.3 mL, 337.79 mmol) was added. The reaction was cooled to +5 OC, and T3P (50% in EtOAc, 274 mL, 460.62 mmol) was added at 5° C. over 15 min. The temperature rose to 13.3° C. over the addition, and the resulting solution was allowed to reach room temperature over 20 minutes and left stirring overnight at room temperature. The mixture was cooled to +5 OC, and an aqueous solution of citric acid (iN) was added, followed by 500 mL of EtOAc. Stirring was continued for 15 min, then stirring was stopped and the layers separated. The organic layer was washed with aqueous citric acid (1000 mL), and then twice with saturated aqueous $NaHCO_3$ (1000 mL), followed by brine (1000 mL). The organic layer was separated and concentrated under reduced pressure (bath temperature 32° C.). The crude material was dissolved in 550 mL of EtOH at rt, and water (440 mL) was slowly added dropwise over 15 min. Seed crystals (20 mg), were added, and the mixture was left overnight at 20° C. The precipitate was isolated by filtration, washed with a 4:1 mixture of $H_2O$/EtOH (220 mL), and dried under high vacuum. The title compound (132 g, quantitative) was used in the next step without further purification.

LC/MS: m/z=581 [M−H]$^−$, 583 [M+H]$^+$. $^1$H NMR (400 MHz, DMSO-$d_6$, mixture of rotamers, 1.9*:1) δ 1.34*, 1.46 (s, 9H), 3.20, 3.21* (s, 3H), 4.69-4.88 (m, 2H), 5.60*, 5.62

(s, 1H), 7.6-7.76 (m, 5H), 7.86-7.92 (m, 1H), 7.98, 8.01* (s, 1H), 8.68*, 8.69 (s, 1H), 10.76 (s, 1H).

The seed crystals were obtained from (R)-tert-butyl 1-((4-(1,1,1,3,3,3-hexafluoro-2-hydroxypropan-2-yl)phenyl)carbamoyl)-5-(methylsulfonyl)isoindoline-2-carboxylate (0.5 g, 0.86 mmol, prepared as described above for the large scale preparation of intermediate 22). This material was dissolved in ethanol (2.5 ml). Water (2 ml) was added until the point the mixture just became turbid. Spontaneous crystallization occured after about 30 seconds, and (R)-tert-butyl 1-((4-(1,1,1,3,3,3-hexafluoro-2-hydroxypropan-2-yl)phenyl)carbamoyl)-5-(methylsulfonyl)isoindoline-2-carboxylate was obtained after filtration and drying as a colorless solid (0.38 g, 76%).

Intermediate 23: (1-Fluorocyclopropyl)methyl methanesulphonate

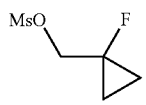

Step 1: (1-Fluorocyclopropyl)methanol

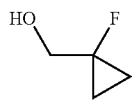

LiAlH$_4$ (0.912 g, 24.02 mmol) was added dropwise to 1-fluorocyclopropane-1-carboxylic acid (2.5 g, 24.02 mmol) in THF (1 mL) cooled to 0° C. under nitrogen. The resulting solution was stirred at rt for 2 hours. The reaction mixture was quenched with Na$_2$SO$_4$·10H$_2$O, extracted with Et$_2$O (3×20 mL), the organic layer was dried over Na$_2$SO$_4$, filtered and evaporated to afford pale yellow oil. The crude product was purified by flash silica chromatography, elution gradient 0 to 20% EtOAc in petroleum ether. Pure fractions were evaporated to dryness to afford (1-fluorocyclopropyl)methanol (0.700 g, 32.3%) as a colourless oil.

$^1$H NMR (400 MHz, DMSO-d$_6$): δ 0.63-0.69 (m, 2H), 0.88-0.97 (m, 2H), 3.62 (dd, 2H), 5.00 (t, 1H).

Step 2: (1-Fluorocyclopropyl)methyl methanesulphonate

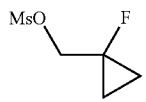

Et$_3$N (0.464 mL, 3.33 mmol) was added to (1-fluorocyclopropyl)methanol (150 mg, 1.66 mmol) and MsCl (0.195 mL, 2.50 mmol) in DCM (2 mL) cooled to 0° C. under nitrogen. The resulting solution was stirred at room temperature for 1 hour. The reaction mixture was quenched with water (5 mL), extracted with DCM (3×5 mL), the organic layer was dried over Na$_2$SO$_4$, filtered and evaporated to afford (1-fluorocyclopropyl)methyl methanesulfonate (250 mg, 89%) as pale yellow oil.

$^1$H NMR (300 MHz, CDCl$_3$) δ 0.86-0.93 (m, 2H), 1.21-1.32 (m, 2H), 3.13 (s, 3H), 4.50 (d, 2H).

Intermediate 24: tert-Butyl 5-{[(1-fluorocyclopropyl)methyl]sulfonyl}-1-{[4-(1,1,1,3,3,3-hexafluoro-2-hydroxypropan-2-yl)phenyl]carbamoyl}-1,3-dihydro-2H-isoindole-2-carboxylate

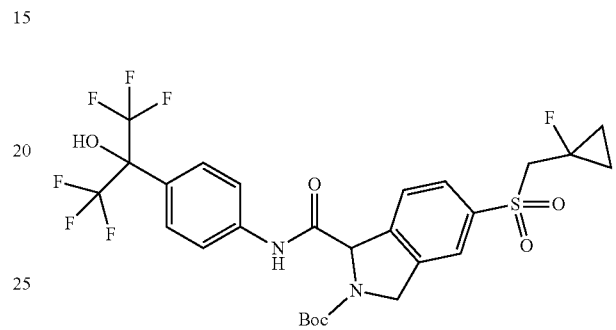

Step 1: tert-Butyl 5-{[(1-fluorocyclopropyl)methyl]sulfanyl}-1-{[4-(1,1,1,3,3,3-hexafluoro-2-hydroxypropan-2-yl)phenyl]carbamoyl}-1,3-dihydro-2H-isoindole-2-carboxylate

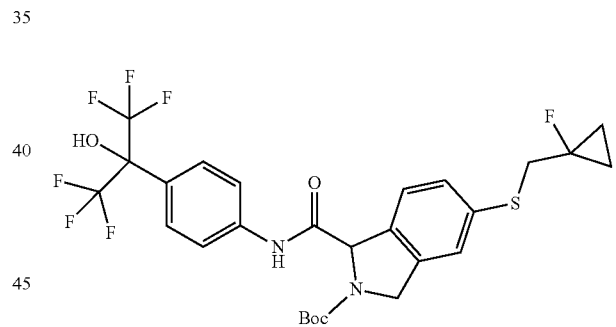

KO$^t$Bu in THF (2.168 mL, 2.17 mmol) was added to tert-butyl 1-((4-(1,1,1,3,3,3-hexafluoro-2-hydroxypropan-2-yl)phenyl)carbamoyl)-5-((3-methoxy-3-oxopropyl)thio)isoindoline-2-carboxylate (450 mg, 0.72 mmol) and (1-fluorocyclopropyl)methyl methanesulfonate (243 mg, 1.45 mmol) in THF (10 mL) cooled to 0° C. under nitrogen. The resulting solution was stirred at 60° C. for 1 hour. The reaction mixture was quenched with water (20 mL), extracted with EtOAc (3×20 mL), the organic layer was dried over Na$_2$SO$_4$, filtered and evaporated to afford tert-butyl 5-(((1-fluorocyclopropyl)methyl)thio)-14-(4-(1,1,1,3,3,3-hexafluoro-2-hydroxypropan-2-yl)phenyl) carbamoyl) isoindoline-2-carboxylate (400 mg, 91%) as an oil. LC/MS: m/z=609 [M+H]$^+$. $^1$H NMR (300 MHz, DMSO-d$_6$, mixture of rotamers, 1.6*:1) δ 0.70-0.78 (m, 2H), 0.99-1.14 (m, 2H), 1.35*, 1.47 (s, 9H), 3.51, 3.52* (d, 2H), 4.50-4.76 (m, 2H), 5.47*, 5.48 (s, 1H), 7.31-7.39 (m, 2H), 7.44-7.49 (m, 1H), 7.59-7.69 (m, 2H), 7.70-7.79 (m, 2H), 8.63*, 8.65 (s, 1H), 10.64 (s, 1H).

Step 2: tert-Butyl 5-{[(1-fluorocyclopropyl)methyl]sulfonyl}-1-{[4-(1,1,1,3,3,3-hexafluoro-2-hydroxypropan-2-yl)phenyl]carbamoyl}-1,3-dihydro-2H-isoindole-2-carboxylate

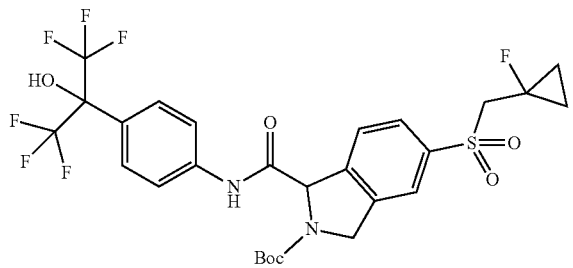 [SMILES: CC(C)(C)OC(=O)N1Cc2cc(S(=O)(=O)CC3(F)CC3)ccc2C1C(=O)Nc1ccc(C(O)(C(F)(F)F)C(F)(F)F)cc1]

mCPBA (247 mg, 1.43 mmol) was added slowly to tert-butyl 5-(((1-fluorocyclopropyl)methyl)thio)-1-((4-(1,1,1,3,3,3-hexafluoro-2-hydroxypropan-2-yl)phenyl)carbamoyl)isoindoline-2-carboxylate (290 mg, 0.48 mmol) in DCM (15 mL) at 0° C. under nitrogen. The resulting solution was stirred at room temperature for 3 hours. The reaction mixture was quenched with water (15 mL), extracted with DCM (3×10 mL), the organic layer was dried over Na$_2$SO$_4$, filtered and evaporated to afford brown oil. The crude product was purified by flash silica chromatography, elution gradient 10 to 20% EtOAc in petroleum ether. Pure fractions were evaporated to dryness to afford tert-butyl 5-(((1-fluorocyclopropyl)methyl)sulfonyl)-1-((4-(1,1,1,3,3,3-hexafluoro-2-hydroxypropan-2-yl)phenyl)carbamoyl)isoindoline-2-carboxylate (200 mg, 65.5%) as a solid.

LC/MS: m/z=641 [M+H]$^+$. $^1$H NMR (300 MHz, DMSO-d$_6$, mixture of rotamers, 1.2*:1) δ 0.69-0.77 (m, 2H), 0.93-1.07 (m, 2H), 1.36*, 1.47 (s, 9H), 3.95-4.04 (m, 2H) 4.72-4.87 (m, 2H), 5.62*, 5.63 (s, 1H), 7.60-7.69 (m, 3H), 7.70-7.77 (m, 2H), 7.85-7.92 (m, 1H), 7.94-8.03 (m, 1H), 8.64*, 8.66 (s, 1H), 10.75 (s, 1H).

Example 100: 5-(Ethylsulfonyl)-N-[4-(1,1,1,3,3,3-hexafluoro-2-hydroxypropan-2-yl)phenyl]-2,3-dihydro-1H-isoindole-1-carboxamide

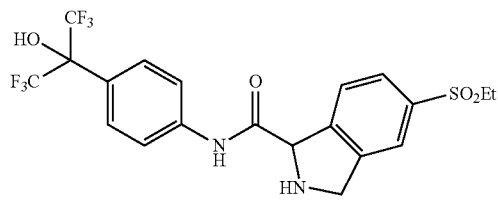

(9H-Fluoren-9-yl)methyl 5-(ethylsulfonyl)-1-((4-(1,1,1,3,3,3-hexafluoro-2-hydroxypropan-2-yl)phenyl)carbamoyl)isoindoline-2-carboxylate (5.4 g, 7.51 mmol) was suspended in acetonitrile (200 mL). Diethylamine (62.8 mL, 601.12 mmol) was added and the reaction stirred at room temperature for 20 min. The reaction was evaporated to dryness and the residue dissolved in methanol. This was loaded on an Isolute™ SCX cartridge (previously flushed with methanol). The SCX was then flushed with methanol and the product eluted with 2M ammonia in methanol. The methanolic ammonia was removed in vacuo to afford 5-(ethylsulfonyl)-N-(4-(1,1,1,3,3,3-hexafluoro-2-hydroxypropan-2-yl)phenyl)isoindoline-1-carboxamide (3.20 g, 86%).

A sample for biological screening was triturated with diethyl ether and the solid obtained was collected by filtration and washed with ether.

HRMS: calculated for (C$_{20}$H$_{18}$F$_6$N$_2$O$_4$S+H)$^+$ 497.0970; found: (ESI [M+H]$^+$) 497.0977. $^1$H NMR (500 MHz, DMSO-d$_6$) δ 1.09 (t, 3H), 3.27 (q, 2H), 3.94 (s, 1H), 4.29-4.48 (m, 2H), 5.09 (s, 1H), 7.60 (d, 2H), 7.7-7.84 (m, 5H), 8.62 (s, 1H), 10.33 (s, 1H).

Example 101: 5-(Ethylsulfonyl)-2-formyl-N-[4-(1,1,1,3,3,3-hexafluoro-2-hydroxypropan-2-yl)phenyl]-2,3-dihydro-1H-isoindole-1-carboxamide

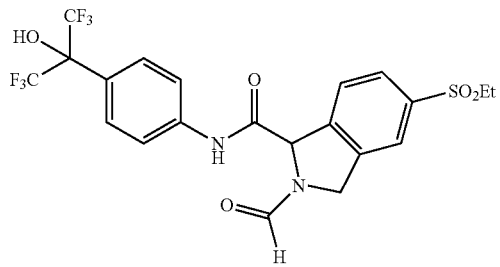

T3P (50% in EtOAc) (0.134 mL, 0.23 mmol) was added to a solution of 5-(ethylsulfonyl)-N-(4-(1,1,1,3,3,3-hexafluoro-2-hydroxypropan-2-yl)phenyl)isoindoline-1-carboxamide (80 mg, 0.16 mmol), formic acid (9.64 mg, 0.21 mmol) and triethylamine (0.045 mL, 0.32 mmol) in dichloromethane (2 mL). The resulting mixture was stirred at room temperature for 1 h. The reaction mixture was partitioned between DCM and sat aq NaHCO$_3$. The layers were separated in a phase separator cartridge and the organic layer was concentrated in vacuo. The residue was purified by flash chromatography eluting with 60%-100% EtOAc in heptane. 5-(Ethylsulfonyl)-2-formyl-N-(4-(1,1,1,3,3,3-hexafluoro-2-hydroxypropan-2-yl)phenyl)isoindoline-1-carboxamide (67.0 mg, 79%) was obtained as a solid.

HRMS: calculated for (C$_{21}$H$_{18}$F$_6$N$_2$O$_5$S+H)$^+$ 525.0919; found: (ESI [M+H]$^+$) 525.0891. $^1$H NMR (500 MHz, DMSO-d$_6$, mixture of rotamers, 2*:1) δ 1.09, 1.10* (t, 3H), 3.27-3.31 (m, 2H), 4.74-4.91, 5.05-5.17* (m, 2H), 5.77*, 5.99 (s, 1H), 7.61-7.67 (m, 2H), 7.7-7.78 (m, 3H), 7.83-7.9 (m, 1H), 7.97-8.03 (m, 1H), 8.39, 8.48* (s, 1H), 8.65 (s, 1H), 10.76*, 10.86 (s, 1H).

Example 102: 2-[(1-Cyanocyclopropyl)acetyl]-5-(ethylsulfonyl)-N-[4-(1,1,1,3,3,3-hexafluoro-2-hydroxypropan-2-yl)phenyl]-2,3-dihydro-1H-isoindole-1-carboxamide

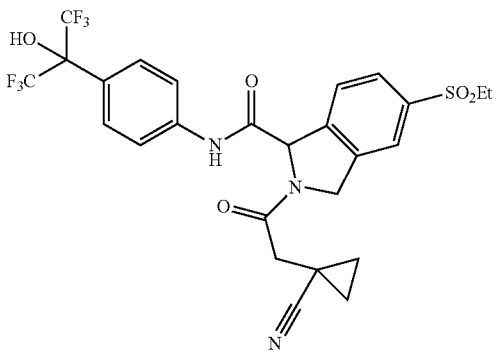

Using the same procedure described in example 101, but using 2-(1-cyanocyclopropyl)acetic acid, the title compound (15.6 mg, 16%) was obtained after purification by RP-HPLC (chromatographic conditions: gradient 5-95% ACN in 0.1M $HCO_2H$, pH3; column: Waters Sunfire C18 ODB 5μ 19×150 mm).

HRMS: calculated for $(C_{26}H_{23}F_6N_3O_5S+H)^+$ 604.1341; found: (ESI [M+H]$^+$) 604.1368.

$^1$H NMR (600 MHz, DMSO-$d_6$, mixture of rotamers, 2*:1) δ 0.87-1.26*(m, 7H), 2.75-2.94, 3.01-3.12* (m, 2H), 3.27-3.32 (m, 2H), 4.97, 5.20* (s, 2H), 5.76-5.8 (m, 1H), 7.6-7.66 (m, 2H), 7.69-7.76 (m, 3H), 7.84-7.89 (m, 1H), 7.94-7.98 (m, 1H), 8.69 (s, 1H), 10.74*, 10.76 (s, 1H).

Example 103: 2-Acetyl-5-(ethylsulfonyl)-N-[4-(1,1,1,3,3,3-hexafluoro-2-hydroxypropan-2-yl)phenyl]-2,3-dihydro-1H-isoindole-1-carboxamide

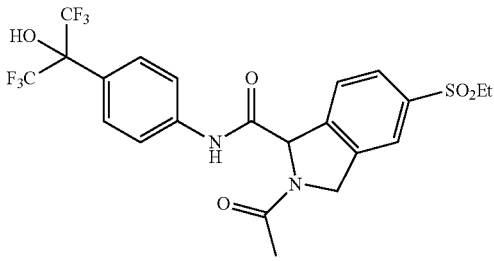

Using the same procedure as in Example 101 but acetic acid instead of formic acid, the title compound (1.0 g, 81%) was obtained after purification by flash chromatography eluting with 50% to 100% EtOAc in heptane.

HRMS: calculated for $(C_{22}H_{20}F_6N_2O_5S+H)^+$ 539.1075; found: (ESI [M+H]$^+$) 539.1077.

$^1$H NMR (600 MHz, DMSO-$d_6$, mixture of rotamers, 4*:1) δ 1.09, 1.10* (t, 3H), 1.99, 2.15* (s, 3H), 3.27-3.32 (m, 2H), 4.77-4.91, 5-5.09* (m, 2H), 5.73*, 5.93 (s, 1H), 7.6-7.66 (m, 2H), 7.69-7.8 (m, 3H), 7.84-7.87 (m, 1H), 7.96*, 7.98 (s, 1H), 8.66*, 8.69 (s, 1H), 10.71*, 10.94 (s, 1H).

The (1R) and the (1S) enantiomers of 2-acetyl-5-(ethylsulfonyl)-N-[4-(1,1,1,3,3,3-hexafluoro-2-hydroxypropan-2-yl)phenyl]-2,3-dihydro-1H-isoindole-1-carboxamide (1230 mg) were separated by a preparative SFC system equipped with a Chiralpak AS column 30% EtOH 100 in $CO_2$ (120 bar); flow: 150 mL/min; injection volume was 1 mL of a 200 mg/mL ethanol solution.

Isomer 1 (peak 1): 624 mg, 99.9% ee by analytical chiral SFC (analytical conditions: Chiralpak AS column, 150×4.6 mm, 3 μm, 3.5 ml/min, 35% EtOH in $CO_2$, 120 bar, 40° C.). [α]$_{D589}$+99° (c=1, $CH_3CN$).

HRMS: calculated for $(C_{22}H_{20}F_6N_2O_5S+H)^+$ 539.1075; found: (ESI [M+H]$^+$) 539.1082.

$^1$H NMR (500 MHz, DMSO-$d_6$, mixture of rotamers, 4*:1) δ 1.10 (t, 3H), 1.99, 2.15* (s, 3H), 3.27-3.32 (m, 2H), 4.77-4.91*, 5-5.09 (m, 2H), 5.73*, 5.93 (s, 1H), 7.6-7.66 (m, 2H), 7.69-7.8 (m, 3H), 7.84-7.87 (m, 1H), 7.96*, 7.98 (s, 1H), 8.66*, 8.69 (s, 1H), 10.71*, 10.94 (s, 1H).

Isomer 2 (peak 2): 612 mg, 99.8% ee by analytical chiral SFC (analytical conditions: Chiralpak AS column, 150×4.6 mm, 3 μm, 3.5 ml/min, 35% EtOH in $CO_2$, 120 bar, 40° C.). [α]$_{D589}$-100° (c=1, $CH_3CN$).

HRMS: calculated for $(C_{22}H_{20}F_6N_2O_5S+H)^+$ 539.1075; found: (ESI [M+H]$^+$) 539.1077.

$^1$H NMR (500 MHz, DMSO-$d_6$, mixture of rotamers, 4*:1) δ 1.10 (t, 3H), 1.99, 2.15* (s, 3H), 3.27-3.32 (m, 2H), 4.77-4.91*, 5-5.09 (m, 2H), 5.73*, 5.93 (s, 1H), 7.6-7.66 (m, 2H), 7.69-7.8 (m, 3H), 7.84-7.87 (m, 1H), 7.96*, 7.98 (s, 1H), 8.66*, 8.69 (s, 1H), 10.71*, 10.94 (s, 1H).

Example 104: 2-[Cyclopropyl(difluoro)acetyl]-5-(ethylsulfonyl)-N-[4-(1,1,1,3,3,3-hexafluoro-2-hydroxypropan-2-yl)phenyl]-2,3-dihydro-1H-isoindole-1-carboxamide

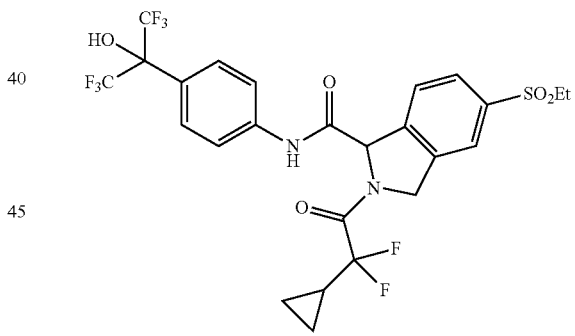

Using the same procedure described in example 101, but using 2-cyclopropyl-2,2-difluoroacetic acid, the title compound (18.5 mg, 37.4%) was obtained after purification by RP-HPLC (chromatographic conditions: gradient 5-95% ACN in 0.1M $HCO_2H$, pH3; column: Waters Sunfire C18 ODB 5 t 19×150 mm).

HRMS: calculated for $(C_{25}H_{22}F_5N_2O_5S+H)^+$ 615.1200; found: (ESI [M+H]$^+$) 615.1200.

$^1$H NMR (600 MHz, DMSO-$d_6$, mixture of rotamers, 5*:1) δ 0.55-0.8 (m, 4H), 1.09, 1.10* (t, 3H), 1.69-1.82 (m, 1H), 3.29 (q, 2H), 4.92-5.1, 5.18-5.29* (m, 2H), 5.91*, 6.17 (s, 1H), 7.61-7.83 (m, 5H), 7.86-7.89 (m, 1H), 7.99*, 8.02 (s, 1H), 8.69 (s, 1H), 10.90, 10.96* (s, 1H).

Example 105: 2-[(1-Cyanocyclopropyl)carbonyl]-5-(ethylsulfonyl)-N-[4-(1,1,1,3,3,3-hexafluoro-2-hydroxypropan-2-yl)phenyl]-2,3-dihydro-1H-isoindole-1-carboxamide

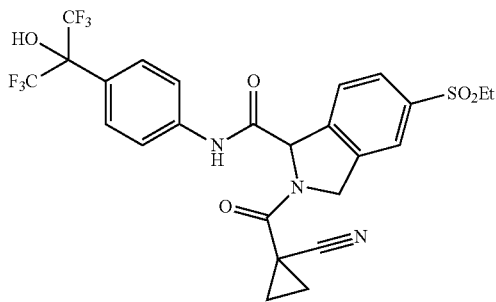

Using the same procedure described in example 101, but using using 1-cyanocyclopropanecarboxylic acid, the title compound (25.2 mg, 70.7%) was obtained after purification by preparative SFC (chromatographic conditions: MeOH/NH$_3$ 20 mM; column: Phenomenex Luna Hilic 5 30×250 mm).

HRMS: calculated for $(C_{25}H_{21}F_6N_3O_5S+H)^+$ 590.1184; found: (ESI [M+H]$^+$) 590.1232.

$^1$H NMR (600 MHz, DMSO-d$_6$, mixture of rotamers, 6*:1, only data for the major rotamer reported) δ 1.11 (t, 3H), 1.53-1.64 (m, 2H), 1.66-1.76 (m, 2H), 3.30 (q, 2H), 5.35-5.4 (m, 2H), 5.85 (s, 1H), 7.61-7.67 (m, 2H), 7.7-7.76 (m, 3H), 7.87-8 (m, 1H), 8.08 (s, 1H), 8.68 (s, 1H), 10.88 (s, 1H).

Examples 106-117

Examples 106-117 (Table 1) were prepared using a similar procedures to those described in the preceding examples.

Example 106: 5-(Ethylsulfonyl)-N-[4-(1,1,1,3,3,3-hexafluoro-2-hydroxypropan-2-yl)phenyl]-2-(3-hydroxy-3-methylbutanoyl)-2,3-dihydro-1H-isoindole-1-carboxamide Example 107: 5-(Ethylsulfonyl)-N-[4-(1,1,1,3,3,3-hexafluoro-2-hydroxypropan-2-yl)phenyl]-2-[(1-hydroxycyclopropyl)acetyl]-2,3-dihydro-1H-isoindole-1-carboxamide Example 108: 5-(Ethylsulfonyl)-2-(3-fluoropropanoyl)-N-[4-(1,1,1,3,3,3-hexafluoro-2-hydroxypropan-2-yl)phenyl]-2,3-dihydro-1H-isoindole-1-carboxamide Example 109: 2-(Cyclobutylacetyl)-5-(ethylsulfonyl)-N-[4-(1,1,1,3,3,3-hexafluoro-2-hydroxypropan-2-yl)phenyl]-2,3-dihydro-1H-isoindole-1-carboxamide Example 110: 5-(Ethylsulfonyl)-N-[4-(1,1,1,3,3,3-hexafluoro-2-hydroxypropan-2-yl)phenyl]-2-(oxetan-2-ylcarbonyl)-2,3-dihydro-1H-isoindole-1-carboxamide Example 111: 2-(3-Cyanopropanoyl)-5-(ethylsulfonyl)-N-[4-(1,1,1,3,3,3-hexafluoro-2-hydroxypropan-2-yl)phenyl]-2,3-dihydro-1H-isoindole-1-carboxamide Example 112: 5-(Ethylsulfonyl)-N-[4-(1,1,1,3,3,3-hexafluoro-2-hydroxypropan-2-yl)phenyl]-2-[(1-methoxycyclopropyl)acetyl]-2,3-dihydro-1H-isoindole-1-carboxamide Example 113: 5-(Ethylsulfonyl)-N-[4-(1,1,1,3,3,3-hexafluoro-2-hydroxypropan-2-yl)phenyl]-2-(tetrahydrofuran-3-ylcarbonyl)-2,3-dihydro-1H-isoindole-1-carboxamide Example 114: 5-(Ethylsulfonyl)-N-[4-(1,1,1,3,3,3-hexafluoro-2-hydroxypropan-2-yl)phenyl]-2-(tetrahydrofuran-2-ylcarbonyl)-2,3-dihydro-1H-isoindole-1-carboxamide Example 115: 2-{[1-(Dimethylamino)cyclopropyl]acetyl}-5-(ethylsulfonyl)-N-[4-(1,1,1,3,3,3-hexafluoro-2-hydroxypropan-2-yl)phenyl]-2,3-dihydro-1H-isoindole-1-carboxamide Example 116: 2-(Cyanoacetyl)-5-(ethylsulfonyl)-N-[4-(1,1,1,3,3,3-hexafluoro-2-hydroxypropan-2-yl)phenyl]-2,3-dihydro-1H-isoindole-1-carboxamide Example 117: 5-(Ethylsulfonyl)-N-[4-(1,1,1,3,3,3-hexafluoro-2-hydroxypropan-2-yl)phenyl]-2-{[1-(hydroxymethyl)cyclopropyl]carbonyl}-2,3-dihydro-1H-isoindole-1-carboxamide

TABLE 1

| Example No. | Structure | NMR + MS |
|---|---|---|
| 106 | 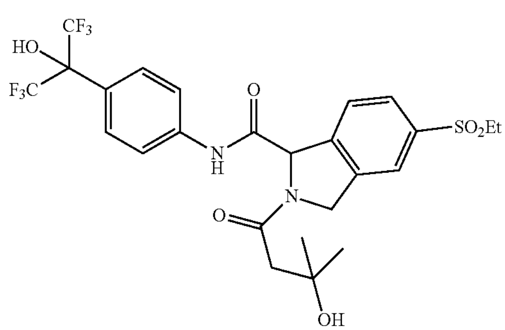 | HRMS: calculated for $(C_{25}H_{26}F_6N_2O_6S + H)^+$ 597.1494; found (ESI [M + H]$^+$) 597.1484. $^1$H NMR (500 MHz DMSO-d$_6$, mixture of rotamers, 5*:1) δ 1.10 (t, 3H), 1.22, 1.26* (s, 6H), 2.52-2.64 (m, 2H), 3.27-3.31 (m, 2H), 4.80 (s, 1H), 4.82-4.96, 5.08-5.19* (m, 2H), 5.78*, 6.10 (s, 1H), 7.6-7.67 (m, 2H), 7.7-7.81 (m, 3H), 7.84-7.88 (m, 1H), 7.95*, 7.98 (s, 1H), 8.65*, 8.67 (s, 1H), 10.66 *, 10.97 (s, 1H). |

TABLE 1-continued

| Example No. | Structure | NMR + MS |
|---|---|---|
| 107 | 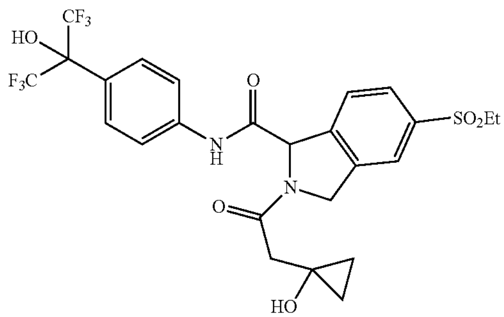 | HRMS: calculated for $(C_{25}H_{24}F_6N_2O_6S + H)^+$ 595.1337; found (ESI [M + H]$^+$) 595.1337. $^1$H NMR (600 MHz, DMSO-d$_6$, mixture of rotamers, 5*:1) δ 0.53-0.63 (m, 4H), 1.09, 1.10 (t, 3H), 2.6-2.67 (m, 1H), 2.78-2.88 (m, 1H), 3.30 (q, 2H), 4.79-4.99, 5.12* (m, 2H), 5.35*, 5.36 (s, 1H), 5.77*, 6.08 (s, 1H), 7.55-7.68 (m, 2H), 7.7-7.83 (m, 3H), 7.83-7.88 (m, 1H), 7.96*, 7.99 (s, 1H), 8.68 (s, 1H), 10.69*, 10.94 (s, 1H). |
| 108 | 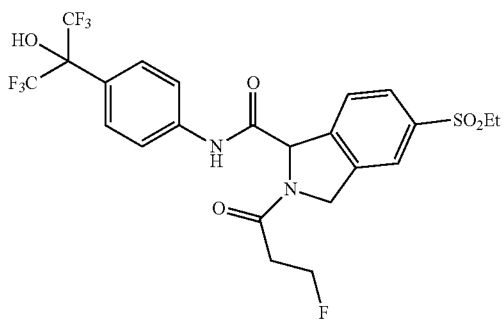 | HRMS: calculated for $(C_{23}H_{21}F_7N_2O_5S + H)^+$ 571.1138; found (ESI [M + H]$^+$) 511.1130. $^1$H NMR (600 MHz, DMSO-d$_6$, mixture of rotamers, 4*:1) δ 1.09, 1.10* (t, 3H), 2.83-3.05 (m, 2H), 3.28-3.32 (m, 2H), 4.66-4.78 (m, 2H), 4.81-4.97, 5.04-5.11* (m, 2H), 5.77*, 5.98 (s, 1H), 7.6-7.67 (m, 2H), 7.7-7.82 (m, 3H), 7.84-7.88 (m, 1H), 7.96*, 7.99 (s, 1H), 8.69*, 8.71 (s, 1H), 10.76*, 10.97 (s, 1H). |
| 109 | 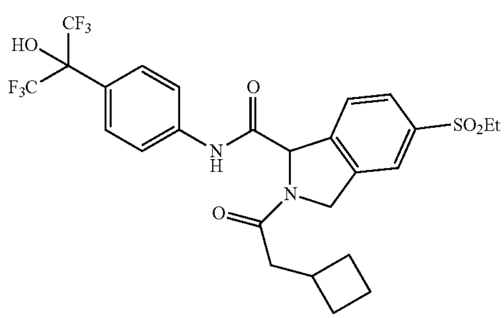 | HRMS: calculated for $(C_{26}H_{26}F_6N_2O_5S + H)^+$ 593.1545; found (ESI [M + H]$^+$) 593.1556. $^1$H NMR (600 MHz, DMSO-d$_6$, mixture of rotamers, 4*:1) δ 1.09, 1.10* (t, 3H), 1.55-1.75 (m, 2H), 1.77-1.89 (m, 2H), 2-2.25 (m, 2H), 2.59 (d, 2H), 2.6-2.71 (m, 1H), 3.26-3.32 (m, 2H), 4.72-4.93, 4.99-5.07* (m, 2H), 5.72*, 5.94 (s, 1H), 7.64 (m, 2H), 7.68-7.8 (m, 3H), 7.82-7.87 (m, 1H), 7.94*, 7.97 (s, 1H), 8.68 (br s, 1H), 10.70*, 10.94 (s, 1H). |
| 110 | 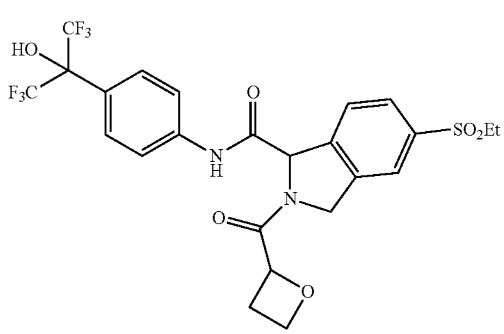 | HRMS: calculated for $(C_{24}H_{22}F_6N_2O_6S + H)^+$ 581.1181; found (ESI [M + H]$^+$) 581.1161. Mixture of diastereomers and rotamers; only major diastereomer/rotamer reported: $^1$H NMR (500 MHz, DMSO-d$_6$) δ 1.10 (t, 3H), 2.71-2.85 (m, 1H), 2.85-2.99 (m, 1H), 3.25-3.3 (m, 2H), 4.46-4.54 (m, 1H), 4.6-4.68 (m, 1H), 4.83-4.91 (m, 1H), 4.99-5.06 (m, 1H), 5.42-5.54 (m, 1H), 5.82 (s, 1H), 7.59-7.66 (m, 2H), 7.71-7.81 (m, 3H), 7.84-7.88 (m, 1H), 7.95 (s, 1H), 8.65 (s, 1H), 10.81 (s, 1H). |

TABLE 1-continued

| Example No. | Structure | NMR + MS |
|---|---|---|
| 111 | 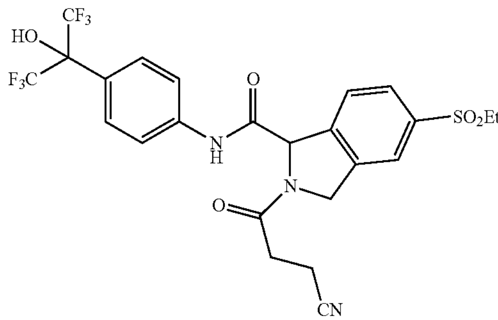 | HRMS: calculated for $(C_{24}H_{21}F_6N_3O_5S + H)^+$ 578.1184; found (ESI [M + H]$^+$) 578.1190. $^1$H NMR (600 MHz, DMSO-d$_6$, mixture of rotamers, 5*:1) δ 1.09, 1.10* (t, 3H), 2.67-2.71 (m, 2H), 2.82-2.97 (m, 2H), 3.31 (q, 2H), 4.81-4.98, 5.02-5.07* (m, 2H), 5.77*, 5.96 (s, 1H), 7.59-7.67 (m, 2H), 7.7-7.82 (m, 3H), 7.83-7.88 (m, 1H), 7.97*, 8.00 (s, 1H), 8.68 (s, 1H), 10.75*, 10.96 (s, 1H). |
| 112 | 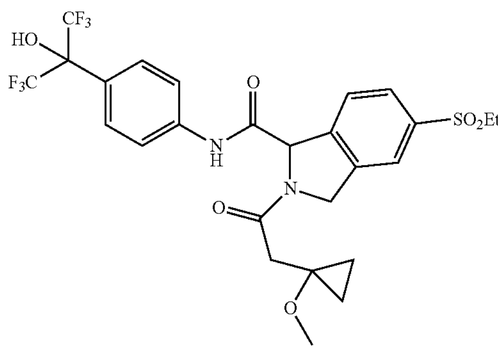 | HRMS: calculated for $(C_{26}H_{26}F_6N_2O_6S + H)^+$ 609.1494; found (ESI [M + H]$^+$) 609.1484. $^1$H NMR (600 MHz, DMSO-d$_6$, mixture of rotamers, 6*:1) δ 0.54-0.79 (m, 4H), 1.09, 1.10 (t, 3H), 2.75-2.92 (m, 2H), 3.14, 3.24* (s, 3H), 3.30 (q, 2H), 4.77-4.96, 5.07-5.18* (m, 2H), 5.75*, 6.01 (s, 1H), 7.6-7.67 (m, 2H), 7.68-7.82 (m, 3H), 7.84-7.88 (m, 1H), 7.97*, 7.99 (s, 1H), 8.66 (br s, 1H), 10.74*, 10.98 (s, 1H). |
| 113 | 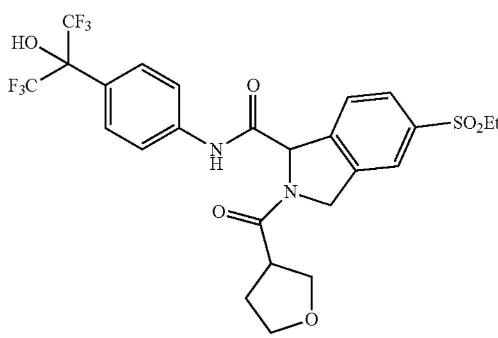 | HRMS: calculated for $(C_{25}H_{24}F_6N_2O_6S + H)^+$ 595.1337; found (ESI [M + H]$^+$) 595.1331. Mixture of diastereomers and rotamers; only major diastereomer/rotamer reported: $^1$H NMR (600 MHz, DMSO-d$_6$) δ 1.04-1.13 (m, 3H), 1.95-2.24 (m, 2H), 3.27-3.32 (m, 2H), 3.42-3.45 (m, 1H), 3.63-3.83 (m, 4H), 5.04-5.16 (m, 2H), 5.74-5.79 (m, 1H), 7.58-7.68 (m, 2H), 7.69-7.81 (m, 3H), 7.84-7.88 (m, 1H), 7.94 (s, 1H), 8.68 (s, 1H), 10.73-10.8 (m, 1H). |
| 114 | 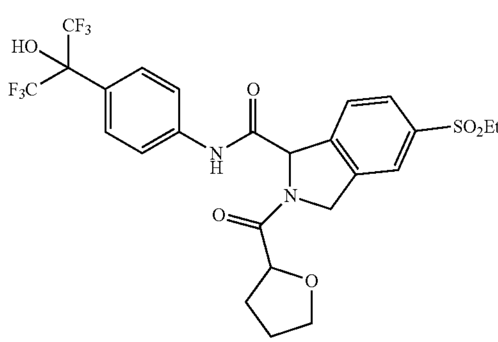 | HRMS: calculated for $(C_{25}H_{24}F_6N_2O_6S + H)^+$ 595.1337; found (ESI [M + H]$^+$) 595.1349. Mixture of diastereomers and rotamers; only major diastereomer/rotamer reported: $^1$H NMR (600 MHz, DMSO-d$_6$) δ 1.04-1.15 (m, 3H), 1.72-2.24 (m, 4H), 3.22-3.31 (m, 2H), 3.75-3.89 (m, 2H), 4.66-4.79 (m, 1H), 5.04-5.24 (m, 2H), 5.75-5.81 (m, 1H), 7.6-7.65 (m, 2H), 7.68-7.76 (m, 3H), 7.84-7.88 (m, 1H), 7.93-7.96 (m, 1H), 8.67 (s, 1H), 10.76-10.81 (m, 1H). |

TABLE 1-continued

| Example No. | Structure | NMR + MS |
|---|---|---|
| 115 | 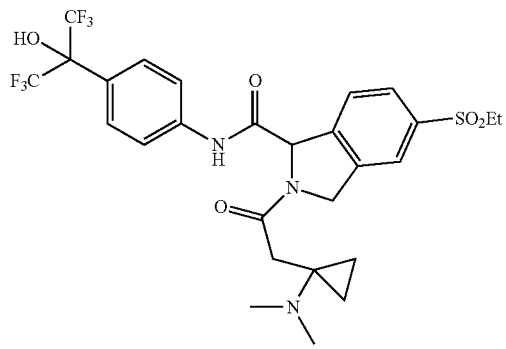 | HRMS: calculated for $(C_{27}H_{29}F_6N_3O_5S + H)^+$ 622.1810; found: 622.1790.<br>$^1$H NMR (600 MHz, DMSO-$d_6$, mixture of rotamers, 7*:1) δ 0.41-0.68 (m, 4H), 1.09, 1.10* (t, 3H), 2.20, 2.32* (s, 6H), 2.58-2.63 (m, 1H), 2.79-2.87 (m, 1H), 3.29 (q, 2H), 4.74-4.93, 5.06-5.18* (m, 2H), 5.72*, 5.97 (s, 1H), 7.59-7.77 (m, 5H), 7.82-7.88 (m, 1H), 7.98, 7.99* (s, 1H), 8.69* 8.72 (s, 1H), 10.79*, 11.01 (s, 1H). |
| 116 | 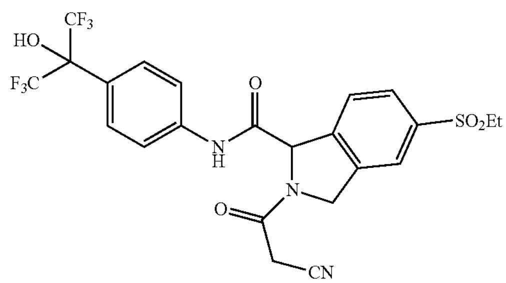 | HRMS: calculated for $(C_{23}H_{19}F_6N_3O_5S + H)^+$ 564.1028; found (ESI [M + H]$^+$) 564.1046.<br>$^1$H NMR (600 MHz, DMSO-$d_6$, mixture of rotamers, 6*:1, only major rotamer reported) δ 1.10 (m, 3H), 3.30 (q, 2H), 4.15-4.3 (m, 2H), 4.96-5.08 (m, 2H), 5.78 (d, 1H), 7.64 (d, 2H), 7.7-7.75 (m, 3H), 7.86-7.89 (m, 1H), 7.99 (s, 1H), 8.70 (s, 1H), 10.81 (s, 1H). |
| 117 | 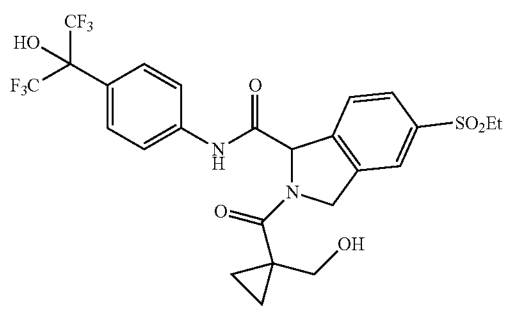 | HRMS: calculated for $(C_{25}H_{24}F_6N_2O_6S + H)^+$ 595.1337; found (ESI [M + H]$^+$) 595.1354.<br>$^1$H NMR (600 MHz, DMSO-$d_6$, mixture of rotamers, 9:1, only major rotamer reported) δ 0.69-0.76 (m, 1H), 0.79-0.83 (m, 1H), 0.85-0.9 (m, 1H), 0.93-0.98 (m, 1H), 1.10 (t, 3H), 3.29 (q, 2H), 3.59 (dd, 1H), 3.71 (dd, 1H), 5.04 (t, 1H), 5.21 (d, 1H), 5.32 (d, 1H), 5.78 (s, 1H), 7.62 (d, 2H), 7.68-7.74 (m, 3H), 7.85 (d, 1H), 7.96 (s, 1H), 8.67 (s, 1H), 10.63 (s, 1H). |

Example 200: 5-[(Cyclopropylmethyl)sulfonyl]-N-[4-(1,1,1,3,3,3-hexafluoro-2-hydroxypropan-2-yl)phenyl]-2,3-dihydro-1H-isoindole-1-carboxamide

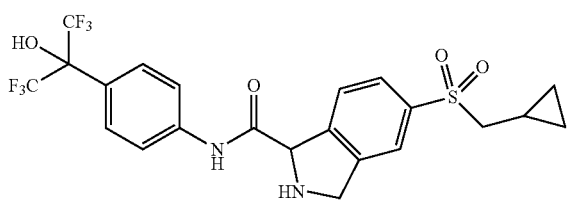 [SMILES: O=C(Nc1ccc(C(O)(C(F)(F)F)C(F)(F)F)cc1)C1NCc2cc(S(=O)(=O)CC3CC3)ccc21]

9H-Fluoren-9-yl 5-[(cyclopropylmethyl)sulfonyl]-1-{[4-(1,1,1,3,3,3-hexafluoro-2-hydroxypropan-2-yl)phenyl]carbamoyl}-1,3-dihydro-2H-isoindole-2-carboxylate (3.2 g, 4.30 mmol) was dissolved in acetonitrile (140 mL). Diethylamine (35.9 mL, 343.76 mmol) was added and the reaction stirred at room temperature for 20 min. The reaction was evaporated to dryness and the residue dissolved in methanol. This was loaded onto Isolute™ SCX (previously flushed with methanol). The resin was flushed with methanol and the product was then eluted with 2M ammonia in methanol. The methanolic ammonia was removed in vacuo to afford 5-((cyclopropylmethyl)sulfonyl)-N-(4-(1,1,1,3,3,3-hexafluoro-2-hydroxypropan-2-yl)phenyl)isoindoline-1-carboxamide (1.918 g, 85%). A sample purified for biological screening was obtained after purification by RP-HPLC (chromatographic conditions: gradient 5-95% ACN in 0.2% NH$_3$, pH10; column: Waters Xbridge, C18 5 ODB 19×150 mm).

HRMS: calculated for $(C_{22}H_{20}F_6N_2O_4S+H)^+$ 523.1126; found: (ESI [M+H]$^+$) 523.1105.

$^1$H NMR (600 MHz, DMSO-$d_6$) δ 0.05-0.15 (m, 2H), 0.42-0.47 (m, 2H), 0.77-0.84 (m, 1H), 3.20-3.27 (m, 2H), 3.96 (br s, 1H), 4.28-4.43 (m, 2H), 5.09 (s, 1H), 7.60 (d, 2H), 7.71 (d, 1H), 7.75-7.85 (m, 4H), 8.65 (br s, 1H), 10.33 (s, 1H).

Example 201: 2-Acetyl-5-[(cyclopropylmethyl)sulfonyl]-N-[4-(1,1,1,3,3,3-hexafluoro-2-hydroxypropan-2-yl)phenyl]-2,3-dihydro-1H-isoindole-1-carboxamide

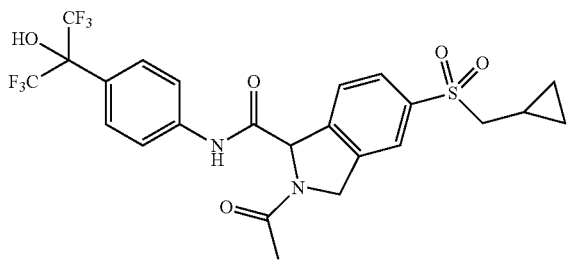 [SMILES: CC(=O)N1Cc2cc(S(=O)(=O)CC3CC3)ccc2C1C(=O)Nc1ccc(C(O)(C(F)(F)F)C(F)(F)F)cc1]

5-[(Cyclopropylmethyl)sulfonyl]-N-[4-(1,1,1,3,3,3-hexafluoro-2-hydroxypropan-2-yl)phenyl]-2,3-dihydro-1H-isoindole-1-carboxamide (300 mg, 0.57 mmol) was dissolved in DCM (15 mL) and to this triethylamine (0.160 mL, 1.15 mmol) and acetic acid (0.036 mL, 0.63 mmol) was added followed by T3P (50% in EtOAc, 0.479 mL, 0.80 mmol). The reaction was stirred at room temperature for 30 min. The reaction mixture was partitioned between DCM and water, the layers were separated using a phase separator cartridge and the solvent was removed in vacuo. The compound was purified by RP-HPLC (chromatographic conditions: gradient 5-95% ACN in 0.1M $HCO_2H$, pH3; column: Waters Sunfire C18 ODB 5μ 19×150 mm) to give 2-acetyl-5-[(cyclopropylmethyl)sulfonyl]-N-[4-(1,1,1,3,3,3-hexafluoro-2-hydroxypropan-2-yl)phenyl]-2,3-dihydro-1H-isoindole-1-carboxamide (189 mg, 58.3%).

HRMS: calculated for $(C_{24}H_{22}F_6N_2O_5S+H)^+$ 565.1232; found: (ESI [M+H]$^+$) 565.1252.

$^1$H NMR (600 MHz, DMSO-$d_6$, mixture of rotamers, 4*:1) δ 0.02-0.18 (m, 2H), 0.41-0.52 (m, 2H), 0.77-0.88 (m, 1H), 1.99*, 2.15 (s, 3H), 3.21-3.31 (m, 2H), 4.76-4.92, 4.98-5.1* (m, 2H), 5.73*, 5.93 (s, 1H), 7.6-7.66 (m, 2H), 7.68-7.79 (m, 3H), 7.85-7.88 (m, 1H), 7.96*, 7.99 (s, 1H), 8.67 (s, 1H), 10.70*, 10.94 (s, 1H).

The (1R) and the (1S) enantiomers of 2-Acetyl-5-[(cyclopropylmethyl)sulfonyl]-N-[4-(1,1,1,3,3,3-hexafluoro-2-hydroxypropan-2-yl)phenyl]-2,3-dihydro-1H-isoindole-1-carboxamide (120 mg) were separated by a preparative SFC system equipped with a Chiralpak IB column 30% IPA in $CO_2$ (120 bar); flow: 80 mL/min; injection volume was 1 mL of a 30 mg/mL ethanol solution.

Isomer 1 (peak 1) 41 mg, 95.4% ee by analytical chiral SFC (analytical conditions: Chiralpak IB column, 150×4.6 mm, 3 m, 3.5 ml/min, 30% IPA in $CO_2$, 120 bar, 40° C.). HRMS: calculated for $(C_{24}H_{22}F_6N_2O_5S+H)^+$ 565.1232; found: (ESI [M+H]$^+$) 565.1234.

$^1$H NMR (500 MHz, MeOD, mixture of rotamers, 4*:1) δ 0.1-0.18 (m, 2H), 0.47-0.56 (m, 2H), 0.9-1.01 (m, 1H), 2.14, 2.27* (s, 3H), 3.11-3.21 (m, 2H), 4.96-5.22 (m, 2H), 5.81*, 5.91 (s, 1H), 7.65-7.77 (m, 5H), 7.9-7.95 (m, 1H), 8.01 (s, 1H).

Isomer 2 (peak 2) 41 mg, 87.3% ee by analytical chiral SFC (analytical conditions: Chiralpak IB column, 150×4.6 mm, 3 m, 3.5 ml/min, 30% IPA in $CO_2$, 120 bar, 40° C.). HRMS: calculated for $(C_{24}H_{22}F_6N_2O_5S+H)^+$ 565.1232; found: (ESI [M+H]$^+$) 565.1250.

$^1$H NMR (500 MHz, MeOD, mixture of rotamers, 4*:1) δ 0.1-0.18 (m, 2H), 0.47-0.56 (m, 2H), 0.9-1.01 (m, 1H), 2.14, 2.27* (s, 3H), 3.1-3.21 (m, 2H), 4.96-5.22 (m, 2H), 5.81*, 5.91 (s, 1H), 7.65-7.77 (m, 5H), 7.9-7.95 (m, 1H), 8.01 (s, 1H).

Example 202: 5-[(Cyclopropylmethyl)sulfonyl]-2-formyl-N-[4-(1,1,1,3,3,3-hexafluoro-2-hydroxypropan-2-yl)phenyl]-2,3-dihydro-1H-isoindole-1-carboxamide

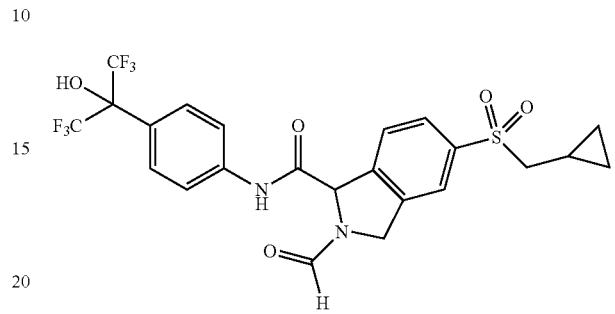

Made using the same procedure as Example 201 but using formic acid instead of acetic acid. The title compound (52 mg, mg, 70.5%) was obtained after purification by RP-HPLC (chromatographic conditions: gradient 5-95% ACN in 0.1M $HCO_2H$, pH3; column: Waters Sunfire C18 ODB 5μ 19×150 mm).

HRMS: calculated for $(C_{23}H_{20}F_6N_2O_5S+H)^+$ 551.1075; found: (ESI [M+H]$^+$) 551.1089.

$^1$H NMR (600 MHz, DMSO-$d_6$, mixture of rotamers, 2*:1) δ 0.07-0.17 (m, 2H), 0.4-0.49 (m, 2H), 0.77-0.88 (m, 1H), 3.2-3.31 (m, 2H), 4.72-4.93, 5.02-5.18* (m, 2H), 5.77*, 5.99 (s, 1H), 7.6-7.67 (m, 2H), 7.71-7.86 (m, 3H), 7.86-7.9 (m, 1H), 7.96, 8.00* (s, 1H), 8.38, 8.48* (m, 1H), 8.67*, 8.68 (s, 1H), 10.76*, 10.86 (s, 1H).

Example 203: 5-[(Cyclopropylmethyl)sulfonyl]-N-[4-(1,1,1,3,3,3-hexafluoro-2-hydroxypropan-2-yl)phenyl]-2-(methoxyacetyl)-2,3-dihydro-1H-isoindole-1-carboxamide

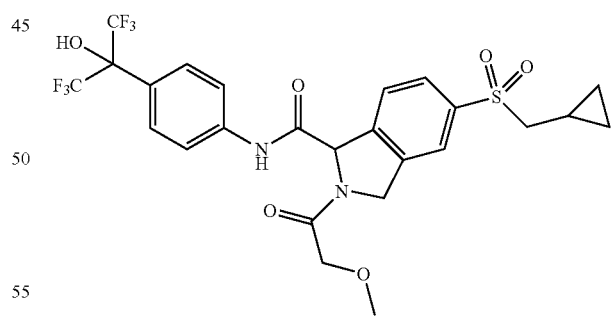

Made using the same procedure as Example 201 but using 2-methoxyacetic acid instead of acetic acid. The title compound (43.1 mg, 54%) was obtained after purification by preparative SFC (chromatographic conditions: MeOH/NH$_3$ 20 mM, EP; column: Waters BEH 2-EP 5 μm 30×250 mm).

HRMS: calculated for $(C_{25}H_{24}F_6N_2O_6S+H)^+$ 595.1337; found: (ESI [M+H]+) 595.1380.

$^1$H NMR (600 MHz, DMSO-$d_6$, mixture of rotamers, 4*:1) δ 0.05-0.18 (m, 2H), 0.37-0.51 (m, 2H), 0.68-0.88 (m, 1H), 3.18-3.32 (m, 5H), 3.93-4.12, 4.17-4.3* (m, 2H), 4.81-5.05 (m, 2H), 5.80*, 5.99 (s, 1H), 7.62-7.65 (m, 2H), 7.7-7.79 (m, 3H), 7.85-7.89 (m, 1H), 7.97*, 8.00 (s, 1H), 8.67 (s, 1H), 10.76*, 10.86 (s, 1H).

Example 204: Ethyl 5-[(cyclopropylmethyl)sulfonyl]-1-{[4-(1,1,1,3,3,3-hexafluoro-2-hydroxypropan-2-yl)phenyl]carbamoyl}-1,3-dihydro-2H-isoindole-2-carboxylate

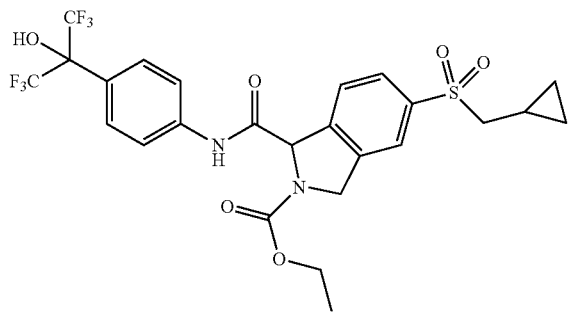 [SMILES: CCOC(=O)N1Cc2cc(S(=O)(=O)CC3CC3)ccc2C1C(=O)Nc1ccc(C(O)(C(F)(F)F)C(F)(F)F)cc1]

Ethyl carbonochloridate (5.19 mg, 0.05 mmol) in acetonitrile (0.25 mL) was added to 5-((cyclopropylmethyl)sulfonyl)-N-(4-(1,1,1,3,3,3-hexafluoro-2-hydroxypropan-2-yl)phenyl)isoindoline-1-carboxamide (25 mg, 0.05 mmol) and DIPEA (0.025 mL, 0.14 mmol) in acetonitrile (1 mL). The reaction was stirred at room temperature for 30 min. The acetonitrile was removed in vacuo and the residue partioned between DCM and water. The layers were separated in a phase separator cartridge and the organic layer was concentrated in vacuo. Purification by preparative SFC (chromatographic conditions: MeOH/NH$_3$ 20 mM; column: Waters Waters BEH 2-EP 5 μm 30×250 mm) gave the title compound (12.0 mg, 42.2%).

HRMS: calculated for $(C_{25}H_{24}F_6N_2O_6S+H)^+$ 595.1337; found: (ESI [M+H]$^+$) 595.1340.

$^1$H NMR (600 MHz, DMSO-d$_6$, mixture of rotamers, 1:1) δ 0.04-0.16 (m, 2H), 0.39-0.53 (m, 2H), 0.77-0.88 (m, 1H), 1.10, 1.26 (t, 3H), 3.19-3.31 (m, 2H), 4.01-4.19 (m, 2H), 4.78-4.92 (m, 2H), 5.64-5.7 (m, 1H), 7.6-7.75 (m, 5H), 7.83-7.88 (m, 1H), 7.96, 7.98 (s, 1H), 8.67 (s, 1H), 10.76, 10.78 (s, 1H).

Example 205: 5-[(Cyclopropylmethyl)sulfonyl]-N-[4-(1,1,1,3,3,3-hexafluoro-2-hydroxypropan-2-yl)phenyl]-2-[(1-methoxycyclopropyl)acetyl]-2,3-dihydro-1H-isoindole-1-carboxamide

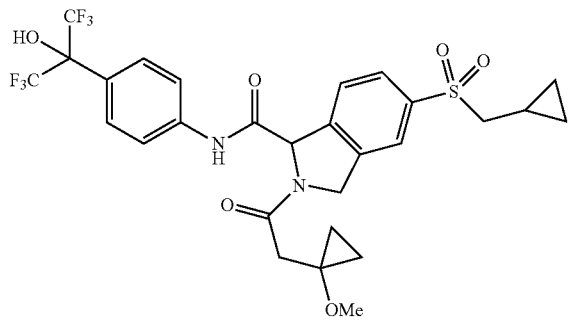 [SMILES: COC1(CC(=O)N2Cc3cc(S(=O)(=O)CC4CC4)ccc3C2C(=O)Nc2ccc(C(O)(C(F)(F)F)C(F)(F)F)cc2)CC1]

Made using the same procedure as Example 201 but using 2-(1-methoxycyclopropyl)acetic acid instead of acetic acid. The title compound (21.2 mg, 23.3%) was obtained after purification by RP-HPLC (chromatographic conditions: gradient 5-95% ACN in 0.1M HCO$_2$H, pH3; column: Waters Sunfire C18 ODB 5μ 19×150 mm).

HRMS: calculated for $(C_{28}H_{28}F_6N_2O_6S+H)^+$ 635.1650; found: (ESI [M+H]$^+$) 635.1699.

$^1$H NMR (600 MHz, DMSO-d$_6$, mixture of rotamers, 6*:1) δ 0.09-0.15 (m, 2H), 0.41-0.48 (m, 2H), 0.56-0.77 (m, 4H), 0.79-0.87 (m, 1H), 2.76-2.92 (m, 2H), 3.14, 3.24* (s, 3H), 3.25-3.31 (m, 2H), 4.8-4.96, 5.08-5.18* (m, 2H), 5.76*, 6.01 (s, 1H), 7.6-7.67 (m, 2H), 7.68-7.81 (m, 3H), 7.85-7.89 (m, 1H), 7.98*, 7.99 (s, 1H), 8.66*, 8.69 (s, 1H), 10.73*, 10.96 (s, 1H).

Examples 206-214

Examples 206-214 (Table 2) were prepared using a similar procedures to those described in the preceding examples.

Example 206: 5-[(Cyclopropylmethyl)sulfonyl]-N-[4-(1,1,1,3,3,3-hexafluoro-2-hydroxypropan-2-yl)phenyl]-2-[(1-hydroxycyclopropyl)acetyl]-2,3-dihydro-1H-isoindole-1-carboxamide Example 207: 5-[(Cyclopropylmethyl)sulfonyl]-N-[4-(1,1,1,3,3,3-hexafluoro-2-hydroxypropan-2-yl)phenyl]-2-(3-hydroxy-3-methylbutanoyl)-2,3-dihydro-1H-isoindole-1-carboxamide Example 208: 5-[(Cyclopropylmethyl)sulfonyl]-N-[4-(1,1,1,3,3,3-hexafluoro-2-hydroxypropan-2-yl)phenyl]-2-(tetrahydrofuran-2-ylcarbonyl)-2,3-dihydro-1H-isoindole-1-carboxamide Example 209: 2-[(1-Cyanocyclopropyl)carbonyl]-5-[(cyclopropylmethyl)sulfonyl]-N-[4-(1,1,1,3,3,3-hexafluoro-2-hydroxypropan-2-yl)phenyl]-2,3-dihydro-1H-isoindole-1-carboxamide Example 210: 5-[(Cyclopropylmethyl)sulfonyl]-N-[4-(1,1,1,3,3,3-hexafluoro-2-hydroxypropan-2-yl)phenyl]-2-(tetrahydrofuran-3-ylcarbonyl)-2,3-dihydro-1H-isoindole-1-carboxamide Example 211: 2-[Amino(cyclopropyl)acetyl]-5-[(cyclopropylmethyl)sulfonyl]-N-[4-(1,1,1,3,3,3-hexafluoro-2-hydroxypropan-2-yl)phenyl]-2,3-dihydro-1H-isoindole-1-carboxamide Example 212: 5-[(Cyclopropylmethyl)sulfonyl]-N-[4-(1,1,1,3,3,3-hexafluoro-2-hydroxypropan-2-yl)phenyl]-2-[(1-methoxycyclopropyl)carbonyl]-2,3-dihydro-1H-isoindole-1-carboxamide Example 213: Methyl 5-[(cyclopropylmethyl)sulfonyl]-1-{[4-(1,1,1,3,3,3-hexafluoro-2-hydroxypropan-2-yl)phenyl]carbamoyl}-1,3-dihydro-2H-isoindole-2-carboxylate Example 214: 2-[Cyclopropyl(difluoro)acetyl]-5-[(cyclopropylmethyl)sulfonyl]-N-[4-(1,1,1,3,3,3-hexafluoro-2-hydroxypropan-2-yl)phenyl]-2,3-dihydro-1H-isoindole-1-carboxamide

TABLE 2

| Example No. | Structure | NMR + MS |
|---|---|---|
| 206 | 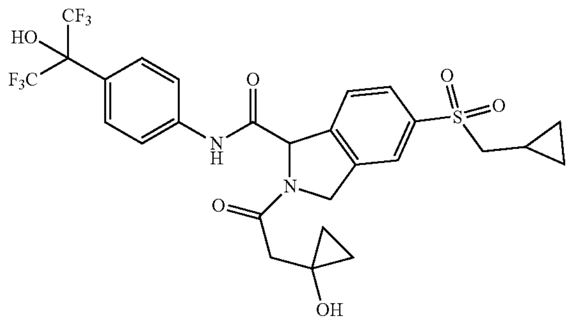 [SMILES: O=C(Nc1ccc(C(O)(C(F)(F)F)C(F)(F)F)cc1)C1c2ccc(S(=O)(=O)CC3CC3)cc2CN1C(=O)CC1(O)CC1] | HRMS: calculated for (C$_{27}$H$_{26}$F$_6$N$_2$O$_6$S + H)$^+$ 621.1494; found (ESI [M + H]$^+$) 621.1501. $^1$H NMR (600 MHz, DMSO-d$_6$, mixture of rotamers, 5*:1) δ 0.07-0.14 (m, 2H), 0.4-0.49 (m, 2H), 0.53-0.64 (m, 4H), 0.79-0.88 (m, 1H), 2.57-2.66 (m, 1H), 2.79-2.89 (m, 1H), 3.22-3.32 (m, 2H), 4.77-4.99, 5.05-5.18* (m, 2H), 5.34*, 5.38 (s, 1H), 5.77*, 6.08 (s, 1H), 7.59-7.67 (m, 2H), 7.68-7.81 (m, 3H), 7.86-7.89 (m, 1H), 7.96*, 7.99 (s, 1H), 8.67 (s, 1H), 10.68*, 10.96 (s, 1H). |
| 207 | 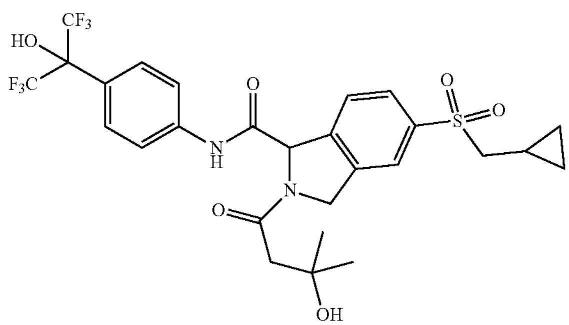 [SMILES: CC(C)(O)CC(=O)N1Cc2cc(S(=O)(=O)CC3CC3)ccc2C1C(=O)Nc1ccc(C(O)(C(F)(F)F)C(F)(F)F)cc1] | HRMS: calculated for (C$_{27}$H$_{28}$F$_6$N$_2$O$_6$S + H)$^+$ 623.1650; found (ESI [M + H]$^+$) 623.1656. $^1$H NMR (600 MHz, DMSO-d$_6$, mixture of rotamers, 6:1, only data for the major rotamer reported) δ 0.09-0.15 (m, 2H), 0.39-0.49 (m, 2H), 0.75-0.88 (m, 1H), 1.26 (s, 6H), 2.55-2.61 (m, 2H), 3.21-3.3 (m, 2H), 5-5.18 (m, 2H), 5.77 (s, 1H), 7.58-7.67 (m, 2H), 7.68-7.8 (m, 3H), 7.83-7.89 (m, 1H), 7.95 (s, 1H), 8.67 (s, 1H), 10.66 (s, 1H). |
| 208 | 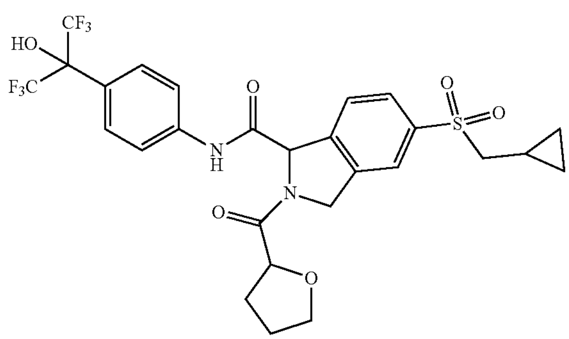 [SMILES: O=C(Nc1ccc(C(O)(C(F)(F)F)C(F)(F)F)cc1)C1c2ccc(S(=O)(=O)CC3CC3)cc2CN1C(=O)C1CCCO1] | HRMS: calculated for (C$_{27}$H$_{26}$F$_6$N$_2$O$_6$S + H)$^+$ 621.1494; found (ESI [M + H]$^+$) 621.1505. Mixture of diastereomers and rotamers; only major diastereomer/rotamer reported: $^1$H NMR (600 MHz, DMSO-d$_6$) δ 0.1-0.14 (m, 2H), 0.42-0.49 (m, 2H), 0.75-0.88 (m, 1H), 1.72-2.23 (m, 4H), 3.2-3.3 (m, 2H), 3.62-3.88 (m, 2H), 4.68-4.78 (m, 1H), 5.01-5.22 (m, 2H), 5.74-5.8 (m, 1H), 7.6-7.65 (m, 2H), 7.68-7.81 (m, 3H), 7.83-7.88 (m, 1H), 7.94-8.01 (m, 1H), 8.68 (s, 1H), 10.76-10.81 (m, 1H). |
| 209 | 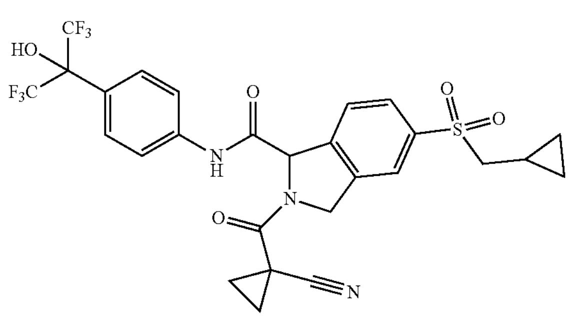 [SMILES: N#CC1(C(=O)N2Cc3cc(S(=O)(=O)CC4CC4)ccc3C2C(=O)Nc2ccc(C(O)(C(F)(F)F)C(F)(F)F)cc2)CC1] | HRMS: calculated for (C$_{27}$H$_{23}$F$_6$N$_3$O$_5$S + H)$^+$ 616.1341.1545; found (ESI [M + H]$^+$) 616.1346. $^1$H NMR (600 MHz, mixture of rotamers, 6:1, only data for the major rotamer reported) δ 0.05-0.15 (m, 2H), 0.35-0.51 (m, 2H), 0.74-0.88 (m, 1H), 1.49-1.82 (m, 4H), 3.18-3.32 (m, 2H), 5.33-5.4 (m, 2H), 5.85 (s, 1H), 7.59-7.68 (m, 2H), 7.69-7.77 (m, 3H), 7.88-8.02 (m, 1H), 8.08 (s, 1H), 8.68 (s, 1H), 10.87 (s, 1H). |

TABLE 2-continued

| Example No. | Structure | NMR + MS |
|---|---|---|
| 210 | (structure) | HRMS: calculated for (C$_{27}$H$_{26}$F$_6$N$_2$O$_6$S + H)$^+$ 621.1494; found (ESI [M + H]$^+$) 621.1490. Mixture of diastereomers and rotamers; Only major diastereomer/rotamer reported: $^1$H NMR (600 MHz, DMSO-d$_6$) δ 0.06-0.17 (m, 2H), 0.41-0.5 (m, 2H), 0.76-0.86 (m, 1H), 1.95-2.24 (m, 2H), 3.2-3.31 (m, 2H), 3.42-3.45 (m, 1H), 3.62-3.84 (m, 4H), 5-5.25 (m, 2H), 5.65-5.83 (m, 1H), 7.6-7.67 (m, 2H), 7.69-7.75 (m, 3H), 7.86-7.89 (m, 1H), 7.95 (s, 1H), 8.69 (s, 1H), 10.61-10.86 (m, 1H). |
| 211 | (structure) | HRMS: calculated for (C$_{27}$H$_{27}$F$_6$N$_3$O$_5$S + H)$^+$ 620.1653; found (ESI [M + H]$^+$) 620.1654. Mixture of diastereomers and rotamers; Only major diastereomer/rotamer reported: $^1$H NMR (600 MHz, DMSO-d$_6$) δ 0.08-0.16 (m, 2H), 0.23-0.53 (m, 6H), 0.77-0.87 (m, 1H), 1.05-1.14 (m, 1H), 3.2-3.31 (m, 3H), 5.02-5.24 (m, 2H), 5.73-5.82 (m, 1H), 7.6-7.66 (m, 2H), 7.67-7.82 (m, 3H), 7.85-7.89 (m, 1H), 7.96 (s, 1H), 8.68 (s, 1H), 10.6-10.83 (m, 1H). |
| 212 | (structure) | HRMS: calculated for (C$_{27}$H$_{26}$F$_6$N$_2$O$_6$S + H)$^+$ 621.1494; found (ESI [M + H]$^+$) 621.1524. $^1$H NMR (600 MHz, mixture of rotamers, 2*:1) δ 0.1-0.17 (m, 2H), 0.43-0.5 (m, 2H), 0.77-0.86 (m, 1H), 0.87-1.19 (m, 4H), 3.2-3.32 (m, 2H), 3.16, 3.35* (s, 3H), 4.8-5.03, 5.19-5.28* (m, 2H), 5.89*, 6.21 (s, 1H), 7.59-7.66 (m, 2H), 7.69-7.82 (m, 3H), 7.85-7.89 (m, 1H), 7.99, 8.01* (s, 1H), 8.65, 8.67* (s, 1H), 10.79, 10.87* (s, 1H). |
| 213 | (structure) | HRMS: calculated for (C$_{24}$H$_{22}$F$_6$N$_2$O$_6$S + H)$^+$ 580.1181; found (ESI [M + H]$^+$) 580.1176. $^1$H NMR (600 MHz, mixture of rotamers, 1.4*:1) δ 0.06-0.15 (m, 2H), 0.39-0.49 (m, 2H), 0.76-0.85 (m, 1H), 3.19-3.3 (m, 2H), 3.63, 3.70* (s, 3H), 4.86 (s, 2H), 5.68*, 5.70 (s, 1H), 7.61-7.65 (m, 2H), 7.68-7.76 (m, 3H), 7.84-7.88 (m, 1H), 7.96*, 7.98 (s, 1H), 8.68 (s, 1H), 10.76, 10.78* (s, 1H). |
| 214 | (structure) | HRMS: calculated for (C$_{27}$H$_{24}$F$_8$N$_2$O$_5$S + H)$^+$ 641.1356; found (ESI [M + H]$^+$) 641.1341 $^1$H NMR (600 MHz, , mixture of rotamers, 4*:1) δ 0.08-0.17 (m, 2H), 0.39-0.51 (m, 2H), 0.54-0.86 (m, 5H), 1.7-1.83 (m, 1H), 3.19-3.3 (m, 2H), 4.91-5.12, 5.16-5.31* (m, 2H), 5.91*, 6.17 (s, 1H), 7.61-7.66 (m, 2H), 7.66-7.82 (m, 3H), 7.87-7.91 (m, 1H), 8.00*, 8.02 (s, 1H), 8.69 (s, 1H), 10.89, 10.95* (s, 1H). |

Example 300: N-[4-(1,1,1,3,3,3-hexafluoro-2-hydroxypropan-2-yl)phenyl]-5-(methylsulfamoyl)-2,3-dihydro-1H-isoindole-1-carboxamide

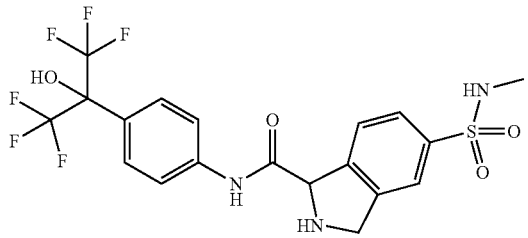 [SMILES: CNS(=O)(=O)c1ccc2c(c1)CNC2C(=O)Nc1ccc(C(O)(C(F)(F)F)C(F)(F)F)cc1]

tert-Butyl 1-((4-(1,1,1,3,3,3-hexafluoro-2-hydroxypropan-2-yl)phenyl)carbamoyl)-5-(N-methylsulfamoyl)isoindoline-2-carboxylate (380 mg, 0.64 mmol) was added to a solution of HCl in dioxane (15 mL, 60.00 mmol) under nitrogen. The resulting mixture was stirred at room temperature for 2 hours. The reaction mixture was basified with saturated NaHCO$_3$. The reaction mixture was quenched with water (50 mL), extracted with EtOAc (3×100 mL), the organic layer was dried over Na$_2$SO$_4$, filtered and evaporated to dryness to afford N-(4-(1,1,1,3,3,3-hexafluoro-2-hydroxypropan-2-yl)phenyl)-5-(N-methylsulfamoyl)isoindoline-1-carboxamide (300 mg, 95%) as an orange solid. LC/MS: m/z=498 [M+H]$^+$.

HRMS: calculated for (C$_{19}$H$_{17}$F$_6$N$_3$O$_4$S+H)$^+$498.0922; found (ESI [M+H]$^+$) 498.0918.

$^1$H NMR (300 MHz, DMSO-d$_6$) δ 2.41 (d, 3H), 4.39 (s, 2H), 5.08 (s, 1H), 7.40-7.49 (m, 1H), 7.58-7.76 (m, 5H), 7.83 (d, 2H), 8.65 (s, 1H), 10.34 (s, 1H).

Example 301: 2-Acetyl-N-[4-(1,1,1,3,3,3-hexafluoro-2-hydroxypropan-2-yl)phenyl]-5-(methylsulfamoyl)-2,3-dihydro-1H-isoindole-1-carboxamide

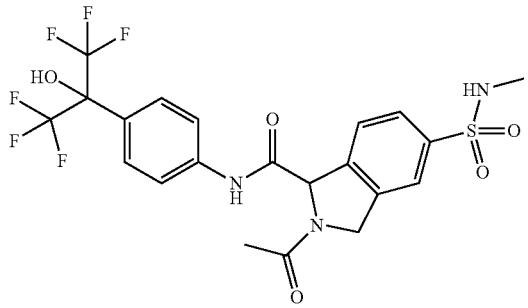 [SMILES: CNS(=O)(=O)c1ccc2c(c1)CN(C(C)=O)C2C(=O)Nc1ccc(C(O)(C(F)(F)F)C(F)(F)F)cc1]

Ac$_2$O (1 mL, 10.60 mmol) was added to N-[4-(1,1,1,3,3,3-hexafluoro-2-hydroxypropan-2-yl)phenyl]-5-(methylsulfamoyl)-2,3-dihydro-1H-isoindole-1-carboxamide (100 mg, 0.20 mmol) in DCM (10 mL) under nitrogen. The resulting mixture was stirred at r.t for 2 hours. The reaction mixture was quenched with water (50 mL), extracted with DCM (3×50 mL), the organic layer was dried over Na$_2$SO$_4$, filtered and evaporated to afford pale yellow solid. The crude product was purified by preparative HPLC (XBridge Prep C18 OBD column, 5 j silica, 19 mm diameter, 100 mm length), using decreasingly polar mixtures of water (containing 0.08% NH$_4$HCO$_3$) and MeCN as eluents. Fractions containing the desired compound were evaporated to dryness to afford 2-acetyl-N-(4-(1,1,1,3,3,3-hexafluoro-2-hydroxypropan-2-yl)phenyl)-5-(N-methylsulfamoyl)isoindoline-1-carboxamide (50.0 mg, 46.1%). LC/MS: m/z=540 [M+H]$^+$.

HRMS: calculated for (C$_{21}$H$_{19}$F$_6$N$_3$O$_5$S+H)$^+$540.1028; found (ESI [M+H]$^+$) 540.1004.

$^1$H NMR (300 MHz, DMSO-d$_6$, mixture of rotamers, 4.3*:1) δ 1.98, 2.14* (s, 3H), 2.42 (s, 3H), 4.77-5.10 (m, 2H), 5.71-5.98 (m, 1H), 7.52-7.88 (m, 8H), 8.69 (s, 1H), 10.71-11.00 (m, 1H).

Example 302: 2-Formyl-N-[4-(1,1,1,3,3,3-hexafluoro-2-hydroxypropan-2-yl)phenyl]-5-(methylsulfamoyl)-2,3-dihydro-1H-isoindole-1-carboxamide

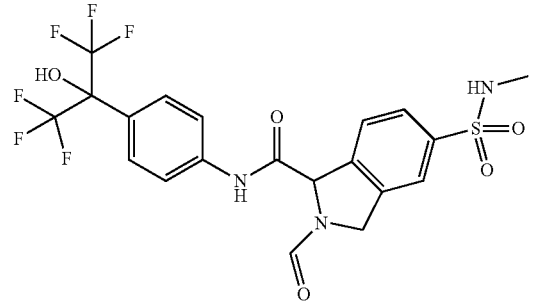 [SMILES: CNS(=O)(=O)c1ccc2c(c1)CN(C=O)C2C(=O)Nc1ccc(C(O)(C(F)(F)F)C(F)(F)F)cc1]

N-[4-(1,1,1,3,3,3-Hexafluoro-2-hydroxypropan-2-yl)phenyl]-5-(methylsulfamoyl)-2,3-dihydro-1H-isoindole-1-carboxamide (90 mg, 0.18 mmol) was added to formic acid (12.49 mg, 0.27 mmol), HATU (103 mg, 0.27 mmol) and DIPEA (0.06 mL, 0.36 mmol) in DCM (5 mL) under nitrogen. The resulting mixture was stirred at room temperatrue for 2 hours. The reaction mixture was quenched with saturated NH$_4$Cl (75 mL), extracted with DCM (3×100 mL), the organic layer was dried over Na$_2$SO$_4$, filtered and evaporated to afford yellow solid. The crude product was purified by flash C18-flash chromatography, elution gradient 5 to 90% MeCN in water. Pure fractions were evaporated to dryness to afford the title compound (80 mg, 84%) as a white solid. LC/MS: m/z=526 [M+H]$^+$. HRMS: calculated for (C$_{20}$H$_{17}$F$_6$N$_3$O$_5$S+H)$^+$526.0871; found (ESI [M+H]$^+$) 526.0864.

$^1$H NMR (300 MHz, DMSO-d$_6$, mixture of rotamers, 2*:1) δ 2.43 (d, 3H), 4.72-4.93, 5.03-5.19* (m, 2H), 5.75*, 5.96 (s, 1H), 7.51-7.87 (m, 8H), 8.38, 8.49* (s, 1H), 8.68*, 8.69 (s, 1H), 10.77*, 10.87 (s, 1H).

115

Example 303: (R,S)—N-[4-(1,1,1,3,3,3-Hexafluoro-2-hydroxypropan-2-yl)phenyl]-2-[(2R)-2-hydroxybutanoyl]-5-(methylsulfamoyl)-2,3-dihydro-1H-isoindole-1-carboxamide

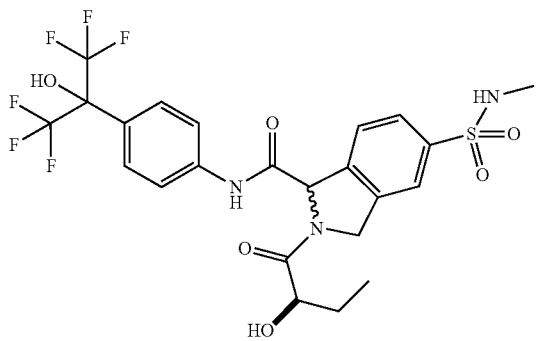 [SMILES: CC[C@@H](O)C(=O)N1Cc2cc(S(=O)(=O)NC)ccc2C1C(=O)Nc1ccc(C(O)(C(F)(F)F)C(F)(F)F)cc1]

N-[4-(1,1,1,3,3,3-Hexafluoro-2-hydroxypropan-2-yl)phenyl]-5-(methylsulfamoyl)-2,3-dihydro-1H-isoindole-1-carboxamide (80.10 mg, 0.16 mmol) was added to (R)-2-hydroxybutanoic acid (21.77 mg, 0.21 mmol), HATU (92.32 mg, 0.24 mmol) and DIPEA (0.056 mL, 0.32 mmol) in DMF (6 mL) under nitrogen. The resulting mixture was stirred at room temperature for 12 hours. The reaction mixture was diluted with DCM (75 mL), and washed sequentially with water (1×75 mL), saturated brine (2×75 mL). The organic layer was dried over $Na_2SO_4$, filtered and evaporated to afford crude product. The crude product was purified by preparative HPLC (XBridge Shield RP18 OBD column, 5p silica, 19 mm diameter, 150 mm length), using decreasingly polar mixtures of water (containing 0.5% formic acid) and MeCN as eluents. Fractions containing the desired compound were evaporated to dryness to afford isomer 1 (15.0 mg, 16%) and isomer 2 (20.0 mg, 21.3%), both as solids.

Isomer 1: LC/MS: m/z=584 $[M+H]^+$.

HRMS: calculated for $(C_{23}H_{23}F_6N_3O_6S+H)^+$ 584.1290; found (ESI $[M+H]^+$) 584.1286.

$^1$H NMR (400 MHz, DMSO-$d_6$, mixture of rotamers, 3*:1) δ 0.80, 0.92* (t, 3H), 1.53-1.71 (m, 2H), 2.39-2.41 (m, 3H), 3.90-3.97, 4.15-4.21* (m, 1H), 4.75-4.98, 5.06-5.19* (m, 2H), 5.12 (s, 1H), 5.73*, 6.17 (s, 1H), 7.45-7.54 (m, 1H), 7.58-7.67 (m, 3H), 7.69-7.76 (m, 4H), 7.82 (d, 1H), 8.61-8.68 (m, 1H), 10.74*, 10.88 (s, 1H).

Isomer 2: LC/MS: m/z=584 $[M+H]^+$.

HRMS: calculated for $(C_{23}H_{23}F_6N_3O_6S+H)^+$ 584.1290; found (ESI $[M+H]^+$) 584.1299.

$^1$H NMR (isomer 2) (400 MHz, DMSO-$d_6$, mixture of rotamers, 7*:1) δ 0.87-0.94 (m, 3H), 1.55-1.75 (m, 2H), 2.38-2.43 (m, 3H), 3.92-4.00, 4.20-4.29* (m, 1H), 4.78-5.21 (m, 3H), 5.78*, 6.04 (s, 1H), 7.45-7.55 (m, 1H), 7.57-7.77 (m, 6H), 7.79-7.86 (d, 1H), 8.67 (m, 1H), 10.76*, 10.91 (s, 1H).

116

Example 304: Methyl 1-{[4-(1,1,1,3,3,3-hexafluoro-2-hydroxypropan-2-yl)phenyl]carbamoyl}-5-(methylsulfamoyl)-1,3-dihydro-2H-isoindole-2-carboxylate

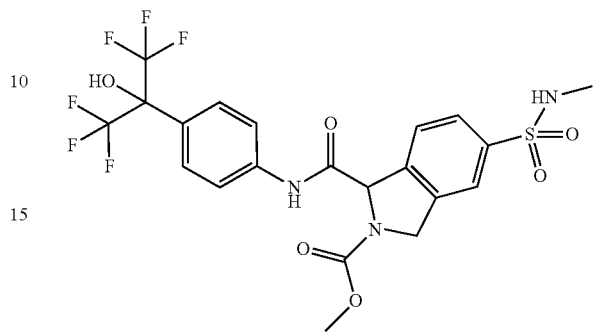

N-[4-(1,1,1,3,3,3-Hexafluoro-2-hydroxypropan-2-yl)phenyl]-5-(methylsulfamoyl)-2,3-dihydro-1H-isoindole-1-carboxamide (90 mg, 0.18 mmol) was added to methyl carbonochloridate (51.3 mg, 0.54 mmol) in DCM (5 mL) under nitrogen. The resulting mixture was stirred at room temperature for 2 hours. The reaction mixture was quenched with water (50 mL), extracted with DCM (3×50 mL), the organic layer was dried over $Na_2SO_4$, filtered and evaporated to afford orange solid. The crude product was purified by flash C18-flash chromatography, elution gradient 5 to 70% MeCN in water. Pure fractions were evaporated to dryness to afford methyl 1-{[4-(1,1,1,3,3,3-hexafluoro-2-hydroxypropan-2-yl)phenyl]carbamoyl}-5-(methylsulfamoyl)-1,3-dihydro-2H-isoindole-2-carboxylate (90 mg, 90%). LC/MS: m/z=556 $[M+H]^+$.

HRMS: calculated for $(C_{21}H_{19}F_6N_3O_6S+H)^+$ 556.0977; found (ESI $[M+H]^+$) 556.0994.

$^1$H NMR (300 MHz, DMSO-$d_6$, mixture of rotamers, 1.3*:1) δ 2.41 (d, 3H), 3.62, 3.70* (s, 3H), 4.84 (br.s, 2H), 5.65 (br.s, 1H), 7.45-7.54 (m, 1H), 7.59-7.69 (m, 1H), 7.70-7.77 (m, 3H), 7.81-7.86 (m, 1H), 8.65 (s, 1H), 10.72-10.78 (m, 1H).

Examples 305-313

Examples 305-313 (Table 3) were Prepared Using a Similar Procedures to Those Described in the Preceding Examples Example 305: Ethyl 1-{[4-(1,1,1,3,3,3-hexafluoro-2-hydroxypropan-2-yl)phenyl]carbamoyl}-5-(methylsulfamoyl)-1,3-dihydro-2H-isoindole-2-carboxylate Example 306: N-[4-(1,1,1,3,3,3-Hexafluoro-2-hydroxypropan-2-yl)phenyl]-2-[(1-methoxycyclopropyl)carbonyl]-5-(methylsulfamoyl)-2,3-dihydro-1H-isoindole-1-carboxamide Example 307, isomer 1: (R) or (S)N-[4-(1,1,1,3,3,3-Hexafluoro-2-hydroxypropan-2-yl)phenyl]-2-[(2S)-2-hydroxybutanoyl]-5-(methylsulfamoyl)-2,3-dihydro-1H-isoindole-1-carboxamide Example 307, isomer 2: (R) or (S)N-[4-(1,1,1,3,3,3-Hexafluoro-2-hydroxypropan-2-yl)phenyl]-2-[(2S)-2-hydroxybutanoyl]-5-(methylsulfamoyl)-2,3-dihydro-1H-isoindole-1-carboxamide Example 308: N-[4-(1,1,1,3,3,3-Hexafluoro-2-hydroxypropan-2-yl)phenyl]-2-(methoxyacetyl)-5-(methylsulfamoyl)-2,3-dihydro-1H-isoindole-1-carboxamide Example 309: N-[4-(1,1,1,3,3,3-Hexafluoro-2-hydroxypropan-2-yl)phenyl]-5-(methylsulfamoyl)-2-(oxetan-2-ylcarbonyl)-2,3-dihydro-1H-isoindole-1-carboxamide Example 310: N-[4-(1,1,1,3,3,3-Hexafluoro-2-hydroxypropan-2-yl)phenyl]-5-(methylsulfamoyl)-2-[(2R)-tetrahydrofuran-2-ylcarbonyl]-2,3-dihydro-1H-isoindole-1-carboxamide Example 311: N-[4-(1,1,1,3,3,3-Hexafluoro-2-hydroxypropan-2-yl)phenyl]-5-(methylsulfamoyl)-2-[(2S)-tetrahydrofuran-2-ylcarbonyl]-2,3-dihydro-1H-isoindole-1-carboxamide Example 312: N-[4-(1,1,1,3,3,3-Hexafluoro-2-hydroxypropan-2-yl)phenyl]-2-(2-methoxybutanoyl)-5-(methylsulfamoyl)-2,3-dihydro-1H-isoindole-1-carboxamide Example 313: N-[4-(1,1,1,3,3,3-Hexafluoro-2-hydroxypropan-2-yl)phenyl]-2-(hydroxyacetyl)-5-(methylsulfamoyl)-2,3-dihydro-1H-isoindole-1-carboxamide

TABLE 3

| Example No. | Structure | NMR +MS |
|---|---|---|
| 305 | 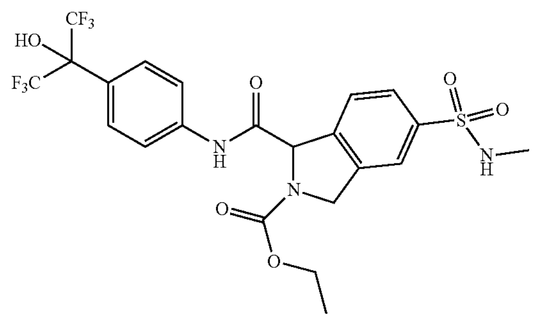 [SMILES: CCOC(=O)N1Cc2cc(S(=O)(=O)NC)ccc2C1C(=O)Nc1ccc(C(O)(C(F)(F)F)C(F)(F)F)cc1] | HRMS: calculated for $(C_{22}H_{21}F_6N_3O_6S + H)^+$ 570.1133; found (ESI [M + H]$^+$) 570.1133. $^1$H NMR (400 MHz, DMSO-d$_6$, mixture of rotamers, 1.2*:1) δ 1.10, 1.26* (t, 3H), 2.42 (d, 3H), 3.99-4.21 (m, 2H), 4.75-4.93 (m, 2H), 5.66 (s, 1H), 7.52 (s, 1H), 7.59-7.70 (m, 3H), 7.70-7.80 (m, 3H), 7.80-7.90 (m, 1H), 8.68 (s, 1H), 10.77, 10.79* (s, 1H). |
| 306 | 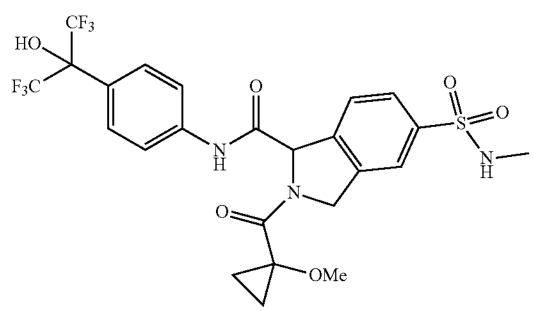 [SMILES: CNS(=O)(=O)c1ccc2c(c1)CN(C(=O)C1(OC)CC1)C2C(=O)Nc1ccc(C(O)(C(F)(F)F)C(F)(F)F)cc1] | HRMS: calculated for $(C_{24}H_{23}F_6N_3O_6S + H)^+$ 596.1290; found (ESI [M + H]$^+$) 596.1295. $^1$H NMR (400 MHz, DMSO-d$_6$, mixture of rotamers, 2.2*:1) δ 0.8-1.25 (m, 4H), 2.39-2.46 (m, 3H), 3.19, 3.36* (s, 3H), 4.85-5.02, 5.17-5.30* (m, 2H), 5.87*, 6.20 (s, 1H), 7.48-7.58 (m, 1H), 7.59-7.81 (m, 6H), 7.84-7.93 (m, 1H), 8.66, 8.68* (s, 1H), 10.81, 10.88* (s, 1H). |
| 307 Isomer 1 | 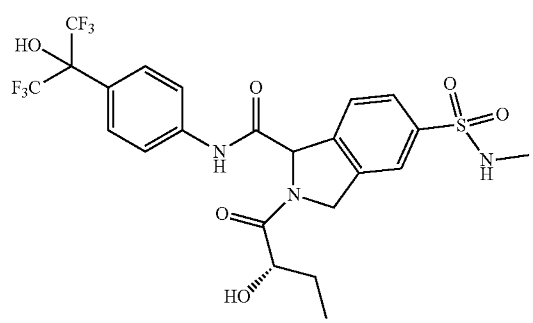 [SMILES: CC[C@H](O)C(=O)N1Cc2cc(S(=O)(=O)NC)ccc2C1C(=O)Nc1ccc(C(O)(C(F)(F)F)C(F)(F)F)cc1] | HRMS: calculated for $(C_{23}H_{23}F_6N_3O_6S + H)^+$ 584.1290; found (ESI [M + H]$^+$) 584.1292. $^1$H NMR (300 MHz, DMSO-d$_6$, mixture of rotamers, 3*:1) δ 0.81, 0.93* (t, 3H), 1.48-1.80 (m, 2H), 2.42 (d, 3H), 3.88-3.99, 4.14-4.26* (m, 1H), 4.76-5.51 (m, 3H), 5.74*, 6.18 (s, 1H), 7.45-7.56 (m, 1H), 7.58-7.78 (m, 6H), 7.79-7.88 (m, 1H), 8.65 (s, 1H), 10.75*, 10.88 (s, 1H). |
| 307 Isomer 2 | 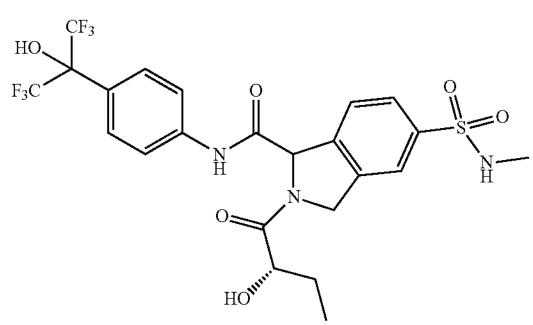 [SMILES: CC[C@H](O)C(=O)N1Cc2cc(S(=O)(=O)NC)ccc2C1C(=O)Nc1ccc(C(O)(C(F)(F)F)C(F)(F)F)cc1] | HRMS: calculated for $(C_{23}H_{23}F_6N_3O_6S + H)^+$ 584.1290; found (ESI [M + H]$^+$) 584.1272. $^1$H NMR (300 MHz, DMSO-d$_6$, mixture of rotamers, 7*:1) δ 0.93 (t, 3H), 1.51-1.8 (m, 2H), 2.42 (s, 3H), 4.2-4.32 (m, 1H), 4.81-5.24 (m, 3H), 5.80*, 6.06 (s, 1H), 7.45-7.56 (m, 1H), 7.56-7.79 (m, 6H), 7.79-7.88 (m, 1H), 8.48, 8.68* (s, 1H), 10.77 (s, 1H). |

| Example No. | Structure | NMR +MS |
|---|---|---|
| 308 | 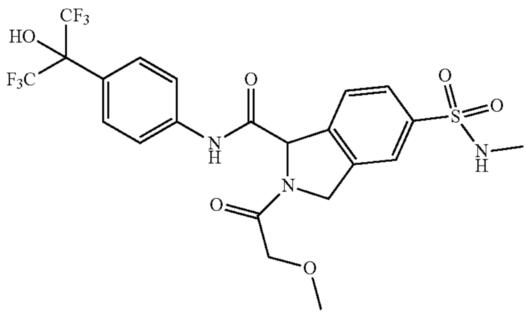 [SMILES: CNS(=O)(=O)c1ccc2c(c1)CN(C(=O)COC)C2C(=O)Nc1ccc(C(O)(C(F)(F)F)C(F)(F)F)cc1] | HRMS: calculated for (C$_{22}$H$_{21}$F$_6$N$_3$O$_6$S + H)$^+$ 570.1133; found (ESI [M + H]$^+$) 570.1127.<br>$^1$H NMR (300 MHz, DMSO-d$_6$, mixture of rotamers, 5*:1) δ 2.43 (d, 3H), 3.28, 3.38* (s, 3H), 3.93-4.13, 4.18-4.33* (m, 2H), 4.80-5.09 (m, 2H), 5.78*, 5.98 (s, 1H), 7.50-7.58 (m, 1H), 7.61-7.81 (m, 6H), 7.83-7.90 (m, 1H), 8.68 (s, 1H), 10.77*, 10.87, (s, 1H). |
| 309 | 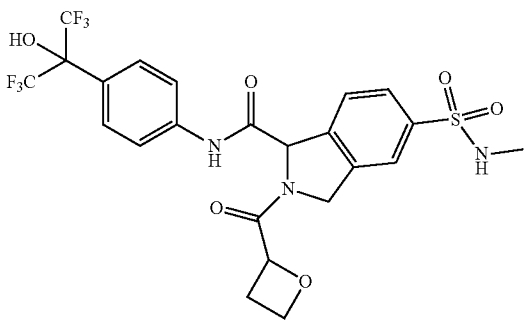 [SMILES: CNS(=O)(=O)c1ccc2c(c1)CN(C(=O)C1CCO1)C2C(=O)Nc1ccc(C(O)(C(F)(F)F)C(F)(F)F)cc1] | HRMS: calculated for (C$_{23}$H$_{21}$F$_6$N$_3$O$_6$S + H)$^+$ 582.1133; found (ESI [M + H]$^+$) 582.1131.<br>Mixture of diastereomers/rotamers; ratio major*: minor = 7.7:1.3:1; only major isomer reported:<br>$^1$H NMR (400 MHz, DMSO-d$_6$) δ 2.42 (d, 3H), 2.71-3.04 (m, 2H), 4.44-4.71 (m, 2H), 4.79-5.08 (m, 2H), 5.42-5.55 (m, 1H), 5.80 (s, 1H), 7.48-7.59 (m, 1H), 7.59-7.8 (m, 6H), 7.80-7.89 (m, 1H), 8.70 (s, 1H), 10.83 (s, 1H). |
| 310 | 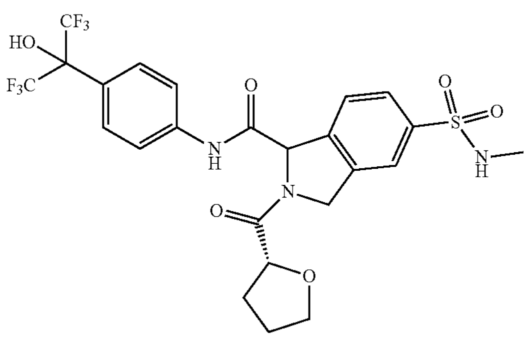 [SMILES: CNS(=O)(=O)c1ccc2c(c1)CN(C(=O)[C@H]1CCCO1)C2C(=O)Nc1ccc(C(O)(C(F)(F)F)C(F)(F)F)cc1] | HRMS: calculated for (C$_{24}$H$_{23}$F$_6$N$_3$O$_6$S + H)$^+$ 596.1290; found (ESI [M + H]$^+$) 596.1307.<br>Mixture of diastereomers/rotamers, 5*:4:1.3:1; only 2 major isomers reported:<br>$^1$H NMR (400 MHz, DMSO-d$_6$) δ 1.7-2.27 (m, 4H), 2.4-2.45 (m, 3H), 3.62-3.91 (m, 2H), 4.68-5.22 (m, 3H), 5.74, 4.76* (s, 1H), 7.48-7.58 (m, 1H), 7.59-7.79 (m, 6H), 7.80-7.89 (m, 1H), 8.68 (s, 1H), 10.77, 10.80* (s, 1H). |
| 311 | 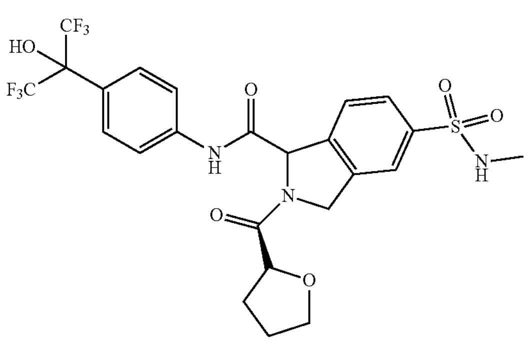 | HRMS: calculated for (C$_{24}$H$_{23}$F$_6$N$_3$O$_6$S + H)$^+$ 596.1290; found (ESI [M + H]$^+$) 596.1311.<br>Mixture of diastereomers/rotamers, 5*:5:2:1; only 2 major isomers reported:<br>$^1$H NMR (400 MHz, DMSO-d$_6$) δ 1.71-2.26 (m, 4H), 2.40-2.43 (m, 3H), 3.73-3.89 (m, 2H), 4.68-5.21 (m, 3H), 5.75, 5.76* (s, 1H), 7.48-7.56 (m, 1H), 7.59-7.79 (m, 6H), 7.81-7.88 (m, 1H), 8.68 (s, 1H), 10.77, 10.80* (s, 1H). |

| Example No. | Structure | NMR +MS |
|---|---|---|
| 312 | 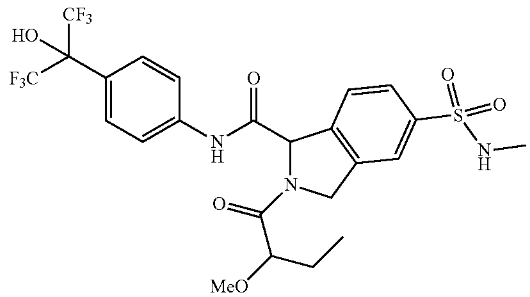 [SMILES: CCC(OC)C(=O)N1Cc2cc(S(=O)(=O)NC)ccc2C1C(=O)Nc1ccc(C(O)(C(F)(F)F)C(F)(F)F)cc1] | HRMS: calculated for $(C_{24}H_{25}F_6N_3O_6S + H)^+$ 598.1447; found (ESI [M + H]$^+$) 598.1470. $^1$H NMR (300 MHz, DMSO-d$_6$, mixture of rotamers, 1.2*:1) δ 0.89-1.00 (m, 3H), 1.63-1.78 (m, 2H), 2.42 (d, J = 4.9 Hz, 3H), 3.27, 3.30* (s, 3H), 3.91-4.13 (m, 1H), 4.93-5.27 (m, 2H), 5.78, 5.84* (s, 1H), 7.47-7.56 (m, 1H), 7.59-7.79 (m, 6H), 7.80-7.88 (m, 1H), 8.65 (s, 1H), 10.80, 10.83* (s, 1H). |
| 313 | 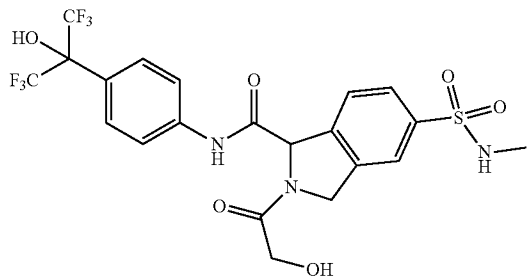 [SMILES: CNS(=O)(=O)c1ccc2c(c1)CN(C(=O)CO)C2C(=O)Nc1ccc(C(O)(C(F)(F)F)C(F)(F)F)cc1] | HRMS: calculated for $(C_{21}H_{19}F_6N_3O_6S + H)^+$ 556.0977; found (ESI [M + H]$^+$) 556.0972. $^1$H NMR (300 MHz, DMSO-d$_6$, mixture of rotamers, 5*:1) δ 2.42 (d, J = 4.6 Hz, 3H), 4.10-4.33 (m, 2H), 4.96 (s, 3H), 5.76*, 5.97 (s, 1H), 7.47-7.55 (m, 1H), 7.58-7.79 (m, 6H), 7.80-7.89 (m, 1H), 8.65*, 8.67 (s, 1H), 10.73*, 10.90 (s, 1H). |

Example 314: N$^2$—Cyclopropyl-N$^1$-[4-(1,1,1,3,3,3-hexafluoro-2-hydroxypropan-2-yl)phenyl]-5-(methylsulfamoyl)-1,3-dihydro-2H-isoindole-1,2-dicarboxamide

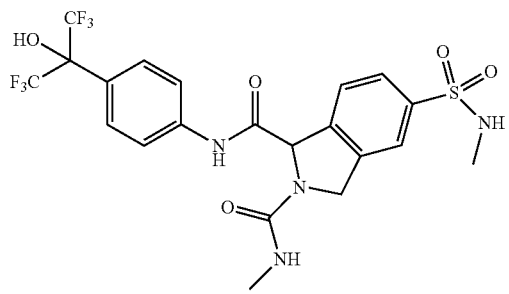 [SMILES: CNC(=O)N1Cc2cc(S(=O)(=O)NC)ccc2C1C(=O)Nc1ccc(C(O)(C(F)(F)F)C(F)(F)F)cc1]

Et$_3$N (0.070 mL, 0.50 mmol) was added to N-(4-(1,1,1,3,3,3-hexafluoro-2-hydroxypropan-2-yl)phenyl)-5-(N-methylsulfamoyl)isoindoline-1-carboxamide (50 mg, 0.10 mmol) and methylcarbamic chloride (37.6 mg, 0.40 mmol) in DCM (4 mL) under nitrogen. The resulting solution was stirred at r.t. for 1 hour. The solvent was removed under reduced pressure. The crude product was purified by preparative HPLC Column: XBridge Prep OBD C18 Column 30×150 mm 5 um; Mobile Phase A: Water (10 mmol/L NH$_4$HCO$_3$), Mobile Phase B: ACN; Flow rate: 60 mL/min; Gradient: 28% B to 43% B in 7 min. Fractions containing the desired compound were evaporated to dryness to afford N$^2$-Cyclopropyl-N$^1$-[4-(1,1,1,3,3,3-hexafluoro-2-hydroxypropan-2-yl)phenyl]-5-(methylsulfamoyl)-1,3-dihydro-2H-isoindole-1,2-dicarboxamide (25 mg, 45%) as a solid. HRMS: calculated for $(C_{21}H_{20}F_6N_4O_5S+H)^+$555.1136; found: (ESI [M+H]$^+$) 555.1147.

$^1$H NMR (300 MHz, DMSO d$_6$) δ 2.42 (d, 2H), 2.64 (d, 3H), 4.73 (d, 1H), 4.82 (d, 1H), 5.64 (d, 1H), 6.58 (q, 1H), 7.49 (q, 1H), 7.59-7.67 (m, 4H), 7.74 (d, 2H), 7.77 (d, 1H), 8.65 (s, 1H), 10.62 (s, 1H).

Example 400: N-[4-(1,1,1,3,3,3-Hexafluoro-2-hydroxypropan-2-yl)phenyl]-5-(methylsulfonyl)-2,3-dihydro-1H-isoindole-1-carboxamide

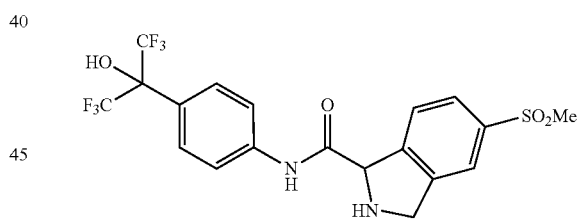

9H-Fluoren-9-yl 1-{[4-(1,1,1,3,3,3-hexafluoro-2-hydroxypropan-2-yl)phenyl]carbamoyl}-5-(methylsulfonyl)-1,3-dihydro-2H-isoindole-2-carboxylate (10.64 g, 15.1 mmol) was dissolved in acetonitrile (300 mL) and to this diethylamine (126 mL, 1208 mmol) was added and the reaction stirred at room temperature for 30 min. The reaction was evaporated to dryness and the residue dissolved in methanol. This was loaded onto Isolute™ SCX resin previously flushed with methanol. The resin was flushed with methanol and the product was then eluted with 2M ammonia in methanol. The methanolic ammonia was removed in vacuo to afford N-(4-(1,1,1,3,3,3-hexafluoro-2-hydroxypropan-2-yl)phenyl)-5-(methylsulfonyl)isoindoline-1-carboxamide (5.16 g, 70.8%).

A sample for biological screening was purified by RP-HPLC (chromatographic conditions: gradient 5-95% ACN in 0.1M HCO$_2$H, pH3; Column: Waters Sunfire C18 ODB 5μ 19×150 mm) to afford the title compound.

HRMS: calculated for $(C_{19}H_{16}F_6N_2O_4S+H)^+$ 483.0813; found: (ESI [M+H]$^+$) 483.0811.

$^1$H NMR (600 MHz, DMSO-d$_6$) δ 3.18 (s, 3H), 4.37 (d, 1H), 4.41 (d, 1H), 5.09 (s, 1H), 7.60 (d, 2H), 7.71 (d, 1H), 7.77-7.83 (m, 3H), 7.87 (s, 1H), 8.65 (s, 1H), 10.33 (s, 1H).

Example 401: 2-Acetyl-N-[4-(1,1,1,3,3,3-hexafluoro-2-hydroxypropan-2-yl)phenyl]-5-(methylsulfonyl)-2,3-dihydro-1H-isoindole-1-carboxamide

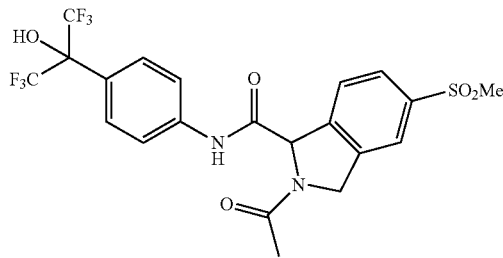 [SMILES: CC(=O)N1Cc2cc(S(C)(=O)=O)ccc2C1C(=O)Nc1ccc(C(O)(C(F)(F)F)C(F)(F)F)cc1]

N-[4-(1,1,1,3,3,3-Hexafluoro-2-hydroxypropan-2-yl)phenyl]-5-(methylsulfonyl)-2,3-dihydro-1H-isoindole-1-carboxamide (4.2 g, 8.71 mmol) was dissolved in DCM (150 mL) and to this triethylamine (2.427 mL, 17.41 mmol) and acetic acid (0.748 mL, 13.06 mmol) was added followed by T3P (50% in EtOAc, 10.37 mL, 17.41 mmol). The reaction was stirred at room temperature for 30 min. The reaction was partitioned between DCM and water, the layers were separated using a phase separator cartridge and the solvent was removed in vacuo.

The residue was purified on silica eluting with 50% to 100% EtOAc in heptane. Product fractions were combined, concentrated in vacuo and a pink gum was obtained. This was triturated with diethyl ether and a solid was formed. This was collected by filtration and washed with diethyl ether to afford 2-acetyl-N-[4-(1,1,1,3,3,3-hexafluoro-2-hydroxypropan-2-yl)phenyl]-5-(methylsulfonyl)-2,3-dihydro-1H-isoindole-1-carboxamide (3.32 g, 72.7%).

HRMS: calculated for $(C_{21}H_8F_6N_2O_5S+H)^+$ 525.0919; found: (ESI [M+H]$^+$) 525.0927.

$^1$H NMR (500 MHz, DMSO-d$_6$, mixture of rotamers, 4*:1) δ 1.99, 2.15* (s, 3H), 3.21, 3.22* (s, 3H), 4.76-4.94, 4.98-5.11* (m, 2H), 5.73*, 5.93 (s, 1H), 7.6-7.81 (m, 5H), 7.87-7.92 (m, 1H), 8.00*, 8.03 (s, 1H), 8.64*, 8.67 (s, 1H), 10.69*, 10.93 (s, 1H).

The (1R) and the (1S) enantiomers of 2-acetyl-N-[4-(1,1,1,3,3,3-hexafluoro-2-hydroxypropan-2-yl)phenyl]-5-(methylsulfonyl)-2,3-dihydro-1H-isoindole-1-carboxamide (4011 mg) were separated by a preparative SFC system equipped with a Chiralpak AS column 25% EtOH 100 in CO$_2$ (120 bar); flow: 150 mL/min; injection volume was 2.5 mL of a 60 mg/mL ethanol/DMSO 9/1 solution.

Isomer 1 (peak 1): 1730 mg, 99.4% ee by analytical chiral SFC (analytical conditions: Chiralpak AS column, 150×4.6 mm, 3 μm, 3.5 ml/min, 30% EtOH in CO$_2$, 120 bar, 40° C.). [α]$_D^{589}$ +13° (c=0.5, CHCl$_3$/DMSO 8/2).

HRMS: calculated for $(C_{21}H_{18}F_6N_2O_5S+H)^+$ 525.0919; found: (ESI [M+H]$^+$) 525.0914.

$^1$H NMR (500 MHz, DMSO-d$_6$, mixture of rotamers, 4*:1) δ 1.99, 2.15* (s, 3H), 3.21, 3.22* (s, 3H), 4.76-4.94, 4.98-5.11* (m, 2H), 5.73*, 5.93 (s, 1H), 7.6-7.81 (m, 5H), 7.87-7.92 (m, 1H), 8.00*, 8.03 (s, 1H), 8.64*, 8.67 (s, 1H), 10.69*, 10.93 (s, 1H). Isomer 2 (peak 2): 1980 mg, 99.5% ee by analytical chiral SFC (analytical conditions: Chiralpak AS column, 150×4.6 mm, 3 m, 3.5 ml/min, 30% EtOH in CO$_2$, 120 bar, 40° C.). [α]$_D^{589}$ −11° (c=0.2, CHCl$_3$/DMSO 8/2).

HRMS: calculated for $(C_{21}H_{18}F_6N_2O_5S+H)^+$ 525.0919; found: (ESI [M+H]$^+$) 525.0916.

$^1$H NMR (600 MHz, DMSO-d$_6$, mixture of rotamers, 4*:1) δ 1.99, 2.15* (s, 2H), 3.21, 3.22* (s, 2H), 4.76-4.94, 4.98-5.11* (m, 2H), 5.73*, 5.93 (s, 1H), 7.6-7.81 (m, 5H), 7.87-7.92 (m, 1H), 8.00*, 8.03 (s, 1H), 8.64*, 8.67 (s, 1H), 10.69*, 10.93 (s, 1H).

Example 402: N-[4-(1,1,1,3,3,3-Hexafluoro-2-hydroxypropan-2-yl)phenyl]-5-(methylsulfonyl)-2-(phenylacetyl)-2,3-dihydro-1H-isoindole-1-carboxamide

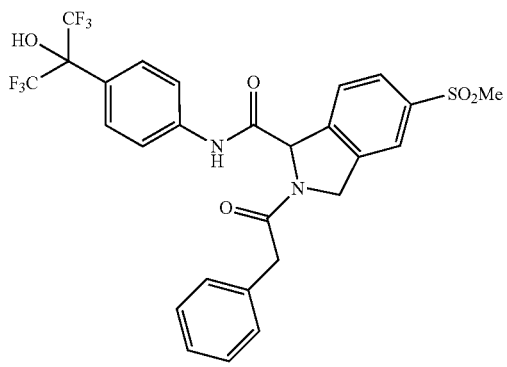 [SMILES: CS(=O)(=O)c1ccc2c(c1)CN(C(=O)Cc1ccccc1)C2C(=O)Nc1ccc(C(O)(C(F)(F)F)C(F)(F)F)cc1]

Prepared using the same procedure as Example 401 but using 2-phenylacetic acid instead of acetic acid. The title compound (14.7 mg, 47%) was obtained after purification by preparative SFC (chromatographic conditions: MeOH/NH$_3$ 20 mM; column: Phenomenex Luna Hilic 5 30×250 mm).

HRMS: calculated for $(C_{27}H_{22}F_6N_2O_5S+H)^+$ 601.1232; found: (ESI [M+H]$^+$) 601.1224.

$^1$HNMR (400 MHz, DMSO-d$_6$, mixture of rotamers, 7*:1) δ $^1$H NMR (600 MHz, DMSO-d$_6$) δ 3.21 (s, 3H), 3.81-3.91 (m, 2H), 4.77-4.99, 5.03-5.17* (m, 2H), 5.79*, 6.05 (s, 1H), 7.18-7.36 (m, 5H), 7.6-7.68 (m, 2H), 7.69-7.76 (m, 3H), 7.88-7.93 (m, 1H), 8.00*, 8.03 (s, 1H), 8.66*, 8.69 (s, 1H), 10.76*, 10.99 (s, 1H).

Example 403: Methyl 1-{[4-(1,1,1,3,3,3-hexafluoro-2-hydroxypropan-2-yl)phenyl]carbamoyl}-5-(methylsulfonyl)-1,3-dihydro-2H-isoindole-2-carboxylate

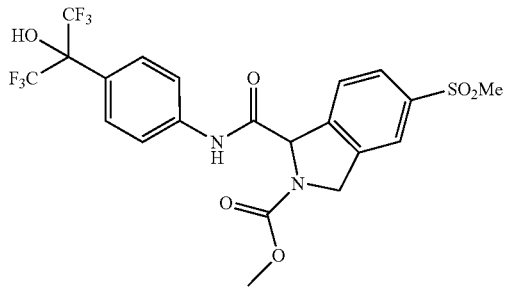 [SMILES: COC(=O)N1Cc2cc(S(C)(=O)=O)ccc2C1C(=O)Nc1ccc(C(O)(C(F)(F)F)C(F)(F)F)cc1]

To a suspension of 5-(methylsulfonyl)isoindoline-1-carboxylic acid, HCl (0.078 g, 0.28 mmol) in acetonitrile (3 mL) was added DIPEA (0.147 mL, 0.84 mmol) and to this methyl carbonochloridate (0.027 g, 0.28 mmol) was added as a solution in acetonitrile (0.25 mL). After 30 mins the reaction was concentrated in vacuo. The residue was dissolved in DCM (4 mL) and to this triethylamine (0.078 mL, 0.56 mmol), 2-(4-aminophenyl)-1,1,1,3,3,3-hexafluoropropan-2-ol (0.073 g, 0.28 mmol) and T3P (50% solution in EtOAc) 0.251 mL, 0.42 mmol) was added. The mixture was stirred at rt for 30 min. The reaction mixture diluted with DCM and washed with water. The layers were separated using a phase separator cartridge and the organic layer was concentrated in vacuo. The title compound (41 mg, 27%) was obtained after purification by preparative SFC (chromatographic conditions: MeOH/NH$_3$ 20 mM; column: Waters BEH 2-EP 5 μm 30×250 mm).

HRMS: calculated for $(C_{21}H_{18}F_6N_2O_6S+H)^+$ 541.0868; found: (ESI [M+H]$^+$) 541.0875.

$^1$H NMR (600 MHz, DMSO-d$_6$, mixture of rotamers, 1:1) δ 3.21 (s, 3H), 3.63, 3.71 (s, 3H), 4.8-4.91 (m, 2H), 5.68, 5.70 (s, 1H), 7.57-7.79 (m, 5H), 7.86-7.93 (m, 1H), 8.00, 8.02 (s, 1H), 10.80 (s, 1H).

Example 404: N-[4-(1,1,1,3,3,3-Hexafluoro-2-hydroxypropan-2-yl)phenyl]-2-[(1-methoxycyclopropyl)carbonyl]-5-(methylsulfonyl)-2,3-dihydro-1H-isoindole-1-carboxamide

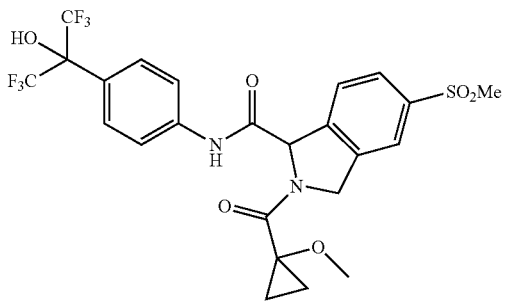 [SMILES: COC1(C(=O)N2Cc3cc(S(C)(=O)=O)ccc3C2C(=O)Nc2ccc(C(O)(C(F)(F)F)C(F)(F)F)cc2)CC1]

Procedure A:

N-[4-(1,1,1,3,3,3-Hexafluoro-2-hydroxypropan-2-yl)phenyl]-5-(methylsulfonyl)-2,3-dihydro-1H-isoindole-1-carboxamide (80 mg, 0.17 mmol) was added to a mixture of 1-methoxycyclopropanecarboxylic acid (28.9 mg, 0.25 mmol), HATU (95 mg, 0.25 mmol) and DIPEA (0.087 mL, 0.50 mmol) in DMF (5 mL) under nitrogen. The resulting mixture was stirred at room temperature for 12 hours. The reaction mixture was quenched with saturated NH$_4$Cl (25 mL) and extracted with EtOAc (3×50 mL). The organic layer was dried over Na$_2$SO$_4$, filtered and evaporated to afford pale yellow solid. The crude product was purified by flash C18-flash chromatography, elution gradient 10 to 90% MeOH in water. Pure fractions were evaporated to dryness to afford the title compound (85 mg, 88%).

HRMS: calculated for $(C_{24}H_{22}F_6N_2O_6S+H)^+$ 581.1181; found: (ESI [M+H]) 581.1199.

$^1$H NMR (300 MHz, DMSO-d$_6$, mixture of rotamers, 2.3*:1) δ 0.84-1.27 (m, 4H), 3.20, 3.23* (s, 3H), 3.37 (s, 3H), 4.85-5.06, 5.18-5.34* (m, 2H), 5.91*, 6.24 (s, 1H), 7.58-7.86 (m, 5H), 7.89-7.96 (m, 1H), 8.02-8.09 (m, 1H), 8.66, 8.67* (s, 1H), 10.82 10.90* (s, 1H).

Procedure B:

The hydrochloride salt of N-[4-(1,1,1,3,3,3-hexafluoro-2-hydroxypropan-2-yl)phenyl]-5-(methylsulfonyl)-2,3-dihydro-1H-isoindole-1-carboxamide (1.2 g, 2.31 mmol) was dissolved in DCM (20 mL) and to this triethylamine (0.967 mL, 6.94 mmol) and 1-methoxycyclopropanecarboxylic acid (0.295 g, 2.54 mmol) was added. T3P (50% in EtOAc, 2.75 mL, 4.63 mmol) was then added. The reaction was stirred at room temperature for 1 hr. LCMS indicated complete conversion to product. The reaction was diluted with DCM and washed with 0.5M HCl. The layers were separated and and the organic layer concentrated in vacuo.

The (1R) and the (1S) enantiomers of N-[4-(1,1,1,3,3,3-hexafluoro-2-hydroxypropan-2-yl)phenyl]-2-[(1-methoxycyclopropyl)carbonyl]-5-(methylsulfonyl)-2,3-dihydro-H-isoindole-1-carboxamide (1400 mg) were separated by a preparative SFC system equipped with a CelluCoat column 20% EtOH in CO$_2$ (120 bar); flow: 150 mL/min; injection volume was 1 mL of a 140 mg/mL ethanol solution.

Isomer 1 (peak 1): 580 mg, 99.8% ee by analytical chiral SFC (analytical conditions: CelluCoat column, 150×4.6 mm, 3 m, 3.5 ml/min, 25% EtOH in CO$_2$, 120 bar, 40° C.). $[α]_D^{589}$ +97° (c=0.6, CH$_3$CN).

HRMS: calculated for $(C_{24}H_{22}F_6N_2O_6S+H)^+$ 581.1181; found: (ESI [M+H]$^+$) 581.1173.

$^1$H NMR (500 MHz, DMSO-d$_6$, mixture of rotamers, 2*:1) δ 0.80-1.23 (m, 4H), 3.17, 3.19* (s, 3H), 3.20, 3.21* (s, 3H), 4.82-5.05, 5.18-5.30* (m, 2H), 5.90*, 6.22 (s, 1H), 7.59-7.83 (m, 5H), 7.86-7.94 (m, 1H), 8.03, 8.06* (s, 1H), 10.80, 10.87* (s, 1H).

Isomer 2 (peak 2): 580 mg, 97.6% ee by analytical chiral SFC (analytical conditions: CelluCoat column, 150×4.6 mm, 3 m, 3.5 ml/min, 25% EtOH in CO$_2$, 120 bar, 40° C.). $[α]D_{589}$ −95° (c=0.6, CH$_3$CN).

HRMS: calculated for $(C_{24}H_{22}F_6N_2O_6S+H)^+$ 581.1181; found: (ESI [M+H]) 581.1163.

$^1$H NMR (500 MHz, DMSO-d$_6$, mixture of rotamers, 2*:1) δ 0.80-1.23 (m, 4H), 3.17, 3.19* (s, 3H), 3.20, 3.21* (s, 3H), 4.82-5.05, 5.18-5.30* (m, 2H), 5.90*, 6.22 (s, 1H), 7.59-7.83 (m, 5H), 7.86-7.94 (m, 1H), 8.03, 8.06* (s, 1H), 10.80, 10.87* (s, 1H).

Example 405: 2-[(1-Cyanocyclopropyl)carbonyl]-N-[4-(1,1,1,3,3,3-hexafluoro-2-hydroxypropan-2-yl)phenyl]-5-(methylsulfonyl)-2,3-dihydro-1H-isoindole-1-carboxamide

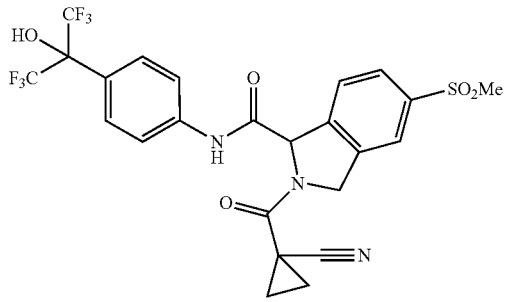 [SMILES: CS(=O)(=O)c1ccc2c(c1)CN(C(=O)C1(C#N)CC1)C2C(=O)Nc1ccc(C(O)(C(F)(F)F)C(F)(F)F)cc1]

Prepared using the same procedure as Example 404 B, but using 1-cyanocyclopropanecarboxylic acid (332 mg, 2.99 mmol). After work-up, about 150 mg (10% of the crude product) were purified by preparative SFC (chromatographic conditions: MeOH/NH$_3$ 20 mM, EP; column: Waters BEH 2-EP 5 μm 30×250 mm) to give the title compound (94 mg, 66%).

HRMS: calculated for $(C_{24}H_{19}F_6N_3O_5S+H)^+$ 576.1028; found: (ESI [M+H]$^+$) 576.1002.

$^1$H NMR (600 MHz, DMSO-d$_6$, mixture of rotamers, 5*:1) δ 1.50-1.65 (m, 2H), 1.65-1.86 (m, 2H), 3.21, 3.22* (s, 3H), 4.85-5, 5.31-5.40* (m, 2H), 5.85*, 6.44 (s, 1H), 7.61-7.76 (m, 5H), 7.91-7.95 (m, 1H), 8.03, 8.12* (s, 1H), 8.69 (br s, 1H), 10.88*, 11.21 (s, 1H).

The remaining material (1200 mg) was subjected to chiral separation using a by a preparative SFC system equipped with a Chiralpak IC 25% EtOH 100 CO$_2$ (120 bar); flow: 70 mL/min; injection volume was 0.6 mL of a 100 mg/mL ethanol solution to give the (1R) and the (1 S) enantiomers.

Isomer 1 (peak 1): 470 mg, 98.3% ee by analytical chiral SFC (analytical conditions: Chiralpak IC, 150×4.6 mm, 3 m, 3.5 ml/min, 25% EtOH in CO$_2$, 120 bar, 40° C.). [α]$_{D589}$+ 78.9° (c=1, CH$_3$CN).

HRMS: calculated for $(C_{24}H_{19}F_6N_3O_5S+H)^+$ 576.1028; found: (ESI [M+H]$^+$) 576.1030.

$^1$H NMR (600 MHz, DMSO-d$_6$, mixture of rotamers, 5*:1) δ 1.50-1.65 (m, 2H), 1.65-1.86 (m, 2H), 3.21, 3.22* (s, 3H), 4.85-5, 5.31-5.40* (m, 2H), 5.85*, 6.44 (s, 1H), 7.61-7.76 (m, 5H), 7.91-7.95 (m, 1H), 8.03, 8.12* (s, 1H), 8.69 (br s, 1H), 10.88*, 11.21 (s, 1H).

Isomer 2 (peak 2): 515 mg, 99.0% ee by analytical chiral SFC (analytical conditions: Chiralpak IC, 150×4.6 mm, 3 m, 3.5 ml/min, 25% EtOH in CO$_2$, 120 bar, 40° C.). [α]$_D^{589}$ −79.4° (c=1, CH$_3$CN).

HRMS: calculated for $(C_{24}H_{19}F_6N_3O_5S+H)^+$ 576.1028; found: (ESI [M+H]$^+$) 576.1057.

$^1$H NMR (600 MHz, DMSO-d$_6$, mixture of rotamers, 5*:1) δ 1.5-1.65 (m, 2H), 1.65-1.86 (m, 2H), 3.21, 3.22* (s, 3H), 4.85-5, 5.31-5.4* (m, 2H), 5.85*, 6.44 (s, 1H), 7.61-7.76 (m, 5H), 7.91-7.95 (m, 1H), 8.03, 8.12* (s, 1H), 8.69 (br s, 1H), 10.88*, 11.21 (s, 1H).

Example 406: 2-Formyl-N-[4-(1,1,1,3,3,3-hexafluoro-2-hydroxypropan-2-yl)phenyl]-5-(methylsulfonyl)-2,3-dihydro-1H-isoindole-1-carboxamide

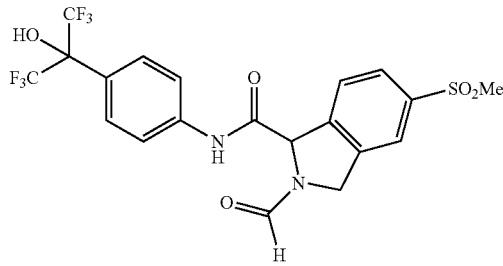 [SMILES: CS(=O)(=O)c1ccc2c(c1)CN(C=O)C2C(=O)Nc1ccc(C(O)(C(F)(F)F)C(F)(F)F)cc1]

N-[4-(1,1,1,3,3,3-Hexafluoro-2-hydroxypropan-2-yl) phenyl]-5-(methylsulfonyl)-2,3-dihydro-1H-isoindole-1-carboxamide (50 mg, 0.10 mmol) was added to a solution of formic acid (6.20 mg, 0.13 mmol), HATU (59.1 mg, 0.16 mmol) and DIPEA (0.054 mL, 0.31 mmol) in DCM (5 mL) under nitrogen. The resulting mixture was stirred at r.t for 2 hours. The reaction mixture was quenched with saturated NH$_4$Cl (50 mL) and extracted with DCM (3×50 mL). The organic layer was dried over Na$_2$SO$_4$, filtered and evaporated to afford pale yellow solid, which was purified by preparative HPLC (XBridge Prep C18 OBD column, 5p silica, 19 mm diameter, 100 mm length), using decreasingly polar mixtures of water (containing 0.08% NH$_4$HCO$_3$) and MeCN as eluents. Fractions containing the desired compound were evaporated to dryness to afford 2-formyl-N-[4-(1,1,1,3,3,3-hexafluoro-2-hydroxypropan-2-yl)phenyl]-5-(methylsulfonyl)-2,3-dihydro-1H-isoindole-1-carboxamide (35.0 mg, 66.2%) as a colorless solid. LC/MS: m/z=511 [M+H]$^+$.

HRMS: calculated for $(C_{20}H_{16}F_6N_2O_5S+H)^+$ 511.0762; found: (ESI [M+H]$^+$) 511.0744.

$^1$H NMR (300 MHz, DMSO-d$_6$, mixture of rotamers, 2*:1) δ 3.21, 3.22* (s, 3H), 4.70-4.91, 5.01-5.18* (m, 2H), 5.76*, 5.99 (s, 1H), 7.59-7.95 (m, 6H), 8.01-8.07 (m, 1H), 8.38, 8.48* (s, 1H), 8.66 (s, 1H), 10.77*, 10.88 (s, 1H).

Example 407: N-[4-(1,1,1,3,3,3-Hexafluoro-2-hydroxypropan-2-yl)phenyl]-5-(methylsulfonyl)-2-(oxetan-2-ylcarbonyl)-2,3-dihydro-1H-isoindole-1-carboxamide

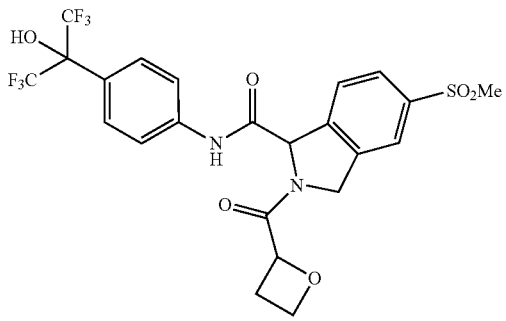 [SMILES: CS(=O)(=O)c1ccc2c(c1)CN(C(=O)C1CCO1)C2C(=O)Nc1ccc(C(O)(C(F)(F)F)C(F)(F)F)cc1]

N-[4-(1,1,1,3,3,3-Hexafluoro-2-hydroxypropan-2-yl) phenyl]-5-(methylsulfonyl)-2,3-dihydro-1H-isoindole-1-carboxamide (80 mg, 0.17 mmol) was added to a solution of oxetane-2-carboxylic acid (25.4 mg, 0.25 mmol), HATU (95 mg, 0.25 mmol) and DIPEA (0.087 mL, 0.50 mmol) in DMF (5 mL) under nitrogen. The resulting mixture was stirred at room temperature for 12 hours. The reaction mixture was quenched with saturated NH$_4$Cl (25 mL) and extracted with EtOAc (3×50 mL). The organic layer was dried over Na$_2$SO$_4$, filtered and evaporated to afford pale yellow solid. The crude product was purified by flash C18-flash chromatography, elution gradient 10 to 90% MeOH in water. Pure fractions were evaporated to dryness to afford N-[4-(1,1,1, 3,3,3-hexafluoro-2-hydroxypropan-2-yl)phenyl]-5-(methylsulfonyl)-2-(oxetan-2-ylcarbonyl)-2,3-dihydro-H-isoindole-1-carboxamide (20.0 mg, 21.3%) as a solid. LC/MS: m/z=567 [M+H]$^+$.

HRMS: calculated for $(C_{23}H_{20}F_6N_2O_6S+H)^+$ 567.1024; found: (ESI [M+H]$^+$) 567.1015.

$^1$H NMR (400 MHz, DMSO-d$_6$, mixture of diastereomers and rotamers; ratio 13:2:2:1; data given for the major rotamer/diastereomer) δ 2.73-3.02 (m, 2H), 3.22 (s, 3H), 4.47-4.68 (m, 2H), 4.82-5.07 (m, 2H), 5.43-5.55 (m, 1H), 5.83 (s, 1H), 7.58-7.84 (m, 5H), 7.88-7.95 (m, 1H), 7.97-8.07 (m, 1H), 8.68 (s, 1H), 10.84 (s, 1H).

Example 408: 2-(3-Fluoro-2-methylpropanoyl)-N-[4-(1,1,1,3,3,3-hexafluoro-2-hydroxypropan-2-yl)phenyl]-5-(methylsulfonyl)-2,3-dihydro-1H-isoindole-1-carboxamide

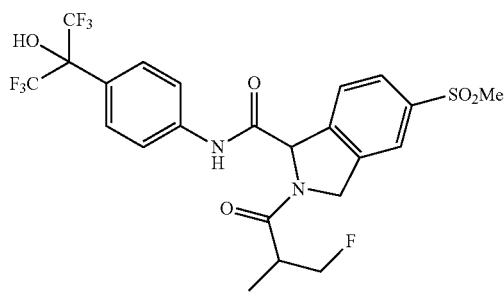 [SMILES: CC(CF)C(=O)N1Cc2cc(S(C)(=O)=O)ccc2C1C(=O)Nc1ccc(C(O)(C(F)(F)F)C(F)(F)F)cc1]

Step 1: N-[4-(1,1,1,3,3,3-Hexafluoro-2-hydroxypropan-2-yl)phenyl]-2-(3-methoxy-2-methylpropanoyl)-5-(methylsulfonyl)isoindoline-1-carboxamide

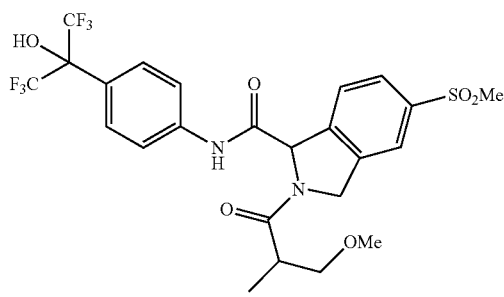 [SMILES: COCC(C)C(=O)N1Cc2cc(S(C)(=O)=O)ccc2C1C(=O)Nc1ccc(C(O)(C(F)(F)F)C(F)(F)F)cc1]

N-[4-(1,1,1,3,3,3-Hexafluoro-2-hydroxypropan-2-yl)phenyl]-5-(methylsulfonyl)-2,3-dihydro-1H-isoindole-1-carboxamide (300 mg, 0.62 mmol) was added to a solution of 3-methoxy-2-methylpropanoic acid (147 mg, 1.24 mmol), HATU (307 mg, 0.81 mmol) and DIPEA (0.326 mL, 1.87 mmol) in DMF (10 mL) under nitrogen. The resulting mixture was stirred at room temperature for 12 hours. The reaction mixture was quenched with saturated $NH_4Cl$ (50 mL), extracted with EtOAc (3×50 mL), the organic layer was dried over $Na_2SO_4$, filtered and evaporated to afford pale yellow solid. The crude product was purified by flash C18-flash chromatography, elution gradient 10 to 90% MeOH in water. Pure fractions were evaporated to dryness to afford N-[4-(1,1,1,3,3,3-hexafluoro-2-hydroxypropan-2-yl)phenyl]-2-(3-methoxy-2-methylpropanoyl)-5-(methylsulfonyl)isoindoline-1-carboxamide (300 mg, 83%) as a solid.

LC/MS: m/z=583 [M+H]$^+$. $^1$HNMR (400 MHz, DMSO-$d_6$, mixture of diastereomers and rotamers; ratio 9.5:5:3:1; data given for the 2 major rotamers/diastereomers) δ 1.06*, 1.09 (d, 3H), 3.02-3.10 (m, 1H), 3.19-3.32 (m, 7H), 3.45-3.58 (m, 1H), 5.08-5.14 (m, 2H), 5.76, 5.77* (s, 1H), 7.62-7.80 (m, 5H), 7.88-8.05 (m, 2H), 8.66 (s, 1H), 10.64, 10.73* (s, 1H).

Step 2: N-(4-(2-(Benzyloxy)-1,1,1,3,3,3-hexafluoropropan-2-yl)phenyl)-2-(3-methoxy-2-methylpropanoyl)-5-(methylsulfonyl)isoindoline-1-carboxamide

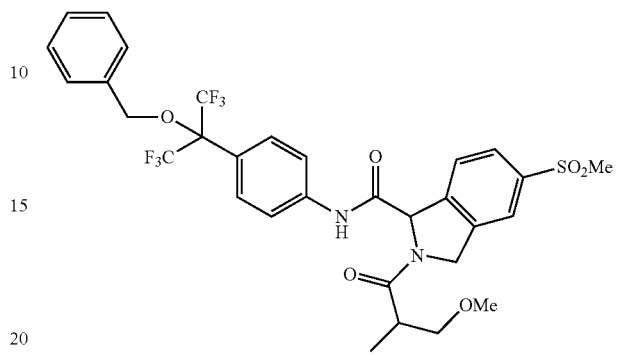

alpha-Bromotoluene (106 mg, 0.62 mmol) was added to N-(4-(1,1,1,3,3,3-hexafluoro-2-hydroxypropan-2-yl)phenyl)-2-(3-methoxy-2-methylpropanoyl)-5-(methylsulfonyl)isoindoline-1-carboxamide (300 mg, 0.52 mmol) and $K_2CO_3$ (142 mg, 1.03 mmol) in DMF (8 mL) under nitrogen. The resulting mixture was stirred at room temperature for 12 hours. The reaction mixture was quenched with water (25 mL), extracted with EtOAc (3×25 mL), the organic layer was dried over $Na_2SO_4$, filtered and evaporated to afford yellow solid. The crude product was purified by flash C18-flash chromatography, elution gradient 10 to 90% MeCN in water. Pure fractions were evaporated to dryness to afford N-(4-(2-(benzyloxy)-1,1,1,3,3,3-hexafluoropropan-2-yl)phenyl)-2-(3-methoxy-2-methylpropanoyl)-5-(methylsulfonyl)isoindoline-1-carboxamide (220 mg, 63.5%).

LC/MS: m/z=673 [M+H]$^+$. $^1$HNMR (300 MHz, DMSO-$d_6$, mixture of diastereomers and rotamers; ratio 10:6:3:1; data given for the 2 major rotamers/diastereomers) δ 1.06-1.10 (m, 3H), 2.97-3.13 (m, 1H), 3.17-3.30 (m, 7H), 3.43-3.60 (m, 1H), 4.61 (s, 2H), 5.02-5.18 (m, 2H), 5.72-5.83 (m, 1H), 7.31-8.04 (m, 12H), 10.75, 10.84* (s, 1H).

Step 3: N-(4-(2-(Benzyloxy)-1,1,1,3,3,3-hexafluoropropan-2-yl)phenyl)-2-(3-hydroxy-2-methylpropanoyl)-5-(methylsulfonyl)isoindoline-1-carboxamide

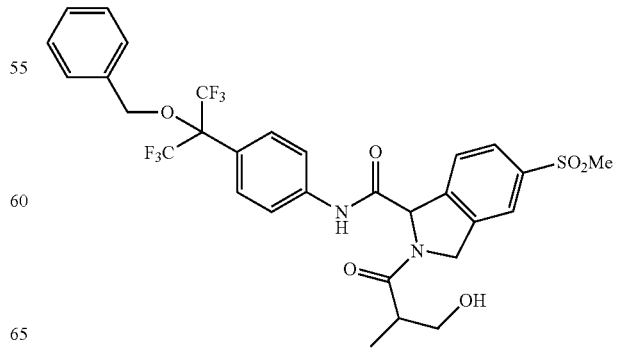

Boron tribromide (410 mg, 1.64 mmol) was added dropwise to a solution of N-(4-(2-(benzyloxy)-1,1,1,3,3,3-hexafluoropropan-2-yl)phenyl)-2-(3-methoxy-2-methylpropanoyl)-5-(methylsulfonyl)isoindoline-1-carboxamide (220 mg, 0.33 mmol) in DCM (10 mL) cooled to −40° C. under nitrogen. The resulting mixture was stirred at 0° C. for 5 hours.

The reaction mixture was quenched with ice water (25 mL), extracted with DCM (3×25 mL), the organic layer was dried over Na$_2$SO$_4$, filtered and evaporated to afford yellow solid. The crude product was purified by flash silica chromatography, elution gradient 0 to 10% MeOH in DCM. Pure fractions were evaporated to dryness to afford N-(4-(2-(benzyloxy)-1,1,1,3,3,3-hexafluoropropan-2-yl)phenyl)-2-(3-hydroxy-2-methylpropanoyl)-5-(methylsulfonyl)isoindoline-1-carboxamide (130 mg, 60.3%).

LC/MS: m/z=659 [M+H]$^+$. $^1$HNMR (300 MHz, DMSO-d$_6$, mixture of diastereomers and rotamers; ratio 5:3:1.6:1; data given for the 2 major rotamers/diastereomers) δ 0.97-1.18 (m, 3H), 2.88-3.05 (m, 1H), 3.16-3.69 (m, 5H), 4.61 (s, 2H), 4.78-5.27 (m, 3H), 5.79 (s, 1H), 7.31-8.12 (m, 12H), 10.61, 10.84* (s, 1H).

Step 4: N-(4-(2-(Benzyloxy)-1,1,1,3,3,3-hexafluoropropan-2-yl)phenyl)-2-(3-fluoro-2-methylpropanoyl)-5-(methylsulfonyl)isoindoline-1-carboxamide

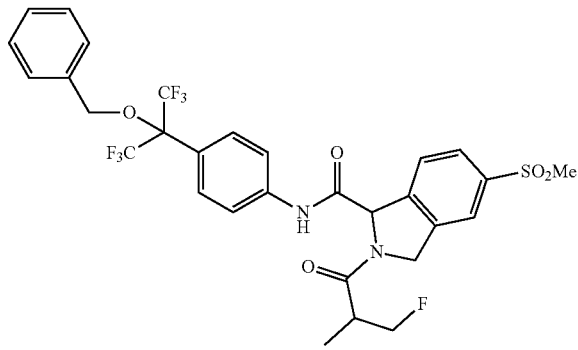 [SMILES: CC(CF)C(=O)N1Cc2cc(S(C)(=O)=O)ccc2C1C(=O)Nc1ccc(C(OCc2ccccc2)(C(F)(F)F)C(F)(F)F)cc1]

DAST (0.047 mL, 0.36 mmol) was added dropwise to a soultion of N-(4-(2-(benzyloxy)-1,1,1,3,3,3-hexafluoropropan-2-yl)phenyl)-2-(3-hydroxy-2-methylpropanoyl)-5-(methylsulfonyl)isoindoline-1-carboxamide (130 mg, 0.20 mmol) in DCM (8 mL) cooled to 0° C. under nitrogen. The resulting mixture was stirred at room temperature for 2 hours. The reaction mixture was quenched with water (15 mL), extracted with DCM (3×20 mL), the organic layer was dried over Na$_2$SO$_4$, filtered and evaporated to afford pale yellow solid. The crude product was purified by flash silica chromatography, elution gradient 0 to 20% MeOH in DCM. Pure fractions were evaporated to dryness to afford N-(4-(2-(benzyloxy)-1,1,1,3,3,3-hexafluoropropan-2-yl)phenyl)-2-(3-fluoro-2-methylpropanoyl)-5-(methylsulfonyl)isoindoline-1-carboxamide (100 mg, 77%).

LC/MS: m/z=661 [M+H]$^+$. $^1$HNMR (300 MHz, DMSO-d$_6$, mixture of diastereomers and rotamers; ratio 5:3:1.6:1; data given for the 2 major rotamers/diastereomers) δ 1.02-1.17 (m, 3H), 3.12-3.29 (m, 4H), 4.27-4.74 (m, 4H), 4.78-5.24 (m, 2H), 5.78, 5.81* (s, 1H), 7.33-8.06 (m, 12H), 10.84, 10.90* (s, 1H).

Step 5: 2-(3-Fluoro-2-methylpropanoyl)-N-[4-(1,1,1,3,3,3-hexafluoro-2-hydroxypropan-2-yl)phenyl]-5-(methylsulfonyl)-2,3-dihydro-1H-isoindole-1-carboxamide

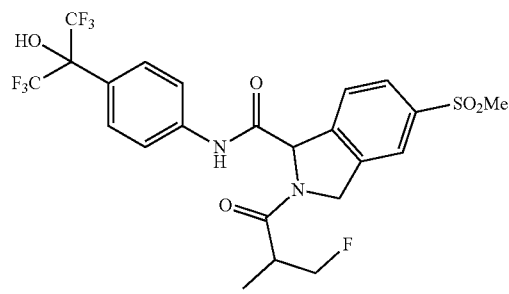 [SMILES: CC(CF)C(=O)N1Cc2cc(S(C)(=O)=O)ccc2C1C(=O)Nc1ccc(C(O)(C(F)(F)F)C(F)(F)F)cc1]

N-[4-(1,1,1,3,3,3-Hexafluoro-2-hydroxypropan-2-yl)phenyl]-5-(methylsulfonyl)-2,3-dihydro-1H-isoindole-1-carboxamide (100 mg, 0.15 mmol) and Pd—C (1,611 mg, 0.02 mmol) in MeOH (10 mL) were stirred under an atmosphere of hydrogen at room temperature for 12 hours. The reaction mixture was filtered through celite. The solvent was removed under reduced pressure. The crude product was purified by flash C18-flash chromatography, elution gradient 10 to 90% MeCN in water. Pure fractions were evaporated to dryness to afford 2-(3-fluoro-2-methylpropanoyl)-N-[4-(1,1,1,3,3,3-hexafluoro-2-hydroxypropan-2-yl)phenyl]-5-(methylsulfonyl)-2,3-dihydro-1H-isoindole-1-carboxamide (60.0 mg, 69.5%).

HRMS: calculated for (C$_{23}$H$_{21}$F$_7$N$_2$O$_5$S+H)$^+$571.1138; found: (ESI [M+H]$^+$) 571.1146.

$^1$H NMR (400 MHz, DMSO-d$_6$, mixture of diastereomers/rotamers, 8*:6:2:1, only data for 2 major isomers reported) δ 1.07-1.16 (m, 3H), 3.19-3.29 (m, 4H), 4.32-4.71 (m, 2H), 4.79-5.21 (m, 2H), 5.77, 5.80* (s, 1H), 7.59-7.83 (m, 5H), 7.89-7.95 (m, 1H), 7.98-8.05 (m, 1H), 8.68 (s, 1H), 10.73, 10.79* (s, 1H).

Example 409: (R,S)—N-[4-(1,1,1,3,3,3-Hexafluoro-2-hydroxypropan-2-yl)phenyl]-2-[(2R)-2-hydroxybutanoyl]-5-(methylsulfonyl)-2,3-dihydro-1H-isoindole-1-carboxamide

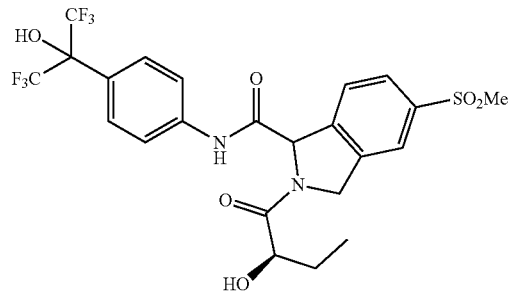 [SMILES: CC[C@@H](O)C(=O)N1Cc2cc(S(C)(=O)=O)ccc2C1C(=O)Nc1ccc(C(O)(C(F)(F)F)C(F)(F)F)cc1]

N-(4-(1,1,1,3,3,3-Hexafluoro-2-hydroxypropan-2-yl)phenyl)-5-(methylsulfonyl)isoindoline-1-carboxamide (90 mg, 0.19 mmol) was added to (R)-2-hydroxybutanoic acid (29.1 mg, 0.28 mmol), HATU (142 mg, 0.37 mmol) and DIPEA (0.098 mL, 0.56 mmol) in DCM (10 mL) under nitrogen. The resulting mixture was stirred at rt for 2 hours.

The reaction mixture was quenched with saturated NH$_4$Cl (50 mL), extracted with DCM (3×50 mL), the organic layer was dried over Na$_2$SO$_4$, filtered and evaporated to afford N-(4-(1,1,1,3,3,3-hexafluoro-2-hydroxypropan-2-yl)phenyl)-2-((R)-2-hydroxybutanoyl)-5-(methylsulfonyl)isoindoline-1-carboxamide (100 mg, 94%). Half of this amount was purified by preparative HPLC (Waters XBridge Prep C18 OBD column, 5µ silica, 19 mm diameter, 100 mm length), using decreasingly polar mixtures of water (containing 0.08% Formic acid) and MeCN as eluents. Fractions containing the desired compound were evaporated to dryness to afford:

Isomer 1, (20.0 mg, 38.0%).
HRMS: calculated for (C$_{23}$H$_{22}$F$_6$N$_2$O$_6$S+H)$^+$569.1181; found (ESI [M+H]$^+$) 569.1193.
$^1$H NMR (400 MHz, DMSO-d$_6$, mixture of rotamers, 3*:1) δ 0.82, 0.94* (t, 3H), 1.50-1.79 (m, 2H), 3.22, 3.23* (s, 3H), 3.91-4.00, 4.17-4.26* (m, 1H), 4.76-5.02, 5.11-5.20* (m, 2H), 5.21-5.28*, 5.58-5.64 (d, 1H), 5.79*, 6.28 (s, 1H), 7.60-7.68 (m, 2H), 7.70-7.83 (m, 3H), 7.91 (m, 1H), 7.98-8.06 (m, 1H), 8.52, 8.86* (s, 1H), 10.85*, 11.13 (s, 1H).

Isomer 2, (20 mg, 38%).
HRMS: calculated for (C$_{23}$H$_{22}$F$_6$N$_2$O$_6$S—H)$^-$ 567.1388; found (ESI [M+H]$^+$) 567.1379.
$^1$H NMR (400 MHz, DMSO-d$_6$, mixture of rotamers, 9*:1) δ 0.89-1.00 (m, 3H), 1.51-1.80 (m, 2H), 3.22, 3.23* (s, 3H), 3.93-4.03, 4.23-4.33* (m, 1H), 4.82-5.24 (m, 3H), 5.84, 6.11 (s, 1H), 7.60-7.81 (m, 5H), 7.88-7.95 (m, 1H), 7.98-8.05 (m, 1H), 8.53, 8.71* (s, 1H), 10.82*, 10.95 (s, 1H).

Examples 410-433

Examples 410-433 (Table 4A) were prepared using a similar procedures to those described in examples 401 to 409.

Example 410: N-[4-(1,1,1,3,3,3-Hexafluoro-2-hydroxypropan-2-yl)phenyl]-2-(3-methylbutanoyl)-5-(methylsulfonyl)-2,3-dihydro-1H-isoindole-1-carboxamide Example 411: 2-(Cyclopropylacetyl)-N-[4-(1,1,1,3,3,3-hexafluoro-2-hydroxypropan-2-yl)phenyl]-5-(methylsulfonyl)-2,3-dihydro-1H-isoindole-1-carboxamide Example 412: N-[4-(1,1,1,3,3,3-Hexafluoro-2-hydroxypropan-2-yl)phenyl]-2-[(1-hydroxycyclopropyl)acetyl]-5-(methylsulfonyl)-2,3-dihydro-1H-isoindole-1-carboxamide Example 413: 2-[(3S)-3-Fluorobutanoyl]-N-[4-(1,1,1,3,3,3-hexafluoro-2-hydroxypropan-2-yl)phenyl]-5-(methylsulfonyl)-2,3-dihydro-1H-isoindole-1-carboxamide Example 414: N-[4-(1,1,1,3,3,3-Hexafluoro-2-hydroxypropan-2-yl)phenyl]-2-(methoxyacetyl)-5-(methylsulfonyl)-2,3-dihydro-1H-isoindole-1-carboxamide Example 415: 2-(3-Fluoropropanoyl)-N-[4-(1,1,1,3,3,3-hexafluoro-2-hydroxypropan-2-yl)phenyl]-5-(methylsulfonyl)-2,3-dihydro-1H-isoindole-1-carboxamide Example 416: 2-[(1-Ethoxycyclopropyl)carbonyl]-N-[4-(1,1,1,3,3,3-hexafluoro-2-hydroxypropan-2-yl)phenyl]-5-(methylsulfonyl)-2,3-dihydro-1H-isoindole-1-carboxamide Example 417: N-[4-(1,1,1,3,3,3-Hexafluoro-2-hydroxypropan-2-yl)phenyl]-2-[(1-methoxycyclopropyl)acetyl]-5-(methylsulfonyl)-2,3-dihydro-1H-isoindole-1-carboxamide Example 418: 2-[(3R)-3-Fluorobutanoyl]-N-[4-(1,1,1,3,3,3-hexafluoro-2-hydroxypropan-2-yl)phenyl]-5-(methylsulfonyl)-2,3-dihydro-1H-isoindole-1-carboxamide Example 419: N-[4-(1,1,1,3,3,3-Hexafluoro-2-hydroxypropan-2-yl)phenyl]-2-(2-methoxy-2-methylpropanoyl)-5-(methylsulfonyl)-2,3-dihydro-1H-isoindole-1-carboxamide Example 420: Propan-2-yl 1-{[4-(1,1,1,3,3,3-hexafluoro-2-hydroxypropan-2-yl)phenyl]carbamoyl}-5-(methylsulfonyl)-1,3-dihydro-2H-isoindole-2-carboxylate Example 421: N-[4-(1,1,1,3,3,3-Hexafluoro-2-hydroxypropan-2-yl)phenyl]-2-(3-hydroxy-3-methylbutanoyl)-5-(methylsulfonyl)-2,3-dihydro-1H-isoindole-1-carboxamide Example 422: N-[4-(1,1,1,3,3,3-Hexafluoro-2-hydroxypropan-2-yl)phenyl]-2-[(2R)-2-hydroxy-3-methylbutanoyl]-5-(methylsulfonyl)-2,3-dihydro-1H-isoindole-1-carboxamide Example 423: N-[4-(1,1,1,3,3,3-Hexafluoro-2-hydroxypropan-2-yl)phenyl]-2-[(2S)-2-hydroxy-3-methylbutanoyl]-5-(methylsulfonyl)-2,3-dihydro-1H-isoindole-1-carboxamide Example 424, isomer 1: N-[4-(1,1,1,3,3,3-Hexafluoro-2-hydroxypropan-2-yl)phenyl]-2-[(2S)-2-hydroxybutanoyl]-5-(methylsulfonyl)-2,3-dihydro-1H-isoindole-1-carboxamide Example 424, isomer 2: N-[4-(1,1,1,3,3,3-Hexafluoro-2-hydroxypropan-2-yl)phenyl]-2-[(2S)-2-hydroxybutanoyl]-5-(methylsulfonyl)-2,3-dihydro-1H-isoindole-1-carboxamide Example 425: N-[4-(1,1,1,3,3,3-Hexafluoro-2-hydroxypropan-2-yl)phenyl]-2-(3-hydroxy-2-methylpropanoyl)-5-(methylsulfonyl)-2,3-dihydro-1H-isoindole-1-carboxamide Example 426: N-[4-(1,1,1,3,3,3-Hexafluoro-2-hydroxypropan-2-yl)phenyl]-5-(methylsulfonyl)-2-(oxetan-3-ylacetyl)-2,3-dihydro-1H-isoindole-1-carboxamide Example 427: 2-[(1-Cyanocyclopropyl)acetyl]-N-[4-(1,1,1,3,3,3-hexafluoro-2-hydroxypropan-2-yl)phenyl]-5-(methylsulfonyl)-2,3-dihydro-1H-isoindole-1-carboxamide Example 428: N-[4-(1,1,1,3,3,3-Hexafluoro-2-hydroxypropan-2-yl)phenyl]-2-[(1-hydroxycyclopropyl)carbonyl]-5-(methylsulfonyl)-2,3-dihydro-1H-isoindole-1-carboxamide Example 429: 2-(3-Cyanopropanoyl)-N-[4-(1,1,1,3,3,3-hexafluoro-2-hydroxypropan-2-yl)phenyl]-5-(methylsulfonyl)-2,3-dihydro-1H-isoindole-1-carboxamide Example 430: N-[4-(1,1,1,3,3,3-Hexafluoro-2-hydroxypropan-2-yl)phenyl]-2-[(trans-3-hydroxycyclobutyl)carbonyl]-5-(methylsulfonyl)-2,3-dihydro-1H-isoindole-1-carboxamide Example 431: N-[4-(1,1,1,3,3,3-Hexafluoro-2-hydroxypropan-2-yl)phenyl]-2-[(cis-3-hydroxycyclobutyl)carbonyl]-5-(methylsulfonyl)-2,3-dihydro-1H-isoindole-1-carboxamide Example 432: N-[4-(1,1,1,3,3,3-Hexafluoro-2-hydroxypropan-2-yl)phenyl]-2-[(3R)-3-hydroxybutanoyl]-5-(methylsulfonyl)-2,3-dihydro-1H-isoindole-1-carboxamide Example 433: N-[4-(1,1,1,3,3,3-Hexafluoro-2-hydroxypropan-2-yl)phenyl]-2-[(3S)-3-hydroxybutanoyl]-5-(methylsulfonyl)-2,3-dihydro-1H-isoindole-1-carboxamide

TABLE 4A

| Example No. | Structure | NMR + MS |
|---|---|---|
| 410 | 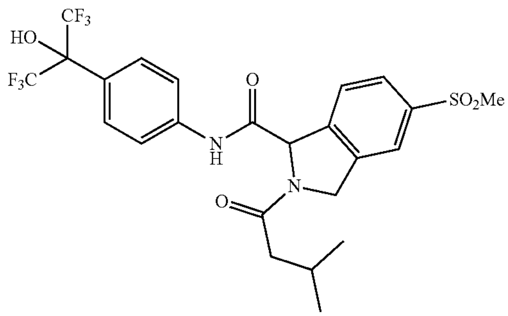 [SMILES: CC(C)CC(=O)N1Cc2cc(S(C)(=O)=O)ccc2C1C(=O)Nc1ccc(C(O)(C(F)(F)F)C(F)(F)F)cc1] | HRMS: calculated for (C$_{24}$H$_{24}$F$_6$N$_2$O$_5$S + H)$^+$ 567.1388; found (ESI [M + H]$^+$) 567.1379. $^1$H NMR (600 MHz, DMSO-d$_6$, mixture of rotamers, 6*:1, only data for major reported) δ 0.96 (d, 3H), 0.97 (d, 3H), 2.04-2.13 (m, 1H), 2.27-2.41 (m, 2H), 3.22 (s, 3H), 5.04 (m, 2H), 5.76 (s, 1H), 7.6-7.68 (m, 2H), 7.68-7.78 (m, 3H), 7.86-7.92 (m, 1H), 7.98 (s, 1H), 8.66 (s, 1H), 10.73 (s, 1H). |
| 411 | 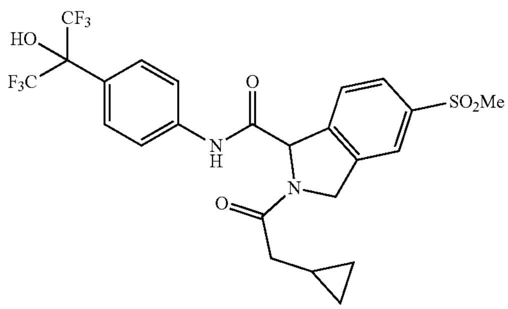 [SMILES: CS(=O)(=O)c1ccc2c(c1)CN(C(=O)CC1CC1)C2C(=O)Nc1ccc(C(O)(C(F)(F)F)C(F)(F)F)cc1] | HRMS: calculated for (C$_{24}$H$_{22}$F$_6$N$_2$O$_5$S + H)$^+$ 565.1232; found (ESI [M + H]$^+$) 565.1236. $^1$H NMR (600 MHz, DMSO-d$_6$, mixture of rotamers, 5*:1) δ 0-0.23 (m, 2H), 0.38-0.52 (m, 2H), 0.94-1.1 (m, 1H), 2.28-2.47 (m, 2H), 0.94-1.1 (m, 1H), 2.28-2.47 (m, 2H), 3.21, 3.22* (s, 3H), 4.79-4.94, 4.95-5.04* (m, 2H), 5.75*, 5.90 (s, 1H), 7.61-7.67 (m, 2H), 7.68-7.78 (m, 3H), 7.88-7.92 (m, 1H), 7.98*, 8.03 (s, 1H), 8.66 (s, 1H), 10.71*, 10.88 (s, 1H). |
| 412 | 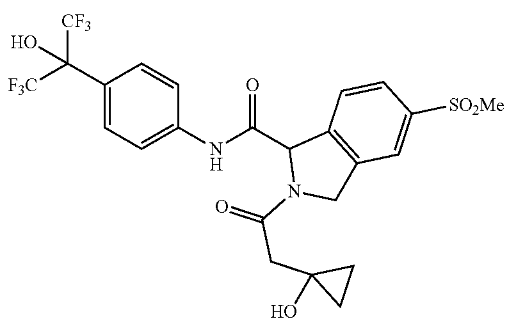 [SMILES: CS(=O)(=O)c1ccc2c(c1)CN(C(=O)CC1(O)CC1)C2C(=O)Nc1ccc(C(O)(C(F)(F)F)C(F)(F)F)cc1] | HRMS: calculated for (C$_{24}$H$_{22}$F$_6$N$_2$O$_6$S + H)$^+$ 581.1181; found (ESI [M + H]$^+$) 581.1160. $^1$H NMR (600 MHz, DMSO-d$_6$, mixture of rotamers, 5*:1) δ 0.40-0.65 (m, 4H), 2.58-2.67 (m, 1H), 2.77-2.87 (m, 1H), 3.21, 3.22* (s, 3H), 4.77-4.98, 5.05-5.2* (m, 2H), 5.35*, 5.36 (s, 1H), 5.77*, 6.07 (s, 1H), 7.6-7.67 (m, 2H), 7.69-7.81 (m, 3H), 7.88-7.92 (m, 1H), 8.00*, 8.03 (s, 1H), 8.66*, 8.69 (s, 1H), 10.68*, 10.94 (s, 1H). |
| 413 | 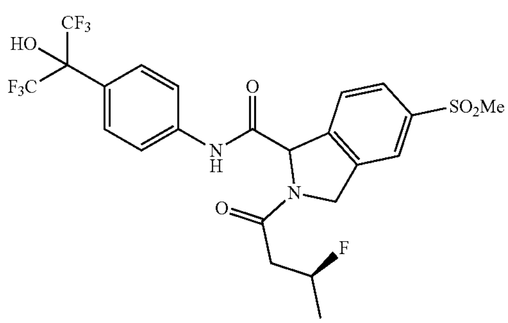 [SMILES: C[C@H](F)CC(=O)N1Cc2cc(S(C)(=O)=O)ccc2C1C(=O)Nc1ccc(C(O)(C(F)(F)F)C(F)(F)F)cc1] | HRMS: calculated for (C$_{23}$H$_{21}$F$_7$N$_2$O$_5$S + H)$^+$ 571.1138; found (ESI [M + H]$^+$) 571.1179. $^1$H NMR (400 MHz, DMSO-d$_6$, mixture of diastereomers and rotamers; data reported for major diastereomer/rotamer) δ 1.34-1.46 (m, 3H), 2.71-3.05 (m, 2H), 3.23 (s, 3H), 4.78-5.24 (m, 3H), 5.78 (s, 1H), 7.59-7.86 (m, 5H), 7.88-7.94 (m, 1H), 7.98-8.06 (m, 1H), 8.69 (s, 1H), 10.71-11.11 (m, 1H). |
| 414 | 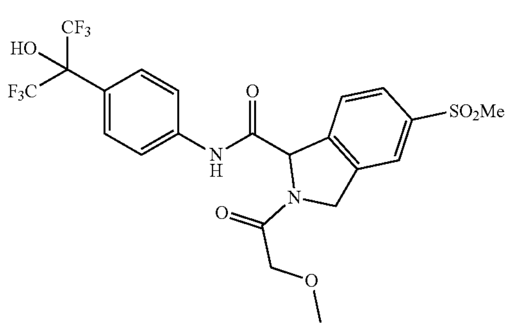 [SMILES: COCC(=O)N1Cc2cc(S(C)(=O)=O)ccc2C1C(=O)Nc1ccc(C(O)(C(F)(F)F)C(F)(F)F)cc1] | HRMS: calculated for (C$_{22}$H$_{20}$F$_6$N$_2$O$_6$S + H)$^+$ 555.1024; found (ESI [M + H]$^+$) 555.1031. $^1$H NMR (600 MHz, DMSO-d$_6$, mixture of rotamers, 4*:1) δ 3.21*, 3.22 (s, 3H), 3.26, 3.36* (s, 3H), 3.92-4.16, 4.17-4.34* (m, 2H), 4.8-5.08 (m, 2H), 5.79*, 5.99 (s, 1H), 7.61-7.66 (m, 2H), 7.71-7.8 (m, 3H), 7.89-7.92 (m, 1H), 8.00* 8.03 (s, 1H), 8.66 (s, 1H), 10.77*, 10.86 (s, 1H). |

TABLE 4A-continued

| Example No. | Structure | NMR + MS |
|---|---|---|
| 415 | 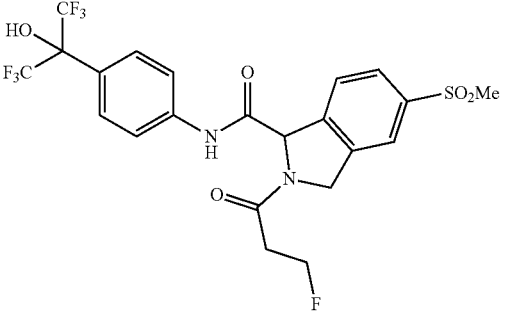 [SMILES: CS(=O)(=O)c1ccc2c(c1)CN(C(=O)CCF)C2C(=O)Nc1ccc(C(O)(C(F)(F)F)C(F)(F)F)cc1] | HRMS: calculated for (C$_{22}$H$_{19}$F$_7$N$_2$O$_6$S + H)$^+$ 557.0981; found (ESI [M + H]$^+$) 557.0993. $^1$H NMR (300 MHz, DMSO-d$_6$, mixture of rotamers, 4.7*:1) δ $^1$H NMR (300 MHz, DMSO) δ 2.85-3.06 (m, 2H), 3.24 (s, 3H), 4.60-4.85 (m, 2H), 4.85-5.16 (m, 2H), 5.79*, 6.01 (s, 1H), 7.58-7.86 (m, 5H), 7.88-7.96 (m, 1H), 7.99-8.08 (m, 1H), 8.69*, 8.72 (s, 1H), 10.77*, 11.01 (s, 1H). |
| 416 | 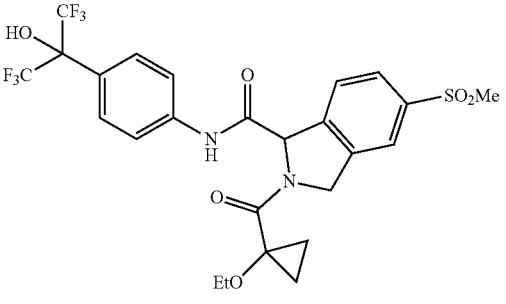 [SMILES: CCOC1(C(=O)N2Cc3cc(S(C)(=O)=O)ccc3C2C(=O)Nc2ccc(C(O)(C(F)(F)F)C(F)(F)F)cc2)CC1] | HRMS: calculated for (C$_{25}$H$_{24}$F$_6$N$_2$O$_6$S + H)$^+$ 595.1337; found (ESI [M + H]$^+$) 595.1368. $^1$H NMR (300 MHz, DMSO-d$_6$, mixture of rotamers, 2.8:1*) δ 0.91-1.27 (m, 7H), 3.23 (s, 3H), 3.40-3.76 (m, 2H), 4.80-5.08, 5.19-5.34* (m, 2H), 5.90*, 6.27 (s, 1H), 7.59-7.96 (m, 6H), 8.01-8.13 (m, 1H), 8.64, 8.66* (s, 1H), 10.81, 10.88* (s, 1H). |
| 417 | 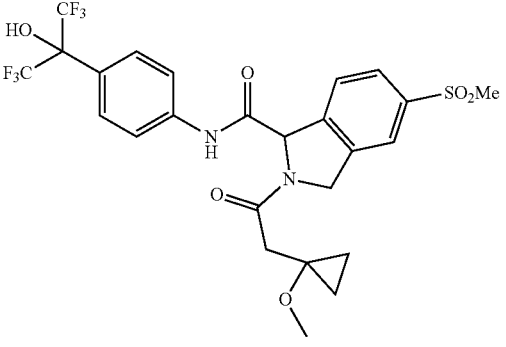 [SMILES: COC1(CC(=O)N2Cc3cc(S(C)(=O)=O)ccc3C2C(=O)Nc2ccc(C(O)(C(F)(F)F)C(F)(F)F)cc2)CC1] | HR1S: calculated for (C$_{25}$H$_{24}$F$_6$N$_2$O$_6$S + H)$^+$ 595.1337; found (ESI [M + H]$^+$) 595.1322. $^1$H NMR (600 MHz, DMSO-d$_6$, mixture of rotamers, 6*:1, only data for major reported) δ 0.55-0.78 (m, 4H), 2.83-2.93 (m, 2H), 3.22 (s, 3H), 3.24 (s, 3H), 5.08-5.17 (m, 2H), 5.75 (s, 1H), 7.57-7.67 (m, 2H), 7.69-7.76 (m, 3H), 7.88-7.92 (m, 1H), 8.01 (s, 1H), 8.66 (s, 1H), 10.74 (s, 1H). |
| 418 | 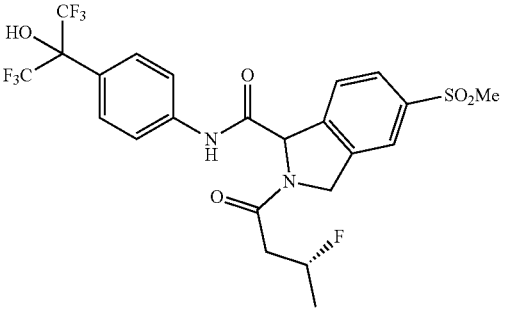 [SMILES: C[C@@H](F)CC(=O)N1Cc2cc(S(C)(=O)=O)ccc2C1C(=O)Nc1ccc(C(O)(C(F)(F)F)C(F)(F)F)cc1] | HRMS: calculated for (C$_{23}$H$_{21}$F$_7$N$_3$O$_5$S + H)$^+$ 571.1138; found (ESI [M + H]$^+$) 571.1144. $^1$H NMR (300 MHz, DMSO-d$_6$, mixture of diastereomers and rotamers; data reported for major diastereomer/rotamer) δ 1.39 (dd, 3H), 2.67-3.06 (m, 2H), 3.22 (s, 3H), 4.76-5.25 (m, 3H), 5.77 (s, 1H), 7.58-7.75 (m, 5H), 7.86-7.94 (m, 1H), 7.96-8.06 (m, 1H), 8.65 (s, 1H), 10.71-10.78 (m, 1H). |

TABLE 4A-continued

| Example No. | Structure | NMR + MS |
|---|---|---|
| 419 | 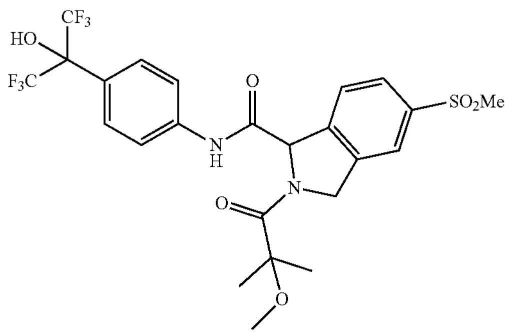 [SMILES: COC(C)(C)C(=O)N1Cc2cc(S(C)(=O)=O)ccc2C1C(=O)Nc1ccc(C(O)(C(F)(F)F)C(F)(F)F)cc1] | HRMS: calculated for (C₂₄H₂₄F₆N₂O₆S + H)⁺ 583.1337; found (ESI [M + H]⁺) 583.1340. ¹H NMR (600 MHz, DMSO-d₆, mixture of rotamers, 10*:1, only data for major reported) δ 1.37 (s, 3H), 1.39 (s, 3H), 3.20 (s, 3H), 3.26 (s, 3H), 5.10-5.29 (m, 2H), 5.86 (s, 1H), 7.60-7.65 (m, 2H), 7.68-7.76 (m, 3H), 7.88-7.91 (m, 1H), 8.01 (s, 1H), 10.88 (s, 1H). |
| 420 | 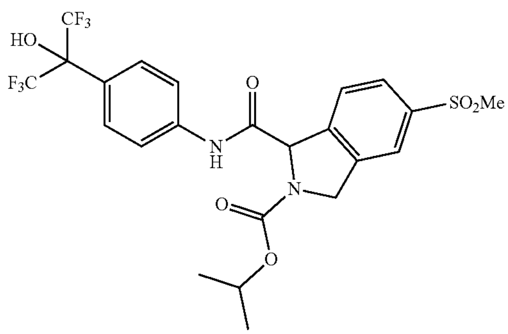 [SMILES: CC(C)OC(=O)N1Cc2cc(S(C)(=O)=O)ccc2C1C(=O)Nc1ccc(C(O)(C(F)(F)F)C(F)(F)F)cc1] | HRMS: calculated for (C₂₃H₂₂F₆N₂O₆S + H)⁺ 569.1181; found (ESI [M + H]⁺) 569.1187. ¹H NMR (400 MHz, DMSO-d₆, mixture of rotamers, 1.2*:1) δ 1.05*, 1.20*, 1.27, 1,28 (2d, 6H), 3.21, 3.22* (s, 3H), 4.75-4.92 (m, 3H), 5.64-5.69 (m, 1H), 7.59-7.79 (m, 5H), 7.88-7.93 (m, 1H), 7.98-8.05 (m, 1H), 8.65*, 8.66 (s, 1H), 10.76*, 10.79 (s, 1H). |
| 421 | 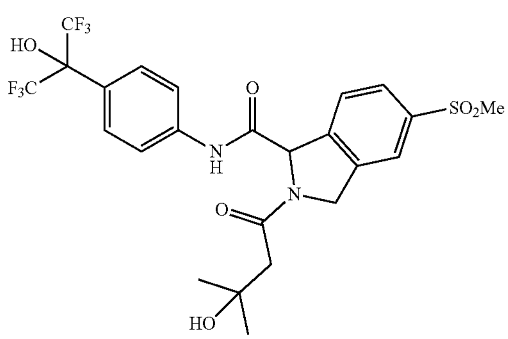 [SMILES: CC(C)(O)CC(=O)N1Cc2cc(S(C)(=O)=O)ccc2C1C(=O)Nc1ccc(C(O)(C(F)(F)F)C(F)(F)F)cc1] | HRMS: calculated for (C₂₄H₂₄F₆N₂O₆S + H)⁺ 583.1337; found (ESI [M + H]⁺) 583.1346. ¹H NMR (300 MHz, DMSO-d₆, mixture of rotamers, 6.5*:1) δ 1.23, 1.27* (s, 6H), 2.55-2.68 (m, 2H), 3.23, 3.24* (s, 3H), 4.83 (s, 1H), 4.77-5.00, 5.09-5.22* (m, 2H), 5.79*, 6.12 (s, 1H), 7.58-7.85 (m, 5H), 7.88-7.967 (m, 1H), 7.98-8.07 (m, 1H), 8.67*, 8.68 (s, 1H), 10.68*, 10.99 (s, 1H). |
| 422 | 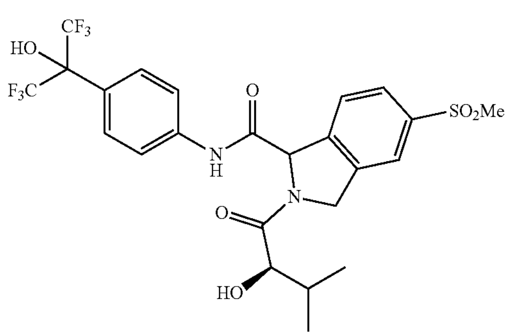 [SMILES: CC(C)[C@@H](O)C(=O)N1Cc2cc(S(C)(=O)=O)ccc2C1C(=O)Nc1ccc(C(O)(C(F)(F)F)C(F)(F)F)cc1] | HRMS: calculated for (C₂₄H₂₄F₆N₂O₆S + H)⁺ 583.1337; found (ESI [M + H]⁺) 583.1343. Mixture of diastereomers and rotamers. Ratio diastereomer 1 major rotamer: diastereomer 2 major rotamer 1.3#:1 Ratio major rotamer: minor rotamer 5:1 only major rotamer reported: ¹H NMR (600 MHz, DMSO-d₆) δ 0.9-0.96 (m, 6H), 1.95-2.06 (m, 1H), 3.21, 3.22# (s, 3H), 3.98, 4.04# (t, 1H), 4.96-5.26 (m, 3H), 5.78, 5.84# (d, 1H), 7.6-7.66 (m, 2H), 7.68-7.75 (m, 3H), 7.88-7.92 (m, 1H), 7.99 (s, 1H), 8.66 (br s, 1H), 10.79, 10.82# (s, 1H). |

TABLE 4A-continued

| Example No. | Structure | NMR + MS |
|---|---|---|
| 423 | 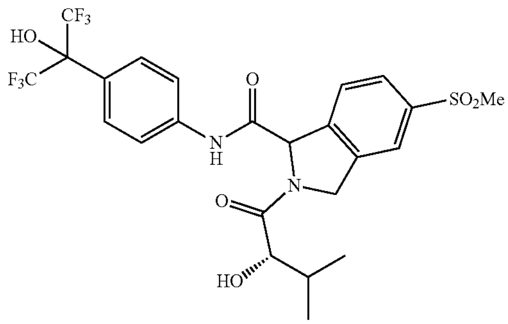 [SMILES: CC(C)[C@H](O)C(=O)N1Cc2cc(S(C)(=O)=O)ccc2C1C(=O)Nc1ccc(C(O)(C(F)(F)F)C(F)(F)F)cc1] | HRMS: calculated for (C$_{24}$H$_{24}$F$_6$N$_2$O$_6$S + H)$^+$ 583.1337; found (ESI [M + H]$^+$) 583.1346. Mixture of diastereomers and rotamers. Ratio diastereomer 1 major rotamer: diastereomer 2 major rotamer 1.2$^\#$: 1 Ratio major rotamer: minor rotamer 5:1 only major rotamer reported: $^1$H NMR (600 MHz, DMSO-d$_6$) δ 0.9-0.96 (m, 6H), 1.97-2.05 (m, 1H), 3.21, 3.22$^\#$ (s, 3H), 3.98, 4.04$^\#$ (d, 1H), 5.06-5.25 (m, 2H), 5.78, 5.84$^\#$ (d, 1H), 7.56-7.65 (m, 2H), 7.66-7.74 (m, 3H), 7.86-7.93 (m, 1H), 7.99 (s, 1H), 8.66 (br s, 1H), 10.78, 10.81$^\#$ (s, 1H). |
| 424 Isomer 1 | 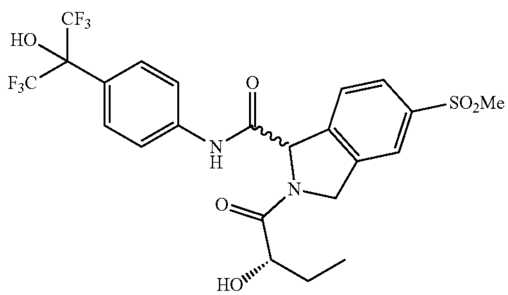 [SMILES: CC[C@H](O)C(=O)N1Cc2cc(S(C)(=O)=O)ccc2C1C(=O)Nc1ccc(C(O)(C(F)(F)F)C(F)(F)F)cc1] | HRMS: calculated for (C$_{23}$H$_{22}$F$_6$N$_2$O$_6$S + H)$^+$ 569.1181; found (ESI [M + H]$^+$) 569.1174. $^1$H NMR (400 MHz, DMSO-d$_6$, mixture of rotamers, 6.5*:1) δ 0.94 (t, 3H), 1.48-1.8 (m, 2H), 3.22 (s, 3H), 3.94-4.03, 4.23-4.31* (m, 1H), 4.81-5.26 (m, 3H), 5.84*, 6.13 (s, 1H), 7.60-7.67 (m, 2H), 7.69-7.82 (m, 3H), 7.87-7.95 (m, 1H), 7.97-8.05 (m, 1H), 8.51, 8.80* (s, 1H), 10.84*, 11.05 (s, 1H). |
| 424 Isomer 2 | 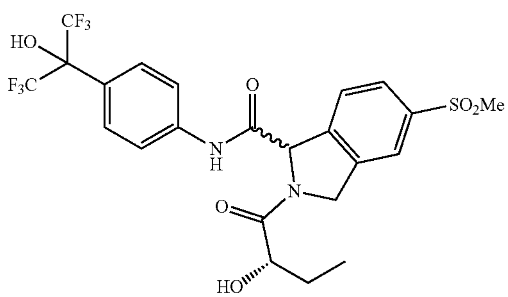 [SMILES: CC[C@H](O)C(=O)N1Cc2cc(S(C)(=O)=O)ccc2C1C(=O)Nc1ccc(C(O)(C(F)(F)F)C(F)(F)F)cc1] | HRMS: calculated for (C$_{23}$H$_{22}$F$_6$N$_2$O$_6$S + H)$^+$ 569.1181; found (ESI [M + H]$^+$) 569.1192. $^1$H NMR (400 MHz, DMSO-d$_6$, mixture of rotamers, 3.2*:1) δ 0.82, 0.94* (t, 3H), 1.5-1.8 (m, 2H), 3.22 (s, 3H), 3.91-4.00, 4.17-4.26* (m, 1H), 4.78-5.2 (m, 2H), 5.22*, 5.58 (d, 1H), 5.78*, 6.25 (s, 1H), 7.58-7.84 (m, 5H), 7.87-7.95 (m, 1H), 7.98-8.07 (m, 1H), 8.53, 8.77* (s, 1H), 10.82*, 11.03 (s, 1H). |
| 425 | 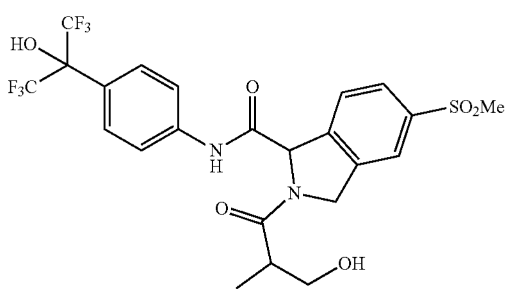 [SMILES: CC(CO)C(=O)N1Cc2cc(S(C)(=O)=O)ccc2C1C(=O)Nc1ccc(C(O)(C(F)(F)F)C(F)(F)F)cc1] | HRMS: calculated for (C$_{23}$H$_{22}$F$_6$N$_2$O$_6$S + H)$^+$ 569.1181; found (ESI [M + H]$^+$) 569.1170. Mixture of diastereomers and rotamers; ratio major: minor = 6:3:1; only major isomer reported: $^1$H NMR (400 MHz, DMSO-d$_6$) δ 1.06 (d, 3H), 2.87-3.03 (m, 1H), 3.23 (s, 3H), 3.43 (s, 1H), 3.51-3.68 (m, 1H), 4.76-5.26 (m, 3H), 5.76 (s, 1H), 7.70 (ddt, 5H), 7.88-7.96 (m, 1H), 7.98-8.07 (m, 1H), 8.68 (s, 1H), 10.49 (s, 1H). |
| 426 | 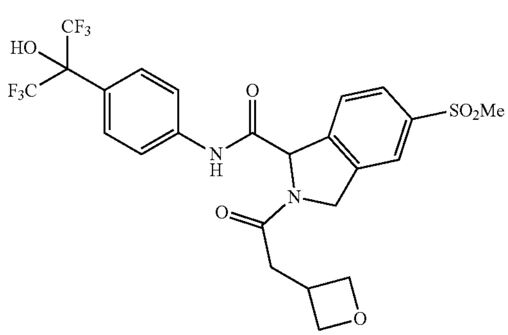 [SMILES: CS(=O)(=O)c1ccc2c(c1)CN(C(=O)CC1COC1)C2C(=O)Nc1ccc(C(O)(C(F)(F)F)C(F)(F)F)cc1] | HRMS: calculated for (C$_{24}$H$_{22}$F$_6$N$_2$O$_6$S + H)$^+$ 581.1181; found (ESI [M + H]$^+$) 581.1191. $^1$H NMR (400 MHz, DMSO-d$_6$, mixture of rotamers, 5*:1) δ 2.86-3.01 (m, 2H), 3.22, 3.24* (s, 3H), 3.26-3.45 (m, 1H), 4.22-4.37 (m, 2H), 4.66-4.73 (m, 2H), 4.75-4.94, 5.02-5.10* (m, 2H), 5.72*, 5.99 (s, 1H), 7.60-7.84 (m, 5H), 7.89-7.95 (m, 1H), 8.00-8.05 (m, 1H), 8.68 (s, 1H), 10.70*, 11.03 (s, 1H). |

TABLE 4A-continued

| Example No. | Structure | NMR + MS |
|---|---|---|
| 427 | 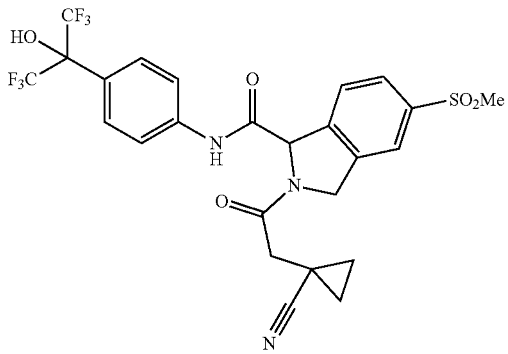 [SMILES: CS(=O)(=O)c1ccc2c(c1)CN(C(=O)CC1(C#N)CC1)C2C(=O)Nc1ccc(C(O)(C(F)(F)F)C(F)(F)F)cc1] | HRMS: calculated for ($C_{25}H_{21}F_6N_3O_5S$ + H)$^+$ 590.1184; found (ESI [M + H]$^+$) 590.1200. $^1$H NMR (400 MHz, DMSO-d$_6$, mixture of rotamers, 5:1, data only for major rotamer) δ 0.85-1.16 (m, 4H), 2.99-3.18 (m, 2H), 3.23 (s, 3H), 5.10-5.29 (m, 2H), 5.79 (s, 1H), 7.59-7.77 (m, 5H), 7.88-7.95 (m, 1H), 7.99-8.03 (m, 1H), 8.74 (s, 1H), 10.77 (s, 1H). |
| 428 | 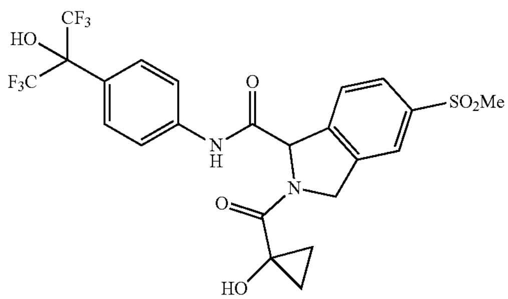 [SMILES: CS(=O)(=O)c1ccc2c(c1)CN(C(=O)C1(O)CC1)C2C(=O)Nc1ccc(C(O)(C(F)(F)F)C(F)(F)F)cc1] | HRMS: calculated for ($C_{23}H_{20}F_6N_2O_6S$ + H)$^+$ 567.1024; found (ESI [M + H]$^+$) 567.1051. $^1$H NMR (300 MHz, DMSO-d$_6$, mixture of rotamers, 1.4*:1) δ 0.74-1.27 (m, 4H), 3.22, 3.23* (s, 3H), 4.82-5.01, 5.27-5.48* (m, 2H), 5.84*, 6.48 (s, 1H), 6.51, 6.53* (s, 1H), 7.57-7.96 (m, 6H), 8.00-8.08 (m, 1H), 8.73 (s, 1H), 10.82*, 10.83 (s, 1H). |
| 429 | 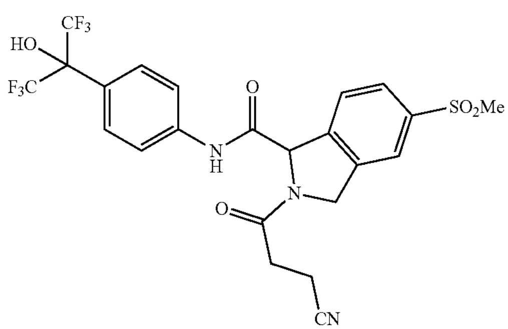 [SMILES: CS(=O)(=O)c1ccc2c(c1)CN(C(=O)CCC#N)C2C(=O)Nc1ccc(C(O)(C(F)(F)F)C(F)(F)F)cc1] | HRMS: calculated for ($C_{23}H_{19}F_6N_3O_5S$ + H)$^+$ 564.1028; found (ESI [M + H]$^+$) 564.1042. $^1$H NMR (400 MHz, DMSO-d$_6$, mixture of rotamers, 6*:1) δ 2.70 (t, 2H), 2.83-2.99 (m, 2H), 3.23, 3.24* (s, 3H), 4.80-5.00, 5.01-5.10* (m, 2H), 5.78*, 5.97 (s, 1H), 7.59-7.85 (m, 5H), 7.89-7.95 (m, 1H), 8.01-8.07 (m, 1H), 8.67*, 8.69 (s, 1H), 10.76*, 10.98 (s, 1H). |
| 430 | 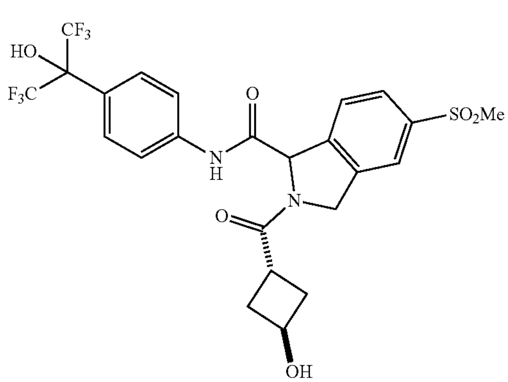 | HRMS: calculated for ($C_{24}H_{22}F_6N_4O_6S$ + H)$^+$ 581.1181; found (ESI [M + H]$^+$) 581.1183. $^1$H NMR (300 MHz, DMSO-d$_6$, mixture of rotamers, 5*:1) δ 2.05-2.22 (m, 2H), 2.41-2.50 (m, 2H), 3.23 (s, 3H), 3.24-3.33 (m, 1H), 4.12-4.26 (m, 1H), 4.78-4.98 (m, 2H), 5.07, 5.16* (d, 1H), 5.77*, 5.85 (s, 1H), 7.60-7.79 (m, 5H), 7.87-7.95 (m, 1H), 7.97-8.06 (m, 1H), 8.69*, 8.71 (s, 1H), 10.77*, 10.95 (s, 1H). |

TABLE 4A-continued

| Example No. | Structure | NMR + MS |
|---|---|---|
| 431 | 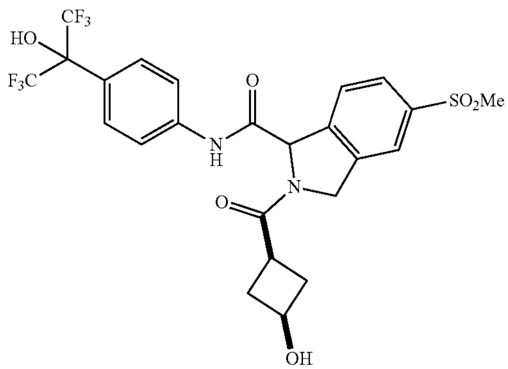 | HRMS: calculated for $(C_{24}H_{22}F_6N_2O_6S + H)^+$ 581.1181; found (ESI [M + H]$^+$) 581.1166. $^1$H NMR (300 MHz, mixture of rotamers, 4.5*:1) δ 1.94-2.12 (m, 2H), 2.38-2.63 (m, 2H), 2.71-2.96 (m, 1H), 3.23 (s, 3H), 3.88-4.15 (m, 1H), 4.76-5.07 (m, 2H), 5.76*, 5.94 (s, 1H), 7.6-7.81 (m, 5H), 7.88-7.95 (m, 1H), 7.97-8.05 (m, 1H), 10.81*, 11.08 (s, 1H). |
| 432 | 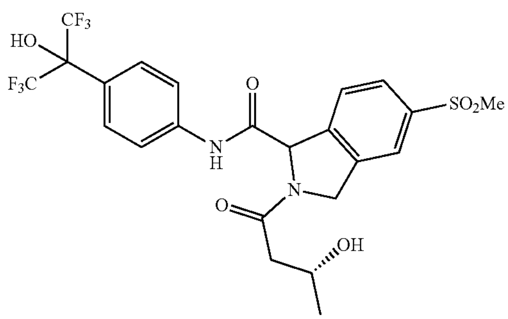 [SMILES: C[C@@H](O)CC(=O)N1Cc2cc(S(C)(=O)=O)ccc2C1C(=O)Nc1ccc(C(O)(C(F)(F)F)C(F)(F)F)cc1] | HRMS: calculated for $(C_{23}H_{22}F_6N_2O_6S + H)^+$ 569.1181; found (ESI [M + H]$^+$) 569.1151. Mixture of diastereomers and rotamers; ratio major*: minor = 7:6:2:1; only 2 major isomers reported: $^1$H NMR (300 MHz, DMSO-d$_6$) δ 1.14-1.21 (m, 3H), 2.41-2.68 (m, 2H), 3.24 (s, 3H), 4.02-4.16 (m, 1H), 5.01-5.19 (m, 2H), 5.77 (s, 1H), 7.59-7.82 (m, 5H), 7.89-7.95 (m, 1H), 7.99-8.03 (m, 1H), 8.67 (s, 1H), 10.66, 10.73* (s, 1H). |
| 433 | 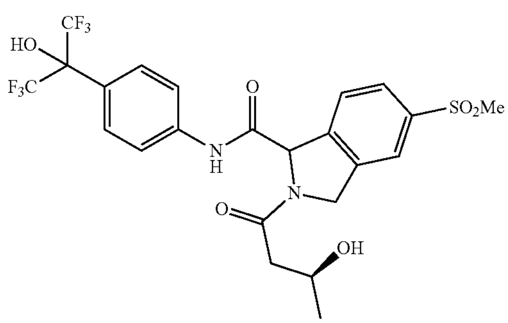 [SMILES: C[C@H](O)CC(=O)N1Cc2cc(S(C)(=O)=O)ccc2C1C(=O)Nc1ccc(C(O)(C(F)(F)F)C(F)(F)F)cc1] | HRMS: calculated for $(C_{23}H_{22}F_6N_2O_6S + H)^+$ 569.1181; found (ESI [M + H]$^+$) 569.1190. Mixture of diastereomers/rotamers; ratio major*: minor = 6:5:2:1, only 2 major isomers reported: $^1$H NMR (400 MHz, DMSO-d$_6$) δ 1.14-1.21 (m, 3H), 2.40-2.55 (m, 1H), 2.58-2.66 (m, 1H), 3.23 (s, 3H), 4.04-4.13 (m, 1H), 4.64-5.15 (m, 3H), 5.76 (s, 1H), 7.58-7.82 (m, 5H), 7.88-7.94 (m, 1H), 7.98-8.05 (m, 1H), 8.66 (s, 1H), 10.66, 10.72* (s, 1H). |
| 434 | 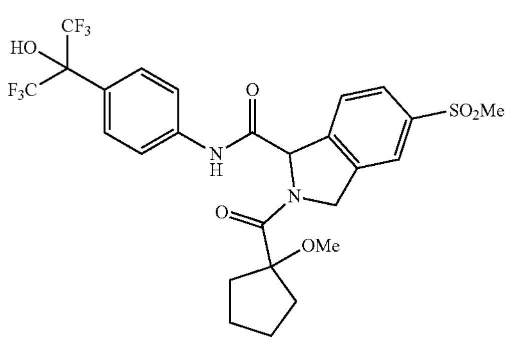 [SMILES: COC1(C(=O)N2Cc3cc(S(C)(=O)=O)ccc3C2C(=O)Nc2ccc(C(O)(C(F)(F)F)C(F)(F)F)cc2)CCCC1] | HRMS: calculated for $(C_{26}H_{26}F_6N_2O_6S + H)^+$ 609.1494; found (ESI [M + H]$^+$) 609.1520. $^1$H NMR (600 MHz, DMSO-d$_6$, mixture of rotamers, 12*:1 only major isomer reported) δ 1.52-1.61 (m, 2H), 1.61-1.71 (m, 2H), 1.88-2.05 (m, 3H), 2.1-2.17 (m, 1H), 3.21 (s, 3H), 3.22 (s, 3H), 5.11-5.23 (m, 2H), 5.86 (s, 1H), 7.6-7.65 (m, 2H), 7.7-7.76 (m, 3H), 7.86-7.92 (m, 1H), 8.01 (s, 1H), 8.67 (br s, 1H), 10.88 (s, 1H). |

Example 435: 2-Acetyl-N-[3-fluoro-4-(1,1,1,3,3,3-hexafluoro-2-hydroxypropan-2-yl)phenyl]-5-(methylsulfonyl)-2,3-dihydro-1H-isoindole-1-carboxamide

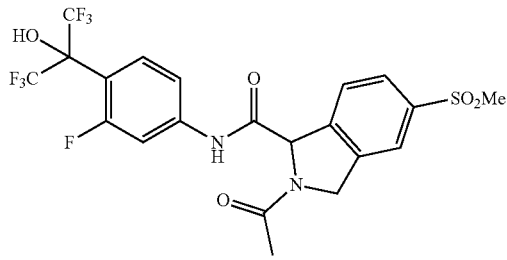 [SMILES: CC(=O)N1Cc2cc(S(C)(=O)=O)ccc2C1C(=O)Nc1ccc(C(O)(C(F)(F)F)C(F)(F)F)c(F)c1]

Step 1: N-[3-Fluoro-4-(1,1,1,3,3,3-hexafluoro-2-hydroxypropan-2-yl)phenyl]-5-(methylsulfonyl)-2,3-dihydro-1H-isoindole-1-carboxamide

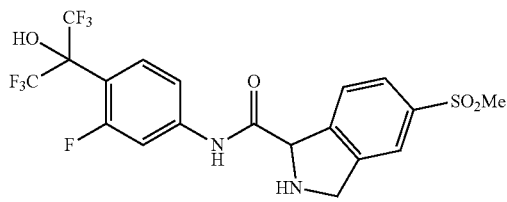 [SMILES: CS(=O)(=O)c1ccc2c(c1)CNC2C(=O)Nc1ccc(C(O)(C(F)(F)F)C(F)(F)F)c(F)c1]

tert-Butyl 1-((3-fluoro-4-(1,1,1,3,3,3-hexafluoro-2-hydroxypropan-2-yl)phenyl)carbamoyl)-5-(methylsulfonyl)isoindoline-2-carboxylate (402 mg, 0.67 mmol) was suspended in isopropyl acetate (15 mL). hydrogen chloride in IPA (1.473 mL, 7.36 mmol) was added. Stirred at rt overnight. The reaction was concentrated in vacuo. The residue was coevaporated with EtOAc (2×25 ml), EtOAc/Hept (1:1, 50 ml) to afford the crude product as its hydrochloride salt. The product was used in the next step without further purification.

LC/MS: m/z=501 [M+H]$^+$.

Step 2: 2-Acetyl-N-[3-fluoro-4-(1,1,1,3,3,3-hexafluoro-2-hydroxypropan-2-yl)phenyl]-5-(methylsulfonyl)-2,3-dihydro-1H-isoindole-1-carboxamide

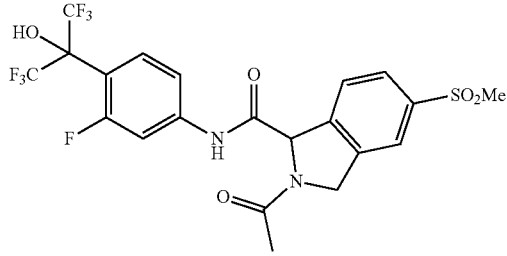 [SMILES: CC(=O)N1Cc2cc(S(C)(=O)=O)ccc2C1C(=O)Nc1ccc(C(O)(C(F)(F)F)C(F)(F)F)c(F)c1]

N-(3-Fluoro-4-(1,1,1,3,3,3-hexafluoro-2-hydroxypropan-2-yl)phenyl)-5-(methylsulfonyl)isoindoline-1-carboxamide, HCl (100 mg, 0.19 mmol) was dissolved in DCM (1 mL) and to this triethylamine (0.078 mL, 0.56 mmol) and acetic acid (13.42 mg, 0.22 mmol) was added followed by T3P (0.222 mL, 0.37 mmol) 50% in EtOAc was then added. The reaction was stirred at rt for 1 hr. LCMS indicated complete conversion to product. The reaction was diluted with DCM and washed with 0.5M HCl. The layers were separated using a phase separator and concentrated in vacuo. The residue was dissolved in DMSO and separated by preparative SFC (chromatographic conditions: MeOH/NH$_3$ 20 mM; column: Waters BEH 5 µm 30×250 mm) to afford 2-acetyl-N-(3-fluoro-4-(1,1,1,3,3,3-hexafluoro-2-hydroxypropan-2-yl)phenyl)-5-(methylsulfonyl)isoindoline-1-carboxamide (79 mg, 78%).

HRMS: calculated for $(C_{21}H_{17}F_7N_2O_5S+H)^+$ 543.0825; found (ESI [M+H]$^+$) 543.0830.

$^1$H NMR (600 MHz, DMSO-d$_6$, mixture of rotamers, 5*:1) δ 1.99, 2.15* (s, 3H), 3.21, 3.22* (s, 3H), 4.73-4.94, 4.99-5.1* (m, 2H), 5.71*, 5.94 (s, 1H), 7.49*, 7.54 (dd, 1H), 7.62-7.71 (m, 2H), 7.76-7.81 (m, 1H), 7.88-7.93 (m, 1H), 8.00*, 8.03 (s, 1H), 8.89 (br s, 1H), 10.92*, 11.15 (s, 1H).

Example 436: 2-[(1-Cyanocyclopropyl)carbonyl]-N-[2-fluoro-4-(1,1,3,3,3-hexafluoro-2-hydroxypropan-2-yl)phenyl]-5-(methylsulfonyl)-2,3-dihydro-1H-isoindole-1-carboxamide

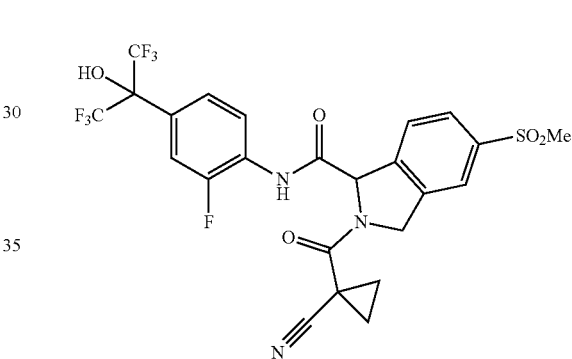

Step 1: N-[2-Fluoro-4-(1,1,1,3,3,3-hexafluoro-2-hydroxypropan-2-yl)phenyl]-5-(methylsulfonyl)-2,3-dihydro-1H-isoindole-1-carboxamide

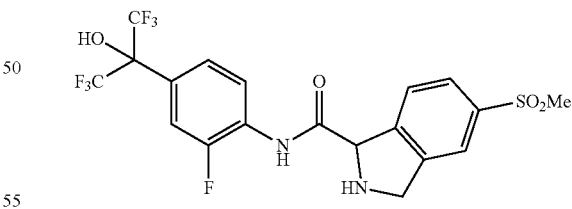

tert-Butyl 1-((2-fluoro-4-(1,1,1,3,3,3-hexafluoro-2-hydroxypropan-2-yl)phenyl)carbamoyl)-5-(methylsulfonyl)isoindoline-2-carboxylate (402 mg, 0.67 mmol) was suspended in isopropyl acetate (1.5 mL). hydrogen chloride in IPA (1.5 mL, 7.50 mmol) was added. Stirred at rt overnight. The reaction was concentrated in vacuo. The residue was coevaporated with EtOAc and then, EtOAc/Hept (1:1). The title compound was obtained as its hydrochloride salt (353 mg, 99%). The pinkish solid was used without further purification in the next step.

LC/MS: m/z=501 [M+H]$^+$.

Step 2: 2-[(1-Cyanocyclopropyl)carbonyl]-N-[2-fluoro-4-(1,1,1,3,3,3-hexafluoro-2-hydroxypropan-2-yl)phenyl]-5-(methylsulfonyl)-2,3-dihydro-1H-isoindole-1-carboxamide

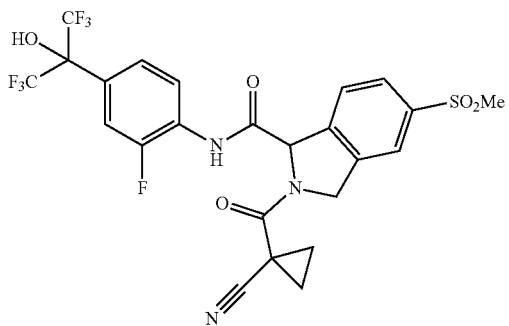 [SMILES: CS(=O)(=O)c1ccc2c(c1)CN(C(=O)C1(C#N)CC1)C2C(=O)Nc1ccc(C(O)(C(F)(F)F)C(F)(F)F)cc1F]

N-(2-Fluoro-4-(1,1,1,3,3,3-hexafluoro-2-hydroxypropan-2-yl)phenyl)-5-(methylsulfonyl)isoindoline-1-carboxamide, HCl (50 mg, 0.09 mmol) was dissolved in DCM (1 mL) and to this triethylamine (0.039 mL, 0.28 mmol) and 1-cyanocyclopropane-1-carboxylic acid (15.52 mg, 0.14 mmol) was added followed by T3P (0.111 mL, 0.19 mmol) 50% in EtOAc was then added. The reaction was stirred at rt for 1 hr. LCMS indicated complete conversion to product. The reaction was diluted with DCM and washed with 0.5M HCl. The layers were separated using a phase separator cartridge and concentrated in vacuo. The residue was dissolved in DMSO and separated by preparative SFC (chromatographic conditions: MeOH/NH$_3$ 20 mM; column: Waters BEH 5 m 30×250 mm) to afford 2-(1-cyanocyclopropane-1-carbonyl)-N-(2-fluoro-4-(1,1,1,3,3,3-hexafluoro-2-hydroxypropan-2-yl)phenyl)-5-(methylsulfonyl)isoindoline-1-carboxamide (31.6 mg, 57.2%).

HRMS: calculated for $(C_{24}H_{18}F_7N_3O_5S+H)^+$ 594.0933; found (ESI [M+H]$^+$) 594.0894.

$^1$H NMR (600 MHz, DMSO-d$_6$, mixture of rotamers, 6*:1) δ 1.44-1.81 (m, 4H), 3.22, 3.23* (s, 3H), 4.86-5.00, 5.32-5.42* (m, 2H), 6.06*, 6.64 (s, 1H), 7.43-7.5 (m, 1H), 7.51-7.56 (m, 1H), 7.76 (d, 1H), 7.93-8.02 (m, 2H), 8.03, 8.12* (s, 1H), 8.96 (br s, 1H), 10.74*, 11.11 (s, 1H).

Examples 437-449

Examples 437-449 (Table 4B) were prepared using a similar procedures to those described in the preceding examples.

Example 437: 2-Acetyl-N-[2-fluoro-4-(1,1,1,3,3,3-hexafluoro-2-hydroxypropan-2-yl)phenyl]-5-(methylsulfonyl)-2,3-dihydro-1H-isoindole-1-carboxamide Example 438: N-[2-Fluoro-4-(1,1,1,3,3,3-hexafluoro-2-hydroxypropan-2-yl)phenyl]-5-(methylsulfonyl)-2,3-dihydro-1H-isoindole-1-carboxamide Example 439: 2-[(1-Cyanocyclopropyl)carbonyl]-N-[3-fluoro-4-(1,1,1,3,3,3-hexafluoro-2-hydroxypropan-2-yl)phenyl]-5-(methylsulfonyl)-2,3-dihydro-1H-isoindole-1-carboxamide Example 440: N-[3-Fluoro-4-(1,1,1,3,3,3-hexafluoro-2-hydroxypropan-2-yl)phenyl]-2-[(1-methoxycyclopropyl)carbonyl]-5-(methylsulfonyl)-2,3-dihydro-1H-isoindole-1-carboxamide Example 441: N-[2-Fluoro-4-(1,1,1,3,3,3-hexafluoro-2-hydroxypropan-2-yl)phenyl]-2-[(1-methoxycyclopropyl)carbonyl]-5-(methylsulfonyl)-2,3-dihydro-1H-isoindole-1-carboxamide Example 442: N-[2-Fluoro-4-(1,1,1,3,3,3-hexafluoro-2-hydroxypropan-2-yl)phenyl]-5-(methylsulfonyl)-2,3-dihydro-1H-isoindole-1-carboxamide Example 443: N-[4-(1,1,1,3,3,3-Hexafluoro-2-hydroxypropan-2-yl)phenyl]-2-[(3-methyloxetan-3-yl)carbonyl-5-(methyl]-5-(methylsulfonyl)-2,3-dihydro-1H-isoindole-1-carboxamide Example 444: N-[4-(1,1,1,3,3,3-Hexafluoro-2-hydroxypropan-2-yl)phenyl]-5-(methylsulfonyl)-2-(oxetan-3-ylcarbonyl)-2,3-dihydro-1H-isoindole-1-carboxamide Example 445: N-[4-(1,1,1,3,3,3-Hexafluoro-2-hydroxypropan-2-yl)phenyl]-2-[(2-methyloxetan-2-yl)carbonyl-5-(methyl]-5-(methylsulfonyl)-2,3-dihydro-1H-isoindole-1-carboxamide Example 446: 2-[(1-Fluorocyclopropyl)carbonyl]-N-[4-(1,1,1,3,3,3-hexafluoro-2-hydroxypropan-2-yl)phenyl]-5-(methylsulfonyl)-2,3-dihydro-1H-isoindole-1-carboxamide Example 447: N-[4-(1,1,1,3,3,3-Hexafluoro-2-hydroxypropan-2-yl)phenyl]-2-(2-methoxybutanoyl)-5-(methylsulfonyl)-2,3-dihydro-1H-isoindole-1-carboxamide Example 448: N-[4-(1,1,1,3,3,3-Hexafluoro-2-hydroxypropan-2-yl)phenyl]-2-[(1-methoxycyclobutyl)carbonyl]-5-(methylsulfonyl)-2,3-dihydro-1H-isoindole-1-carboxamide Example 449: N-[4-(1,1,1,3,3,3-Hexafluoro-2-hydroxypropan-2-yl)phenyl]-2-[(2R)-2-methoxypropanoyl]-5-(methylsulfonyl)-2,3-dihydro-1H-isoindole-1-carboxamide

TABLE 4B

| Example No. | Structure | NMR + MS |
|---|---|---|
| 437 | 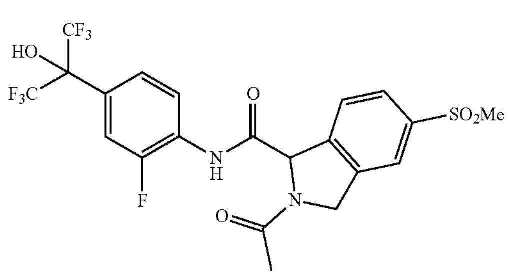 [SMILES: CC(=O)N1Cc2cc(S(C)(=O)=O)ccc2C1C(=O)Nc1ccc(C(O)(C(F)(F)F)C(F)(F)F)cc1F] | HRMS: calculated for $(C_{21}H_{17}F_7N_2O_5S + H)^+$ 543.0825; found (ESI [M + H]$^+$) 543.0825. $^1$H NMR (600 MHz, DMSO-d$_6$, mixture of rotamers, 4*:1) δ 2.01, 2.15* (s, 3H), 3.22, 3.23* (s, 3H), 4.75-4.92, 4.99-5.07* (m, 2H), 5.95*, 6.12 (s, 1H), 7.43-7.57 (m, 2H), 7.71*, 7.77 (d, 1H), 7.89-7.95 (m, 1H), 7.99-8.04 (m, 2H), 8.93 (br s, 1H), 10.58*, 10.82 (s, 1H). |

TABLE 4B-continued

| Example No. | Structure | NMR + MS |
|---|---|---|
| 438 | 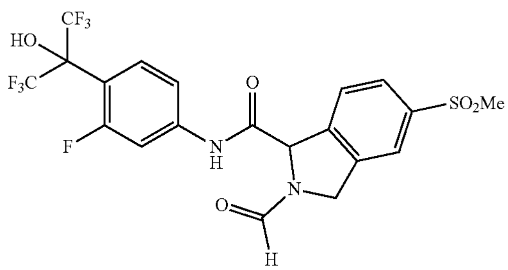 [SMILES: CS(=O)(=O)c1ccc2c(c1)CN(C=O)C2C(=O)Nc1ccc(C(O)(C(F)(F)F)C(F)(F)F)c(F)c1] | HRMS: calculated for (C₂₄H₂₂F₆N₂O₆S + H)⁺ 581.1181; found (ESI [M + H]⁺) 581.1160. 1H NMR (600 MHz, DMSO-d₆, mixture of rotamers, 2*:1) δ 3.21, 3.22* (s, 3H), 4.71-4.92, 5.04-5.16* (m, 2H), 5.76*, 6.00 (s, 1H), 7.05*, 7.54 (dd, 1H), 7.62-7.87 (m, 3H), 7.89-7.93 (m, 1H), 8.03, 8.05* (s, 1H), 8.39, 8.49* (s, 1H) 8.88 (br s, 1H), 10.98*, 11.08 (s, 1H). |
| 439 | 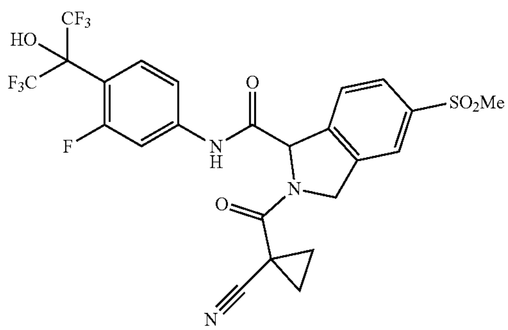 [SMILES: CS(=O)(=O)c1ccc2c(c1)CN(C(=O)C1(C#N)CC1)C2C(=O)Nc1ccc(C(O)(C(F)(F)F)C(F)(F)F)c(F)c1] | HRMS: calculated for (C₂₄H₁₈F₇N₃O₅S + H)⁺ 594.0933; found (ESI [M + H]⁺) 594.0890. ¹H NMR (600 MHz, DMSO-d₆, mixture of rotamers, 6*:1) δ 1.49-1.87 (m, 4H), 3.21, 3.23* (s, 3H), 4.86-5, 5.33-5.43* (m, 2H), 5.84*, 6.43 (s, 1H), 7.45-7.55 (m, 1H), 7.6-7.69 (m, 1H), 7.73-7.84 (m, 2H), 7.89-7.97 (m, 1H), 8.04, 8.13* (s, 1H), 8.89 (s, 1H), 11.09*, 11.40 (s, 1H). |
| 440 | 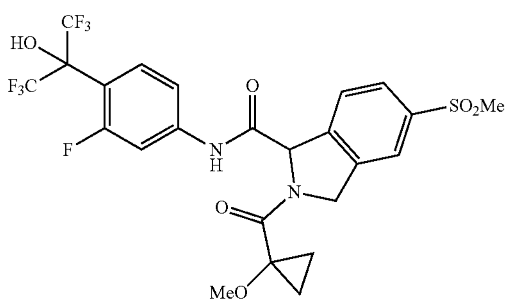 [SMILES: COC1(C(=O)N2Cc3cc(S(C)(=O)=O)ccc3C2C(=O)Nc2ccc(C(O)(C(F)(F)F)C(F)(F)F)c(F)c2)CC1] | HRMS: calculated for (C₂₄H₂₁F₇N₂O₆S + H)⁺ 599.1086; found (ESI [M + H]⁺) 599.17. ¹H NMR (600 MHz, DMSO-d₆, mixture of rotamers, 1*:1) δ 0.78-1.20 (m, 4H), 3.18, 3.22* (s, 3H), 3.21, 3.35* (s, 3H), 4.83-5.05, 5.16-5.31* (m, 2H), 5.88*, 6.20 (s, 1H), 7.45-7.52 (m, 1H), 7.64 (dd, 1H), 7.7-7.82 (m, 2H), 7.87-7.93 (m, 1H), 8.03, 8.06* (s, 1H), 8.88 (s, 1H), 11.02, 11.10* (s, 1H). |
| 441 | 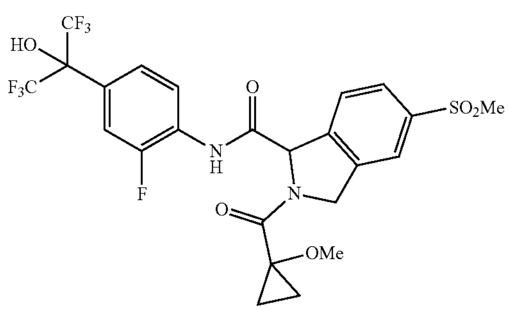 [SMILES: COC1(C(=O)N2Cc3cc(S(C)(=O)=O)ccc3C2C(=O)Nc2ccc(C(O)(C(F)(F)F)C(F)(F)F)cc2F)CC1] | HRMS: calculated for (C₂₄H₂₁F₇N₂O₆S + H)⁺ 599.1086; found (ESI [M + H]⁺) 599.1094. ¹H NMR (600 MHz, DMSO-d₆, mixture of rotamers, 2:1 only major reported) δ 0.84-1.2 (m, 4H), 3.22 (d, 3H), 3.33 (s, 3H), 5.13-5.31 (m, 2H), 6.10 (s, 1H), 7.46 (d, 1H), 7.49-7.56 (m, 1H), 7.76 (d, 1H), 7.89-7.95 (m, 1H), 7.98-8.07 (m, 2H), 8.95 (s, 1H), 10.71 (s, 1H). |
| 442 | 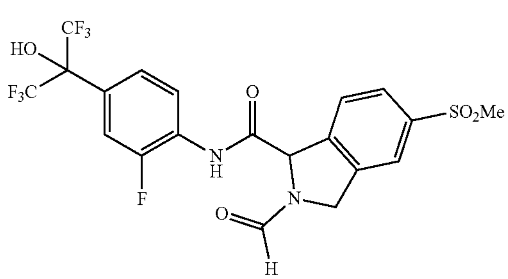 [SMILES: CS(=O)(=O)c1ccc2c(c1)CN(C=O)C2C(=O)Nc1ccc(C(O)(C(F)(F)F)C(F)(F)F)cc1F] | HRMS: calculated for (C₂₀H₁₅F₇N₂O₅S + H)⁺ 529.0668; found (ESI [M + H]⁺) 529.0647. ¹H NMR (600 MHz, DMSO-d₆, mixture of rotamers, 2:1 only major reported) δ δ 3.23 (s, 3H), 5.02-5.16 (m, 2H), 5.99 (s, 1H), 7.47 (m, 1H), 7.54 (d, 1H), 7.74 (d, 1H), 7.92-8.04 (m, 3H), 8.48 (s, 1H), 8.95 (br s, 1H), 10.66 (s, 1H). |

TABLE 4B-continued

| Example No. | Structure | NMR + MS |
|---|---|---|
| 443 | 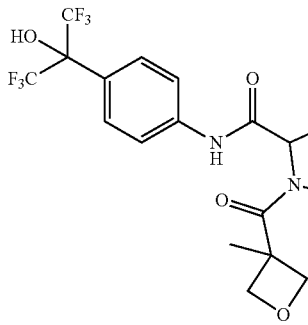 | HRMS: calculated for (C₂₄H₂₂F₆N₂O₆S + H)⁺ 581.1181; found (ESI [M + H]⁺) 581.1180. ¹H NMR (600 MHz, DMSO-d₆, mixture of rotamers >10:1 only major reported) δ 1.68 (s, 3H), 3.20 (s, 3H), 4.27-4.32 (m, 2H), 4.73-4.9 (m, 2H), 4.94 (dd, 2H), 5.81 (d, 1H), 7.63 (d, 2H), 7.71-7.76 (m, 3H), 7.91 (d, 1H), 7.95 (s, 1H), 8.68 (s, 1H), 10.82 (s, 1H). |
| 444 | 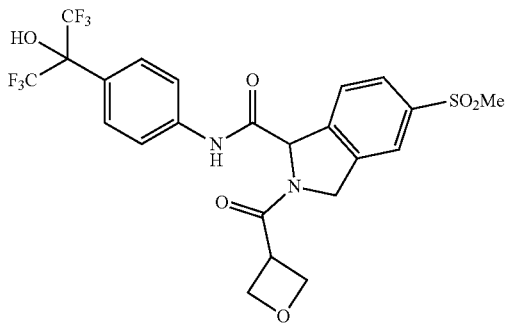 [SMILES: CS(=O)(=O)c1ccc2c(c1)CN(C(=O)C1COC1)C2C(=O)Nc1ccc(C(O)(C(F)(F)F)C(F)(F)F)cc1] | HRMS: calculated for (C₂₃H₂₀F₆N₂O₆S + H)⁺ 567.1024; found (ESI [M + H]⁺) 567.1061. ¹H NMR (600 MHz, DMSO-d₆, mixture of rotamers, 4:1 only major reported) δ 3.20 (s, 3H), 4.2-4.28 (m, 1H), 4.43-4.97 (m, 6H), 5.79 (s, 1H), 7.61-7.68 (m, 2H), 7.7-7.8 (m, 3H), 7.90 (d, 1H), 7.96 (s, 1H), 8.71 (br s, 1H), 10.80 (s, 1H). |
| 445 | 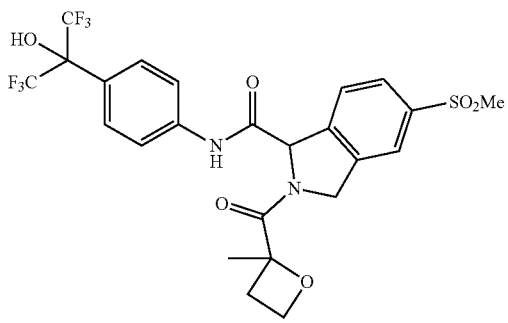 [SMILES: CC1(C(=O)N2Cc3cc(S(C)(=O)=O)ccc3C2C(=O)Nc2ccc(C(O)(C(F)(F)F)C(F)(F)F)cc2)CCO1] | HRMS: calculated for (C₂₄H₂₂F₆N₂O₆S + H)⁺ 581.1181; found (ESI [M + H]⁺) 581.1178. ¹H NMR (600 MHz, DMSO-d₆, 1:1 mixture of diastereomers, and 1:1 ratio of rotamers, for each diastereomer) δ 1.51 (s, 0.75H), 1.61 (s, 0.75H), 1.63 (s, 0.75H), 1.64 (s, 0.75H), 2.55-2.65 (m, 1H), 2.84 (m, 0.5H), 2.97 (m, 0.5H), 3.19 (s, 0.5H), 3.20 (s, 2.5H), 4.05-4.11 (m, 0.25H), 4.25-4.3 (m, 0.25H), 4.34-4.51 (m, 1.5H), 4.82-4.93 (m, 0.25H), 4.95-5.03 (m, 1.25H), 5.24 (d, 0.25H), 5.32 (d, 0.25H), 5.84 (d, 0.25H), 5.85 (d, 0.25H), 5.95 (d, 0.25H), 6.49 (d, 0.25H), 7.58-7.65 (m, 2H), 7.69-7.77 (m, 2.5H), 7.81 (d, 0.5H), 7.87-7.91 (m, 1H), 7.99 (s, 0.5H), 8.01 (s, 0.25H), 8.03 (s, 0.25H), 8.6-8.69 (m, 1H), 10.58 (s, 0.25H), 10.81 (s, 0.5H), 10.87 (s, 0.25H). |
| 446 | 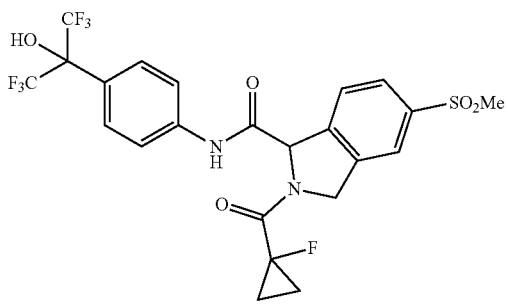 [SMILES: CS(=O)(=O)c1ccc2c(c1)CN(C(=O)C1(F)CC1)C2C(=O)Nc1ccc(C(O)(C(F)(F)F)C(F)(F)F)cc1] | HRMS: calculated for (C₂₃H₁₉F₇N₂O₅S + H)⁺ 569.0981; found (ESI [M + H]⁺) 569.1009. ¹H NMR (600 MHz, DMSO-d₆, mixture of rotamers, 2:1 only major reported) δ 1.18-1.48 (m, 4H) 3.22 (s, 3H), 5.22-5.32 (m, 2H), 5.90 (s, 1H), 7.6-7.65 (m, 2H), 7.69-7.83 (m, 3H), 7.88-7.94 (m, 1H), 8.02-8.07 (m, 1H), 8.65 (s, 1H), 10.85 (s, 1H). |

TABLE 4B-continued

| Example No. | Structure | NMR + MS |
|---|---|---|
| 447 | 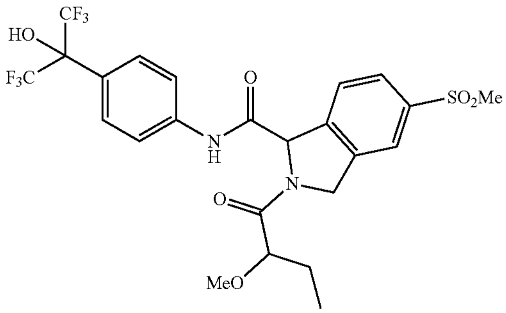 [SMILES: CCC(OC)C(=O)N1Cc2cc(S(C)(=O)=O)ccc2C1C(=O)Nc1ccc(C(O)(C(F)(F)F)C(F)(F)F)cc1] | HRMS: calculated for $(C_{24}H_{24}F_6N_2O_6S + H)^+$ 583.1337; found (ESI [M + H]$^+$) 583.1317. $^1$H NMR (600 MHz, DMSO-d$_6$, 1:1 mixture of diastereomers and approximately 6:1 ratio of rotamers for each diastereomer; only major rotamer for each diastereomer reported) δ 0.91-0.97 (m, 3H), 1.64-1.75 (m, 2H), 3.2-3.22 (m, 3H), 3.27 (s, 1.5H), 3.31 (s, 1.5H), 3.99-4.06 (m, 1H), 5.08 (dd, 1H), 5.19 (t, 1H), 5.81 (d, 0.5H), 5.87 (d, 0.5H), 7.59-7.66 (m, 2H), 7.7-7.76 (m, 3H), 7.87-7.95 (m, 1H), 8.00 (s, 1H), 8.67 (s, 1H), 10.82 (s, 0.5H), 10.85 (s, 0.5H). |
| 448 | 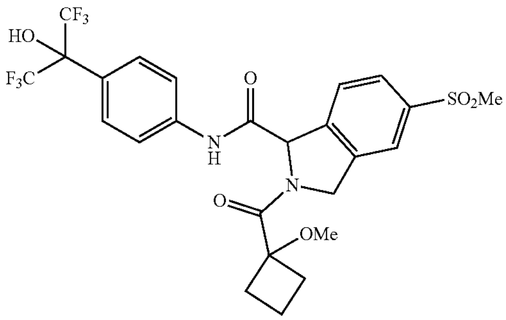 [SMILES: COC1(C(=O)N2Cc3cc(S(C)(=O)=O)ccc3C2C(=O)Nc2ccc(C(O)(C(F)(F)F)C(F)(F)F)cc2)CCC1] | HRMS: calculated for $(C_{25}H_{24}F_6N_2O_6S + H)^+$ 595.1337; found (ESI [M + H]$^+$) 595.1374. $^1$H NMR (600 MHz, DMSO-d$_6$, mixture of rotamers, 7:1 only major reported) δ 1.52-1.61 (m, 1H), 1.76-1.86 (m, 1H), 2.04-2.11 (m, 1H), 2.15-2.26 (m, 1H), 2.44-2.49 (m, 1H), 2.57-2.65 (m, 1H), 3.15 (s, 3H), 3.20 (s, 3H), 4.92-5.09 (m, 2H), 5.88 (d, 1H), 7.59-7.66 (m, 2H), 7.69-7.78 (m, 3H), 7.89 (d, 1H), 8.01 (s, 1H), 8.67 (s, 1H), 10.90 (s, 1H). |
| 449 | 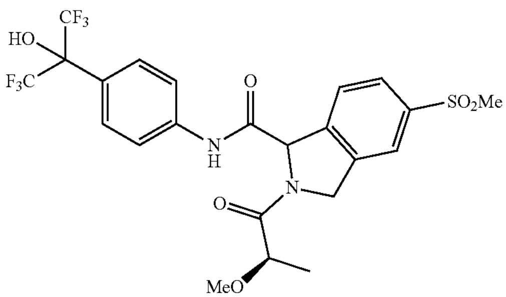 [SMILES: CO[C@H](C)C(=O)N1Cc2cc(S(C)(=O)=O)ccc2C1C(=O)Nc1ccc(C(O)(C(F)(F)F)C(F)(F)F)cc1] | HRMS: calculated for $(C_{23}H_{22}F_6N_2O_6S + H)^+$ 569.1181; found (ESI [M + H]$^+$) 569.1174. $^1$H NMR (600 MHz, DMSO d$_6$, 1:1 mixture of diastereomers and approximately 6:1 ratio of rotamers for each diastereomer; only major rotamer for each diastereomer reported) δ 1.29 (d, 1.5H), 1.32 (d, 1.5H), 3.21 (s, 3H), 3.27 (s, 1.5H), 3.31 (s, 1.5H), 4.20 (q, 0.5H), 4.27 (q, 0.5H), 5.03-5.1 (m, 1H), 5.12-5.24 (m, 1H), 5.80 (s, 1H), 5.84 (d, 1H), 7.56-7.66 (m, 2H), 7.69-7.76 (m, 3H), 7.91 (d, 1H), 8.00 (s, 1H), 10.82 (s, 0.5H), 10.83 (s, 0.5H). |

Example 450: 2-Acetyl-N-[4-(1,1,1,3,3,3-hexafluoro-2-hydroxypropan-2-yl)phenyl]-5-(methylsulfonyl)(1-$^2$H)-2,3-dihydro-1H-isoindole-1-carboxamide

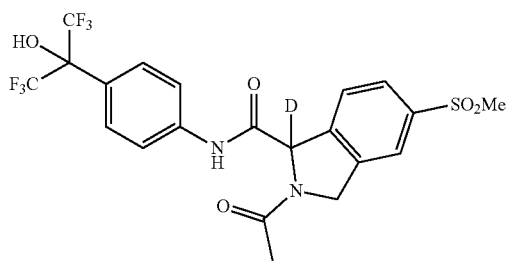 [SMILES: [2H]C1(C(=O)Nc2ccc(C(O)(C(F)(F)F)C(F)(F)F)cc2)c2ccc(S(C)(=O)=O)cc2CN1C(C)=O]

2-Acetyl-N-(4-(1,1,1,3,3,3-hexafluoro-2-hydroxypropan-2-yl)phenyl)-5-(methylsulfonyl)isoindoline-1-carboxamide (0.156 g, 0.30 mmol) was mixed with CD$_3$OD (2 mL) and triethylamine (0.082 mL, 0.59 mmol) was added. The resulting mixture was stirred at ambient temperature for 18 h. A precipitate had formed and the mixture was diluted with more CD$_3$OD (3 mL) and heated at 50° C. for 3 h. The mixture was then stirred at ambient temperature for 20 h. Acetic acid (2.1 equiv.) was added and the mixture was partitioned between water (5 mL) and dichloromethane (50 mL). The layers were separated in a phase separator and the organic layer was concentrated under reduced pressure to give a white solid (0.160 g, 102%).

HRMS: calculated for $(C_{21}H_{17}DF_6N_2O_5S+H)^+$ 526.0982; found: (ESI [M+H]+) 526.0964.

$^1$H NMR (500 MHz, MeOD) δ 2.27 (s, 3H), 3.12-3.15 (m, 3H), 5.06-5.2 (m, 2H), 7.66-7.76 (m, 5H), 7.94-7.98 (m, 1H), 8.02-8.06 (m, 1H).

Separation of the (1R) and the (1S) Enantiomers:

The racemate (0.14 g) was separated into the enatiomers by a preparative SFC system equipped with a YMC SA (IA) column, 250×20, 35% isopropyl alcohol 100 in CO$_2$ (120 bar), flow: 70 mL/min; injection volume was 5.0 mL of a 14 mg/mL ethanol/dichloromethane 1/1 solution.

Isomer 1 (peak 1): 0.065 g, 99.4% ee by analytical chiral SFC (analytical conditions: YMC SA (IA) column, 150×3 mm, 3 m, 3.5 ml/min, 40% IPA in CO2, 120 bar, 40° C.). HRMS: calculated for $(C_{21}H_{17}DF_6N_2O_5S+H)^+$ 526.0982; found: (ESI [M+H]$^+$) 526.0989.

$^1$H NMR (500 MHz, MeOD, mixture of rotamers, 6:1, only data for major rotamer reported) δ 2.26 (s, 3H), 3.12 (s, 3H), 5.06 (d, 1H), 5.16 (d, 1H), 7.66-7.69 (m, 4H), 7.70 (d, 1H), 7.93 (d, 1H), 8.02 (s, 1H).

Isomer 2 (peak 2): 0.073 g, 96.6% ee by analytical chiral SFC (analytical conditions: YMC SA (IA) column, 150×3 mm, 3 m, 3.5 ml/min, 40% IPA in $CO_2$, 120 bar, 40° C.). HRMS: calculated for $(C_{21}H_{17}DF_6N_2O_5S+H)^+$ 526.0982; found: (ESI $[M+H]^+$) 526.0978.

$^1$H NMR (500 MHz, MeOD, mixture of rotamers, 6:1, only data for major rotamer reported) δ 2.26 (s, 3H), 3.13 (s, 3H), 5.07 (d, 1H), 5.16 (d, 1H), 7.66-7.69 (m, 4H), 7.70 (d, 1H), 7.94 (d, 1H), 8.02 (s, 1H).

Example 451: (1R)-2-Acetyl-N-[4-(1,1,1,3,3,3-hexafluoro-2-hydroxypropan-2-yl)phenyl]-5-(methylsulfonyl)-2,3-dihydro-1H-isoindole-1-carboxamide

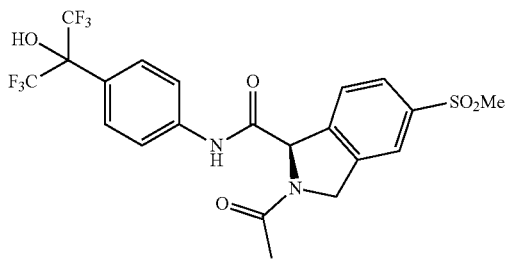 [SMILES: CC(=O)N1Cc2cc(S(C)(=O)=O)ccc2[C@@H]1C(=O)Nc1ccc(C(O)(C(F)(F)F)C(F)(F)F)cc1]

Step 1: (1R)—N-[4-(1,1,1,3,3,3-Hexafluoro-2-hydroxypropan-2-yl)phenyl]-5-(methylsulfonyl)-2,3-dihydro-1H-isoindole-1-carboxamide

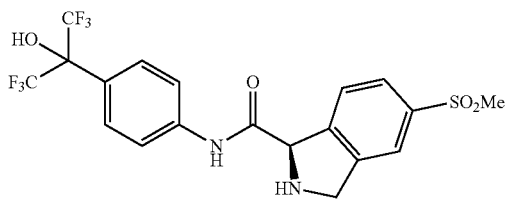 [SMILES: CS(=O)(=O)c1ccc2c(c1)CN[C@H]2C(=O)Nc1ccc(C(O)(C(F)(F)F)C(F)(F)F)cc1]

(R)-tert-Butyl 1-((4-(1,1,1,3,3,3-hexafluoro-2-hydroxypropan-2-yl)phenyl)carbamoyl)-5-(methylsulfonyl)isoindoline-2-carboxylate (132 g, 226.6 mmol) was suspended in isopropyl acetate (500 mL). Hydrogen chloride in isopropyl alcohol (500 ml, 2500.00 mmol) was added. The resulting mixture was stirred at 20° C. for 16½ h and then transferred to an evaporation flask. The solvents were removed under reduced pressure at a bath temperature of 30° C. and the residue was coevaporated with EtOAc (2×500 ml), EtOAc/Hept (1:1 800 ml) and heptane (2×400 ml), and subsequently dried under vacuum for 20 h. The hydrochloride salt of (R)—N-(4-(1,1,1,3,3,3-hexafluoro-2-hydroxypropan-2-yl)phenyl)-5-(methylsulfonyl)isoindoline-1-carboxamide (125 g, 106%) was obtained as a solid and used without further purification in the next step.

LC/MS: m/z=483 $[M+H]^+$. $^1$H NMR (400 MHz, DMSO-$d_6$) δ 3.23 (s, 3H), 4.72 (d, 1H), 4.80 (d, 1H), 5.96 (s, 1H), 7.68 (d, 2H), 7.81 (d, 2H), 7.97 (d, 1H), 8.02 (d, 1H), 8.06 b (s, 1H), 8.71 (s, 1H), 9.75 (bs, 1H), 10.96 (bs, 1H) 11.93 (s, 1H).

Step 2: (1R)-2-Acetyl-N-[4-(1,1,1,3,3,3-hexafluoro-2-hydroxypropan-2-yl)phenyl]-5-(methylsulfonyl)-2,3-dihydro-1H-isoindole-1-carboxamide

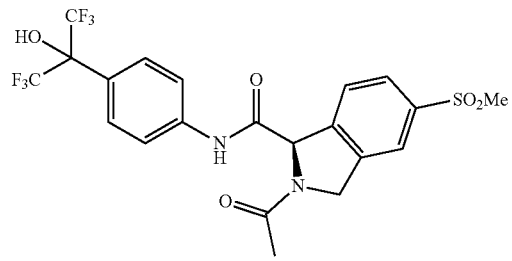 [SMILES: CC(=O)N1Cc2cc(S(C)(=O)=O)ccc2[C@@H]1C(=O)Nc1ccc(C(O)(C(F)(F)F)C(F)(F)F)cc1]

(1R)—N-(4-(1,1,1,3,3,3-Hexafluoro-2-hydroxypropan-2-yl)phenyl)-5 (methylsulfonyl)isoindoline-1-carboxamide hydrochloride (125 g, 216.82 mmol) was dissolved in ethyl acetate (1250 mL). Acetic acid (24.82 mL, 433.64 mmol) and pyridine (73.8 mL, 867.29 mmol) was added. T3P in ethyl acetate (50% in EtOAc, 258 mL, 433.64 mmol) was added slowly over 10 min and the resultant mixture was stirred for 30 min. The reaction mixture was diluted with EtOAc (500 mL) and washed with an aqueous solution of citric acid (1M, 2×750 ml), aqueous $NaHCO_3$ (4%, 2×750 ml) and water (500 ml). The organic layer was evaporated and the resulting greyish foam crushed and dried under vacuum overnight. The crude solid (123 g) was dissolved in EtOAc (300 mL) and the material was filtered through a plug of silica gel (450 g) and eluted with EtOAc (1000 mL). The filtrate was evaporated, and the crude was dissolved in EtOAc (600 mL) and cooled to 10° C. n-Heptane (275 mL) was added slowly. Seed crystals were added after addition of half of the heptane. After addition, the temperature of the mixture was raised to 55° C. for 50 min. The cycling between 10 and 55° C. was then repeated two more times. The precipitate was filtered off using a P3 glas filter and the solid was washed with EtOAc/heptane (1:1 400 ml) and heptane (200 ml), and then dried in the funnel for 30 min, before being dried in the vacuum oven at 30° C. for 2 h. (1R)-2-Acetyl-N-(4-(1,1,1,3,3,3-hexafluoro-2-hydroxypropan-2-yl)phenyl)-5-(methylsulfonyl)isoindoline-1-carboxamide (62.6 g, 51.5%) was obtained as a solid (mp=228° C.).

Analytical chiral SFC 99.9% ee (analytical conditions: 1 mg of compound/ml in ACN; CelluCoat column, 150×4.6 mm, 3 m, 3.5 ml/min, 25% IPA in $CO_2$, 120 bar, 40° C., 240 nm). $[α]D_{589}+108°$ (c=1.0, $CH_3CN$, 20° C.).

HRMS: calculated for $(C_{21}H_{18}F_6N_2O_5S+H)^+$ 525.0919; found: (ESI $[M+H]^+$) 525.0917.

$^1$H NMR (400 MHz, DMSO-$d_6$, mixture of rotamers, 4*:1) δ 1.99, 2.15* (s, 3H), 3.22, 3.23* (s, 3H), 4.79 (d, 1H), 4.89 (d, 1H), 4.98-5.11* (m, 2H), 5.73*, 5.93 (s, 1H), 7.6-7.81 (m, 5H), 7.88-7.92 (m, 1H), 8.00*, 8.03 (s, 1H), 8.64*, 8.67 (s, 1H), 10.70*, 10.92 (s, 1H).

The mother liqour was evaporated and the solid was dissolved in ethyl acetate (200 mL) and heptane (90 mL) was slowly added. After about half of the heptane was added, seed crystal were added, and the mixture was heated to 55° C. for 64 h. The solid was filtered off and washed with EtOAc/Hept (1:1, 120 ml) and Heptane (2×120 ml), dried in the funnel for 15 min and then under vacuum at 40° C. for 72 h. A second batch of (1R)-2-acetyl-N-(4-(1,1,1,3,3,3-hexafluoro-2-hydroxypropan-2-yl)phenyl)-5-(methylsulfonyl)isoindoline-1-carboxamide (30.0 g, 24.7%) was thus obtained as a solid. 98.3% ee by analytical chiral SFC (analytical conditions: 1 mg of compound/ml in ACN; CelluCoat column, 150×4.6 mm, 3 m, 3.5 ml/min, 25% IPA 100 in $CO_2$, 120 bar, 40° C., 240 nm). $[\alpha]_D^{589}$+1030 (c=1.0, ACN).

The seed crystals were obtained from 440 mg crude (1R)-2-Acetyl-N-[4-(1,1,1,3,3,3-hexafluoro-2-hydroxypropan-2-yl)phenyl]-5-(methylsulfonyl)-2,3-dihydro-1H-isoindole-1-carboxamide, prepared as described above, by crystallization from EtOAc and heptane, and leaving the mixture stirring overnight. The solid was filtered off to give a colorless solid (377 mg, 85%) and washed with EtOAc/heptane (1:4, 1.3 ml) and heptane (1 ml).

Example 452: (1R)—N-[4-(1,1,1,3,3,3-Hexafluoro-2-hydroxypropan-2-yl)phenyl]-2-[(2-methyloxetan-2-yl)carbonyl]-5-(methylsulfonyl)-2,3-dihydro-1H-isoindole-1-carboxamide

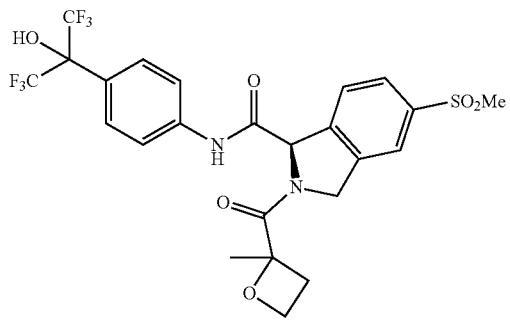 [SMILES: CC1(C(=O)N2Cc3cc(S(C)(=O)=O)ccc3[C@@H]2C(=O)Nc2ccc(C(O)(C(F)(F)F)C(F)(F)F)cc2)CCO1]

(R)—N-(4-(1,1,1,3,3,3-hexafluoro-2-hydroxypropan-2-yl)phenyl)-5-(methylsulfonyl)isoindoline-1-carboxamide, HCl (620 mg, 1.19 mmol) was suspended in DCM (10 mL) and to this 2-methyloxetane-2-carboxylic acid (278 mg, 2.39 mmol) and pyridine (0.242 mL, 2.99 mmol) was added followed by T3P (1.423 mL, 2.39 mmol, 50% in EtOAc). The reaction was stirred at RT for 1 hr. LCMS indicated complete conversion to product. The reaction was diluted with DCM and washed with 0.5M HCl. The layers were separated using a phase sep and concentrated in vacuo. The crude product (690 mg) was purified on a preparative SFC system equipped with a YMC SA (IA) column, 250×20, 5 μM, 18% IPA in $CO_2$ (160 bar), flow: 70 mL/min; injection volume was 0.30 mL of a 138 mg/mL ethanol solution.

Isomer 1 (peak 1): 160 mg, 23% yield; 99.9% ee by analytical chiral SFC (analytical conditions: YMC SA (IA) column, 150×4.6 mm, 3 μm, 3.5 ml/min, 25% IPA in $CO_2$, 120 bar, 40° C.). $[\alpha]_D^{589}$+92° (c=0.6, $CH_3CN$).

HRMS: calculated for $(C_{24}H_{22}F_6N_2O_6S+H)^+$ 581.1181; found (ESI $[M+H]^+$) 581.1182.

$^1$H NMR (500 MHz, DMSO-$d_6$, 1:1 ratio of rotamers) δ 1.51 (s, 1.5H), 1.63 (s, 1.5H), 2.51-2.7 (m, 1H), 2.77-2.88 (m, 0.5H), 2.87-2.97 (m, 0.5H), 3.17 (s, 1.5H), 3.20 (s, 1.5H), 4.34-4.56 (m, 2H), 4.89 (d, 0.5H), 4.99 (d, 1H), 5.24 (d, 0.5H), 5.85 (s, 0.5H), 6.49 (s, 0.5H), 7.63 (dd, 2H), 7.69-7.78 (m, 2.5H), 7.81 (d, 0.5H), 7.90 (d, 1H), 7.99 (s, 0.5H), 8.03 (s, 0.5H), 8.66 (s, 1H), 10.80 (s, 0.5H), 10.86 (s, 0.5H).

Isomer 2 (peak 2): 172 mg, 25% yield; 98.5% ee by analytical chiral SFC (analytical conditions: YMC SA (IA) column, 150×4.6 mm, 3 m, 3.5 ml/min, 25% IPA in $CO_2$, 120 bar, 40° C.). $[\alpha]_D^{589}$+94° (c=0.6, $CH_3CN$).

HRMS: calculated for $(C_{24}H_{22}F_6N_2O_6S+H)^+$ 581.1181; found (ESI [M+H]+) 581.1159.

$^1$H NMR (500 MHz, DMSO-$d_6$, 1:1 ratio of rotamers) δ 1.61 (s, 1.5H), 1.64 (s, 1.5H), 2.51-2.64 (m, 1H), 2.81-2.88 (m, 0.5H), 2.97-3.03 (m, 0.5H), 3.19 (s, 1.5H), 3.2 (s, 1.5H), 4.04-4.12 (m, 0.5H), 4.25-4.31 (m, 0.5H), 4.33-4.4 (m, 0.5H), 4.46-4.52 (m, 0.5H), 4.87 (d, 0.5H), 4.96 (s, 0.5H), 5.02 (d, 0.5H), 5.33 (d, 0.5H), 5.84 (s, 0.5H), 5.95 (s, 0.5H), 7.61 (dd, 2H), 7.73 (dd, 2.5H), Example 453: $N^1$-[4-(1,1,1,3,3,3-Hexafluoro-2-hydroxypropan-2-yl)phenyl]-$N^2$-methyl-5-(methylsulfonyl)-1,3-dihydro-2H-isoindole-1,2-dicarboxamide

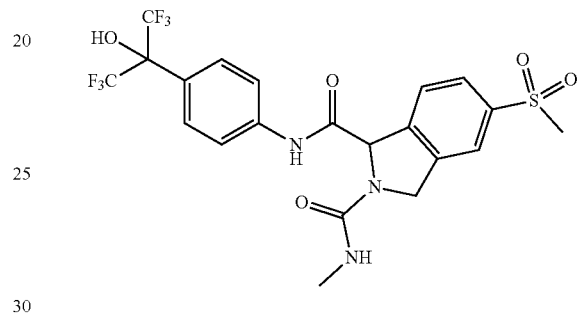

Methyl isocyanate (21.99 mg, 0.39 mmol) was added to a mixture of N-(4-(1,1,1,3,3,3-hexafluoro-2-hydroxypropan-2-yl)phenyl)-5-(methylsulfonyl)isoindoline-1-carboxamide, HCl (100 mg, 0.19 mmol) and triethylamine (0.081 mL, 0.58 mmol) in DCM (1 mL)/THF (1 mL). The reaction was stirred at room temperature for 15 min. The reaction mixture was diluted with EtOAc and washed with saturated brine. The layers were separated and the organic layer was dried using a phase separator cartridge. The solvent was removed in vacuo and the residue triturated with DCM. The solid obtained was collected by filtration and washed with DCM before being dried under vacuum. The title compound (84 mg, 81%) was obtained as a colorless solid.

HRMS: calculated for $(C_{21}H_{19}F_6N_3O_5S+H)^+$ 540.1028; found: (ESI $[M+H]^+$) 540.1050.

$^1$H NMR (500 MHz, DMSO $d_6$) δ 2.64 (d, 3H), 3.22 (s, 3H), 4.75 (d, 1H), 4.82 (dd, 1H), 5.66 (d, 1H), 6.59 (q, 1H), 7.61 (d, 2H), 7.68 (d, 1H), 7.73 (d, 2H), 7.88 (dd, 1H), 7.96 (s, 1H), 8.62 (s, 1H), 10.60 (s, 1H).

Examples 454-456

Examples 454-456 (Table 4C) were prepared using a similar procedures to those described in the preceding examples.

Example 454: $N^2$-Ethyl-$N^1$-[4-(1,1,1,3,3,3-hexafluoro-2-hydroxypropan-2-yl)phenyl]-5-(methylsulfonyl)-1,3-dihydro-2H-isoindole-1,2-dicarboxamide Example 455: $N^1$-[4-(1,1,1,3,3,3-Hexafluoro-2-hydroxypropan-2-yl)phenyl]-5-(methylsulfonyl)-1,3-dihydro-2H-isoindole-1,2-dicarboxamide Example 456: $N^2$—Cyclopropyl-$N^1$-[4-(1,1,1,3,3,3-hexafluoro-2-hydroxypropan-2-yl)phenyl]-5-(methylsulfonyl)-1,3-dihydro-2H-isoindole-1,2-dicarboxamide

TABLE 4C

| Example No. | Structure | NMR + MS |
|---|---|---|
| 454 | (structure: 4-(1,1,1,3,3,3-hexafluoro-2-hydroxypropan-2-yl)phenyl carboxamide isoindoline with 5-methylsulfonyl and N-ethyl urea) | HRMS: calculated for (C$_{22}$H$_{21}$F$_6$N$_3$O$_5$S + H)$^+$ 554.1184; found (ESI [M + H]$^+$) 554.1165. $^1$H NMR (600 MHz, DMSO d$_6$) δ 1.06 (t, 3H), 3.05-3.17 (m, 2H), 3.22 (s, 3H), 4.75 (d, 1H), 4.82 (dd, 1H), 5.66 (d, 1H), 6.63 (t, 1H), 7.61 (d, 2H), 7.68 (d, 1H), 7.72 (d, 2H), 7.88 (d, 1H), 7.95 (s, 1H), 8.66 (s, 1H), 10.62 (s, 1H). |
| 455 | (structure: same scaffold with primary urea NH$_2$) | HRMS: calculated for (C$_{20}$H$_{17}$F$_6$N$_3$O$_5$S + H)$^+$ 526.0871; found (ESI [M + H]$^+$) 526.0860. $^1$H NMR (500 MHz, DMSO-d$_6$) δ 3.22 (s, 3H), 4.77 (d, 1H), 4.84 (dd, 1H), 5.64 (d, 1H), 6.23 (s, 2H), 7.61 (d, 2H), 7.68 (d, 1H), 7.73 (d, 2H), 7.87 (d, 1H), 7.94 (s, 1H), 8.62 (s, 1H), 10.59 (s, 1H). |
| 456 | (structure: same scaffold with N-cyclopropyl urea) | HRMS: calculated for (C$_{23}$H$_{21}$F$_6$N$_3$O$_5$S + H)$^+$ 566.1184; found (ESI [M + H]$^+$) 566.1182. $^1$H NMR (600 MHz, DMSO d6) δ 0.39-0.52 (m, 2H), 0.54-0.63 (m, 2H), 2.55-2.58 (m, 1H), 3.21 (s, 3H), 4.71 (d, 1H), 4.79 (dd, 1H), 5.66 (d, 1H), 6.77 (d, 1H), 7.62 (d, 2H), 7.67 (d, 1H), 7.72 (d, 2H), 7.87 (d, 1H), 7.92 (s, 1H), 8.67 (s, 1H), 10.62 (s, 1H). |

Example 500: 2-Acetyl-5-(cyclopropylsulfamoyl)-N-[4-(1,1,1,3,3,3-hexafluoro-2-hydroxypropan-2-yl)phenyl]-2,3-dihydro-1H-isoindole-1-carboxamide

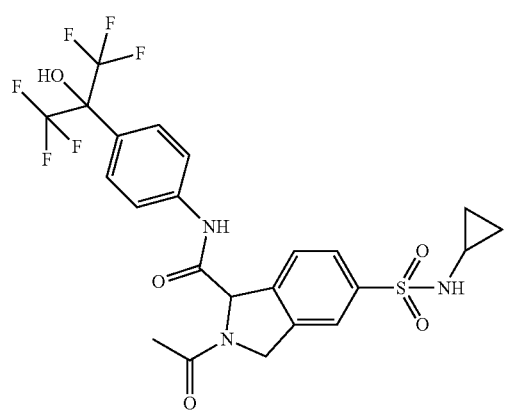 [SMILES: CC(=O)N1Cc2cc(S(=O)(=O)NC3CC3)ccc2C1C(=O)Nc1ccc(C(O)(C(F)(F)F)C(F)(F)F)cc1]

DIPEA (0.162 mL, 0.92 mmol) was added to 2-acetyl-5-(cyclopropylsulfamoyl)-2,3-dihydro-1H-isoindole-1-carboxylic acid (100 mg, 0.31 mmol), 2-(4-aminophenyl)-1,1,1,3,3,3-hexafluoropropan-2-ol (88 mg, 0.34 mmol) and HATU (129 mg, 0.34 mmol) in DCM (5 mL) under nitrogen. The resulting solution was stirred at room temperature for 1 hour. The reaction mixture was quenched with saturated NH$_4$Cl (20 mL), extracted with DCM (3×20 mL), the organic layer was dried over Na$_2$SO$_4$, filtered and evaporated to afford dark solid. The crude product was purified by flash silica chromatography, elution gradient 0 to 100% EtOAc in petroleum ether. Pure fractions were evaporated to dryness to afford 2-acetyl-5-(cyclopropylsulfamoyl)-N-[4-(1,1,1,3,3,3-hexafluoro-2-hydroxypropan-2-yl)phenyl]-2,3-dihydro-1H-isoindole-1-carboxamide (40.0 mg, 22.94%) as a colorless solid. LC/MS: m/z=566 [M+H]$^+$.

HRMS: calculated for (C$_{23}$H$_{21}$F$_6$N$_3$O$_5$S+H)$^+$ 566.1184; found (ESI [M+H]$^+$) 566.1185.

$^1$H NMR (400 MHz, DMSO-d$_6$, mixture of rotamers, 4.5*:1) δ 0.36-0.54 (m, 4H), 1.99, 2.15* (s, 3H), 2.08-2.10 (m, 1H), 4.76-4.93, 5.00-5.09* (m, 2H), 5.71*, 5.91 (s, 1H) 7.61-7.70 (m, 3H), 7.71-7.82 (m, 3H), 7.84-7.92 (m, 1H), 8.00, 8.02* (d, 1H), 8.67*, 8.69 (s, 1H), 10.71*, 10.94 (s, 1H).

Example 600: 5-(Cyclopropylsulfonyl)-N-[4-(1,1,1,3,3,3-hexafluoro-2-hydroxypropan-2-yl)phenyl]-2,3-dihydro-1H-isoindole-1-carboxamide

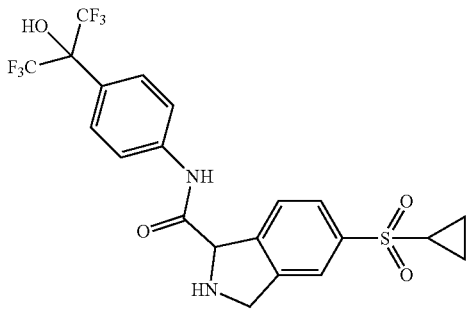 [SMILES: O=C(Nc1ccc(C(O)(C(F)(F)F)C(F)(F)F)cc1)C1NCc2cc(S(=O)(=O)C3CC3)ccc21]

HCl (gas) was bubbled into a solution of tert-butyl 5-(cyclopropylsulfonyl)-1-((4-(1,1,1,3,3,3-hexafluoro-2-hydroxypropan-2-yl)phenyl)carbamoyl)isoindoline-2-carboxylate (1.3 g, 2.14 mmol) in DCM (20 mL) at room temperature and the resulting mixture was stirred at room temperature for 3 hours. The reaction mixture was basified with saturated Na$_2$CO$_3$. The reaction mixture was extracted with DCM (3×25 mL), the organic layer was dried over Na$_2$SO$_4$, filtered and evaporated to afford yellow oil. The crude product was purified by flash C18-flash chromatography, elution gradient 0 to 30% MeCN in water. Pure fractions were evaporated to dryness to afford 5-(cyclopropylsulfonyl)-N-(4-(1,1,1,3,3,3-hexafluoro-2-hydroxypropan-2-yl)phenyl)isoindoline-1-carboxamide (0.750 g, 69.1%) as a pale yellow solid.

HRMS: calculated for (C$_{21}$H$_{18}$F$_6$N$_2$O$_4$S+H)$^+$ 509.0970; found (ESI [M+H]$^+$) 509.0957.

$^1$H NMR (300 MHz, DMSO-d$_6$) δ 0.98-1.2 (m, 4H), 2.76-2.95 (m, 1H), 3.87-4.11 (m, 1H), 4.24-4.53 (m, 2H), 5.10 (s, 1H), 7.59-7.66 (m, 2H), 7.7-7.76 (m, 1H), 7.77-7.88 (m, 4H), 8.65 (s, 1H), 10.35 (s, 1H).

Example 601: 2-Acetyl-5-(cyclopropylsulfonyl)-N-[4-(1,1,1,3,3,3-hexafluoro-2-hydroxypropan-2-yl)phenyl]-2,3-dihydro-1H-isoindole-1-carboxamide

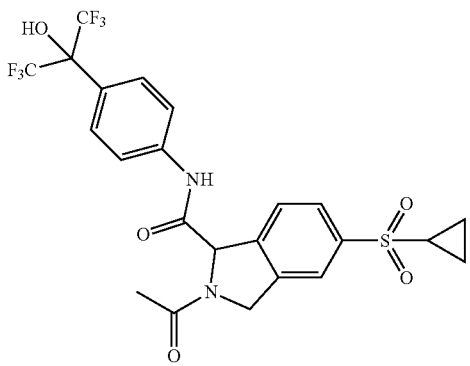 [SMILES: CC(=O)N1Cc2cc(S(=O)(=O)C3CC3)ccc2C1C(=O)Nc1ccc(C(O)(C(F)(F)F)C(F)(F)F)cc1]

5-(Cyclopropylsulfonyl)-N-(4-(1,1,1,3,3,3-hexafluoro-2-hydroxypropan-2-yl)phenyl)isoindoline-1-carboxamide (50 mg, 0.10 mmol) was added to AcOH (6.2 μl, 0.11 mmol), HATU (41.1 mg, 0.11 mmol) and DIPEA (0.052 mL, 0.30 mmol) in DCM (2 mL) under nitrogen. The resulting solution was stirred at room temperature for 1 hour. The reaction mixture was quenched with saturated NH$_4$Cl (10 mL), extracted with DCM (3×10 mL), the organic layer was dried over Na$_2$SO$_4$, filtered and evaporated to afford yellow oil. The crude product was purified by flash silica chromatography, elution gradient 0 to 70% EtOAc in petroleum ether. Pure fractions were evaporated to dryness to afford the title compound (50 mg, 78%) as a white solid. LC/MS: m/z=551 [M+H]$^+$. HRMS: calculated for (C$_{23}$H$_{20}$F$_6$N$_2$O$_5$S+H)$^+$ 551.1075; found (ESI [M+H]$^+$) 551.1071.

$^1$H NMR (300 MHz, DMSO-d$_6$, mixture of rotamers, 4.5*:1) 0.97-1.27 (m, 4H), 1.98, 2.14* (s, 3H), 2.68-2.91 (m, 1H), 4.73-5.11 (m, 2H), 5.72*, 5.92 (s, 1H), 7.58-7.84 (m, 5H), 7.84-7.92 (m, 1H), 7.94-8.03 (m, 1H), 8.66, 8.68 (s, 1H), 10.71*, 10.94 (s, 1H).

Example 602: Methyl 5-(cyclopropylsulfonyl)-1-{[4-(1,1,1,3,3,3-hexafluoro-2-hydroxypropan-2-yl)phenyl]carbamoyl}-1,3-dihydro-2H-isoindole-2-carboxylate

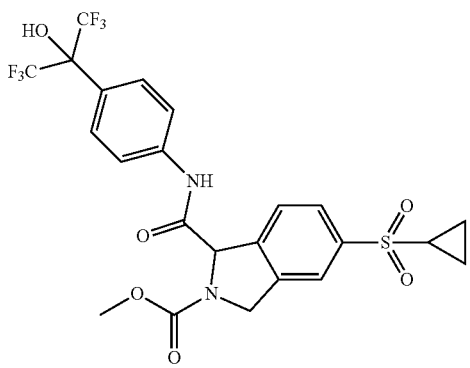 [SMILES: COC(=O)N1Cc2cc(S(=O)(=O)C3CC3)ccc2C1C(=O)Nc1ccc(C(O)(C(F)(F)F)C(F)(F)F)cc1]

Methyl carbonochloridate (22.30 mg, 0.24 mmol) was added dropwise to 5-(cyclopropylsulfonyl)-N-(4-(1,1,1,3,3,3-hexafluoro-2-hydroxypropan-2-yl)phenyl)isoindoline-1-carboxamide (60 mg, 0.12 mmol) in DCM (5 mL) cooled to 0° C. under nitrogen. The resulting mixture was stirred at room temperature for 2 hours. The reaction mixture was quenched with water (20 mL), extracted with DCM (3×25 mL), the organic layer was dried over Na$_2$SO$_4$, filtered and evaporated to afford yellow solid. The crude product was purified by flash C18-flash chromatography, elution gradient 10 to 80% MeCN in water. Pure fractions were evaporated to dryness to afford the title compound (40 mg, 59.8%) as a solid. LC/MS: m/z=567 [M+H]$^+$.

HRMS: calculated for (C$_{23}$H$_{20}$F$_6$N$_2$O$_6$S+H)$^+$ 567.1024; found (ESI [M+H]$^+$) 567.1041.

$^1$H NMR (400 MHz, DMSO-d$_6$, mixture of rotamers, 1.3*:1) δ 0.98-1.21 (m, 4H), 2.81-2.91 (m, 1H), 3.64, 3.71* (s, 3H), 4.79-4.91 (m, 2H), 5.68*, 5.70 (s, 1H), 7.61-7.68 (m, 2H), 7.69-7.78 (m, 3H), 7.84-7.9 (m, 1H), 7.96-8.02 (m, 1H), 8.68 (s, 1H), 10.79*, 10.81 (s, 1H).

Examples 603-609

Examples 603-609 (Table 6) were prepared using similar procedures to those described in the preceding examples. Example 610 was prepared using a similar procedure to those described for Examples 314 or 453.

Example 603: 5-(Cyclopropylsulfonyl)-N-[4-(1,1,1,3,3,3-hexafluoro-2-hydroxypropan-2-yl)phenyl]-2-[(1-methoxycyclopropyl)carbonyl]-2,3-dihydro-1H-isoindole-1-carboxamide Example 604: 5-(Cyclopropylsulfonyl)-2-formyl-N-[4-(1,1,1,3,3,3-hexafluoro-2-hydroxypropan-2-yl)phenyl]-2,3-dihydro-1H-isoindole-1-carboxamide Example 605: 5-(Cyclopropylsulfonyl)-N-[4-(1,1,1,3,3,3-hexafluoro-2-hydroxypropan-2-yl)phenyl]-2-(hydroxyacetyl)-2,3-dihydro-1H-isoindole-1-carboxamide Example 606: 5-(Cyclopropylsulfonyl)-N-[4-(1,1,1,3,3,3-hexafluoro-2-hydroxypropan-2-yl)phenyl]-2-(methoxyacetyl)-2,3-dihydro-1H-isoindole-1-carboxamide Example 607: 2-[(1-Cyanocyclopropyl)carbonyl]-5-(cyclopropylsulfonyl)-N-[4-(1,1,1,3,3,3-hexafluoro-2-hydroxypropan-2-yl)phenyl]-2,3-dihydro-1H-isoindole-1-carboxamide Example 608: 5-(Cyclopropylsulfonyl)-N-[4-(1,1,1,3,3,3-hexafluoro-2-hydroxypropan-2-yl)phenyl]-2-[(2S)-tetrahydrofuran-2-ylcarbonyl]-2,3-dihydro-1H-isoindole-1-carboxamide Example 609: 5-(Cyclopropylsulfonyl)-N-[4-(1,1,1,3,3,3-hexafluoro-2-hydroxypropan-2-yl)phenyl]-2-[(2R)-tetrahydrofuran-2-ylcarbonyl]-2,3-dihydro-1H-isoindole-1-carboxamide Example 610: 5-(Cyclopropylsulfonyl)-N'-[4-(1,1,1,3,3,3-hexafluoro-2-hydroxypropan-2-yl)phenyl]-$N^2$-methyl-1,3-dihydro-2H-isoindole-1,2-dicarboxamide

TABLE 6

| Example No. | Structure | NMR + MS |
|---|---|---|
| 603 | 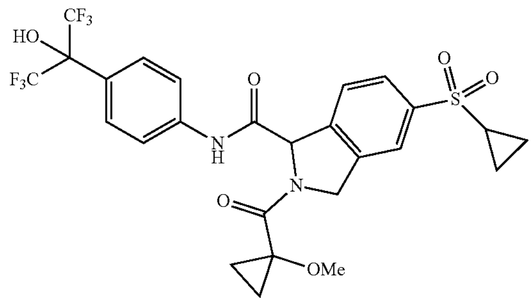 [SMILES: COC1(C(=O)N2Cc3cc(S(=O)(=O)C4CC4)ccc3C2C(=O)Nc2ccc(C(O)(C(F)(F)F)C(F)(F)F)cc2)CC1] | HRMS: calculated for ($C_{26}H_{24}F_6N_2O_6S$ + H)$^+$ 607.1337; found (ESI [M + H]$^+$) 607.1351. $^1$H NMR (400 MHz, DMSO-$d_6$, mixture of rotamers, 2.3*:1) δ 0.84-1.21 (m, 8H), 2.80-2.90 (m, 1H), 3.19, 3.36* (s, 3H), 4.85-5.04, 5.19-5.31* (m, 2H), 5.90*, 6.22 (s, 1H), 7.60-7.69 (m, 2H), 7.70-7.84 (m, 3H), 7.86-7.91 (m, 1H), 8.00-8.06 (m, 1H), 8.66, 8.68* (s, 1H), 10.83, 10.90* (s, 1H). |
| 604 | 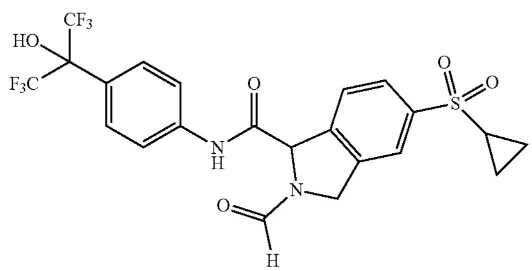 [SMILES: O=CN1Cc2cc(S(=O)(=O)C3CC3)ccc2C1C(=O)Nc1ccc(C(O)(C(F)(F)F)C(F)(F)F)cc1] | HRMS: calculated for ($C_{22}H_{18}F_6N_2O_5S$ + H)$^+$ 537.0919; found (ESI [M + H]$^+$) 537.0928. $^1$H NMR (400 MHz, DMSO-$d_6$, mixture of rotamers, 1.8*:1) δ 0.98-1.32 (m, 4H), 2.86 (s, 1H), 4.74-4.94, 5.04-5.19* (m, 2H), 5.78*, 5.99 (s, 1H), 7.61-7.69 (m, 2H), 7.71-7.93 (m, 4H), 7.98-8.06 (m, 1H), 8.40, 8.49* (s, 1H), 8.66*, 8.67 (s, 1H), 10.77*, 10.87 (s, 1H). |
| 605 | 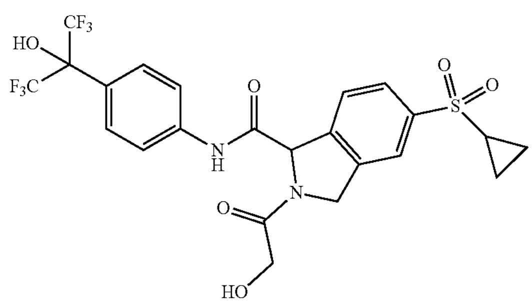 [SMILES: O=C(Nc1ccc(C(O)(C(F)(F)F)C(F)(F)F)cc1)C1c2ccc(S(=O)(=O)C3CC3)cc2CN1C(=O)CO] | HRMS: calculated for ($C_{23}H_{20}F_6N_2O_6S$ + H)$^+$ 567.1024; found (ESI [M + H]$^+$) 567.1004. $^1$H NMR (300 MHz, DMSO-$d_6$, mixture of rotamers, 5*:1) δ 0.98-1.21 (m, 4H), 2.81-2.93 (m, 1H), 3.87-4.34 (m, 2H), 4.81-5.25 (m, 3H), 5.80*, 6.01 (s, 1H), 7.58-7.84 (m, 5H), 7.89 (d, J = 9.0 Hz, 1H), 8.00 (d, J = 12.1 Hz, 1H), 8.67*, 8.69 (s, 1H), 10.77*, 10.95 (s, 1H). |
| 606 | 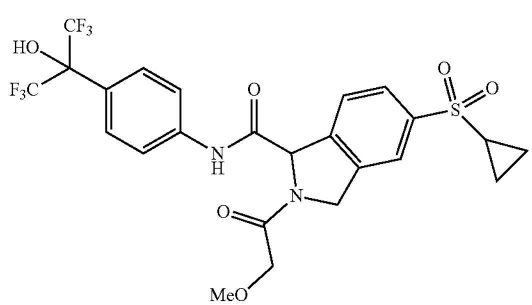 [SMILES: COCC(=O)N1Cc2cc(S(=O)(=O)C3CC3)ccc2C1C(=O)Nc1ccc(C(O)(C(F)(F)F)C(F)(F)F)cc1] | HRMS: calculated for ($C_{24}H_{22}F_6N_2O_6S$ + H)$^+$ 581.1181; found (ESI [M + H]$^+$) 581.1175. $^1$H NMR (300 MHz, DMSO-$d_6$, mixture of rotamers, 5*:1) δ 0.97-1.29 (m, 5H), 2.80-2.92 (m, 1H), 3.27, 3.36* (s, 3H), 3.93-4.13, 4.16-4.34* (m, 2H), 4.81-5.07 (m, 2H), 5.80*, 5.99 (s, 1H), 7.64 (d, J = 8.3 Hz, 2H), 7.7-7.81 (m, 3H), 7.88 (d, J = 8.0 Hz, 1H), 7.97-8.03 (m, 1H), 8.67 (s, 1H), 10.78*, 10.88 (s, 1H). |

TABLE 6-continued

| Example No. | Structure | NMR + MS |
|---|---|---|
| 607 | 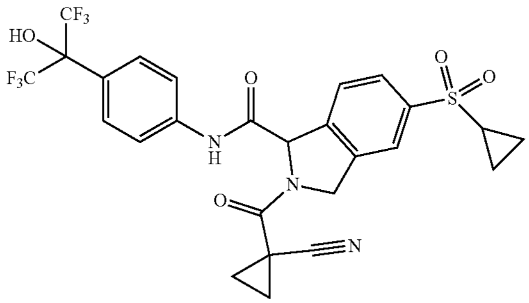 [SMILES: N#CC1(C(=O)N2Cc3cc(S(=O)(=O)C4CC4)ccc3C2C(=O)Nc2ccc(C(O)(C(F)(F)F)C(F)(F)F)cc2)CC1] | HRMS: calculated for (C$_{26}$H$_{21}$F$_6$N$_3$O$_5$S + H)$^+$ 602.1184; found (ESI [M + H]$^+$) 602.1210. $^1$H NMR (300 MHz, DMSO-d$_6$, mixture of rotamers, 6*:1) δ 0.98-1.17 (m, 4H), 1.52-1.65 (m, 2H), 1.65-1.78 (m, 2H), 2.80-2.92 (m, 1H), 4.86-5.00, 5.32-5.43* (m, 2H), 5.85*, 6.44 (s, 1H), 7.60-7.69 (m, 2H), 7.69-7.81 (m, 3H), 7.86-7.99 (m, 1H), 8.00-8.14 (m, 1H), 8.67 (s, 1H), 10.89*, 11.22 (s, 1H). |
| 608 | 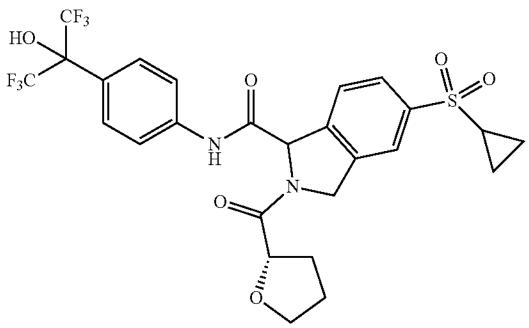 [SMILES: O=C(Nc1ccc(C(O)(C(F)(F)F)C(F)(F)F)cc1)C1c2ccc(S(=O)(=O)C3CC3)cc2CN1C(=O)[C@@H]1CCCO1] | HRMS: calculated for (C$_{26}$H$_{24}$F$_6$N$_2$O$_6$S + H)$^+$ 607.1337; found (ESI [M + H]$^+$) 607.1342. 1H NMR (300 MHz, DMSO-d$_6$, mixture of 4 isomers, only 2 main isomers reported) δ 0.97-1.27 (m, 4H), 1.72-2.00 (m, 2H), 2.00-2.27 (m, 2H), 2.80-2.91 (m, 1H), 3.75-3.91 (m, 2H), 4.69-4.78 (m, 1H), 5.00-5.24 (m, 2H), 5.77*, 5.79 (s, 1H), 7.63 (d, J = 8.7 Hz, 2H), 7.68-7.77 (m, 3H), 7.84-7.91 (m, 1H), 7.95-8.01 (m, 1H), 8.67 (s, 1H), 10.78*, 10.80 (s, 1H). |
| 609 | 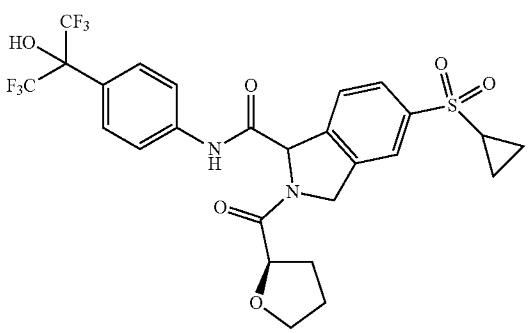 [SMILES: O=C(Nc1ccc(C(O)(C(F)(F)F)C(F)(F)F)cc1)C1c2ccc(S(=O)(=O)C3CC3)cc2CN1C(=O)[C@H]1CCCO1] | HRMS: calculated for (C$_{26}$H$_{24}$F$_6$N$_2$O$_6$S + H)$^+$ 607.1337; found (ESI [M + H]$^+$) 607.1320. 1H NMR (300 MHz, DMSO-d$_6$, mixture of 4 isomers, only 2 main isomers reported) δ 1.00-1.16 (m, 4H), 1.81-1.93 (m, 2H), 2.00-2.27 (m, 2H), 2.79-2.9 (m, 1H), 3.73-3.92 (m, 2H), 4.68-4.79 (m, 1H), 5.00-5.13 (m, 1H), 5.13-5.24 (m, 1H), 5.77*, 5.78 (s, 1H), 7.63 (d, J = 8.6 Hz, 2H), 7.68-7.77 (m, 3H), 7.84-7.90 (m, 1H), 7.95-8.01 (m, 1H), 8.63-8.72 (m, 1H), 10.78*, 10.80 (s, 1H). |
| 610 | 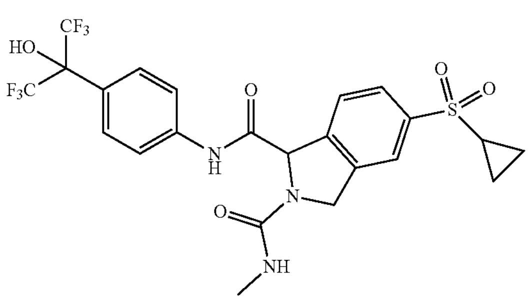 [SMILES: CNC(=O)N1Cc2cc(S(=O)(=O)C3CC3)ccc2C1C(=O)Nc1ccc(C(O)(C(F)(F)F)C(F)(F)F)cc1] | HRMS: calculated for (C$_{23}$H$_{21}$F$_6$N$_3$O$_5$S + H)$^+$ 566.1184; found (ESI [M + H]$^+$) 566.1199. $^1$H NMR (300 MHz, DMSO-d$_6$) δ 0.98-1.08 (m, 2H), 2.65 (d, 3H), 2.81-2.94 (m, 1H), 4.75 (d, 1H), 4.83 (dd, 1H), 5.67 (d, 1H), 6.60 (q, 1H), 7.62 (d, 2H), 7.68 (d, 1H), 7.75 (d, 2H), 7.85 (dd, 1H), 7.94 (s, 1H), 8.65 (s, 1H), 10.63 (s, 1H). |

Example 700: N-[4-(1,1,1,3,3,3-Hexafluoro-2-hydroxypropan-2-yl)phenyl]-5-[(2-methoxyethyl)sulfonyl]-2,3-dihydro-1H-isoindole-1-carboxamide

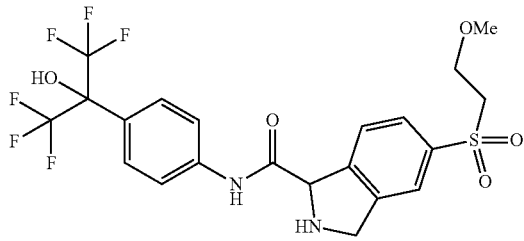 [SMILES: COCCS(=O)(=O)c1ccc2c(c1)CNC2C(=O)Nc1ccc(C(O)(C(F)(F)F)C(F)(F)F)cc1]

HCl (gas) (0.171 mL, 5.63 mmol) was passsed through a solution of tert-butyl 1-((4-(1,1,1,3,3,3-hexafluoro-2-hydroxypropan-2-yl)phenyl)carbamoyl)-5-((2-methoxyethyl)sulfonyl)isoindoline-2-carboxylate (3.53 g, 5.63 mmol) in DCM (35 mL). The resulting mixture was stirred at room temperature for 3 hours. The reaction mixture was basified with saturated NaHCO$_3$. The reaction mixture was extracted with DCM (3×50 mL), the organic layer was dried over Na$_2$SO$_4$, filtered and evaporated to afford brown oil. The crude product was purified by flash C18-flash chromatography, elution gradient 0 to 50% MeCN in water. Pure fractions were evaporated to dryness to afford the title compound (2.110 g, 71.1%) as a solid. LC/MS: m/z=527 [M+H]$^+$.

HRMS: calculated for (C$_{21}$H$_{20}$F$_6$N$_2$O$_5$S+H)$^+$527.1075; found (ESI [M+H]$^+$) 527.1071.

$^1$H NMR (300 MHz, DMSO-d$_6$) δ 3.10 (s, 3H), 3.51-3.65 (m, 4H), 4.38 (s, 2H), 5.08 (s, 1H), 7.60 (d, 2H), 7.70 (d, 1H), 7.74-7.89 (m, 4H), 8.63 (s, 1H), 10.33 (s, 1H).

Example 701: 2-Formyl-N-[4-(1,1,1,3,3,3-hexafluoro-2-hydroxypropan-2-yl)phenyl]-5-[(2-methoxyethyl)sulfonyl]-2,3-dihydro-1H-isoindole-1-carboxamide

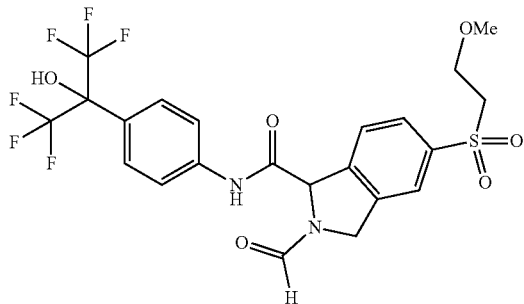 [SMILES: COCCS(=O)(=O)c1ccc2c(c1)CN(C=O)C2C(=O)Nc1ccc(C(O)(C(F)(F)F)C(F)(F)F)cc1]

DIPEA (0.080 mL, 0.46 mmol) was added to N-(4-(1,1,1,3,3,3-hexafluoro-2-hydroxypropan-2-yl)phenyl)-5-((2-methoxyethyl)sulfonyl)isoindoline-1-carboxamide (80 mg, 0.15 mmol), formic acid (13.99 mg, 0.30 mmol) and HATU (63.6 mg, 0.17 mmol) in DCM (10 mL) under nitrogen. The resulting solution was stirred at room temperature for 5 hours. The reaction mixture was quenched with saturated NH$_4$Cl (15 mL), extracted with DCM (3×20 mL), the organic layer was dried over Na$_2$SO$_4$, filtered and evaporated to afford yellow solid. The crude product was purified by flash C18-flash chromatography, elution gradient 0 to 50% MeCN in water. Pure fractions were evaporated to dryness to afford the title compound (67.0 mg, 80%) as a white solid. LC/MS: m/z=555 [M+H]$^+$. HRMS: calculated for (C$_{22}$H$_{20}$F$_6$N$_2$O$_6$S+H)$^+$555.1024; found (ESI [M+H]$^+$) 555.117.

$^1$H NMR (300 MHz, DMSO-d$_6$, mixture of rotamers, 1.7*:1) δ 3.11 (s, 3H), 3.63 (s, 4H), 4.72-4.94, 5.03-5.21* (m, 2H), 5.78*, 6.00 (s, 1H), 7.59-7.94 (m, 6H), 8.02 (s, 1H), 8.40, 8.50* (s, 1H), 8.68 (s, 1H), 10.79*, 10.89 (s, 1H).

Example 702: 2-Acetyl-N-[4-(1,1,1,3,3,3-hexafluoro-2-hydroxypropan-2-yl)phenyl]-5-[(2-methoxyethyl)sulfonyl]-2,3-dihydro-1H-isoindole-1-carboxamide

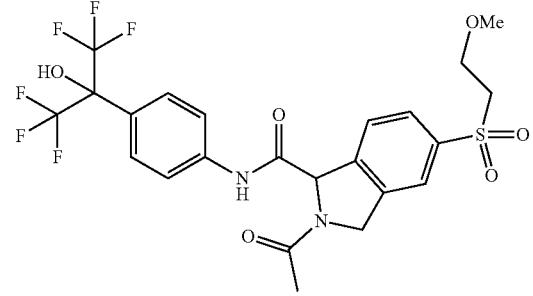 [SMILES: COCCS(=O)(=O)c1ccc2c(c1)CN(C(C)=O)C2C(=O)Nc1ccc(C(O)(C(F)(F)F)C(F)(F)F)cc1]

Following the procedure in example 701 but using acetic acid instead of formic acid, a brown oil was obtained after work-up. The crude product was purified by flash C18-flash chromatography, elution gradient 0 to 30% MeCN in water. Pure fractions were evaporated to dryness to afford the title compound (20 mg, 6.67%) as a white solid. LC/MS: m/z=569 [M+H]$^+$.

HRMS: calculated for (C$_{23}$H$_{22}$F$_6$N$_2$O$_6$S+H)$^+$569.1181; found (ESI [M+H]$^+$) 569.1197.

$^1$H NMR (300 MHz, DMSO-d$_6$, mixture of rotamers, 4.2*:1) δ 1.98, 2.14* (s, 3H), 3.06-3.11 (m, 3H), 3.60 (s, 4H), 4.72-5.08 (m, 2H), 5.72*, 5.95 (s, 1H), 7.57-7.80 (m, 5H), 7.82-7.88 (m, 1H), 7.93-8.00 (m, 1H), 8.66 (s, 1H), 10.73*, 11.01 (s, 1H).

Example 703: N-[4-(1,1,1,3,3,3-hexafluoro-2-hydroxypropan-2-yl)phenyl]-2-[(1-methoxycyclopropyl)carbonyl]-5-[(2-methoxyethyl)sulfonyl]-2,3-dihydro-1H-isoindole-1-carboxamide

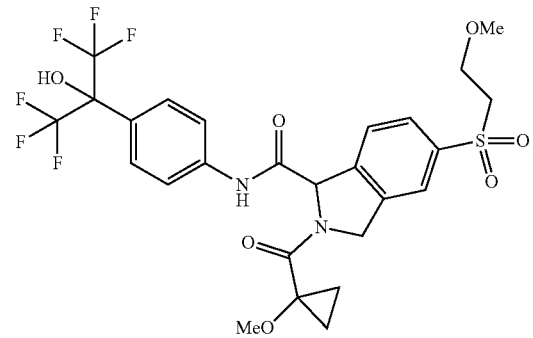 [SMILES: COCCS(=O)(=O)c1ccc2c(c1)CN(C(=O)C1(OC)CC1)C2C(=O)Nc1ccc(C(O)(C(F)(F)F)C(F)(F)F)cc1]

Following the procedure in example 701 but using 1-methoxycyclopropanecarboxylic acid instead of formic acid afforded a colorless solid as the crude product, which was purified by flash C18-flash chromatography, elution gradient 0 to 70% MeCN in water. Pure fractions were evaporated to dryness to afford N-(4-(1,1,1,3,3,3-hexafluoro-2-hydroxypropan-2-yl)phenyl)-2-(1-methoxycyclopropanecarbonyl)-5-((2-methoxyethyl)sulfonyl)isoindoline-1-carboxamide (50.8 mg, 86%) as a colorless solid.

HRMS: calculated for $(C_{26}H_{26}F_6N_2O_7S+H)^+$ 625.1443; found (ESI [M+H]$^+$) 625.1461.

$^1$H NMR (400 MHz, DMSO-d$_6$, mixture of rotamers, 2.2*:1) δ 0.83-1.27 (m, 4H), 3.11, 3.12* (s, 3H), 3.19, 3.36* (s, 3H), 3.55-3.66 (m, 4H), 4.86-5.04, 5.18-5.31* (m, 2H), 5.90*, 6.22 (s, 1H), 7.60-7.68 (m, 2H), 7.7-7.82 (m, 3H), 7.84-7.91 (m, 1H), 7.98-8.05 (m, 1H), 8.66, 8.68* (s, 1H), 10.82, 10.90* (s, 1H).

Examples 704-706 (Table 7) were prepared using similar procedures to those described in the preceding examples. Example 707 was prepared using a similar procedure to those described for Examples 314 or 453.

Example 704: Methyl 1-{[4-(1,1,1,3,3,3-hexafluoro-2-hydroxypropan-2-yl)phenyl]carbamoyl}-5-[(2-methoxyethyl)sulfonyl]-1,3-dihydro-2H-isoindole-2-carboxylate Example 705: N-[4-(1,1,1,3,3,3-Hexafluoro-2-hydroxypropan-2-yl)phenyl]-2-(hydroxyacetyl)-5-[(2-methoxyethyl)sulfonyl]-2,3-dihydro-1H-isoindole-1-carboxamide Example 706: N-[4-(1,1,1,3,3,3-Hexafluoro-2-hydroxypropan-2-yl)phenyl]-2-(methoxyacetyl)-5-[(2-methoxyethyl)sulfonyl]-2,3-dihydro-1H-isoindole-1-carboxamide Example 707: N'-[4-(1,1,1,3,3,3-Hexafluoro-2-hydroxypropan-2-yl)phenyl]-5-[(2-methoxyethyl) sulfonyl]-N$^2$-methyl-1,3-dihydro-2H-isoindole-1,2-dicarboxamide

TABLE 7

| Example No. | Structure | NMR + MS |
|---|---|---|
| 704 | *[structure]* | HRMS: calculated for $(C_{23}H_{22}F_6N_2O_7S + H)^+$ 585.1130; found (ESI [M + H]$^+$) 585.1130. $^1$H NMR (300 MHz, DMSO-d$_6$, mixture of rotamers, 1.4*:1) δ 3.09 (s, 3H), 3.56-3.73 (m, 7H), 4.80-4.91 (m, 2H), 5.68 (m, 1H), 7.56-7.77 (m, 5H), 7.86 (d, J = 8.1 Hz, 1H), 7.97 (d, J = 6.1 Hz, 1H), 8.67 (s, 1H), 10.77, 10.79* (s, 1H). |
| 705 | *[structure]* | HRMS: calculated for $(C_{23}H_{22}F_6N_2O_7S + H)^+$ 585.1130; found (ESI [M + H]$^+$) 585.1145. $^1$H NMR (300 MHz, DMSO-d$_6$, mixture of rotamers, 5*:1) δ 3.09 (s, 3H), 3.57-3.64 (m, 4H), 3.86-4.33 (m, 2H), 4.80-5.10 (m, 3H), 5.79*, 6.00 (s, 1H), 7.59-7.66 (m, 2H), 7.68-7.80 (m, 3H), 7.83-7.91 (m, 1H), 7.93-8.02 (s, 1H), 8.66*, 8.68 (s, 1H), 10.75*, 10.92 (s, 1H). |
| 706 | *[structure]* | HRMS: calculated for $(C_{24}H_{24}F_6N_2O_7S + H)^+$ 599.1287; found (ESI [M + H]$^+$) 599.1309. $^1$H NMR (300 MHz, DMSO-d$_6$, mixture of rotamers, 4*:1) δ 3.09 (s, 3H), 3.26, 3.36* (s, 3H), 3.61 (s, 4H), 3.93-4.12, 4.17-4.32* (m, 2H), 4.78-5.16 (m, 2H), 5.79*, 5.99 (s, 1H), 7.64 (d, J = 8.7 Hz, 2H), 7.68-7.81 (m, 3H), 7.87 (d, J = 8.1 Hz, 1H), 7.95-8.01 (m, 1H), 8.68 (s, 1H), 10.79* 10.89 (s, 1H). |

TABLE 7-continued

| Example No. | Structure | NMR + MS |
|---|---|---|
| 707 | 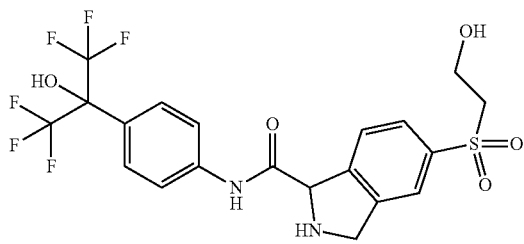 [SMILES: O=C(Nc1ccc(C(O)(C(F)(F)F)C(F)(F)F)cc1)C1NCc2cc(S(=O)(=O)CCO)ccc21] | HRMS: calculated for $(C_{23}H_{23}F_6N_3O_6S + H)^+$ 584.1290; found (ESI [M + H]$^+$) 584.1282. 1H NMR (300 MHz, DMSO-d$_6$) δ 2.65 (d, 3H), 3.11 (s, 3H), 3.63 (s, 4H), 4.75 (d, 1H), 4.84 (d, 1H), 5.67 (d, 1H), 6.62 (d, 1H), 7.63 (d, 2H), 7.68 (d, 1H), 7.75 (d, 2H), 7.85 (dd, 1H), 7.94 (s, 1H), 8.66 (s, 1H), 10.64 (s, 1H). |

Example 800: N-[4-(1,1,1,3,3,3-Hexafluoro-2-hydroxypropan-2-yl)phenyl]-5-[(2-hydroxyethyl)sulfonyl]-2,3-dihydro-1H-isoindole-1-carboxamide Example 801: 2-Acetyl-N-[4-(1,1,1,3,3,3-hexafluoro-2-hydroxypropan-2-yl)phenyl]-5-[(2-hydroxyethyl)sulfonyl]-2,3-dihydro-1H-isoindole-1-carboxamide

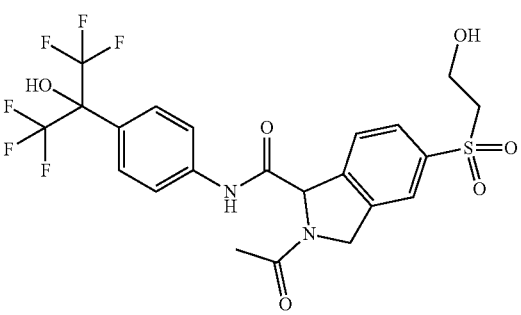 [SMILES: CC(=O)N1Cc2cc(S(=O)(=O)CCO)ccc2C1C(=O)Nc1ccc(C(O)(C(F)(F)F)C(F)(F)F)cc1]

Diethylamine (59.7 mg, 0.82 mmol) was added to (9H-fluoren-9-yl)methyl 1-((4-(1,1,1,3,3,3-hexafluoro-2-hydroxypropan-2-yl)phenyl)carbamoyl)-5-((2-hydroxyethyl)sulfonyl)isoindoline-2-carboxylate (60 mg, 0.08 mmol) in DCM (3 mL) at 25° C. over a period of 10 minutes under nitrogen. The resulting solution was stirred at 25° C. for 4 hours. The solvent was removed under reduced pressure. The crude product was purified by flash silica chromatography, elution gradient 50 to 70% EtOAc in petroleum ether. Pure fractions were evaporated to dryness to afford N-(4-(1,1,1,3,3,3-hexafluoro-2-hydroxypropan-2-yl)phenyl)-5-((2-hydroxyethyl)sulfonyl)isoindoline-1-carboxamide (25.0 mg, 59.7%) as a white solid. LC/MS: m/z=513 [M+H]$^+$.

HRMS: calculated for $(C_{20}H_{18}F_6N_2O_5S+H)^+$513.0919; found (ESI [M+H]$^+$) 513.0927.

$^1$H NMR (400 MHz, DMSO-d$_6$, mixture of rotamers, 4.5*:1, only major isomer reported) δ 3.43 (t, 2H), 3.67 (q, 2H), 3.94 (br.s, 1H), 4.33-4.46 (m, 2H), 4.86 (t, 1H), 5.09 (s, 1H), 7.57-7.65 (m, 2H), 7.68-7.74 (m, 1H), 7.76-7.87 (m, 4H), 8.64 (s, 1H), 10.34 (s, 1H).

Tribromoborane (485 mg, 1.93 mmol) was added dropwise to 2-acetyl-N-(4-(1,1,1,3,3,3-hexafluoro-2-hydroxypropan-2-yl)phenyl)-5-((2-methoxyethyl)sulfonyl)isoindoline-1-carboxamide (220 mg, 0.39 mmol) in DCM (20 mL) cooled to −40° C. over a period of 30 minutes under nitrogen. The resulting solution was stirred at 0° C. for 1 hour. The reaction mixture was quenched with saturated NaHCO$_3$ (25 mL), extracted with DCM (3×25 mL). The precipitate was collected by filtration, washed with DCM (20 mL) and dried under vacuum to afford 2-acetyl-N-(4-(1,1,1,3,3,3-hexafluoro-2-hydroxypropan-2-yl)phenyl)-5-((2-hydroxyethyl)sulfonyl)isoindoline-1-carboxamide (42.0 mg, 17.95%) as a white solid. LC/MS: m/z=555 [M+H]$^+$.

HRMS: calculated for $(C_{22}H_{20}F_6N_2O_6S+H)^+$555.1024; found (ESI [M+H]$^+$) 555.1019.

$^1$H NMR (300 MHz, DMSO-d$_6$, mixture of rotamers, 4.4*:1) δ 1.98, 2.14* (s, 3H), 3.45 (t, 2H), 3.67 (q, 2H), 4.78-4.91, 5.00-5.07* (m, 3H), 5.74* (s, 1H), 7.58-7.78 (m, 5H) 7.83-7.89 (m, 1H), 7.93-8.00 (m, 1H), 8.64*, 8.67 (s, 1H), 10.70*, 10.94 (s, 1H).

Example 802: N-[4-(1,1,1,3,3,3-Hexafluoro-2-hydroxypropan-2-yl)phenyl]-5-[(2-hydroxyethyl)sulfonyl]-2-[(1-methoxycyclopropyl)carbonyl]-2,3-dihydro-1H-isoindole-1-carboxamide

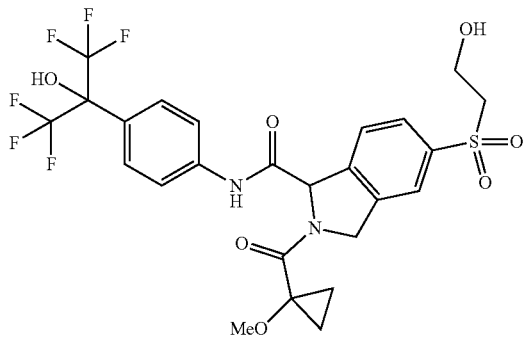 [SMILES: COC1(C(=O)N2Cc3cc(S(=O)(=O)CCO)ccc3C2C(=O)Nc2ccc(C(O)(C(F)(F)F)C(F)(F)F)cc2)CC1]

Step 1: 5-((2-((tert-Butyldimethylsilyl)oxy)ethyl)sulfonyl)-N-(4-(1,1,1,3,3,3-hexafluoro-2-hydroxypropan-2-yl)phenyl)-2-(1-methoxycyclopropanecarbonyl)isoindoline-1-carboxamide

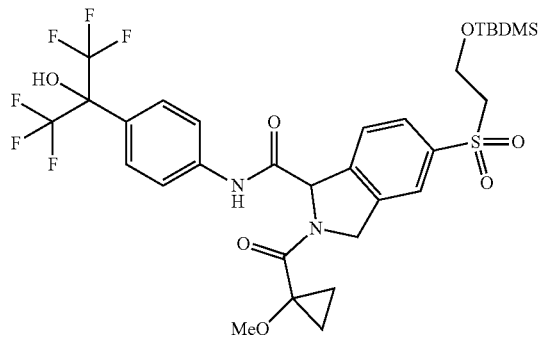 [SMILES: COC1(C(=O)N2Cc3cc(S(=O)(=O)CCO[Si](C)(C)C(C)(C)C)ccc3C2C(=O)Nc2ccc(C(O)(C(F)(F)F)C(F)(F)F)cc2)CC1]

DIPEA (0.084 ml, 0.48 mmol) was added to 5-((2-((tert-butyldimethylsilyl)oxy)ethyl)sulfonyl)-N-(4-(1,1,1,3,3,3-hexafluoro-2-hydroxypropan-2-yl)phenyl)isoindoline-1-carboxamide (100 mg, 0.16 mmol), 1-methoxycyclopropanecarboxylic acid (37.1 mg, 0.32 mmol) and HATU (66.7 mg, 0.18 mmol) in under nitrogen. The resulting solution was stirred at room temperature for 2 hours. The crude product was purified by flash silica chromatography, elution gradient 0 to 70% EtOAc in petroleum ether. Pure fractions were evaporated to dryness to afford the title compound (120 mg, 104%) as a colourless dry film.

LC/MS: m/z=725 [M+H]+.

Step 2: N-[4-(1,1,1,3,3,3-Hexafluoro-2-hydroxypropan-2-yl)phenyl]-5-[(2-hydroxyethyl)sulfonyl]-2-[(1-methoxycyclopropyl)carbonyl]-2,3-dihydro-1H-isoindole-1-carboxamide

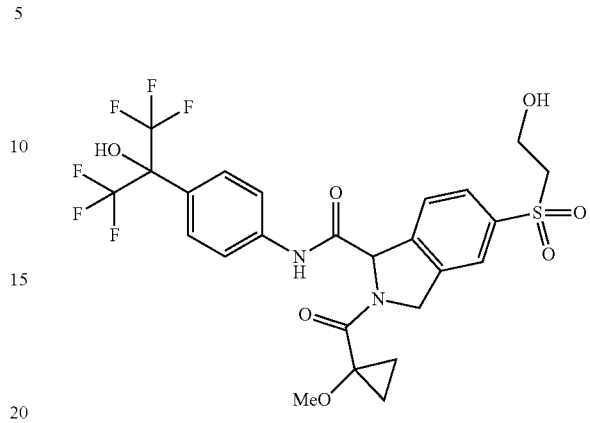

Triethylamine trihydrofluoride (0.270 mL, 1.66 mmol) was added to 5-((2-((tert-butyldimethylsilyl)oxy)ethyl)sulfonyl)-N-(4-(1,1,1,3,3,3-hexafluoro-2-hydroxypropan-2-yl)phenyl)-2-(1-methoxycyclopropanecarbonyl)isoindoline-1-carboxamide (120 mg, 0.17 mmol) in THF (6 mL) under nitrogen. The resulting solution was stirred at room temperature for 2 hours. The crude product was purified by preparative HPLC (XBridge Prep C18 OBD column using decreasingly polar mixtures of water (containing 0.1% TFA) and MeCN as eluents. Fractions containing the desired compound were evaporated to dryness to afford the title compound (32.0 mg, 31.7%) as a colorless solid.

HRMS: calculated for $(C_{25}H_{24}F_6N_2O_7S+H)^+$ 611.1287; found (ESI [M+H]+) 611.1304.

$^1$H NMR (400 MHz, DMSO-$d_6$, mixture of rotamers, 2.2*:1) δ 0.87-1.22 (m, 4H), 3.20, 3.36* (s, 3H), 3.46 (t, 2H), 3.69 (q, 2H), 4.85-5.31 (m, 3H), 5.90*, 6.22 (s, 1H), 7.61-7.68 (m, 2H), 7.71-7.82 (m, 3H), 7.86-7.91 (m, 1H), 7.98-8.04 (m, 1H), 8.66, 8.68* (s, 1H), 10.82, 10.89* (s, 1H).

Example 900: 5-{[(1-Cyanocyclopropyl)methyl]sulfonyl}-N-[4-(1,1,1,3,3,3-hexafluoro-2-hydroxypropan-2-yl)phenyl]-2,3-dihydro-1H-isoindole-1-carboxamide

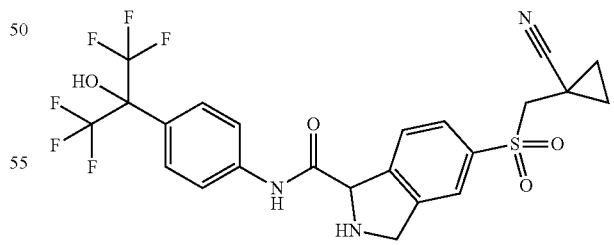

Diethylamine (1.5 mL, 0.19 mmol) was added to (9H-fluoren-9-yl)methyl 5-(((1-cyanocyclopropyl)methyl)sulfonyl)-1-((4-(1,1,1,3,3,3-hexafluoro-2-hydroxypropan-2-yl)phenyl)carbamoyl)isoindoline-2-carboxylate (150 mg, 0.19 mmol) in DCM (15 mL) under nitrogen. The resulting solution was stirred at rt for 14 hours. 5-(((1-cyanocyclopropyl)methyl)sulfonyl)-N-(4-(1,1,1,3,3,3-hexafluoro-2-hydroxypropan-2-yl)phenyl)isoindoline-1-carboxamide (100 mg, 94%) was detected by LCMS. The solvent was removed under reduced pressure. The crude product was purified by flash C18-flash chromatography, elution gradient 0 to 40% MeCN in water. Pure fractions were evaporated to dryness to afford 5-(((1-cyanocyclopropyl)methyl)sulfonyl)-N-(4-(1,1,1,3,3,3-hexafluoro-2-hydroxypropan-2-yl)phenyl) isoindoline-1-carboxamide (100 mg, 94%). LC/MS: m/z=548 [M+H]$^+$. HRMS: calculated for $(C_{23}H_{19}F_6N_3O_4S+H)^+$548.1087; found (ESI [M+H]$^+$) 548.1098. $^1$H NMR (300 MHz, DMSO-d$_6$) δ 0.99-1.13 (m, 2H), 1.27-1.31 (m, 2H), 3.69 (s, 2H), 4.42 (s, 2H), 5.12 (s, 1H), 7.60-7.89 (m, 7H), 8.64 (s, 1H), 10.34 (s, 1H).

Example 901: 2-Acetyl-5-{[(1-cyanocyclopropyl)methyl]sulfonyl}-N-[4-(1,1,1,3,3,3-hexafluoro-2-hydroxypropan-2-yl)phenyl]-2,3-dihydro-1H-isoindole-1-carboxamide

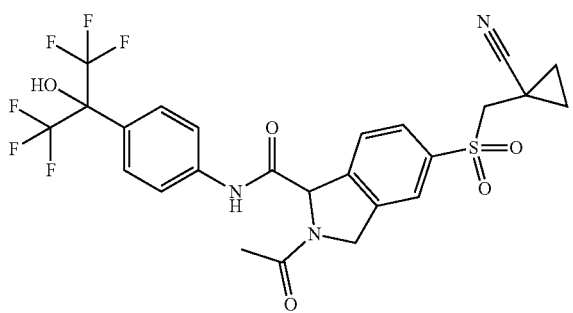 [SMILES: CC(=O)N1Cc2cc(S(=O)(=O)CC3(C#N)CC3)ccc2C1C(=O)Nc1ccc(C(O)(C(F)(F)F)C(F)(F)F)cc1]

Ac$_2$O (0.138 mL, 1.46 mmol) was added to 5-(((1-cyanocyclopropyl)methyl)sulfonyl)-N-(4-(1,1,1,3,3,3-hexafluoro-2-hydroxypropan-2-yl)phenyl)isoindoline-1-carboxamide (80 mg, 0.15 mmol) in DCM (5 mL) at 0° C. under nitrogen. The resulting solution was stirred at room temperature for 3 hours. The reaction mixture was treated with water (5 mL), extracted with DCM (3×10 mL), the organic layer was dried over Na$_2$SO$_4$, filtered and evaporated to afford white solid. The crude product was purified by preparative HPLC Column: XBridge Prep C18 OBD Column, 5 um, 19*150 mm; Mobile Phase A: Waters (0.05% TFA), Mobile Phase B: ACN; Flow rate: 20 mL/min; Gradient: 10% B to 54% B in 7 min; 254/220 nm. Fractions containing the desired compound were evaporated to dryness to afford 2-acetyl-5-(((1-cyanocyclopropyl)methyl)sulfonyl)-N-(4-(1,1,1,3,3,3-hexafluoro-2-hydroxypropan-2-yl)phenyl)isoindoline-1-carboxamide (60.0 mg, 69.7%). LC/MS: m/z=590 [M+H]$^+$. HRMS: calculated for $(C_{25}H_{21}F_6N_3O_5S+H)^+$590.1184; found (ESI [M+H]$^+$) 590.1185. $^1$H NMR (300 MHz, DMSO-d$_6$, mixture of rotamers, 4*:1) δ 1.00-1.04 (m, 2H), 1.29-1.33 (m, 2H), 2.00, 2.16* (s, 3H), 3.73 (s, 2H), 4.85-5.07 (m, 2H), 5.75*, 5.96 (s, 1H), 7.62-8.04 (m, 7H), 8.66*, 8.68 (s, 1H), 10.71*, 10.93 (s, 1H).

Example 902: Methyl 5-{[(1-cyanocyclopropyl)methyl]sulfonyl}-1-{[4-(1,1,1,3,3,3-hexafluoro-2-hydroxypropan-2-yl)phenyl]carbamoyl}-1,3-dihydro-2H-isoindole-2-carboxylate

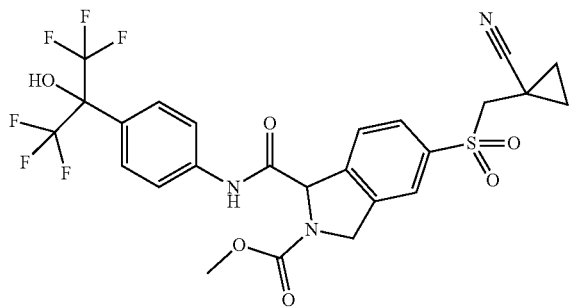 [SMILES: COC(=O)N1Cc2cc(S(=O)(=O)CC3(C#N)CC3)ccc2C1C(=O)Nc1ccc(C(O)(C(F)(F)F)C(F)(F)F)cc1]

Methyl carbonochloridate (69.0 mg, 0.73 mmol) was added dropwise to 5-(((1-cyanocyclopropyl)methyl)sulfonyl)-N-(4-(1,1,1,3,3,3-hexafluoro-2-hydroxypropan-2-yl)phenyl)isoindoline-1-carboxamide (80 mg, 0.15 mmol) in DCM (10 mL) at 0° C. over a period of 10 minutes under nitrogen. The resulting solution was stirred at room temperature for 12 hours. The reaction mixture was treated with water (10 mL), extracted with DCM (3×10 mL), the organic layer was dried over Na$_2$SO$_4$, filtered and evaporated to afford brown oil. The crude product was purified by preparative HPLC, Column: XSelect CSH Prep C18 OBD Column, 19*250 mm, 5 um; Mobile Phase A:Water (0.1% FA), Mobile Phase B: ACN; Flow rate: 25 mL/min; Gradient: 52% B to 52% B in 6 min; 254/220 nm; Rt: 5.50 min. Fractions containing the desired compound were evaporated to dryness to afford methyl 5-(((1-cyanocyclopropyl)methyl)sulfonyl)-1-((4-(1,1,1,3,3,3-hexafluoro-2-hydroxypropan-2-yl)phenyl)carbamoyl)isoindoline-2-carboxylate (60.0 mg, 67.8%).

LC/MS: m/z=606 [M+H]$^+$. HRMS: calculated for $(C_{25}H_{21}F_6N_3O_6S+H)^+$606.1133; found (ESI [M+H]$^+$) 606.1160. $^1$H NMR (300 MHz, DMSO-d$_6$, mixture of rotamers, 1.5*:1) δ 1.00-1.01 (m, 2H), 1.26-1.30 (m, 2H), 3.61-3.76 (m, 5H), 4.87 (s, 2H), 5.67-5.74 (m, 1H), 7.63 (d, J=8.7 Hz, 2H), 7.72-7.76 (m, 3H), 7.90 (d, J=8.1 Hz, 1H), 8.01 (d, J=5.7 Hz, 1H), 8.67 (s, 1H), 10.78*, 10.80 (s, 1H).

Example 1000: N-[4-(1,1,1,3,3,3-hexafluoro-2-hydroxypropan-2-yl)phenyl]-5-[(2-methylpropyl)sulfonyl]-2,3-dihydro-1H-isoindole-1-carboxamide

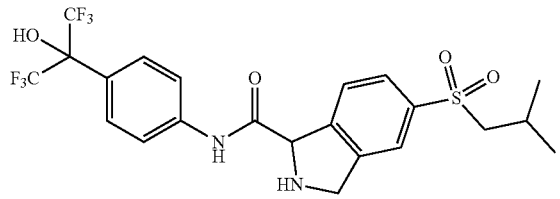 [SMILES: CC(C)CS(=O)(=O)c1ccc2c(c1)CNC2C(=O)Nc1ccc(C(O)(C(F)(F)F)C(F)(F)F)cc1]

tert-Butyl 1-{[4-(1,1,1,3,3,3-hexafluoro-2-hydroxypropan-2-yl)phenyl]carbamoyl}-5-[(2-methylpropyl)sulfonyl]-1,3-dihydro-2H-isoindole-2-carboxylate (130 mg, 0.21 mmol) was dissolved in isopropyl acetate (1 mL). 5M hydrogen chloride in IPA (1 ml, 5.00 mmol) was added and the reaction stirred at room temperature overnight. The reaction was concentrated in vacuo and the residue was co-evaporated with EtOAc/Hept (1:1 20 ml). N-[4-(1,1,1,3,3,3-hexafluoro-2-hydroxypropan-2-yl)phenyl]-5-[(2-methylpropyl)sulfonyl]-2,3-dihydro-1H-isoindole-1-carboxamide HCl salt (100 mg, 92%) was obtained as an off-white solid. The material was used without further purification.
LC/MS: m/z=525 [M+H]$^+$.

Example 1001: 2-Acetyl-N-[4-(1,1,1,3,3,3-hexafluoro-2-hydroxypropan-2-yl)phenyl]-5-[(2-methylpropyl) sulfonyl]-2,3-dihydro-1H-isoindole-1-carboxamide

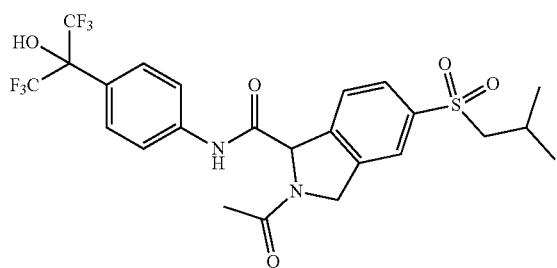 [SMILES: CC(=O)N1Cc2cc(S(=O)(=O)CC(C)C)ccc2C1C(=O)Nc1ccc(C(O)(C(F)(F)F)C(F)(F)F)cc1]

N-[4-(1,1,1,3,3,3-Hexafluoro-2-hydroxypropan-2-yl)phenyl]-5-[(2-methylpropyl)sulfonyl]-2,3-dihydro-1H-isoindole-1-carboxamide HCl salt (60 mg, 0.11 mmol) was dissolved in DCM (5 mL) and to this triethylamine (0.045 mL, 0.32 mmol) and acetic acid (7.35 µl, 0.13 mmol) were added followed by T3P (50% solution in EtOAc) (0.127 mL, 0.21 mmol). The reaction was stirred at room temperature for 30 min. The reaction was diluted with DCM and washed with saturated aqueous NaHCO$_3$. The layers were separated using a phase separator cartridge and the DCM removed in vacuo. A sample for biological screening was purified: Instrument: SFC-MS. Chromatographic conditions: MeOH/NH$_3$ 20 mM. Column: Waters Acquity UPC2 BEH 2-EP 3.5 µm 3×100 mm. 2-Acetyl-N-[4-(1,1,1,3,3,3-hexafluoro-2-hydroxypropan-2-yl)phenyl]-5-[(2-methylpropyl)sulfonyl]-2,3-dihydro-1H-isoindole-1-carboxamide (42.5 mg, 70.1%) HRMS: calculated for (C$_{24}$H$_{24}$F$_6$N$_2$O$_5$S+H)$^+$567.1388; found: (ESI [M+H]$^+$) 567.1381.
$^1$H NMR (600 MHz, DMSO-d$_6$, mixture of rotamers, 4*:1) δ 0.96 (d, 3H), 0.98 (d, 3H), 1.99-2.05 (m, 1H), 1.99, 2.14* (s, 3H), 3.20, 3.22* (d, 2H), 4.75-4.91, 5-5.09* (m, 2H), 5.72*, 5.92 (s, 1H), 7.6-7.79 (m, 5H), 7.87 (d, 1H), 7.97*, 8.00 (s, 1H), 8.68 (br s, 1H), 10.71*, 10.94 (s, 1H).

Example 1100: N-[4-(1,1,1,3,3,3-Hexafluoro-2-hydroxypropan-2-yl)phenyl]-5-{[(1-hydroxycyclopropyl)methyl]sulfonyl}-2,3-dihydro-1H-isoindole-1-carboxamide

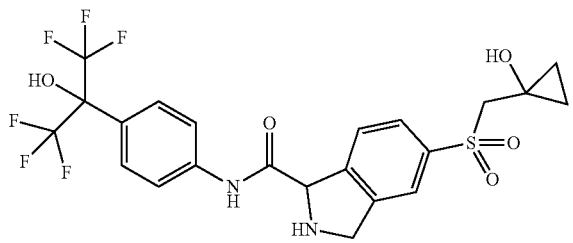 [SMILES: O=C(Nc1ccc(C(O)(C(F)(F)F)C(F)(F)F)cc1)C1NCc2cc(S(=O)(=O)CC3(O)CC3)ccc21]

TFA (3 mL, 40 mmol) was added to tert-butyl 5-(((1-((tert-butyldimethylsilyl)oxy)cyclopropyl)methyl)sulfonyl)-1-((4-(1,1,1,3,3,3-hexafluoro-2-hydroxypropan-2-yl)phenyl)carbamoyl)isoindoline-2-carboxylate (60 mg, 0.08 mmol) in DCM (3 mL) at 0° C. under nitrogen. The resulting solution was stirred at room temperature for 1 hour. The solvent was removed under reduced pressure. The crude product was purified by preparative HPLC Column: XBridge Prep C18 OBD Column, 5 um, 19*150 mm; Mobile Phase A:Waters (0.05% TFA), Mobile Phase B: ACN; Flow rate: 20 mL/min; Gradient: 10% B to 54% B in 7 min; 254/220 nm. Fractions containing the desired compound were evaporated to dryness to afford N-(4-(1,1,1,3,3,3-hexafluoro-2-hydroxypropan-2-yl)phenyl)-5-(((1-hydroxycyclopropyl)methyl)sulfonyl)isoindoline-1-carboxamide (TFA salt) (40.0 mg, 61.5%).
LC/MS: m/z=539[M+H]$^+$. HRMS: calculated for (C$_{22}$H$_{20}$F$_6$N$_2$O$_5$S+H)$^+$539.1075; found: (ESI [M+H]$^+$) 539.1069. $^1$H NMR (300 MHz, DMSO-d$_6$) δ 0.51-0.61 (m, 4H), 3.56 (s, 2H), 4.76 (dd, J=25.2, 15.0 Hz, 2H), 5.35 (brs, 1H), 5.74 (s, 1H), 7.69-7.79 (m, 4H), 7.82-7.88 (m, 1H), 7.92-7.98 (m, 1H), 8.03 (s, 1H), 8.73 (s, 1H), 11.28 (s, 1H).

Example 1101: 2-Acetyl-N-[4-(1,1,1,3,3,3-hexafluoro-2-hydroxypropan-2-yl)phenyl]-5-{[(1-hydroxycyclopropyl)methyl]sulfonyl}-2,3-dihydro-1H-isoindole-1-carboxamide

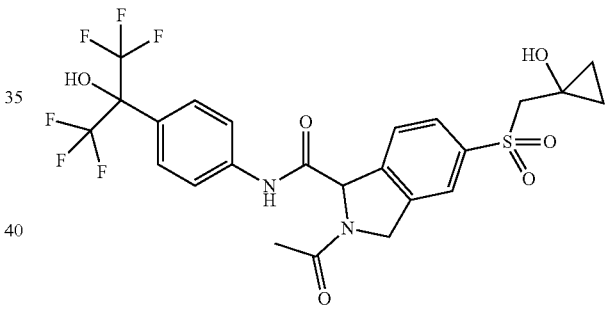

Ac$_2$O (15.17 mg, 0.15 mmol) was added to N-(4-(1,1,1,3,3,3-hexafluoro-2-hydroxypropan-2-yl)phenyl)-5-(((1-hydroxycyclopropyl)methyl)sulfonyl)isoindoline-1-carboxamide (80 mg, 0.15 mmol) in DCM (1 mL) at 0° C. under nitrogen. The resulting solution was stirred at room temperature for 1 hour. The solvent was removed under reduced pressure. The crude product was purified by preparative HPLC Column: XBridge Prep C18 OBD Column, 5 um, 19*150 mm; Mobile Phase A: Waters (0.05% TFA), Mobile Phase B: ACN; Flow rate: 20 mL/min; Gradient: 10% B to 54% B in 7 min; 254/220 nm. Fractions containing the desired compound were evaporated to dryness to afford 2-acetyl-N-(4-(1,1,1,3,3,3-hexafluoro-2-hydroxypropan-2-yl)phenyl)-5-(((1-hydroxycyclopropyl)methyl)sulfonyl) isoindoline-1-carboxamide (40.0 mg, 46.4%).
LC/MS: m/z=581[M+H]$^+$. HRMS: calculated for (C$_{24}$H$_{22}$F$_6$N$_2$O$_6$S+H)$^+$581.1181; found: (ESI [M+H]$^+$) 581.1208. $^1$H NMR (300 MHz, DMSO-d$_6$, mixture of rotamers, 4*:1) δ 0.48-0.60 (m, 4H), 2.00, 2.16* (s, 3H), 3.53 (s, 2H), 4.76-5.10 (m, 2H), 5.34, 5.35* (s, 1H), 5.73*, 5.93 (s, 1H), 7.62-7.77 (m, 5H), 7.85-7.91 (m, 1H), 7.95-8.00 (m, 1H), 8.65*, 8.67 (s, 1H), 10.70*, 10.93 (s, 1H).

Example 1102: 2-Formyl-N-[4-(1,1,1,3,3,3-hexafluoro-2-hydroxypropan-2-yl)phenyl]-5-{[(1-hydroxycyclopropyl)methyl]sulfonyl}-2,3-dihydro-1H-isoindole-1-carboxamide

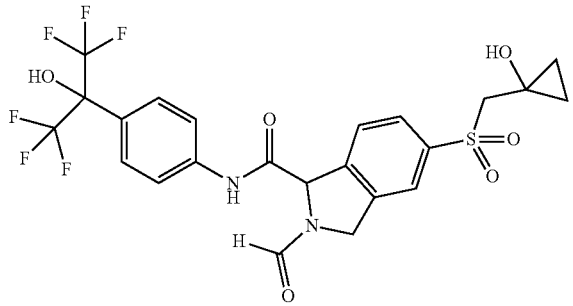 [SMILES: O=CN1Cc2cc(S(=O)(=O)CC3(O)CC3)ccc2C1C(=O)Nc1ccc(C(O)(C(F)(F)F)C(F)(F)F)cc1]

DIPEA (0.052 mL, 0.30 mmol) was added to N-(4-(1,1,1,3,3,3-hexafluoro-2-hydroxypropan-2-yl)phenyl)-5-(((1-hydroxycyclopropyl)methyl)sulfonyl)isoindoline-1-carboxamide (80 mg, 0.15 mmol), formic acid (68.4 mg, 1.49 mmol) and HATU (169 mg, 0.45 mmol) in DCM (1 mL) under nitrogen. The resulting solution was stirred at room temperature for 1 hour. The solvent was removed under reduced pressure. The crude product was purified by preparative HPLC Column: XBridge Prep C18 OBD Column, 5 um, 19*150 mm; Mobile Phase A: Waters (0.05% TFA), Mobile Phase B: ACN; Flow rate: 20 mL/min; Gradient: 10% B to 54% B in 7 min; 254/220 nm. Fractions containing the desired compound were evaporated to dryness to afford 2-formyl-N-(4-(1,1,1,3,3,3-hexafluoro-2-hydroxypropan-2-yl)phenyl)-5-(((1-hydroxycyclopropyl)methyl)sulfonyl)isoindoline-1-carboxamide (62.0 mg, 59.0%).

LC/MS: m/z=567 [M+H]$^+$. HRMS: calculated for $(C_{23}H_{20}F_6N_2O_6S+H)^+$ 567.1024; found: (ESI [M+H]$^+$) 567.1004. $^1$H NMR (300 MHz, DMSO-$d_6$, mixture of rotamers, 1.7*:1) δ 0.48-0.61 (m, 4H), 3.53 (s, 2H), 4.74-4.92, 5.02-5.18* (m, 2H), 5.34, 5.35* (s, 1H), 5.77*, 5.99 (s, 1H), 7.63-7.84 (m, 5H), 7.87-7.93 (m, 1H), 8.00 (s, 1H), 8.40, 8.49* (s, 1H), 8.65*, 8.67 (s, 1H), 10.76*, 10.86 (s, 1H).

Example 1103: N-[4-(1,1,1,3,3,3-Hexafluoro-2-hydroxypropan-2-yl)phenyl]-2-(hydroxyacetyl)-5-{[(1-hydroxycyclopropyl)methyl]sulfonyl}-2,3-dihydro-1H-isoindole-1-carboxamide

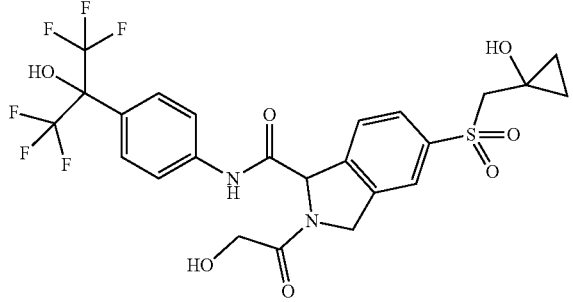 [SMILES: O=C(Nc1ccc(C(O)(C(F)(F)F)C(F)(F)F)cc1)C1c2ccc(S(=O)(=O)CC3(O)CC3)cc2CN1C(=O)CO]

DIPEA (0.058 mL, 0.33 mmol) was added to N-(4-(1,1,1,3,3,3-hexafluoro-2-hydroxypropan-2-yl)phenyl)-5-(((1-hydroxycyclopropyl)methyl)sulfonyl)isoindoline-1-carboxamide (60 mg, 0.11 mmol), 2-hydroxyacetic acid (42.4 mg, 0.56 mmol) and HATU (169 mg, 0.45 mmol) in DCM (2 mL) under nitrogen. The resulting solution was stirred at room temperature for 2 hours. The reaction mixture was treated with NH$_4$Cl (5 mL), extracted with DCM (3×10 mL), the organic layer was dried over Na$_2$SO$_4$, filtered and evaporated to afford colourless dry film. The crude product was purified by preparative HPLC Column: CHIRALPAK IF, 2*25 cm, 5 m; Mobile Phase A: Hex—HPLC, Mobile Phase B: EtOH—HPLC; Flow rate: 20 mL/min; Gradient: 30 B to 30 B in 16 min; 220/254 nm; Fractions containing the desired compound were evaporated to dryness to afford N-(4-(1,1,1,3,3,3-hexafluoro-2-hydroxypropan-2-yl)phenyl)-2-(2-hydroxyacetyl)-5-(((1-hydroxycyclopropyl)methyl)sulfonyl)isoindoline-1-carboxamide (18.00 mg, 27.1%).

LC/MS: m/z=597 [M+H]$^+$. HRMS: calculated for $(C_{24}H_{22}F_6N_2O_7S+H)^+$ 597.1130; found: (ESI [M+H]$^+$) 597.1130. $^1$H NMR (400 MHz, DMSO-$d_6$, mixture of rotamers, 5*:1) δ 0.49-0.59 (m, 4H), 3.53 (s, 2H), 3.85-4.31 (m, 2H), 4.83-5.21 (m, 3H), 5.35, 5.36* (s, 1H), 5.79*, 6.00 (s, 1H), 7.63-7.78 (m, 5H), 7.88 (d, J=8.1 Hz, 1H), 7.94-8.01 (m, 1H), 8.67*, 8.68 (s, 1H), 10.76*, 10.93 (s, 1H).

Example 1200: 2-Acetyl-N-[4-(1,1,1,3,3,3-hexafluoro-2-hydroxypropan-2-yl)phenyl]-5-[(2-hydroxypropyl)sulfonyl]-2,3-dihydro-1H-isoindole-1-carboxamide

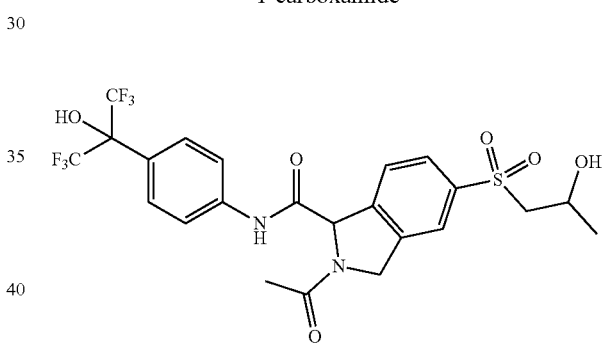

Step 1: 2-Acetyl-N-(4-(1,1,1,3,3,3-hexafluoro-2-hydroxypropan-2-yl)phenyl)-5-((2-hydroxypropyl)thio)isoindoline-1-carboxamide

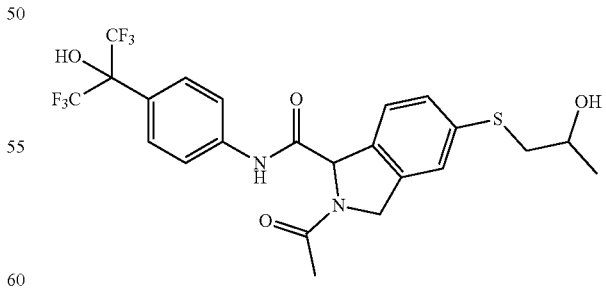

A solution of 2-acetyl-5-bromo-N-(4-(1,1,1,3,3,3-hexafluoro-2-hydroxypropan-2-yl)phenyl)isoindoline-1-carboxamide (83 mg, 0.16 mmol) in dioxane (1.5 mL) was degassed before, Xantphos (9.14 mg, 0.02 mmol), DIPEA (0.033 mL, 0.19 mmol), Pd$_2$(dba)$_3$ (7.24 mg, 7.90 μmol) and 1-mercaptopropan-2-ol (102 mg, 1.11 mmol) was added.

The reaction was heated to 80° C. for 40 min. The reaction was concentrated in vacuo and the residue was purified by flash chromatography eluting with 0-40% EtOAc in heptane. 2-Acetyl-N-(4-(1,1,1,3,3,3-hexafluoro-2-hydroxypropan-2-yl)phenyl)-5-((2-hydroxypropyl)thio)isoindoline-1-carboxamide (60.0 mg, 70.8%) was obtained as a foam.

LC/MS: m/z=535 [M−H]⁻. ¹H NMR (500 MHz, DMSO d₆, mixture of rotamers, 4*:1) δ 1.15 (d, 3H), 1.96, 2.12* (s, 3H), 2.87-2.96 (m, 1H), 2.98-3.04 (m, 1H), 3.72-3.8 (m, 1H), 4.63-4.97 (m, 3H), 5.56*, 5.74 (s, 1H), 7.24-7.44 (m, 3H), 7.59-7.66 (m, 2H), 7.69-7.76 (m, 2H), 8.62*, 8.65 (s, 1H), 10.55*, 10.78 (s, 1H).

Step 2: 2-Acetyl-N-[4-(1,1,1,3,3,3-hexafluoro-2-hydroxypropan-2-yl)phenyl]-5-[(2-hydroxypropyl)sulfonyl]-2,3-dihydro-1H-isoindole-1-carboxamide

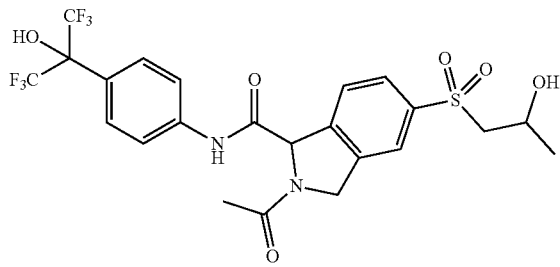 [SMILES: CC(=O)N1Cc2cc(S(=O)(=O)CC(C)O)ccc2C1C(=O)Nc1ccc(C(O)(C(F)(F)F)C(F)(F)F)cc1]

2-Acetyl-N-(4-(1,1,1,3,3,3-hexafluoro-2-hydroxypropan-2-yl)phenyl)-5-((2-hydroxypropyl)thio)isoindoline-1-carboxamide (60 mg, 0.11 mmol) was dissolved in DCM (2 mL) and to this mCPBA (≥77%) (60.2 mg, 0.27 mmol) was added and the reaction stirred at room temperature for 30 min. Sulphoxide could still be seen in the LCMS. mCPBA (≥77%) (25.06 mg, 0.11 mmol) was added and the reaction stirred at room temperature for another 30 min. The reaction was diluted with EtOAc and washed with 1M aq NaOH. The layers were separated and the aqueous was extracted twice with EtOAc. The combined organic extracts were dried using a phase separator cartridge and the solvent was removed in vacuo. Sample for biological screening was purified: Instrument: SFC2-MS. Chromatographic conditions: MeOH/NH₃ 20 mM. Column: Phenomenex Luna Hilic 5 30×250 mm. 2-Acetyl-N-[4-(1,1,1,3,3,3-hexafluoro-2-hydroxypropan-2-yl)phenyl]-5-[(2-hydroxypropyl)sulfonyl]-2,3-dihydro-1H-isoindole-1-carboxamide (28.4 mg, 44.7%). HRMS: calculated for (C₂₃H₂₂F₆N₂O₆S+H)⁺ 569.1181; found: (ESI [M+H]⁺) 569.1178.

¹H NMR (600 MHz, DMSO-d₆, mixture of rotamers, 4*:1) δ 1.09-1.15 (m, 3H), 1.99, 2.15* (s, 3H), 3.96-4.07 (m, 1H), 4.76-4.88, 4.99-5.08* (m, 2H), 4.90 (d, 1H), 5.72*, 5.92 (s, 1H), 7.59-7.78 (m, 5H), 7.86 (d, 1H), 7.95*, 7.98 (s, 1H), 8.67*, 8.70 (s, 1H), 10.70*, 10.94 (d, 1H).

Example 1300: 5-{[(1-Fluorocyclopropyl)methyl]sulfonyl}-N-[4-(1,1,1,3,3,3-hexafluoro-2-hydroxypropan-2-yl)phenyl]-2,3-dihydro-1H-isoindole-1-carboxamide

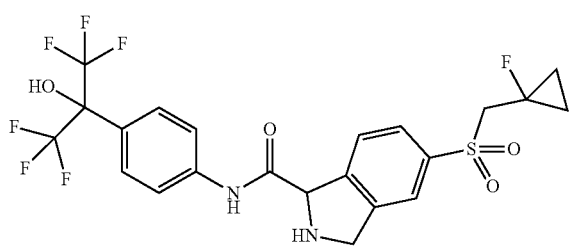 [SMILES: O=C(Nc1ccc(C(O)(C(F)(F)F)C(F)(F)F)cc1)C1NCc2cc(S(=O)(=O)CC3(F)CC3)ccc21]

TFA (1 mL, 12.98 mmol) was added to tert-butyl 5-(((1-fluorocyclopropyl)methyl)sulfonyl)-1-((4-(1,3,3,3-h1,1,1,3,3,3-hexafluoro-2-hydroxypropan-2-yl)phenyl)carbamoyl)isoindoline-2-carboxylate (200 mg, 0.31 mmol) in DCM (5 mL) cooled to 0° C. under nitrogen. The resulting solution was stirred at room temperature for 3 hours. The reaction mixture was quenched with saturated NaHCO₃ (10 mL), extracted with DCM (3×20 mL), the organic layer was dried over Na₂SO₄, filtered and evaporated to afford 5-(((1-fluorocyclopropyl)methyl)sulfonyl)-N-(4-(1,1,1,3,33-hexafluoro-2-hydroxypropan-2-yl)phenyl)isoindoline-1-carboxamide (100 mg, 59.3%) as an oil.

HRMS: calculated for (C₂₂H₁₉F₇N₂O₄S+H)⁺541.1032; found: (ESI [M+H]⁺) 541.1049.

¹H NMR (300 MHz, DMSO d₆) δ 0.69-0.77 (m, 2H), 0.92-1.05 (m, 2H), 3.96 (d, 2H), 4.34-4.44 (m, 2H), 5.09 (s, 1H), 7.60 (d, 2H), 7.60 (d, 1H), 7.77-7.90 (m, 4H), 8.63 (s, 1H), 10.33 (s, 1H).

Example 1301: 2-Acetyl-5-{[(1-fluorocyclopropyl)methyl]sulfonyl}-N-[4-(1,1,1,3,3,3-hexafluoro-2-hydroxypropan-2-yl)phenyl]-2,3-dihydro-1H-isoindole-1-carboxamide

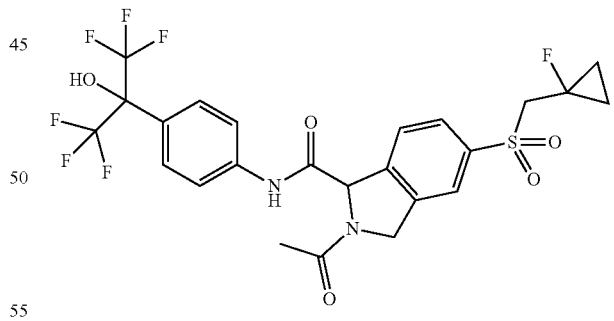

Acetic anhydride (151 mg, 1.48 mmol) was added dropwise to 5-(((1-fluorocyclopropyl)methyl)sulfonyl)-N-(4-(1,1,1,3,3,3-hexafluoro-2-hydroxypropan-2-yl)phenyl)isoindoline-1-carboxamide (80 mg, 0.15 mmol) in DCM (5 mL) at 0° C. over a period of 10 minutes under nitrogen. The resulting solution was stirred at room temperature for 4 hours. The reaction mixture was quenched with ice/water (5 mL), extracted with DCM (3×10 mL), the organic layer was dried over Na₂SO₄, filtered and evaporated to afford brown oil. The crude product was purified by preparative HPLC, Column: XBridge Prep C18 OBD Column 19×150 mm 5 um; Mobile Phase A: Water (0.05% TFA), Mobile Phase B: ACN; Flow rate: 20 mL/min; Gradient: 39% B to 47% B in 7 min; 254/220 nm; Rt: 6.33 min. Fractions containing the desired compound were evaporated to dryness to afford 2-acetyl-5-(((1-fluorocyclopropyl)methyl)sulfonyl)-N-(4-(1,1,1,3,3,3-hexafluoro-2-hydroxypropan-2-yl)phenyl) isoindoline-1-carboxamide (54 mg, 62%) as a solid.

HRMS: calculated for $(C_{24}H_{21}F_7N_2O_5S+H)^+$ 583.1138; found: (ESI [M+H]$^+$) 583.1135.

$^1$H NMR (300 MHz, DMSO-d$_6$, mixture of rotamers, 3.5*:1) δ 0.66-0.79 (m, 2H), 0.92-1.06 (m, 2H), 1.99, 2.14* (s, 3H), 4.00 (d, 2H), 4.78-4.90, 5.01-5.07* (m, 2H), 5.73*, 5.93 (s, 1H), 7.58-7.81 (m, 5H), 7.88-7.91 (m, 1H), 7.98-8.01 (m, 1H), 8.64*, 8.66 (s, 1H), 10.69*, 10.94 (s, 1H).

Biological Data

Compounds according to Formula I are RORγ modulators and their activities were determined in one of the following assays.

RORγ Radioligand Competition Binding Assay (SPA)

The aim of this assay is to identify compounds which bind to the RORγ ligand binding domain, by competing with tritiated 2-(4-(ethylsulfonyl)phenyl)-N-(4-(2-(methoxymethyl)phenyl)thiophen-2-yl)acetamide.

Preparation of tritiated 2-(4-(Ethylsulfonyl)phenyl)-N-(4-(2-(methoxymethyl)phenyl) thiophen-2-yl) acetamide

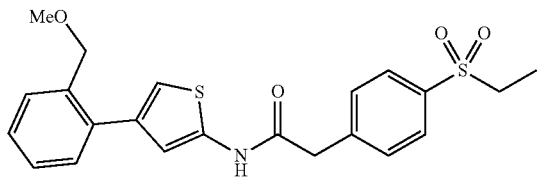 [SMILES: CCS(=O)(=O)c1ccc(CC(=O)Nc2cc(-c3ccccc3COC)cs2)cc1]

Step 1: N-(4-Bromothiophen-2-yl)-2-(4-(ethylsulfonyl)phenyl)acetamide

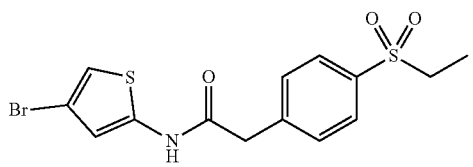 [SMILES: CCS(=O)(=O)c1ccc(CC(=O)Nc2cc(Br)cs2)cc1]

The trifluoroacetate salt of 4-bromothiophen-2-amine (2.45 g, 8.42 mmol, obtained by deprotection of tert-butyl N-(4-bromo-2-thienyl)carbamate with TFA in DCM) was added to 2-(4-(ethylsulfonyl)phenyl)acetic acid (2 g, 8.76 mmol), EDC (2.016 g, 10.51 mmol) and DMAP (3.21 g, 26.29 mmol) in DCM (30 mL) under nitrogen. The resulting mixture was stirred at rt for 12 hours. The reaction mixture was diluted with EtOAc (100 mL), and washed sequentially with water (150 mL) and saturated brine (125 mL). The organic layer was dried over Na$_2$SO$_4$, filtered and evaporated to afford the crude product. The crude product was purified by flash silica chromatography, elution gradient 10% to 60% EtOAc in petroleum ether. Pure fractions were evaporated to dryness to afford N-(4-bromothiophen-2-yl)-2-(4-(ethylsulfonyl)phenyl)acetamide (2.0 g, 61%) as a solid. LC/MS: m/z=535 [M−H]$^-$. $^1$H NMR (400 MHz, DMSO-d$_6$) δ 1.09, (t, 3H), 3.26 (q, 2H), 3.85 (s, 2H), 6.63 (d, 1H), 7.06, (d, 1H), 7.58 (d, 2H), 7.84 (d, 2H), 11.64 (s, 1H).

Step 2: 2-(4-(Ethylsulfonyl)phenyl)-N-(4-(2-(methoxymethyl)phenyl)thiophen-2-yl)acetamide

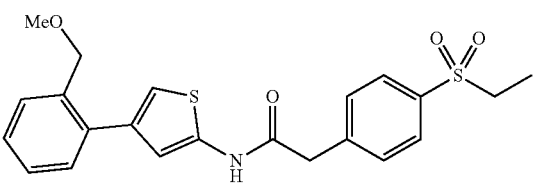 [SMILES: CCS(=O)(=O)c1ccc(CC(=O)Nc2cc(-c3ccccc3COC)cs2)cc1]

PdCl$_2$(dppf) (9.42 mg, 0.01 mmol) was added to N-(4-bromothiophen-2-yl)-2-(4-(ethylsulfonyl)phenyl)acetamide (100 mg, 0.26 mmol), (2-(methoxymethyl)phenyl)boronic acid (85 mg, 0.52 mmol) and K$_2$CO$_3$ (107 mg, 0.77 mmol) in 1,4-dioxane (4 mL) and water (0.5 mL) at 25° C. under nitrogen. The resulting mixture was stirred at 100° C. for 5 hours. The reaction mixture was quenched with water (10 mL) and extracted with EtOAc (30×2 mL). The organic layer was dried over Na$_2$SO$_4$, filtered and evaporated to afford yellow solid. The crude product was purified by flash C18-flash chromatography, elution gradient 5 to 50% MeCN in water. Pure fractions were evaporated to dryness to afford 2-(4-(ethylsulfonyl)phenyl)-N-(4-(2-(methoxymethyl)phenyl)thiophen-2-yl)acetamide (81 mg, 73.2%) as a solid.

HRMS: calculated for $(C_{22}H_{23}NO_4S+H)^+$ 430.1133; found: (ESI [M+H]$^+$) 430.1147.

$^1$H NMR (300 MHz, CDCl$_3$) δ 1.29 (t, 3H), 3.11 (q, 2H), 3.38 (s, 3H), 3.82 (s, 2H), 4.38 (s, 2H), 6.80 (s, 1H), 6.92 (s, 1H), 7.28-7.39 (m, 3H), 7.43-7.47 (m, 1H), 7.51 (d, 2H), 7.85 (d, 2H), 8.35 (s, 1H).

Step 3: Tritiation of 2-(4-(ethylsulfonyl)phenyl)-N-(4-(2-(methoxymethyl)phenyl)thiophen-2-yl)acetamide 2-(4-(Ethylsulfonyl)phenyl)-N-(4-(2-(methoxymethyl) phenyl)thiophen-2-yl)acetamide (2.3 mg, 5.35 μmol) and 1-iodopyrrolidine-2,5-dione (1.3 mg, 5.78 μmol) were dissolved in DCM (0.2 mL) and TFA (0.02 mL) was added. The reaction mixture was stirred for 5 minutes, then concentrated by a stream of nitrogen. The residue was dissolved in EtOH (0.4 mL), triethylamine (20 μl, 144.28 μmol) was added and the solution was transferred to a tritiation vial containing Pd/C (3 mg, 2.82 μmol, 10% Pd). The vial was degassed by 3 freeze-pump-thaw-cycles. The flask was filled with T$_2$ gas (290 GBq). The reaction mixture was stirred at rt for 2.5 h. T$_2$ gas was recovered via the washing bed and the reaction mixture was concentrated by a stream of nitrogen. MeOH (0.7 mL) were added and the reaction mixture was concentrated by a stream of nitrogen. This procedure was repeated 3 times. The reaction mixture was filtered and dissolved in MeOH (15 mL total). After evaporation, the crude product was dissolved in DMSO and purified by preparative HPLC on a XBridge C18 column (10 m, 250×19 mm) using a gradient of 5-95% acetonitrile in H$_2$O/ACN/HOAc 95/5/0.5 buffer over 40 minutes with a flow of 15 mL/min. The product was detected by UV at 244 nm. Yield: 1717 MBq.

Protein Production

Human RORγ (Ligand Binding Domain (RORγ LBD) was expressed in *E. coli* (BL21DE3 Star) as a fusion protein: N-6×HN-Avi-GST-TCS-hRORγ LBD (S258-K518) subcloned into pET24a(+). The LBD (258-518) is underlined in the protein sequence:

(SEQ ID NO: 1)
HNHNHNHNHNHNGGLNDIFEAQKIEWHEGSPILGYWKIKGLVQPTRLLLE

YLEEKYEEHLYERDEGDKWRNKKFELGLEFPNLPYYIDGDVKLTQSMAII

RYIADKHNMLGGCPKERAEISMLEGAVLDIRYGVSRIAYSKDFETLKVDF

LSKLPEMLKMFEDRLCHKTYLNGDHVTHPDFMLYDALDVVLYMDPMCLDA

FPKLVCFKKRIEAIPQIDKYLKSSKYIAWPLQGWQATFGGGDHPPKSDYD

IPTTGSGSGSLVPRGSTPEAPYASLTEIEHLVQSVCKSYRETCQLRLEDL

LRQRSNIFSREEVTGYQRKSMWEMWERCAHHLTEAIQYVVEFAKRLSGFM

ELCQNDQIVLLKAGAMEVVLVRMCRAYNADNRTVPPEGKYGGMELFRALG

CSELISSIFDFSHSLSALHFSEDEIALYTALVLINAHRPGLQEKRKVEQL

QYNLELAFHHHLCKTHRQSILAKLPPKGKLRSLCSQHVERLQIFQHLHPI

VVQAAFPPLYKELFSTETESPVGLSK.

The bacteria was grown in TB with Autoinduction media (Stock 50×ZYM-5052: 25% Glycerol, 2.5% Glucose, 10% Lactose), 3 mM MgOAc and 100 ug/ml Kan A. The culture was incubated at 180 rpm, at 37° C. At OD600 1.9, the temperature was decreased to 20° C. and at OD600 7.9 the cells were harvested. After centrifugation the bacterial pellet was resuspended in ice cold Lysis Buffer (20 mM Tris pH8.0, 250 mM NaCl, 10% (v/v) Glycerol, 0.5% CHAPS (w/v), 20 mM Imidazole, 1 mM TCEP, 1x Protease inhibitor (Complete, Roche), 1ul Benzonase/100 ml buffer (E1014, Sigma)). Lysis was performed on ice at 30 kpsi using a Cell disruptor. To remove cell debris the sample was centrifuged at 48 000 xg (20 000 rpm) for 20 minutes, at 4° C.

The protein was purified in two steps at room temperature. The 6×HN tag was utilized in the first affinity purification step where lysate was run over a HisTrap 5 ml Crude column (Amersham Pharmacia) using AKTA FPLC system (Amersham Pharmacia). After washing with Affinity purification buffer A (20 mM Tris pH8.0, 250 mM NaCl, 10% (v/v) Glycerol, 0.5% CHAPS (w/v), 20 mM Imidazole, 1 mM TCEP), proteins were eluted with a step gradient (50-100-150-200-250-300-500 mM Imidazole). Fractions of 0.5 ml volume were collected and analysed with SDS-PAGE (Novex system) and Coomassie staining. Fractions containing protein with expected molecular weight (from 50 mM Imidazole elution step) were pooled. The pool also contained protein with molecular weight corresponding to free GST. To separate GST from GST-RORγ a second size exclusion purification step was performed using a SEC Sephadex200 16/60 column (Amersham Pharmacia) at 0.8 ml/min in Size Exclusion/Storage Buffer (20 mM Tris pH8.0, 150 mM KCl, 0.5 mM EDTA, 20% (v/v) Glycerol, 0.5% (w/v) CHAPS, 1mM TCEP). Fractions of 0.5 ml volume were collected and were analysed on a gel as described above. Fractions with no or low levels of the band corresponding to free GST, were pooled, frozen in liquid nitrogen and stored at −80° C. for use in the SPA binding assay.

Assay Protocol

The scintillation proximity assay (SPA) was run in white polystyrene flat-bottom 384-well plates (Greiner, cat. No. 781075). Assays were carried out in 40 μl reaction volumes. Various concentrations of test ligands in 0.4 microlitres of DMSO were added to assay plates using an acoustic liquid dispenser. 4 nM purified N—(HN)6-GST-TCS-hRORγ (258-518) was mixed with 40 micrograms Yttrium oxide (YOx) glutathione SPA imaging beads in assay buffer (20 mM Tris, 150 mM NaCl, 10% Glycerol, 0.25% CHAPS, 1 mM TCEP) prior to adding 30 microlitres to test ligands. Assay plates were incubated for one hour at room temperature before adding 10 microlitres tritiated 2-(4-(ethylsulfonyl)phenyl)-N-(4-(2-(methoxymethyl)phenyl)thiophen-2-yl)acetamide to test plates in assay buffer (final concentration, 25 nM). Test plates were incubated for 16 hours and read using a LEADseeker Multimodality imaging instrument.

The raw data was analysed and IC50 and Ki values for the compounds were calculated using Genedata Screener software. Raw data was transformed to % effect using equation 1:

Compound % effect=100*[(*X*−min)/(max−min)], where X represents the normalized value for the compound based on the Min (vehicle) and Max (reference compound) inhibition controls.

The concentration of test ligand that inhibited radioligand binding by 50% (i.e., the $IC_{50}$) was calculated by plotting the % effect versus test ligand concentration and fitting the data using the Genedata Screener Smart fit algorithm. $K_i$ is calculated from the $IC_{50}$ value using the equation Ki=IC50/1+[L]/Kd) where [L]=25 nmol/L and $K_d$=17 nmol/L RORγ Co-Factor Recruitment Assay (FRET)

A high throughput coactivator binding assay for the identification of inverse agonists of the recruitment of peptide SRC-1 (NCOA1_677-_700) to the RORγ ligand binding domain was established.

Protein Production

The ligand binding domain (LBD) of human RORγ was expressed in *E. coli* (BL21DE3 Star) as a fusion protein: N-6×HN-MBP-Avi-TCS-hRORγLBD(P260-K518) subcloned into pET24a(+). The LBD (P260-K518) is underlined in the protein sequence:

(SEQ ID NO: 2)
MHNHNHNHNHNHNGGLNDIFEAQKIEWHEGMKIEEGKLVIWINGDKGYNG

LAEVGKKFEKDTGIKVTVEHPDKLEEKFPQVAATGDGPDIIFWAHDRFGG

YAQSGLLAEITPDKAFQDKLYPFTWDAVRYNGKLIAYPIAVEALSLIYNK

DLLPNPPKTWEEIPALDKELKAKGKSALMFNLQEPYFTWPLIAADGGYAF

KYENGKYDIKDVGVDNAGAKAGLTFLVDLIKNKHMNADTDYSIAEAAFNK

GETAMTINGPWAWSNIDTSKVNYGVTVLPTFKGQPSKPFVGVLSAGINAA

SPNKELAKEFLENYLLTDEGLEAVNKDKPLGAVALKSYEEELAKDPRIAA

TMENAQKGEIMPNIPQMSAFWYAVRTAVINAASGRQTVDEALKDAQTGSD

YDIPTTGSGSGSLVPRGSTPEAPYASLTEIEHLVQSVCKSYRETCQLRLE

DLLRQRSNIFSREEVTGYQRKSMWEMWERCAHHLTEAIQYVVEFAKRLSG

FMELCQNDQIVLLKAGAMEVVLVRMCRAYNADNRTVFFEGKYGGMELFRA

LGCSELISSIFDFSHSLSALHFSEDEIALYTALVLINAHRPGLQEKRKVE

-continued

QLQYNLELAFHHHLCKTHRQSILAKLPPKGKLRSLCSQHVERLQIFQHLH

PIVVQAAFPPLYKELFSTETESPVGLSK.

Bacterial colonies were picked and inoculated in 16×500 mL TB medium supplemented with 25 mM $(NH_4)_2SO_4$, 50 mM $KH_2PO_4$, 50 mM $Na_2HPO_4$, 0.8% v/v Glycerol, 0.05% w/v Glucose, 0.2% w/v α-Lactose, 1 mM $MgSO_4$ and 200 µg/ml Kanamycin to promote autoinduction. After incubation at 37° C. at 200 rpm for two hours the temperature was decreased to 20° C. When the OD600 was 12.4, the temperature was further decreased to 16° C. Cells were harvested at OD600 24 by centrifugation at 4000 rpm for 10 minutes at 4° C. The pellet, approximately ~320 g was stored at −80° C.

The pellet was resuspended in 1600 mL Lysis Buffer (50 mM Tris-HCl, 10% v/v Glycerol, 1 mM TCEP, 2 tablets Protease Inhibitor/100 mL Lysis Buffer (Complete, Roche), 4 1 Benzonase/100 mL Lysis Buffer (E1014, Sigma), pH 8.0). Lysis was performed at 25 kpsi using Cell disruptor (Constant Cell Disruptor Systems). The sample was kept on ice during the whole lysis procedure For removal of cell debris, the lysed cells were ultracentrifuged at 143719×g (43000 rpm) for 45 minutes at 4° C. The supernatant was stored at −80° C.

The thawed supernatant was captured utilizing the N-6× HN tag with washed 100 mL NiNTA Superflow resin (Qiagen) in Wash Buffer (50 mM Tris-HCl, 50 mM NaCl, 30 mM Imidazole, 10% v/v Glycerol, 1 mM TCEP, pH 8.0) and slowly stirred with a magnetic bar at room temperature. After 1.5 hours the supernatant was removed by vacuum suction through a porcelain funnel (sieve size 2). The resin, with the captured protein was washed with 700 mL Wash Buffer and transferred to three PD columns with filter (GE). Each column was eluted with 10 mL+90 mL Elution Buffer (50 mM Tris-HCl, 50 mM NaCl, 300 mM Imidazole, 10% v/v Glycerol, 1 mM TCEP, pH 8.0) and collected. All fractions from the columns were pooled and analyzed with SDS-PAGE (Novex System) and stained in commassie. The pooled sample was concentrated to ~30 mL using concentrators with 30K cutoff (Amicon, Millipore) at 4000 rpm and at 4° C. The concentrated sample was clarified at 30000×g for 15 minutes at 4° C. After centrifugation a small pellet of aggregated protein was visible which was discarded. In a size exclusion column (XK50/60, GE) 1000 mL Superdex 200 resin (GE) was equilibrated with GF Buffer (20 mM Tris-HCl, 150 mM NaCl, 10% v/v Glycerol, 1 mM TCEP, pH 8.0). The concentrated sample was loaded onto the column at the flow rate 6 mL/min and 14 mL fractions were collected. The fractions were analyzed on a gel as described above. Fractions containing the major band which corresponded to the expected molecular weight for N-6×HN-MBP-Avi-TCS-hRORγLBD(P260-K518) (75.9 kDa) were collected and pooled. To further verify the mass, the pooled sample was analysed using mass spectrometry (Waters) and the mass corresponded to the expected mass. From 8 litres culture (~320 g bacteria cells) 348 mg of N-6×HN-MBP-Avi-TCS-hRORγLBD(P260-K518) was purified. Purified protein was flash frozen in liquid nitrogen and stored at −80° C.

Protein N-6×HN-MBP-Avi-TCS-hRORγLBD(P260-K518), 42 µM (223 mg) purified as described above was incubated with 15000 units BirA/L (Avidity LLC) in 70 mL Biotinylation Buffer (200 µM Biotin, 10 mM ATP, 10 mM $Mg_2OAc$) at room temperature whilst slowly stirring with a magnetic bar for 9 hours. The reaction was analyzed using mass spectrometry and the mass determined to be 76.2 kDa corresponding to biotinylated N-6×HN-MBP-Avi-TCS-hRORγLBD(P260-K518). After centrifugation at 19000 rpm for 15 minutes at 4° C. precipitation was visible which was discarded. The sample was concentrated as described above to ~25 mL. The reaction was polished in size exclusion columns (HiLoad Superdex 200 26/60, GE) equilibrated with GF Buffer using aflow rate of 2.5 mL/min and 2 mL/fractions were collected. The fractions were analyzed on a gel as described above. Fractions containing the major band which corresponded to the expected molecular weight for biotinylated N-6×HN-MBP-Avi-TCS-hRORγ LBD (P260-K518) (76.2 kDa) were collected and pooled. The estimated yield was ~185 mg. Biotinylated protein was flash frozen in liquid nitrogen and stored at −80° C.

Assay Protocol

The assay was run in black 384 well plates (Greiner cat no: 784900). Various concentrations of test ligands in 0.1 microlitres DMSO were dispensed to assay plates using an Echo acoustic dispenser. Two pre-mixes were prepared and incubated for 1 h at room temp in the dark. Pre-mix 1 comprised 100 nM Protein (Biotinylated HN-Avi-MBP-TCS-hRORγ (258-518)) and 60 nM Streptavidin APC in assay buffer, 50 mM MOPS pH7.4, 50 mM KF, 0.003% (w/v) CHAPS, 10 mM DTT and 0.01% (w/v) BSA and pre-mix 2 comprised 160 nM biotinylated SRC-1 peptide (NCOA1-677-700) and 20 nM Europium-W8044 labelled Streptavidin in assay buffer. Five microlitres of pre-mix 2 was dispensed to assay plates containing 0.1 microlitres of test compound and was incubated for 15 minutes prior to adding five microlitres of pre-mix 1. Plates were incubated at room temperature for 1 hour in the dark, prior to reading in a Pherastar multi-mode plate reader using HTRF filter set (ex 320, em 612 and 665). The FRET signal at 665 nm was divided by the signal at 612 nm and multiplied by 10,000 to generate a signal ratio value for each well. The raw data was transformed to % effect using the equation:

$$\text{Compound \% effect} = 100 * [(X-\min)/(\max-\min)],$$

where X represents the normalized value for the compound based on the Min (vehicle) and Max (reference compound) inhibition control.

The concentration of test ligand that inhibited the activity by 50% (i.e., the $IC_{50}$) was calculated by plotting the % effect versus test ligand concentration and fitting the data using the Genedata Screener Smart fit algorithm.

Inhibition of IL-17 Release from Human $T_H17$ Cells (IL-17 Release)

This test is designed to screen compounds for their inhibitory effect on the release of IL-17 from isolated and cultured human $T_H17$ cells.

Peripheral blood mononuclear cells (PBMC) were isolated from heparin treated human whole blood fromhealthy donors by density gradient centrifugation. $T_H17$ cells (CD4+ CXCR3-CCR6+) were enriched using a human $T_H17$ Cell Enrichment Kit (Stemcell Technologies) according to the manufacturer's protocol. The isolated $T_H17$ cells were activated with aCD3aCD28 beads (MACS Miltenyi) and cultured in X-Vivo15 medium (Lonza) supplemented with L-glutamine, β-mercaptoethanol and a cytokine cocktail consisting of; IL-2, IL-23, IL-1β, IL-6, TGF-β. Cells were seeded at 8000 cells/well in a 384-plate (Corning, #3707) in the presence of compounds or DMSO and cultured for 4 days (37° C., 5% $CO_2$). On day 4 supernatants were collected and IL-17A was measured using a Human IL-17 HTRF Assay kit (Cisbio Bioassays) according to the manufacturer's protocol. The $IC_{50}$ values for the tested compounds was calculated using Genedata Screener® software (Genedata) using the following calculation method;

Compound % effect=100*[(X−min)/(max−min)], where X represents the normalized value for the compound based on the Min (DMSO) and Max (compound 3-(1,3-benzodioxol-5-yl)-1-(3,5-dimethylpiperidin-1-yl)-3-(2-hydroxy-4,6-dimethoxyphenyl)propan-1-one at 10 jM, described in J. R. Hu et al. ACS Med. Chem. Lett. 2013, 4, 79-84) inhibition controls.

Results

All exemplified compounds were tested in the FRET assay described above. All of the exemplified compounds were also tested in the SPA assay. Selected compounds were further characterized for the inhibition of 11-17 release in the cell assay. Results are summarized in the table below.

TABLE

Screening results of exemplified compounds

| Example No. | $pIC_{50}$ (FRET) | $pIC_{50}$ (SPA) | $pIC_{50}$ IL-17 release |
|---|---|---|---|
| 100 | 7.2 | 6.4 | 7.4 |
| 101 | 7.3 | 7.5 | 7.9 |
| 102 | 6.7 | 7.1 | 7.1 |
| 103 racemate | 7.2 | 7.5 | 7.9 |
| 103 isomer 1 | 7.2 | 7.5 | 7.9 |
| 103 isomer 2 | 6.5 | 6.8 | 7.6 |
| 104 | 6.7 | 7.1 | 7.7 |
| 105 | 6.4 | 6.9 | 7.7 |
| 106 | 6.5 | 6.9 | 7.2 |
| 107 | 6.8 | 7.2 | 7.3 |
| 108 | 7.0 | 7.4 | 7.4 |
| 109 | 7.0 | 7.2 | 7.7 |
| 110 | 7.1 | 7.1 | 7.7 |
| 111 | 6.9 | 7.4 | 7.2 |
| 112 | 7.0 | 7.1 | 7.5 |
| 113 | 6.4 | 6.9 | 7.1 |
| 114 | 6.7 | 7.0 | 7.5 |
| 115 | 6.3 | 6.5 | 7.2 |
| 116 | 6.7 | 7.2 | 6.7 |
| 117 | 7.3 | 7.4 | 7.1 |
| 200 | 7.2 | 7.8 | 7.5 |
| 201, racemate | 7.2 | 7.9 | 8.1 |
| 201, isomer 1 | 6.3 | 7.0 | 7.4 |
| 201, isomer 2 | 7.4 | 8.2 | 8.2 |
| 202 | 7.5 | 8.1 | 8.2 |
| 203 | 7.2 | 7.9 | 8.0 |
| 204 | 7.0 | 7.6 | 8.1 |
| 205 | 6.9 | 7.7 | 7.8 |
| 206 | 7.1 | 7.8 | 7.4 |
| 207 | 7.1 | 7.6 | 7.4 |
| 208 | 7.0 | 7.5 | 7.7 |
| 209 | 7.0 | 7.8 | 7.6 |
| 210 | 6.7 | 7.4 | 7.6 |
| 211 | 6.7 | 7.3 | 6.7 |
| 212 | 6.6 | 7.3 | 7.8 |
| 213 | 7.5 | 7.8 | 8.1 |
| 214 | 6.8 | 7.7 | 8.0 |
| 300 | 7.3 | 6.5 | 7.6 |
| 301 | 7.3 | 7.3 | 7.7 |
| 302 | 7.2 | 7.6 | 8.2 |
| 303, isomer 1 | 6.3 | 6.9 | 6.7 |
| 303, isomer 2 | 6.9 | 7.4 | 7.5 |
| 304 | 6.8 | 7.0 | 7.9 |
| 305 | 7.0 | 6.1 | 8.0 |
| 306 | 6.6 | 7.2 | 7.7 |
| 307, isomer 1 | 7.1 | 7.4 | 7.5 |
| 307, isomer 2 | 6.3 | 6.7 | 6.5 |
| 308 | 7.3 | 7.3 | 7.5 |
| 309 | 6.9 | 7.3 | 7.3 |
| 310 | 6.6 | 7.4 | 7.5 |
| 311 | 6.8 | 7.1 | 7.5 |
| 312 | 6.4 | 6.0 | 7.4 |
| 313 | 7.1 | 7.5 | 7.0 |
| 314 | 7.0 | 7.5 | 7.2 |
| 400 | 6.7 | 5.7 | 6.5 |
| 401, racemate | 7.0 | 6.8 | 7.6 |
| 401, isomer 1 | 7.4 | 7.1 | 7.8 |
| 401, isomer 2 | 5.7 | <5.4 | 6.9 |
| 402 | 7.0 | 7.6 | 7.9 |
| 403 | 7.2 | 6.6 | 7.6 |
| 404, racemate | 6.7 | 6.7 | 7.5 |
| 404, isomer 1 | 6.8 | 6.9 | 7.6 |
| 404, isomer 2 | 4.8 | 5.2 | 6.5 |
| 405, racemate | 6.6 | 6.7 | 7.4 |
| 405, isomer 1 | 6.9 | 7.1 | 7.8 |
| 405, isomer 2 | 4.7 | <5.2 | <6.8 |
| 406 | 7.3 | 6.8 | 7.6 |
| 407 | 7.1 | 6.6 | 7.2 |
| 408 | 6.5 | 6.8 | 7.9 |
| 409, isomer 1 | 6.4 | 6.3 | 7.2 |
| 409, isomer 2 | 7.1 | 6.8 | 7.1 |
| 410 | 6.9 | 6.9 | 7.7 |
| 411 | 7.0 | 6.8 | 7.6 |
| 412 | 6.8 | 6.5 | 7.6 |
| 413 | 6.7 | 7.1 | 7.5 |
| 414 | 7.2 | 6.7 | 7.5 |
| 415 | 7.0 | 7.1 | 7.5 |
| 416 | 6.4 | 6.6 | 7.5 |
| 417 | 6.9 | 6.4 | 7.5 |
| 418 | 6.5 | 6.9 | 7.4 |
| 419 | 6.2 | 6.5 | 7.3 |
| 420 | 6.1 | 6.2 | 7.1 |
| 421 | 6.8 | 6.4 | 7.0 |
| 422 | 6.8 | 6.6 | 7.4 |
| 423 | 7.0 | 6.6 | 7.1 |
| 424, isomer 1 | 6.8 | 6.5 | 6.8 |
| 424, isomer 2 | 6.4 | 6.3 | 6.5 |
| 425 | 6.7 | 6.7 | 7.1 |
| 426 | 6.5 | 6.0 | 6.5 |
| 427 | 6.6 | 6.8 | 7.0 |
| 428 | 6.9 | 7.0 | 6.9 |
| 429 | 7.1 | 7.0 | 6.9 |
| 430 | 6.6 | 6.7 | 6.9 |
| 431 | 6.8 | 6.7 | 6.6 |
| 432 | 6.8 | 6.4 | 6.8 |
| 433 | 6.9 | 6.8 | 7.1 |
| 434 | 6.3 | 6.7 | 7.6 |
| 435 | 7.0 | 7.1 | 7.7 |
| 436 | 6.6 | 6.7 | 7.8 |
| 437 | 6.8 | 6.6 | 7.7 |
| 438 | 7.2 | 7.0 | 7.7 |
| 439 | 6.5 | 7.2 | 7.6 |
| 440 | 6.4 | 6.9 | 7.5 |
| 441 | 6.3 | 6.6 | 7.6 |
| 442 | 7.2 | 6.6 | 7.3 |
| 443 | 6.0 | 6.3 | 7.0 |
| 444 | 6.5 | 6.7 | 7.2 |
| 445 | 6.7 | 6.7 | 7.6 |
| 446 | 6.7 | 6.5 | 7.5 |
| 447 | 6.1 | 6.3 | 7.3 |
| 448 | 6.1 | 6.5 | 7.1 |
| 449 | 6.3 | 6.6 | 7.1 |
| 450, racemate | 6.9 | 6.8 | 7.6 |
| 450, isomer 1 | 7.3 | 7.0 | 7.9 |
| 450, isomer 2 | 6.1 | 6.2 | 7.0 |
| 452, isomer 1 | 6.8 | 7.0 | 7.7 |
| 452, isomer 2 | 6.7 | 6.8 | 7.3 |
| 453 | 6.8 | 6.9 | 7.4 |
| 454 | 6.9 | 6.9 | 7.4 |
| 455 | 7.0 | 7.0 | 7.0 |
| 456 | 6.8 | 6.6 | 7.9 |
| 500 | 7.3 | 7.7 | 8.0 |
| 600 | 6.4 | 5.4 | — |
| 601 | 7.4 | 6.6 | 7.5 |
| 602 | 7.1 | 6.6 | 7.6 |
| 603 | 6.6 | <5.8 | 7.5 |
| 604 | 7.2 | 6.6 | 7.3 |
| 605 | 7.2 | 6.9 | 6.9 |
| 606 | 7.0 | 6.6 | 7.5 |

TABLE-continued

Screening results of exemplified compounds

| Example No. | pIC$_{50}$ (FRET) | pIC$_{50}$ (SPA) | pIC$_{50}$ IL-17 release |
|---|---|---|---|
| 607 | 6.8 | 6.6 | 7.4 |
| 608 | 6.7 | 6.4 | 7.4 |
| 609 | 6.6 | 6.6 | 7.3 |
| 610 | 7.1 | 6.8 | 7.2 |
| 700 | 6.4 | 5.7 | 7.0 |
| 701 | 7.1 | 7.0 | 7.8 |
| 702 | 7.2 | 6.8 | 7.5 |
| 703 | 6.4 | 6.7 | 7.6 |
| 704 | 7.0 | 6.9 | 7.6 |
| 705 | 7.0 | 7.1 | 7.0 |
| 706 | 6.8 | 7.0 | 7.3 |
| 707 | 7.0 | 7.1 | 7.3 |
| 800 | 6.2 | 5.4 | — |
| 801 | 6.7 | 6.7 | 7.1 |
| 802 | 6.2 | 6.5 | 7.1 |
| 900 | 6.3 | 5.5 | — |
| 901 | 7.1 | 6.8 | 7.1 |
| 902 | 7.1 | 6.4 | 7.3 |
| 1001 | 6.9 | 6.2 | 7.0 |
| 1100 | 7.2 | 6.0 | 6.7 |
| 1101 | 7.0 | 7.1 | 7.2 |
| 1102 | 7.2 | 7.2 | 7.5 |
| 1103 | 6.8 | 7.1 | 6.3 |
| 1200 | 6.7 | 6.7 | 6.8 |
| 1300 | 7.4 | 7.5 | 6.6 |
| 1301 | 7.2 | 7.9 | 6.8 |

The above description of illustrative embodiments is intended only to acquaint others skilled in the art with the Applicant's specification, its principles, and its practical application so that others skilled in the art may readily adapt and apply the specification in its numerous forms, as they may be best suited to the requirements of a particular use. This description and its specific examples, while indicating embodiments of this specification, are intended for purposes of illustration only. This specification, therefore, is not limited to the illustrative embodiments described in this specification, and may be variously modified. In addition, it is to be appreciated that various features of the specification that are, for clarity reasons, described in the context of separate embodiments, also may be combined to form a single embodiment. Conversely, various features of the specification that are, for brevity reasons, described in the context of a single embodiment, also may be combined to form sub-combinations thereof.

The invention claimed is:

1. A method of treating a disease state in a human suffering from said disease state, which comprises administering to the human in need of such treatment a therapeutically effective amount of (1R)-2-acetyl-N-[4-(1,1,1,3,3,3-hexafluoro-2-hydroxypropan-2-yl)phenyl]-5-(methylsulfonyl)-2,3-dihydro-1H-isoindole-1-carboxamide, or a pharmaceutically acceptable salt thereof, and wherein the disease state is selected from ulcerative cholitis, Crohn's disease, multiple sclerosis, inflammatory bowel disease, rheumatoid arthritis, graft versus host disease, systemic lupus erythematosis, and lupus nephritis.

2. The method of treating according to claim 1, wherein the disease state is ulcerative cholitis.

3. The method of treating according to claim 1, wherein the disease state is Crohn's disease.

4. The method of treating according to claim 1, wherein the disease state is multiple sclerosis.

5. The method of treating according to claim 1, wherein the disease state is inflammatory bowel disease.

6. The method of treating according to claim 1, wherein the disease state is rheumatoid arthritis.

7. The method of treating according to claim 1, wherein the disease state is graft versus host disease.

8. The method of treating according to claim 1, wherein the disease state is systemic lupus erythematosis.

9. The method of treating according to claim 1, wherein the disease state is lupus nephritis.

* * * * *